US006641814B1

(12) United States Patent
Andersen et al.

(10) Patent No.: US 6,641,814 B1
(45) Date of Patent: Nov. 4, 2003

(54) NUCLEIC ACIDS FRAGMENTS AND POLYPEPTIDE FRAGMENTS DERIVED FROM M. TUBERCULOSIS

(75) Inventors: Peter Andersen, Brønshøj (DK); Rikke Nielsen, Frederiksberg (DK); Thomas Oettinger, Hellerup (DK); Peter Birk Rasmussen, København (DK); Ida Rosenkrands, København (DK); Karin Weldingh, København (DK); Walter Florio, Frederiksberg (DK)

(73) Assignee: Statens Serum Institut, Copenhagen (DK)

( * ) Notice: Subject to any disclaimer, the term of this patent is extended or adjusted under 35 U.S.C. 154(b) by 0 days.

(21) Appl. No.: 09/050,739

(22) Filed: Mar. 30, 1998

Related U.S. Application Data

(60) Provisional application No. 60/044,624, filed on Apr. 18, 1997.

(30) Foreign Application Priority Data

Apr. 2, 1997 (DK) .............................. 0376/97

(51) Int. Cl.[7] .................. A61K 39/02; A61K 39/40; A61K 39/04; C12N 1/12; C12M 1/34

(52) U.S. Cl. .................. 424/190.1; 424/168.1; 424/248.1; 435/91.1; 435/253.1; 435/287.2; 536/22.1

(58) Field of Search .................. 424/190.1, 248.1, 424/168.1; 435/253.1, 91.1, 287.2; 536/22.1; 935/77, 95

(56) References Cited

FOREIGN PATENT DOCUMENTS

| WO | WO 95/01441 | 1/1995 |
|---|---|---|
| WO | WO 96/37219 | 11/1996 |
| WO | WO 97/09428 | 3/1997 |
| WO | WO 97/09429 | 3/1997 |

OTHER PUBLICATIONS

Wiegeshaus, E.H., et al "Evaluation of the Protective Potency of New Tuberculosis Vaccines", Reviews of Infectious Diseases, vol. 11, supplement 2, pp. S484–S490, Mar. 1989.*
Orme, I.M., "New Vaccines against Tuberculosis", Infectious Disease Clinics of North America, vol. 13, No. 1, pp. 169–185, Mar. 1999.*
Infection and Immunity vol. 59, No. 6, Jun. 1991, Washington US pp. 1905–1910 Peter Andersen et al. 'Proteins released from *Mycobacterium tuberculosis* during growth'.
Stryhn, A., et al., 1996, Peptide binding specificity of major histocompatibility complex class I resolved into an array of apparently independent subspecificites: quantitation by peptide libraries and improved prediction of binding, Eur. J. Immunol. 26:1911–1918.

Ulrichs, T. et al., 1998, Differential T cell responses to *Mycobacterium tuberculosis* ESAT6 in tuberculosis patients and healthy donors, Eur. J. Immunol. 28:3949–3958.
P. Andersen et al., Identification of Immunodominant antigens during infection with *Mycobacterium tuberculosis*, J. Immunol, 36, 823–831, 1992.
Peter Andersen et al., Proteins released from *Mycobacterium tuberculosis* during growth, Infection and Immunity, Jun. 1991, vol. 59, No. 6, p. 1905–1910.
Peter Andersen et al., Specificity of a protective memory immune response against *Mycobacterium tuberculosis*, Infection and Immunity, Mar. 1993, vol. 61, No. 3, p. 844–851.
Peter Andersen et al., T–cell proliferatiive response to antigens secreted by *Mycobacterium tuberculosis*, Infection and Immunity, Apr. 1991, vol. 59, No. 4, p. 1558–1563.
Kris Huygen et al., Spleen cell cytokine secretion in *Mycobacterium bovis* BCG–infected mice, infection and immunity, Jul. 1992, vol. 60, No. 7, p. 2880–2886.
Christiane Abou–Zeid et al., Characterization of fibronectin–binding antigens released by *Mycobacterium tuberculosis* and *Mycobacterium bovis* BCG, Infection and Immunity, Dec. 1988, vol. 56, No. 12, p. 3046–3051.
Martine Borremans et al., Cloning sequence determination, and expression of a 32– kilodalton–protein gene of *Mycobacterium tuberculosis*, Infection and Immunity, Oct. 1989, vol. 57, No. 10, p. 3123–3130.
Peter Andersen, Effective vaccination of mice against *Mycobacterium tuberculosis* infection with a soluble mixture of secreted *Mycobacterial proteins*, Infection and Immunity, Jun. 1994, vol. 62, No. 6.
Andersen, P. et al., Jun. 1991, Proteins released from *Mycobacterium tuberculosis* during growth, Infect. Immun. 59(6): 1905–1910.
Baldwin, S.L. et al., Jun. 1998, Evaluation of new vaccines in the mouse and guinea pig model of tuberculosis, Infect. Immun. 66(6):2951–2959.
Boesen, H. et al., Apr. 1995, Human T–cell responses to secreted antigen fractions of *Mycobacterium tuberculosis*, Infect. Immun. 63(4): 1491–1497.

(List continued on next page.)

*Primary Examiner*—Rodney P Swartz
(74) *Attorney, Agent, or Firm*—Frommer Lawrence & Haug; Thomas J. Kowalski

(57) ABSTRACT

The present invention is based on the identification and characterization of a number of *M. tuberculosis* derived novel proteins and protein fragments (SEQ ID NOs: 2, 4, 6, 8, 10, 12, 14, 16, 17–23, 42, 48, 50, 52, 54, 56, 58, 60, 62, 64, 66, 68, 70, 72–86, 88, 90, 92, 94, 141, 143, 145, 147, 149, 151, 153, and 168–171). The invention is directed to the polypeptides and immunologically active fragments thereof, the genes encoding them, immunological compositions such as vaccines and skin test reagents containing the polypeptides. Another part of the invention is based on the surprising discovery that fusions between ESAT-6 and MPT59 are superior immunogens compared to each of the unfused proteins, respectively.

43 Claims, 6 Drawing Sheets

OTHER PUBLICATIONS

Figure 1:
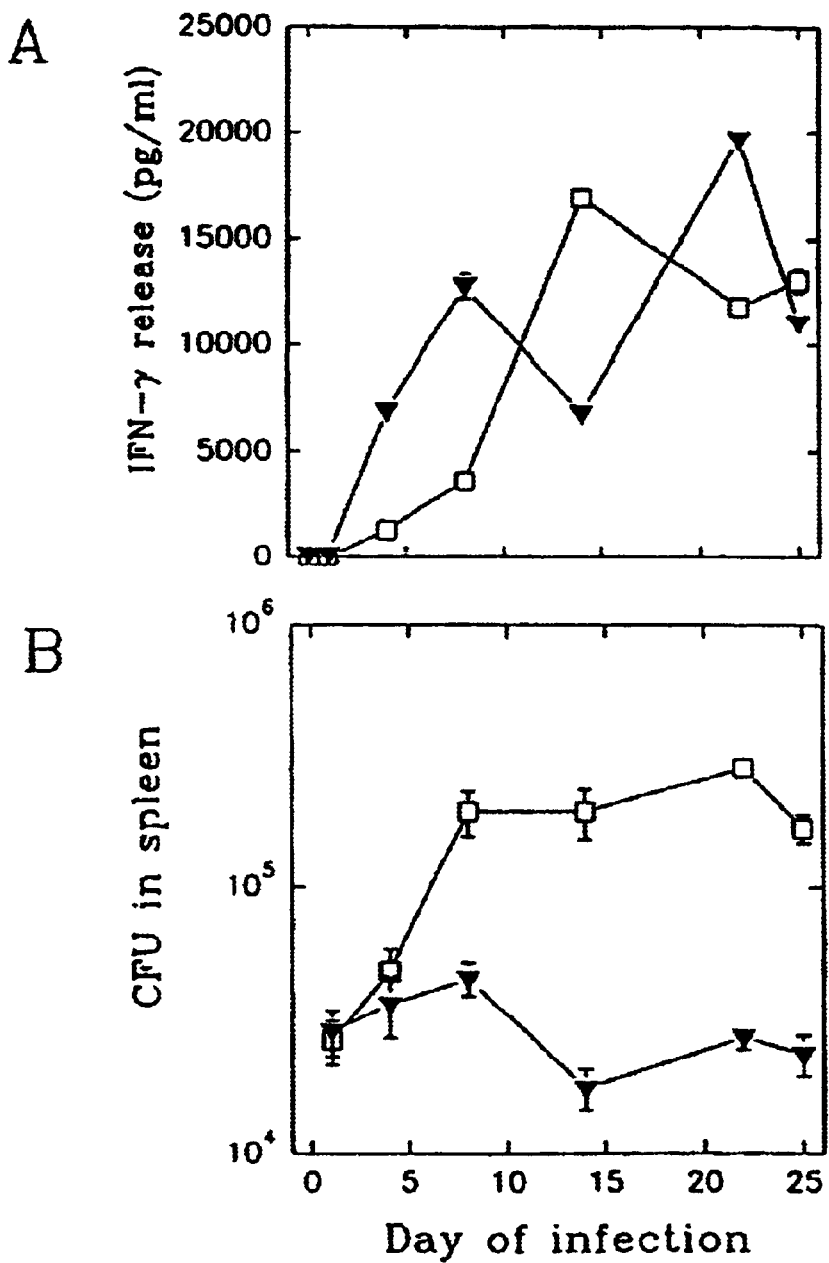
Figure 2:
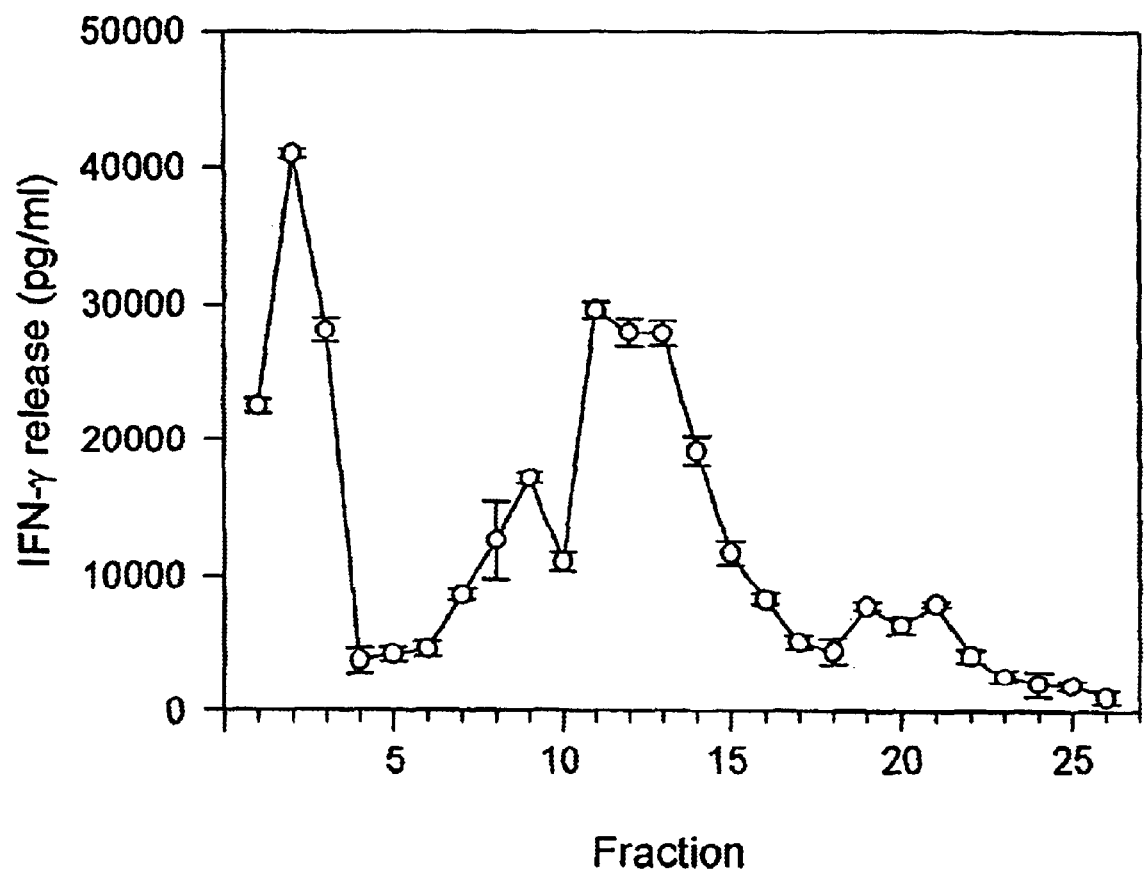

Brandt et al., 1996, Key epitopes on the ESAT–6 antigen recognized in mice during the recall of protective immunity to *Mycobacterium tuberculosis*, J. Immunol. 157:3527–3533.

Brandt L. et al., Feb. 2000, ESAT–6 subunit vaccination against *Mycobacterium tuberculosis*, Infect. Immun. 68:791–795.

Cole, S.T. et al., Jun. 1998, Deciphering the biology of *Mycobacterium tuberculosis* from the complete genome sequence, Nature 393:537–544.

Horwitz et al., Feb. 1995, Protective immunity against tuberculosis induced by vaccination with major extracellular proteins of *Mycobacterium tuberculosis*, Proc. Natl. Acad. Sci.USA.92:1530–1534.

Olsen A.W. et al., Jun. 2000, Efficient protection against *Mycobacterium tuberculosis* by vaccination with a single subdominant epitope from the ESAT–6 antigen, Eur J. Immunol. 30(6):1724–1732.

Ravn, P. et al., Mar. 1999, Human T Cell responses to ESAT–6 antigen from *Mycobacterium tuberculosis*, J. Infect. Dis. 179:637–645.

Roche, P.W. et al. Dec. 1994, T–cell determinants and antibody binding sites on the major mycobacterial secretory protein MPB59 of *Mycobacterium bovis*, Infect. Immun.62(12):5319–5326.

Rosenkrands, I., et al., Identification and characterization of a 29–kilodalton protein from *Mycobacterium tuberculosis* culture filtrate recognized by mouse memory effector cells, Infect. Immun 66(6); 2728–2735.

Skjøt, R.L.V., et al., Jan. 2000, Comparative evaluation of low–molecular–mass proteins from *Mycobacterium tuberculosis* identifies members of the ESAT–6 family as immunodominant T–cell antigens, Infect. Immun. 68(1):214–220.

Andersen et al., J. Immunol. Methods, vol. 161, pp. 29–39, No Dates.

Andersen et al., Infect. Immun., vol. 60, pp. 2317–2323, No Dates.

Andersen, Infect. Immun. vol. 62, pp. 2536–2544, No Dates.

Andersen et al., J. Immunol. vol. 154, pp. 3359–3372, No Dates.

Barkholt et al., Anal. Biochem., vol. 177, pp. 318–322, No Dates.

Borodovsky et al., Computers Chem., vol. 17, pp. 123–133, No Dates.

Brown, EMBL Sequence database, No Dates.

Crabtree et al., EMBL Sequence database, No Dates.

Van Dyke et al., Gene, pp. 99–104, No Dates.

Gosselin et al., J. Immunol., vol. 149, pp. 3477–3481, No Dates.

Harboe et al., Infect. Immun. vol. 64, pp. 16–22, No dates.

Von Heijne et al., J. Mol. Biol., vol. 173, pp. 243–251, No dates.

Hochstrasser et al., Annal Biochem., vol. 173, pp. 424–435, No dates.

Kohler et al., Nature, vol. 256, pp. 495–497, No dates.

Li et al., Infect. Immun., vol. 61, pp. 1730–1734, No dates.

Lindblad et al., Infect. Immun., vol. 65, pp. 623–629, No dates.

Mahairs et al., J. Bacteriol., vol. 178, pp. 1274–1282, No dates.

Nagai et al., Infect. Immun., vol. 59, pp. 372–382, No dates.

Oettinger et al., Infect. Immun., vol. 62, pp. 2058–2064, No dates.

Ohara et al., Scand. J. Immunol., vol. 41, pp. 433–442, No dates.

Pal et al., Infect. Immun., vol. 60, pp. 4781–4792, No dates.

Pearson et al., Proc. Natl. Acad. Sci., USA, vol. 85, pp. 2444–2448, No dates.

Ploug et al., Anal Biochem., vol. 181, pp. 33–39, No dates.

Porath et al., FEBS Lett., vol. 185, pp. 306–310, No dates.

Roberts et al., Immunol., vol. 85, pp. 502–508, No dates.

Rosenkrands et al., Infect. Immun., vol. 66, No. 6, pp. 2728–2735, No dates.

Rosenkrands et al., EMBL: 007812, No dates.

Rosenkrands et al., EMBL: Y12820, No dates.

Sorensen et al., Infect. Immun., vol. 63, pp. 1710–1717, No dates.

Theisen et al., Clinical and Diagnostic Laboratory Immunology, vol. 2, pp. 30–34, No dates.

Valdes–Stauber et al., Appl. Environ. Microbiol., vol. 60, pp. 3809–3814, No dates.

Williams, Science, 272:27, No dates.

Young et al., Proc. Natl. Acad. Sci. USA, vol. 82, pp. 2583–2587, No dates.

* cited by examiner

```
1    GGCGCGCCGGT ACCTATGTGG CCGCCGATGC TGCGGNCGCG TCGACCTATA CCGGGTTCTG      60
                 -35 region                              -10 region 61   ATCGAACCCT GCTGACCGAG AGGACTTGTG ATG TCG CAA ATC ATG TAC AAC TAC CCC GCG  120
                          Shine Delgarno M   S   Q   I   M   Y   N   Y   P   A 121  ATG TTG GGT CAC GCC GGG GAT ATG GCC GGA TAT GCC GGC ACG CTG CAG AGC TTG GGT GCC  180
     M   L   G   H   A   G   D   M   A   G   Y   A   G   T   L   Q   S   L   G   A 181  GAG ATC GCC GTG GAG CAG GCC GCG CTG CAG TGG CAG AGT GCG TGG CAG GAT ACC GGG ATC ACG  240
     E   I   A   V   E   Q   A   A   L   Q   W   Q   S   A   W   Q   D   T   G   I   T 241  TAT CAG GCG TGG CAG GCA CAG TGG CAG AAC CAG GCC ATG GAA GAT TTG GTG CGG GCC TAT CAT  300
     Y   Q   A   W   Q   A   Q   W   Q   N   Q   A   M   E   D   L   V   R   Y   H 301  GCG ATG TCC AGC ACC CAT GAA GCC AAC ACC ATG GCG ATG ATG GCC CGC GAC ACC GCC GAA  360
     A   M   S   S   T   H   E   A   N   T   M   A   M   M   A   R   D   T   A   E 361  GCC GCC AAA TGG GGC TAG                                              381
     A   A   K   W   G   G   *
```

Fig. 3

```
  1   GGGTAGCCCG ACCACGGCTG GGCAAAGATG TGCAGGCCGC CATCAAGGCG GTCAAGGCCG    60
          -35 region 61   GCGACGGCGT CATAAACCCG GACGGCCACCT TGTTGGCGGG CCCCGCGGTG CTGACGCCCG   120
                  -10 region 121   ACGAGTACAA CTCCCGGCTG GTG GCC GCC GAC CCG GAG TCC ACC GCG GCG       170
        Shine Delgarno       V   A   A   D   P   E   S   T   A   A 171   TTG CCC GAC GGC GCC GGG CTG GTC GTT CTG GAT GGC ACC GTC ACT GCC GAA CTC GAA GCC   230
       L   P   D   G   A   G   L   V   V   L   D   G   T   V   T   A   E   L   E   A 231   GAG GGC TGG GCC AAA GAT CGC GAT CGG CAA GAG CTG CGT AAG TCG ACC GGG CTG         290
       E   G   W   A   K   D   R   I   R   Q   E   L   R   K   S   T   G   L 291   GAC GTT TCC GAC CGC ATC CGG GTG ATG TCG GTG CCT GCG GAA CGC GAA GAC TGG GCG      350
       D   V   S   D   R   I   R   V   M   S   V   P   A   E   R   E   D   W   A 351   CGC ACC CAT CGC GAC CTC ATT GCC GGA GAA ATC TTG GCT ACC GAC TTC GAA TTC GCC GAC  410
       R   T   H   R   D   L   I   A   G   E   I   L   A   T   D   F   E   F   A   D 411   CTC GCC GAT GGT GTG GCC ATC GGC GAC GTG CGG GTA AGC ATC GAA AAG ACC TGA         467
       L   A   D   G   V   A   I   G   D   V   R   V   S   I   E   K   T   *
```

Fig. 4

```
  1 GAATTCGCCGGGTGCACACAGCCTTACACGACGGAGGTGGACACATGAAG   50
                                                      M  K
 51 GGTCGGTCGGCGCTGCTGCGGGCGCTCTGGATTGCCGCACTGTCATTCGG  100
     G  R  S  A  L  L  R  A  L  W  I  A  A  L  S  F  G
101 GTTGGGCGGTGTCGCGGTAGCCGCGGAACCCACCGCCAAGGCCGCCCCAT  150
     L  G  G  V  A  V  A  A  E  P  T  A  K  A  A  P
151 ACGAGAACCTGATGGTGCCGTCGCCCTCGATGGGCCGGGACATCCCGGTG  200
     Y  E  N  L  M  V  P  S  P  S  M  G  R  D  I  P  V
201 GCCTTCCTAGCCGGTGGGCCGCACGCGGTGTATCTGCTGGACGCCTTCAA  250
     A  F  L  A  G  G  P  H  A  V  Y  L  L  D  A  F  N
251 CGCCGGCCCGGATGTCAGTAACTGGGTCACCGCGGGTAACGCGATGAACA  300
     A  G  P  D  V  S  N  W  V  T  A  G  N  A  M  N
301 CGTTGGCGGGCAAGGGGATTTCGGTGGTGGCACCGGCCGGTGGTGCGTAC  350
     T  L  A  G  K  G  I  S  V  V  A  P  A  G  G  A  Y
351 AGCATGTACACCAACTGGGAGCAGGATGGCAGCAAGCAGTGGGACACCTT  400
     S  M  Y  T  N  W  E  Q  D  G  S  K  Q  W  D  T  F
401 CTTGTCCGCTGAGCTGCCCGACTGGCTGGCCGCTAACCGGGGCTTGGCCC  450
     L  S  A  E  L  P  D  W  L  A  A  N  R  G  L  A
451 CCGGTGGCCATGCGGCCGTTGGCGCCGCTCAGGGCGGTTACGGGGCGATG  500
     P  G  G  H  A  A  V  G  A  A  Q  G  G  Y  G  A  M
501 GCGCTGGCGGCCTTCCACCCCGACCGCTTCGGCTTCGCTGGCTCGATGTC  550
     A  L  A  A  F  H  P  D  R  F  G  F  A  G  S  M  S
551 GGGCTTTTTGTACCCGTCGAACACCACCACCAACGGTGCGATCGCGGCGG  600
     G  F  L  Y  P  S  N  T  T  T  N  G  A  I  A  A
601 GCATGCAGCAATTCGGCGGTGTGGACACCAACGGAATGTGGGGAGCACCA  650
     G  M  Q  Q  F  G  G  V  D  T  N  G  M  W  G  A  P
651 CAGCTGGGTCGGTGGAAGTGGCACGACCCGTGGGTGCATGCCAGCCTGCT  700
     Q  L  G  R  W  K  W  H  D  P  W  V  H  A  S  L  L
701 GGCGCAAAACAACACCCGGGTGTGGGTGTGGAGCCCGACCAACCCGGGAG  750
     A  Q  N  N  T  R  V  W  V  W  S  P  T  N  P  G
751 CCAGCGATCCCGCCGCCATGATCGGCCAAACCGCCGAGGCGATGGGTAAC  800
     A  S  D  P  A  A  M  I  G  Q  I  A  E  A  M  G  N
801 AGCCGCATGTTCTACAACCAGTATCGCAGCGTCGGCGGGCACAACGGACA  850
     S  R  M  F  Y  N  Q  Y  R  S  V  G  G  H  N  G  H
851 CTTCGACTTCCCAGCCAGCGGTGACAACGGCTGGGGCTCGTGGGCGCCCC  900
     F  D  F  P  A  S  G  D  N  G  W  G  S  W  A  P
901 AGCTGGGCGCTATGTCGGGCGATATCGTCGGTGCGATCCGCTAAGCGAAT  950
     Q  L  G  A  M  S  G  D  I  V  G  A  I  R
951 TC                                                  952
```

Fig. 5

US 6,641,814 B1

NUCLEIC ACIDS FRAGMENTS AND POLYPEPTIDE FRAGMENTS DERIVED FROM *M. TUBERCULOSIS*

RELATED APPLICATIONS

Reference is made to U.S. Provisional application 60/044,624, filed Apr. 18, 1997, and Danish application Serial No. 0376/97, filed Apr. 2, 1997, priority from both of which are claimed; and, each of which are hereby incorporated herein by reference. All documents cited in the following text are also hereby incorporated herein by reference.

FIELD OF THE INVENTION

The present invention relates to a number of immunologically active, novel polypeptide fragments derived from the *Mycobacterium tuberculosis*, vaccines and other immunologic compositions containing the fragments as immunogenic components, and methods of production and use of the polypeptides. The invention also relates to novel nucleic acid fragments derived from *M. tuberculosis* which are useful in the preparation of the polypeptide fragments of the invention or in the diagnosis of infection with *M. tuberculosis*. The invention further relates to certain fusion polypeptides, notably fusions between ESAT-6 and MPT59.

BACKGROUND OF THE INVENTION

Human tuberculosis (hereinafter designated "TB") caused by *Mycobacterium tuberculosis* is a severe global health problem responsible for approximately 3 million deaths annually, according to the WHO. The worldwide incidence of new TB cases has been progressively falling for the last decade but the recent years has markedly changed this trend due to the advent of AIDS and the appearance of multidrug resistant strains of *M. tuberculosis*.

The only vaccine presently available for clinical use is BCG, a vaccine which efficacy remains a matter of controversy. BCG generally induces a high level of acquired resistance in animal models of TB, but several human trials in developing countries have failed to demonstrate significant protection. Notably, BCG is not approved by the FDA for use in the United States.

This makes the development of a new and improved vaccine against TB an urgent matter which has been given a very high priority by the WHO. Many attempts to define protective mycobacterial substances have been made, and from 1950 to several investigators reported an increased resistance after experimental vaccination. However, the demonstration of a specific long-term protective immune response with the potency of BCG has not yet been achieved by administration of soluble proteins or cell wall fragments, although progress is currently being made by relying on polypeptides derived from short term-culture filtrate, cf. the discussion below.

Immunity to *M. tuberculosis* is characterized by three basic features; i) Living bacilli efficiently induces a protective immune response in contrast to killed preparations; ii) Specifically sensitized T lymphocytes mediate this protection; iii) The most important mediator molecule seems to be interferon gamma (INF-γ). Short term-culture filtrate (ST-CF) is a complex mixture of proteins released from *M. tuberculosis* during the first few days of growth in a liquid medium (Andersen et al., 1991). Culture filtrates has been suggested to hold protective antigens recognized by the host in the first phase of TB infection (Andersen et al. 1991, Orme et al. 1993). Recent data from several laboratories have demonstrated that experimental subunit vaccines based on culture filtrate antigens can provide high levels of acquired resistance to TB (Pal and Horwitz, 1992; Roberts et al., 1995; Andersen, 1994; Lindblad et al., 1997). Culture filtrates are, however, complex protein mixtures and until now very limited information has been available on the molecules responsible for this protective immune response. In this regard, only two culture filtrate antigens have been described as involved in protective immunity, the low mass antigen ESAT-6 (Andersen et al., 1995 and EP-A-0 706 571) and the 31 kDa molecule Ag85B (EP-0 432 203).

There is therefore a need for the identification of further antigens involved in the induction of protective immunity against TB in order to eventually produce an effective sub-unit vaccine.

OBJECT OF THE INVENTION

It is an object of the invention to provide novel antigens which are effective as components in a subunit vaccine against TB or which are useful as components in diagnostic compositions for the detection of infection with mycobacteria, especially virulence-associated mycobacteria. The novel antigens may also be important drug targets.

SUMMARY OF THE INVENTION

The present invention is i.a. based on the identification and characterization of a number of previously uncharacterized culture filtrate antigens from *M. tuberculosis*. In animal models of TB, T cells mediating immunity are focused predominantly to antigens in the regions 6–12 and 17–30 kDa of STCF. In the present invention 8 antigens in the low molecular weight region (CFP7, CFP7A, CFP7B, CFP8A, CFP8B, CFP9, CFP10A, and CFP11) and 18 antigens (CFP16, CFP17, CFP19, CFP19B, CFP20, CFP21, CFP22, CFP22A, CFP23, CFP23A, CFP23B, CFP25, CFP26, CFP27, CFP28, CFP29, CFP30A, and CFP30B) in the 17–30 kDa region have been identified. Of these, CFP19A and CFP23 have been selected because they exhibit relatively high homologies with CFP21 and CFP25, respectively, in so far that a nucleotide homology sequence search in the Sanger Database (cf. below) with the genes encoding CFP21 and CFP25, (cfp25 and cfp21 respectively), shows homology to two *M. tuberculosis* DNA sequences, orf19A and orf23. The two sequences, orf19a and orf23, encode to putative proteins CFP19A and CFP23 with the molecular weights of approx. 19 and 23 kDa respectively. The identity, at amino acid level, to CFP21 and CFP25 is 46% and 50%, respectively, for both proteins. CFP21 and CFP25 have been shown to be dominant T-cell antigens, and it is therefore believed that CFP19A and CFP23 are possible new T-cell antigens.

Furthermore, a 50 kDa antigen (CFP50) has been isolated from culture filtrate and so has also an antigen (CWP32) isolated from the cell wall in the 30 kDa region.

The present invention is also based on the identification of a number of putative antigens from *M. tuberculosis* which are not present in *Mycobacterium bovis* BCG strains. The nucleotide sequences encoding these putative antigens are: rd1-orf2, rd1-orf3, rd1-orf4, rd1-orf5, rd1-orf8, rd1-orf9a, and rd1-orf9b.

Finally, the invention is based on the surprising discovery that fusions between ESAT-6 and MPT59 are superior immunogens compared to the unfused proteins, respectively.

The encoding genes for 33 of the antigens have been determined, the distribution of a number of the antigens in various mycobacterial strains investigated and the biological activity of the products characterized. The panel hold antigens with potential for vaccine purposes as well as for diagnostic purposes, since the antigens are all secreted by metabolizing mycobacteria.

The following table lists the antigens of the invention by the names used herein as well as by reference to relevant SEQ ID NOs of N-terminal sequences, full amino acid sequences and sequences of DNA encoding the antigens:

| Antigen | N-terminal sequence SEQ ID NO: | Nucleotide sequence SEQ ID NO: | Amino acid sequence SEQ ID NO: |
| --- | --- | --- | --- |
| CFP7 | | 1 | 2 |
| CFP7A | 81 | 47 | 48 |
| CFP7B | 168 | 146 | 147 |
| CFP8A | 73 | 148 | 149 |
| CFP8B | 74 | 150 | 151 |
| CFP9 | | 3 | 4 |
| CFP10A | 169 | 140 | 141 |
| CFP11 | 170 | 142 | 143 |
| CFP16 | 79 | 63 | 64 |
| CFP17 | 17 | 5 | 6 |
| CFP19 | 82 | 49 | 50 |
| CFP19A | | 51 | 52 |
| CFP19B | 80 | | |
| CFP20 | 18 | 7 | 8 |
| CFP21 | 19 | 9 | 10 |
| CFP22 | 20 | 11 | 12 |
| CFP22A | 83 | 53 | 54 |
| CFP23 | | 55 | 56 |
| CFP23A | 76 | | |
| CFP23B | 75 | | |
| CFP25 | 21 | 13 | 14 |
| CFP25A | 78 | 65 | 66 |
| CFP27 | 84 | 57 | 58 |
| CFP28 | 22 | | |
| CFP29 | 23 | 15 | 16 |
| CFP30A | 85 | 59 | 60 |
| CFP30B | 171 | 144 | 145 |
| CFP50 | 86 | 61 | 62 |
| MPT51 | | 41 | 42 |
| CWP32 | 77 | 152 | 153 |
| RD1-ORF8 | | 67 | 68 |
| RD1-ORF2 | | 71 | 72 |
| RD1-ORF9B | | 69 | 70 |
| RD1-ORF3 | | 87 | 88 |
| RD1-ORF9A | | 93 | 94 |
| RD1-ORF4 | | 89 | 90 |
| RD1-ORF5 | | 91 | 92 |
| MPT59-ESAT6 | | | 172 |
| ESAT6-MPT59 | | | 173 |

It is well-known in the art that T-cell epitopes are responsible for the elicitation of the acquired immunity against TB, whereas B-cell epitopes are without any significant influence on acquired immunity and recognition of mycobacteria in vivo. Since such T-cell epitopes are linear and are known to have a minimum length of 6 amino acid residues, the present invention is especially concerned with the identification and utilisation of such T-cell epitopes.

Hence, in its broadest aspect the invention relates to a substantially pure polypeptide fragment which a) comprises an amino acid sequence selected from the sequences shown in SEQ ID NO: 2, 4, 6, 8, 10, 12, 14, 16, any one of 17–23, 42, 48, 50, 52, 54, 56, 58, 60, 62, 64, 66, 68, 70, any one of 72–86, 88, 90, 92, 94, 141, 143, 145, 147, 149, 151, 153, and any one of 168–171, b) comprises a subsequence of the polypeptide fragment defined in a) which has a length of at least 6 amino acid residues, said subsequence being immunologically equivalent to the polypeptide defined in a) with respect to the ability of evoking a protective immune response against infections with mycobacteria belonging to the tuberculosis complex or with respect to the ability of eliciting a diagnostically significant immune response indicating previous or ongoing sensitization with antigens derived from mycobacteria belonging to the tuberculosis complex, or c) comprises an amino acid sequence having a sequence identity with the polypeptide defined in a) or the subsequence defined in b) of at least 70% and at the same time being immunologically equivalent to the polypeptide defined in a) with respect to the ability of evoking a protective immune response against infections with mycobacteria belonging to the tuberculosis complex or with respect to the ability of eliciting a diagnostically significant immune response indicating previous or ongoing sensitization with antigens derived from mycobacteria belonging to the tuberculosis complex, with the proviso that i) the polypeptide fragment is in essentially pure form when consisting of the amino acid sequence 1–96 of SEQ ID NO: 2 or when consisting of the amino acid sequence 87–108 of SEQ ID NO: 4 fused to β-galactosidase, ii) the degree of sequence identity in c) is at least 95% when the polypeptide comprises a homologue of a polypeptide which has the amino acid sequence SEQ ID NO: 12 or a subsequence thereof as defined in b), and iii) the polypeptide fragment contains a threonine residue corresponding to position 213 in SEQ ID NO: 42 when comprising an amino acid sequence of at least 6 amino acids in SEQ ID NO: 42.

Other parts of the invention pertains to the DNA fragments encoding a polypeptide with the above definition as well as to DNA fragments useful for determining the presence of DNA encoding such polypeptides.

DETAILED DISCLOSURE OF THE INVENTION

In the present specification and claims, the term "polypeptide fragment" denotes both short peptides with a length of at least two amino acid residues and at most 10 amino acid residues, oligopeptides (11–100 amino acid residues), and longer peptides (the usual interpretation of "polypeptide", i.e. more than 100 amino acid residues in length) as well as proteins (the functional entity comprising at least one peptide, oligopeptide, or polypeptide which may be chemically modified by being glycosylated, by being lipidated, or by comprising prosthetic groups). The definition of polypeptides also comprises native forms of peptides/proteins in mycobacteria as well as recombinant proteins or peptides in any type of expression vectors transforming any kind of host, and also chemically synthesized peptides.

In the present context the term "substantially pure polypeptide fragment" means a polypeptide preparation which contains at most 5% by weight of other polypeptide material with which it is natively associated (lower percentages of other polypeptide material are preferred, e.g. at most 4%, at most 3%, at most 2%, at most 1%, and at most ½%). It is preferred that the substantially pure polypeptide is at least 96% pure, i.e. that the polypeptide constitutes at least 96% by weight of total polypeptide material present in the preparation, and higher percentages are preferred, such as at least 97%, at least 98%, at least 99%, at least 99.25%, at least 99.5%, and at least 99.75%. It is especially preferred that the polypeptide fragment is in "essentially pure form", i.e. that the polypeptide fragment is essentially free of any other antigen with which it is natively associated, i.e. free of any other antigen from bacteria belonging to the tuberculosis complex. This can be accomplished by preparing the polypeptide fragment by means of recombinant methods in a non-mycobacterial host cell as will be described in detail below, or by synthesizing the polypeptide fragment by the well-known methods of solid or liquid phase peptide synthesis. e.g. by the method described by Merrifield or variations thereof.

The term "subsequence" when used in connection with a polypeptide of the invention having a SEQ ID NO selected from 2, 4, 6, 8, 10, 12, 14, 16, any one of 17–23, 42, 48, 50, 52, 54, 56, 58, 60, 62, 64, 66, 68, 70, any one of 72–86, 88, 90, 92, 94, 141, 143, 145, 147, 149, 151, 153, and any one of 168–171 denotes any continuous stretch of at least 6 amino acid residues taken from the *M. tuberculosis* derived polypeptides in SEQ ID NO: 2, 4, 6, 8, 10, 12, 14, 16, any one of 17–23, 42, 48, 50, 52, 54, 56, 58, 60, 62, 64, 66, 68, 70, any one of 72–86, 88, 90, 92, 94, 141, 143, 145, 147, 149, 151, 153, or any one of 168–171 and being immunological equivalent thereto with respect to the ability of conferring increased resistance to infections with bacteria belonging to the tuberculosis complex. Thus, included is also a polypeptide from different sources, such as other bacteria or even from eukaryotic cells.

Figure 6:
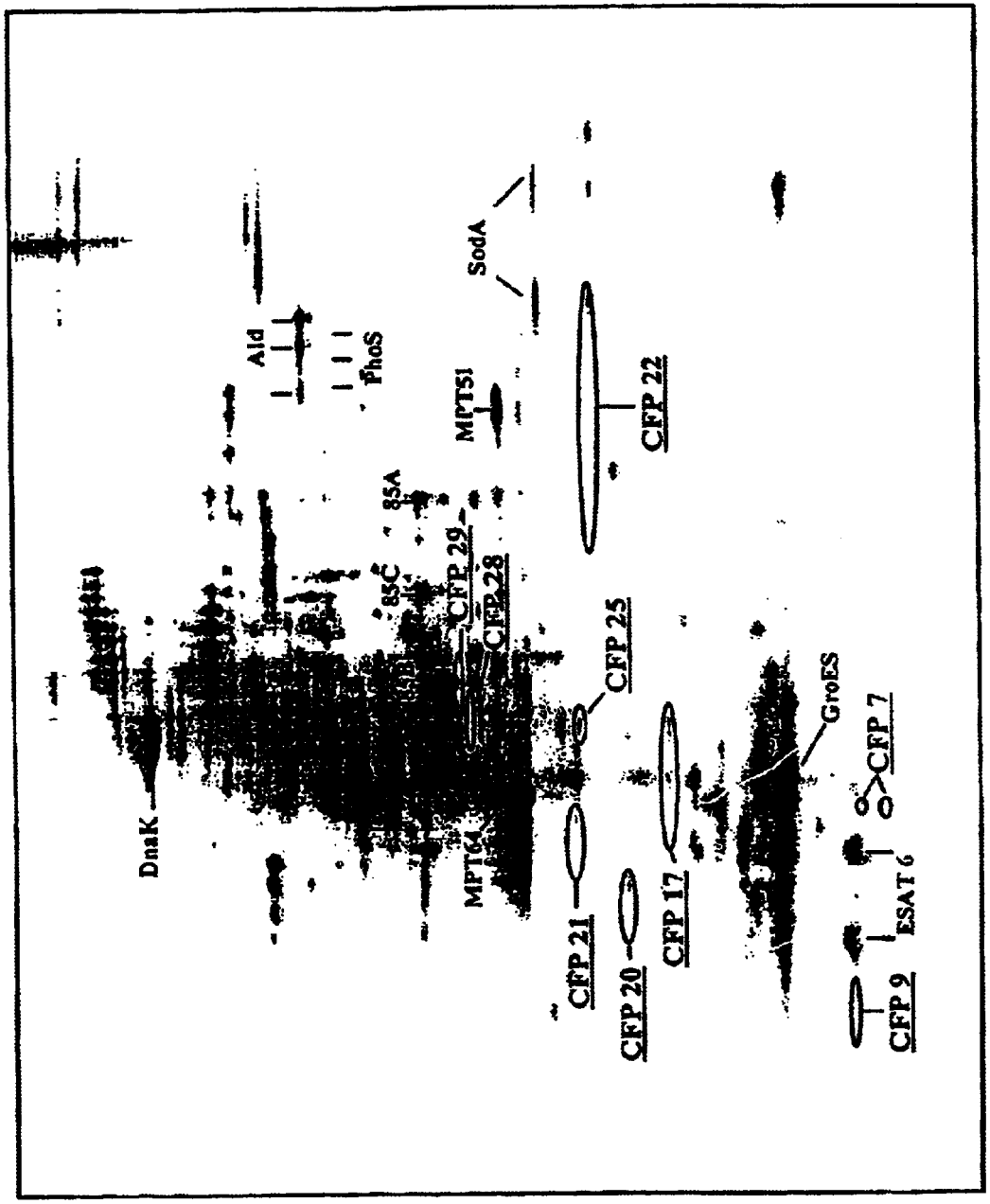

When referring to an "immunologically equivalent" polypeptide is herein meant that the polypeptide, when formulated in a vaccine or a diagnostic agent (i.e. together with a pharmaceutically acceptable carrier or vehicle and optionally an adjuvant), will I) confer, upon administration (either alone or as an immunologically active constituent together with other antigens), an acquired increased specific resistance in a mouse and/or in a guinea pig and/or in a primate such as a human being against infections with bacteria belonging to the tuberculosis complex which is at least 20% of the acquired increased resistance conferred by *Mycobacterium bovis* BCG and also at least 20% of the acquired increased resistance conferred by the parent polypeptide comprising SEQ ID NO: 2, 4, 6, 8, 10, 12, 14, 16, any one of 17–23, 42, 48, 50, 52, 54, 56, 58, 60, 62, 64, 66, 68, 70, any one of 72–86, 88, 90, 92, 94, 141, 143, 145, 147, 149, 151, 153, or any one of 168–171 (said parent polypeptide having substantially the same relative location and pattern in a 2DE gel prepared as the 2DE gel shown in FIG. 6, cf. the examples), the acquired increased resistance being assessed by the observed reduction in mycobacterial counts from spleen, lung or other organ homogenates isolated from the mouse or guinea pig receiving a challenge infection with a virulent strain of *M. tuberculosis,* or, in a primate such as a human being, being assessed by determining the protection against development of clinical tuberculosis in a vaccinated group versus that observed in a control group receiving a placebo or BCG (preferably the increased resistance is higher and corresponds to at least 50% of the protective immune response elicited by *M. bovis* BCG, such as at least 60%, or even more preferred to at least 80% of the protective immune response elicited by *M. bovis* BCG, such as at least 90%; in some cases it is expected that the increased resistance will supersede that conferred by *M. bovis* BCG, and hence it is preferred that the resistance will be at least 100%, such as at least 110% of said increased resistance); and/or II) elicit a diagnostically significant immune response in a mammal indicating previous or ongoing sensitization with antigens derived from mycobacteria belonging to the tuberculosis complex; this diagnostically significant immune response can be in the form of a delayed type hypersensitivity reaction which can e.g. be determined by a skin test, or can be in the form of IFN-γ release determined e.g. by an IFN-γ assay as described in detail below. A diagnostically significant response in a skin test setup will be a reaction which gives rise to a skin reaction which is at least 5 mm in diameter and which is at least 65% (preferably at least 75% such as at the least 85%) of the skin reaction (assessed as the skin reaction diameter) elicited by the parent polypeptide comprising SEQ ID NO: 2, 4, 6, 8, 10, 12, 14, 16, any one of 17–23, 42, 48, 50, 52, 54, 56, 58, 60, 62, 64, 66, 68, 70, any one of 72–86, 88, 90, 92, 94, 141, 143, 145, 147, 149, 151, 153, or any one of 168–171.

The ability of the polypeptide fragment to confer increased immunity may thus be assessed by measuring in an experimental animal, e.g. a mouse or a guinea pig, the reduction in mycobacterial counts from the spleen, lung or other organ homogenates isolated from the experimental animal which have received a challenge infection with a virulent strain of mycobacteria belonging to the tuberculosis complex after previously having been immunized with the polypeptide, as compared to the mycobacterial counts in a control group of experimental animals infected with the same virulent strain, which experimental animals have not previously been immunized against tuberculosis. The comparison of the mycobacterial counts may also be carried out with mycobacterial counts from a group of experimental animals receiving a challenge infection with the same virulent strain after having been immunized with *Mycobacterium bovis* BCG.

The mycobacterial counts in homogenates from the experimental animals immunized with a polypeptide fragment according to the present invention must at the most be 5 times the counts in the mice or guinea pigs immunized with *Mycobacterium bovis* BCG, such as at the most 3 times the counts, and preferably at the most 2 times the counts.

A more relevant assessment of the ability of the polypeptide fragment of the invention to confer increased resistance is to compare the incidence of clinical tuberculosis in two groups of individuals (e.g. humans or other primates) where one group receives a vaccine as described herein which contains an antigen of the invention and the other group receives either a placebo or an other known TB vaccine (e.g. BCG). In such a setup, the antigen of the invention should give rise to a protective immunity which is significantly higher than the one provided by the administration of the placebo (as determined by statistical methods known to the skilled artisan).

The "tuberculosis-complex" has its usual meaning, i.e. the complex of mycobacteria causing TB which are *Mycobacterium tuberculosis, Mycobacterium bovis, Mycobacterium bovis* BCG, and *Mycobacterium africanum.*

In the present context the term "metabolizing mycobacteria" means live mycobacteria that are multiplying logarithmically and releasing polypeptides into the culture medium wherein they are cultured.

The term "sequence identity" indicates a quantitative measure of the degree of homology between two amino acid sequences or between two nucleotide sequences of equal length: The sequence identity can be calculated as $$\frac{(N_{ref} - N_{dif})100}{N_{ref}},$$

wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{dif}$=2 and $N_{ref}$=8).

The sequence identity is used here to illustrate the degree of identity between the amino acid sequence of a given polypeptide and the amino acid sequence shown in SEQ ID NO: 2, 4, 6, 8, 10, 12, 14, 16, any one of 17–23, 42, 48, 50, 52, 54, 56, 58, 60, 62, 64, 66, 68, 70, any one of 72–86, 88, 90, 92, 94, 141, 143, 145, 147, 149, 151, 153, or any one of 168–171. The amino acid sequence to be compared with the amino acid sequence shown in SEQ ID NO: 2, 4, 6, 8, 10, 12, 14, 16, any one of 17–23, 42, 48, 50, 52, 54, 56, 58, 60, 62, 64, 66, 68, 70, any one of 72–86, 88, 90, 92, 94, 141, 143, 145, 147, 149, 151, 153, or any one of 168–171 may be deduced from a DNA sequence, e.g. obtained by hybridization as defined below, or may be obtained by conventional amino acid sequencing methods. The sequence identity is preferably determined on the amino acid sequence of a mature polypeptide, i.e. without taking any leader sequence into consideration.

As appears from the above disclosure, polypeptides which are not identical to the polypeptides having SEQ ID NO: 2, 4, 6, 8, 10, 12, 14, 16, any one of 17–23, 42, 48, 50, 52, 54, 56, 58, 60, 62, 64, 66, 68, 70, any one of 72–86, 88, 90, 92, 94, 141, 143, 145, 147, 149, 151, 153, or any one of 168–171 are embraced by the present invention. The invention allows for minor variations which do not have an adverse effect on immunogenicity compared to the parent sequences and which may give interesting and useful novel binding properties or biological functions and immunogenicities etc.

Each polypeptide fragment may thus be characterized by specific amino acid and nucleic acid sequences. It will be understood that such sequences include analogues and variants produced by recombinant methods wherein such nucleic acid and polypeptide sequences have been modified by substitution, insertion, addition and/or deletion of one or more nucleotides in said nucleic acid sequences to cause the substitution, insertion, addition or deletion of one or more amino acid residues in the recombinant polypeptide. When the term DNA is used in the following, it should be understood that for the number of purposes where DNA can be substituted with RNA, the term DNA should be read to include RNA embodiments which will be apparent for the man skilled in the art. For the purposes of hybridization, PNA may be used instead of DNA, as PNA has been shown to exhibit a very dynamic hybridization profile (PNA is described in Nielsen P E et al., 1991, Science 254: 1497–1500).

In both immunodiagnostics and vaccine preparation, it is often possible and practical to prepare antigens from segments of a known immunogenic protein or polypeptide. Certain epitopic regions may be used to produce responses similar to those produced by the entire antigenic polypeptide. Potential antigenic or immunogenic regions may be identified by any of a number of approaches, e.g., Jameson-Wolf or Kyte-Doolittle antigenicity analyses or Hopp and Woods (1981) hydrophobicity analysis (see, e.g., Jameson and Wolf, 1988; Kyte and Doolittle, 1982; or U.S. Pat. No. 4,554,101). Hydrophobicity analysis assigns average hydrophilicity values to each amino acid residue from these values average hydrophilicities can be calculated and regions of greatest hydrophilicity determined. Using one or more of these methods, regions of predicted antigenicity may be derived from the amino acid sequence assigned to the polypeptides of the invention.

Alternatively, in order to identify relevant T-cell epitopes which are recognized during an immune response, it is also possible to use a "brute force" method: Since T-cell epitopes are linear, deletion mutants of polypeptides having SEQ ID NO: 2, 4, 6, 8, 10, 12, 14, 16, any one of 17–23, 42, 48, 50, 52, 54, 56, 58, 60, 62, 64, 66, 68, 70, any one of 72–86, 88, 30 90, 92, 94, 141, 143, 145, 147, 149, 151, 153, or any one of 168–171 will, if constructed systematically, reveal what regions of the polypeptides are essential in immune recognition, e.g. by subjecting these deletion mutants to the IFN-γ assay described herein. Another method utilises overlapping oligomers (preferably synthetic having a length of e.g. 20 amino acid residues) derived from polypeptides having SEQ ID NO: 2, 4, 6, 8, 10, 12, 14, 16, any one of 17–23, 42, 48, 50, 52, 54, 56, 58, 60, 62, 64, 66, 68, 70, any one of 72–86, 88, 90, 92, 94, 141, 143, 145, 147, 149, 151, 153, or any one of 168–171. Some of these will give a positive response in the IFN-γ assay whereas others will not.

In a preferred embodiment of the invention, the polypeptide fragment of the invention comprises an epitope for a T-helper cell.

Although the minimum length of a T-cell epitope has been shown to be at least 6 amino acids, it is normal that such epitopes are constituted of longer stretches of amino acids. Hence it is preferred that the polypeptide fragment of the invention has a length of at least 7 amino acid residues, such as at least 8, at least 9, at least 10, at least 12, at least 14, at least 16, at least 18, at least 20, at least 22, at least 24, and at least 30 amino acid residues.

As will appear from the examples, a number of the polypeptides of the invention are natively translation products which include a leader sequence (or other short peptide sequences), whereas the product which can be isolated from short-term culture filtrates from bacteria belonging to the tuberculosis complex are free of these sequences. Although it may in some applications be advantageous to produce these polypeptides recombinantly and in this connection facilitate export of the polypeptides from the host cell by including information encoding the leader sequence in the gene for the polypeptide, it is more often preferred to either substitute the leader sequence with one which has been shown to be superior in the host system for effecting export, or to totally omit the leader sequence (e.g. when producing the polypeptide by peptide synthesis. Hence, a preferred embodiment of the invention is a polypeptide which is free from amino acid residues −30 to −1 in SEQ ID NO: 6 and/or −32 to −1 in SEQ ID NO: 10 and/or −8 to −1 in SEQ ID NO: 12 and/or −32 to −1 in SEQ ID NO: 14 and/or −33 to −1 in SEQ ID NO: 42 and/or −38 to −1 in SEQ ID NO: 52 and/or −33 to −1 in SEQ ID NO: 56 and/or −56 to −1 in SEQ ID NO: 58 and/or −28 to −1 in SEQ ID NO: 151.

In another preferred embodiment, the polypeptide fragment of the invention is free from any signal sequence; this is especially interesting when the polypeptide fragment is produced synthetically but even when the polypeptide fragments are produced recombinantly it is normally acceptable that they are not exported by the host cell to the periplasm or the extracellular space; the polypeptide fragments can be recovered by traditional methods (cf. the discussion below) from the cytoplasm after disruption of the host cells, and if there is need for refolding of the polypeptide fragments, general refolding schemes can be employed, cf. e.g. the disclosure in WO 94/18227 where such a general applicable refolding method is described.

A suitable assay for the potential utility of a given polypeptide fragment derived from SEQ ID NO: 2, 4, 6, 8, 10, 12, 14, 16, any one of 17–23, 42, 48, 50, 52, 54, 56, 58, 60, 20 62, 64, 66, 68, 70, any one of 72–86, 88, 90, 92, 94, 141, 143, 145, 147, 149, 151, 153, or any one of 168–171 is to assess the ability of the polypeptide fragment to effect IFN-γ release from primed memory T-lymphocytes. Polypeptide fragments which have this capability are according to the invention especially interesting embodiments of the invention: It is contemplated that polypeptide fragments which stimulate T lymphocyte immune response shortly after the onset of the infection are important in the control of the mycobacteria causing the infection before the mycobacteria have succeeded in multiplying up to the number of bacteria that would have resulted in fulminant infection.

Thus, an important embodiment of the invention is a polypeptide fragment defined above which 1) induces a release of IFN-γ from primed memory T-lymphocytes withdrawn from a mouse within 2 weeks of primary infection or within 4 days after the mouse has been rechallenge infected with mycobacteria belonging to the tuberculosis complex, the induction performed by the addition of the polypeptide to a suspension comprising about 200,000 spleen cells per ml, the addition of the polypeptide resulting in a concentration of 1–4 μg polypeptide per ml suspension, the release of IFN-γ being assessable by determination of IFN-γ in supernatant harvested 2 days after the addition of the polypeptide to the suspension, and/or 2) induces a release of IFN-γ of at least 1,500 pg/ml above background level from about 1,000,000 human PBMC (peripheral blood mononuclear cells) per ml isolated from TB patients in the first phase of infection, or from healthy BCG vaccinated donors, or from healthy contacts to TB patients, the induction being performed by the addition of the polypeptide to a suspension comprising the about 1,000,000 PBMC per ml, the addition of the polypeptide resulting in a concentration of 1–4 μg polypeptide per ml suspension, the release of IFN-γ being assessable by determination of IFN-γ in supernatant harvested 2 days after the addition of the polypeptide to the suspension; and/or 3) induces an IFN-γ release from bovine PBMC derived from animals previously sensitized with mycobacteria belonging to the tuberculosis complex, said release being at least two times the release observed from bovine PBMC derived from animals not previously sensitized with mycobacteria belonging to the tuberculosis complex.

Preferably, in alternatives 1 and 2, the release effected by the polypeptide fragment gives rise to at least 1,500 pg/ml IFN-γ in the supernatant but higher concentrations are preferred, e.g. at least 2,000 pg/ml and even at least 3,000 g/ml IFN-γ in the supernatant. The IFN-γ release from bovine PBMC can e.g. be measured as the optical density (OD) index over background in a standard cytokine ELISA and should thus be at least two, but higher numbers such as at least 3, 5, 8, and 10 are preferred.

The polypeptide fragments of the invention preferably comprises an amino acid sequence of at least 6 amino acid residues in length which has a higher sequence identity than 70 percent with SEQ ID NO: 2, 4, 6, 8, 10, 12, 14, 16, any one of 17–23, 42, 48, 50, 52, 54, 56, 58, 60, 62, 64, 66, 68, 70, any one of 72–86, 88, 90, 92, 94, 141, 143, 145, 147, 149, 151, 153, or any one of 168–171. A preferred minimum percentage of sequence identity is at least 80%, such as at least 85%, at least 90%, at least 91%, at least 92%, at least 93%, at least 94%, at least 95%, at least 96%, at least 97%, at least 98%, at least 99%, and at least 99.5%.

As mentioned above, it will normally be interesting to omit the leader sequences from the polypeptide fragments of the invention. However, by producing fusion polypeptides, superior characteristics of the polypeptide fragments of the invention can be achieved. For instance, fusion partners which facilitate export of the polypeptide when produced recombinantly, fusion partners which facilitate purification of the polypeptide, and fusion partners which enhance the immunogenicity of the polypeptide fragment of the invention are all interesting possibilities. Therefore, the invention also pertains to a fusion polypeptide comprising at least one polypeptide fragment defined above and at least one fusion partner. The fusion partner can, in order to enhance immunogenicity, e.g. be selected from the group consisting of another polypeptide fragment as defined above (so as to allow for multiple expression of relevant epitopes), and an other polypeptide derived from a bacterium belonging to the tuberculosis complex, such as ESAT-6, MPB64, MPT64, and MPB59 or at least one T-cell epitope of any of these antigens. Other immunogenicity enhancing polypeptides which could serve as fusion partners are T-cell epitopes (e.g. derived from the olypeptides ESAT-6, MPB64, MPT64, or MPB59) or other immunogenic epitopes enhancing the immunogenicity of the target gene product, e.g. lymphokines such as INF-γ, IL-2 and IL-12. In order to facilitate expression and/or purification the fusion partner can e.g. be a bacterial fimbrial protein, e.g. the pilus components pilin and papA; protein A; the ZZ-peptide (ZZ-fusions are marketed by Pharmacia in Sweden); the maltose binding protein; gluthatione S-transferase; β-galactosidase; or polyhistidine.

Other interesting fusion partners are polypeptides which are lipidated and thereby effect that the immunogenic polypeptide is presented in a suitable manner to the immune system. This effect is e.g. known from vaccines based on the *Borrelia burgdorferi* OspA polypeptide, wherein the lipidated membrane anchor in the polypeptide confers a self-adjuvating effect to the polypeptide (which is natively lipidated) when isolated from cells producing it. In contrast, the OspA polypeptide is relatively silent immunologically when prepared without the lipidation anchor.

As evidenced in Example 6A, the fusion polypeptide consisting of MPT59 fused directly N-terminally to ESAT-6 enhances the immunogenicity of ESAT-6 beyond what would be expected from the immunogenicities of MPT59 and ESAT-6 alone. The precise reason for this surprising finding is not yet known, but it is expected that either the presence of both antigens lead to a synergistic effect with respect to immunogenicity or the presence of a sequence N-terminally to the ESAT-6 sequence protects this immune dominant protein from loss of important epitopes known to be present in the N-terminus. A third, alternative, possibility is that the presence of a sequence C-terminally to the MPT59 sequence enhances the immunologic properties of this antigen.

Hence, one part of the invention pertains to a fusion polypeptide fragment which comprises a first amino acid sequence including at least one stretch of amino acids constituting a T-cell epitope derived from the *M. tuberculosis* protein ESAT-6 or MPT59, and a second amino acid sequence including at least one T-cell epitope derived from a *M. tuberculosis* protein different from ESAT-6 (if the first stretch of amino acids are derived from ESAT-6) or MPT59 (if the first stretch of amino acids are derived from MPT59) and/or including a stretch of amino acids which protects the first amino acid sequence from in vivo degradation or post-translational processing. The first amino acid sequence may be situated N- or C-terminally to the second amino acid sequence, but in line with the above considerations regarding protection of the ESAT-6 N-terminus it is preferred that the first amino acid sequence is C-terminal to the second when the first amino acid sequence is derived from ESAT-6.

Although only the effect of fusion between MPT59 and ESAT6 has been investigated at present, it is believed that ESAT6 and MPT59 or epitopes derived therefrom could be advantageously be fused to other fusion partners having substantially the same effect on overall immunogenicity of the fusion construct. Hence, it is preferred that such a fusion polypeptide fragment according of the invention is one, wherein the at least one T-cell epitope included in the second amino acid sequence is derived from a *M. tuberculosis* polypeptide (the "parent" polypeptide) selected from the group consisting of a polypeptide fragment according to the present invention and described in detail above and in the examples, or the amino acid sequence could be derived from any one of the *M. tuberculosis* proteins DnaK, GroEL, urease, glutamine synthetase, the proline rich complex, L-alanine dehydrogenase, phosphate binding protein, Ag 85 complex, HBHA (heparin binding hemagglutinin), MPT51, MPT64, superoxide dismutase, 19 kDa lipoprotein, α-crystallin, GroES, MPT59 (when the first amino acid sequence is derived from ESAT-6), and ESAT-6 (when the first amino acid sequence is derived from MPT59). It is preferred that the first and second T-cell epitopes each have a sequence identity of at least 70% with the natively occurring sequence in the proteins from which they are derived and it is even further preferred that the first and/or second amino acid sequence has a sequence identity of at least 70% with the protein from which they are derived. A most preferred embodiment of this fusion polypeptide is one wherein the first amino acid sequence is the amino acid sequence of ESAT-6 or MPT59 and/or the second amino acid sequence is the full-length amino acid sequence of the possible "parent" polypeptides listed above.

In the most preferred embodiment, the fusion polypeptide fragment comprises ESAT-6 fused to MPT59 (advantageously, ESAT-6 is fused to the C-terminus of MPT59) and in one special embodiment, there are no linkers introduced between the two amino acid sequences constituting the two parent polypeptide fragments.

Another part of the invention pertains to a nucleic acid fragment in isolated form which 1) comprises a nucleic acid sequence which encodes a polypeptide or fusion polypeptide as defined above, or comprises a nucleic acid sequence complementary there-to, and/or 2) has a length of at least 10 nucleotides and hybridizes readily under stringent hybridization conditions (as defined in the art, i.e. 5–10° C. under the melting point $T_m$, cf. Sambrook et al, 1989, pages 11.45–11.49) with a nucleic acid fragment which has a nucleotide sequence selected from SEQ ID NO: 1 or a sequence complementary thereto,
SEQ ID NO: 3 or a sequence complementary thereto,
SEQ ID NO: 5 or a sequence complementary thereto,
SEQ ID NO: 7 or a sequence complementary thereto,
SEQ ID NO: 9 or a sequence complementary thereto,
SEQ ID NO: 11 or a sequence complementary thereto,
SEQ ID NO: 13 or a sequence complementary thereto,
SEQ ID NO: 15 or a sequence complementary thereto,
SEQ ID NO: 41 or a sequence complementary thereto,
SEQ ID NO: 47 or a sequence complementary thereto,
SEQ ID NO: 49 or a sequence complementary thereto,
SEQ ID NO: 51 or a sequence complementary thereto,
SEQ ID NO: 53 or a sequence complementary thereto,
SEQ ID NO: 55 or a sequence complementary thereto,
SEQ ID NO: 57 or a sequence complementary thereto,
SEQ ID NO: 59 or a sequence complementary thereto,
SEQ ID NO: 61 or a sequence complementary thereto,
SEQ ID NO: 63 or a sequence complementary thereto,
SEQ ID NO: 65 or a sequence complementary thereto,
SEQ ID NO: 67 or a sequence complementary thereto,
SEQ ID NO: 69 or a sequence complementary thereto,
SEQ ID NO: 71 or a sequence complementary thereto,
SEQ ID NO: 87 or a sequence complementary thereto,
SEQ ID NO: 89 or a sequence complementary thereto,
SEQ ID NO: 91 or a sequence complementary thereto,
SEQ ID NO: 93 or a sequence complementary thereto,
SEQ ID NO: 140 or a sequence complementary thereto,
SEQ ID NO: 142 or a sequence complementary thereto,
SEQ ID NO: 144 or a sequence complementary thereto,
SEQ ID NO: 146 or a sequence complementary thereto,
SEQ ID NO: 148 or a sequence complementary thereto,
SEQ ID NO: 150 or a sequence complementary thereto, and
SEQ ID NO: 152 or a sequence complementary thereto, with the proviso that when the nucleic acid fragment comprises a subsequence of SEQ ID NO: 41, then the nucleic acid fragment contains an A corresponding to position 781 in SEQ ID NO: 41 and when the nucleic acid fragment comprises a subsequence of a nucleotide sequence exactly complementary to SEQ ID NO: 41, then the nucleic acid fragment comprises a T corresponding to position 781 in SEQ ID NO: 41.

It is preferred that the nucleic acid fragment is a DNA fragment.

To provide certainty of the advantages in accordance with the invention, the preferred nucleic acid sequence when employed for hybridization studies or assays includes sequences that are complementary to at least a 10 to 40, or so, nucleotide stretch of the selected sequence. A size of at least 10 nucleotides in length helps to ensure that the fragment will be of sufficient length to form a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained.

Hence, the term "subsequence" when used in connection with the nucleic acid fragments of the invention is intended to indicate a continuous stretch of at least 10 nucleotides exhibits the above hybridization pattern. Normally this will require a minimum sequence identity of at least 70% with a subsequence of the hybridization partner having SEQ ID NO: 1, 3, 5, 7, 9, 11, 12, 15, 21, 41, 47, 49, 51, 53, 55, 57, 59, 61, 63, 65, 67, 69, 71, 87, 89, 91, 93, 140, 142, 144, 146, 148, 150, or 152. It is preferred that the nucleic acid fragment is longer than 10 nucleotides, such as at least 15, at least 20, at least 25, at least 30, at least 35, at least 40, at least 45, at least 50, at least 55, at least 60, at least 65, at least 70, and at least 80 nucleotides long, and the sequence identity should preferable also be higher than 70%, such as at least 75%, at least 80%, at least 85%, at least 90%, at least 92%, at least 94%, at least 96%, and at least 98%. It is most preferred that the sequence identity is 100%. Such fragments may be readily prepared by, for example, directly synthesizing the fragment by chemical means, by application of nucleic acid reproduction technology, such as the PCR technology of U.S. Pat. No. 4,603,102, or by introducing selected sequences into recombinant vectors for recombinant production.

It is well known that the same amino acid may be encoded by various codons, the codon usage being related, inter alia, to the preference of the organisms in question expressing the nucleotide sequence. Thus, at least one nucleotide or codon of a nucleic acid fragment of the invention may be exchanged by others which, when expressed, result in a polypeptide identical or substantially identical to the polypeptide encoded by the nucleic acid fragment in question. The invention thus allows for variations in the sequence such as substitution, insertion (including introns), addition, deletion and rearrangement of one or more nucleotides, which variations do not have any substantial effect on the polypeptide encoded by the nucleic acid fragment or a subsequence thereof. The term "substitution" is intended to mean the replacement of one or more nucleotides in the full nucleotide sequence with one or more different nucleotides, "addition" is understood to mean the addition of one or more nucleotides at either end of the full nucleotide sequence, "insertion" is intended to mean the introduction of one or more nucleotides within the full nucleotide sequence, "deletion" is intended to indicate that one or more nucleotides have been deleted from the full nucleotide sequence whether at either end of the sequence or at any suitable point within it, and "re-arrangement" is intended to mean that two or more nucleotide residues have been exchanged with each other.

The nucleotide sequence to be modified may be of cDNA or genomic origin as discussed above, but may also be of synthetic origin. Furthermore, the sequence may be of mixed cDNA and genomic, mixed cDNA and synthetic or genomic and synthetic origin as discussed above. The sequence may have been modified, e.g. by site-directed mutagenesis, to result in the desired nucleic acid fragment encoding the desired polypeptide. The following discussion focused on modifications of nucleic acid encoding the polypeptide should be understood to encompass also such possibilities, as well as the possibility of building up the nucleic acid by ligation of two or more DNA fragments to obtain the desired nucleic acid fragment, and combinations of the above-mentioned principles.

The nucleotide sequence may be modified using any suitable technique which results in the production of a nucleic acid fragment encoding a polypeptide of the invention.

The modification of the nucleotide sequence encoding the amino acid sequence of the polypeptide of the invention should be one which does not impair the immunological function of the resulting polypeptide.

A preferred method of preparing variants of the antigens disclosed herein is site-directed mutagenesis. This technique is useful in the preparation of individual peptides, or biologically functional equivalent proteins or peptides, derived from the antigen sequences, through specific mutagenesis of the underlying nucleic acid. The technique further provides a ready ability to prepare and test sequence variants, for example, incorporating one or more of the foregoing considerations, by introducing one or more nucleotide sequence changes into the nucleic acid. Site-specific mutagenesis allows the production of mutants through the use of specific oligonucleotide sequences which encode the nucleotide sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art as exemplified by publications (Adelman et al., 1983). As will be appreciated, the technique typically employs a phage vector which exists in both a single stranded and double stranded form. Typical vectors useful in site-directed mutagenesis include vectors such as the M13 phage (Messing et al., 1981). These phage are readily commercially available and their use is generally well known to those skilled in the art.

In general, site-directed mutagenesis in accordance herewith is performed by first obtaining a single-stranded vector which includes within its sequence a nucleic acid sequence which encodes the polypeptides of the invention. An oligonucleotide primer bearing the desired mutated sequence is prepared, generally synthetically, for example by the method of Crea et al. (1978). This primer is then annealed with the single-stranded vector, and subjected to DNA polymerizing enzymes such as $E.$ $coli$ polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as $E.$ $coli$ cells, and clones are selected which include recombinant vectors bearing the mutated sequence arrangement.

The preparation of sequence variants of the selected nucleic acid fragments of the invention using site-directed mutagenesis is provided as a means of producing potentially useful species of the genes and is not meant to be limiting as there are other ways in which sequence variants of the nucleic acid fragments of the invention may be obtained. For example, recombinant vectors encoding the desired genes may be treated with mutagenic agents to obtain sequence variants (see, e.g., a method described by Eichenlaub, 1979) for the mutagenesis of plasmid DNA using hydroxylamine.

The invention also relates to a replicable expression vector which comprises a nucleic acid fragment defined above, especially a vector which comprises a nucleic acid fragment encoding a polypeptide fragment of the invention.

The vector may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication; examples of such a vector are a plasmid, phage, cosmid, mini-chromosome or virus. Alternatively, the vector may be one which, when introduced in a host cell, is integrated in the host cell genome and replicated together with the chromosome(s) into which it has been integrated.

Expression vectors may be constructed to include any of the DNA segments disclosed herein. Such DNA might encode an antigenic protein specific for virulent strains of mycobacteria or even hybridization probes for detecting mycobacteria nucleic acids in samples. Longer or shorter DNA segments could be used, depending on the antigenic protein desired. Epitopic regions of the proteins expressed or encoded by the disclosed DNA could be included as relatively short segments of DNA. A wide variety of expression vectors is possible including, for example, DNA segments encoding reporter gene products useful for identification of heterologous gene products and/or resistance genes such as antibiotic resistance genes which may be useful in identifying transformed cells.

The vector of the invention may be used to transform cells so as to allow propagation of the nucleic acid fragments of the invention or so as to allow expression of the polypeptide fragments of the invention. Hence, the invention also pertains to a transformed cell harbouring at least one such vector according to the invention, said cell being one which does not natively harbour the vector and/or the nucleic acid fragment of the invention contained therein. Such a transformed cell (which is also a part of the invention) may be any suitable bacterial host cell or any other type of cell such as a unicellular eukaryotic organism, a fungus or yeast, or a cell derived from a multicellular organism, e.g. an animal or a plant. It is especially in cases where glycosylation is desired that a mammalian cell is used, although glycosylation of proteins is a rare event in prokaryotes. Normally, however, a prokaryotic cell is preferred such as a bacterium belonging to the genera Mycobacterium, Salmonella, Pseudomonas, Bacillus and Eschericia. It is preferred that the transformed cell is an *E. coli, B. subtilis,* or *M. bovis* BCG cell, and it is especially preferred that the transformed cell expresses a polypeptide according of the invention. The latter opens for the possibility to produce the polypeptide of the invention by simply recovering it from the culture containing the transformed cell. In the most preferred embodiment of this part of the invention the transformed cell is *Mycobacterium* bovis BCG strain: Danish 1331, which is the *Mycobacterium bovis* strain Copenhagen from the Copenhagen BCG Laboratory, Statens Seruminstitut, Denmark.

The nucleic acid fragments of the invention allow for the recombinant production of the polypeptides fragments of the invention. However, also isolation from the natural source is a way of providing the polypeptide fragments as is peptide synthesis.

Therefore, the invention also pertains to a method for the preparation of a polypeptide fragment of the invention, said method comprising inserting a nucleic acid fragment as defined above into a vector which is able to replicate in a host cell, introducing the resulting recombinant vector into the host cell (transformed cells may be selected using various techniques, including screening by differential hybridization, identification of fused reporter gene products, resistance markers, anti-antigen antibodies and the like), culturing the host cell in a culture medium under conditions sufficient to effect expression of the polypeptide (of course the cell may be cultivated under conditions appropriate to the circumstances, and if DNA is desired, replication conditions are used), and recovering the polypeptide from the host cell or culture medium; or isolating the polypeptide from a short-term culture filtrate as defined in claim 1; or isolating the polypeptide from whole mycobacteria of the tuberculosis complex or from lysates or fractions thereof, e.g. cell wall containing fractions, or synthesizing the polypeptide by solid or liquid phase peptide synthesis.

The medium used to grow the transformed cells may be any conventional medium suitable for the purpose. A suitable vector may be any of the vectors described above, and an appropriate host cell may be any of the cell types listed above. The methods employed to construct the vector and effect introduction thereof into the host cell may be any methods known for such purposes within the field of recombinant DNA. In the following a more detailed description of the possibilities will be given:

In general, of course, prokaryotes are preferred for the initial cloning of nucleic sequences of the invention and constructing the vectors useful in the invention. For example, in addition to the particular strains mentioned in the more specific disclosure below, one may mention by way of example, strains such as *E. coli* K12 strain 294 (ATCC No. 31446), *E. coli* B, and *E. coli* X 1776 (ATCC No. 31537). These examples are, of course, intended to be illustrative rather than limiting.

Prokaryotes are also preferred for expression. The aforementioned strains, as well as *E. coli* W3110 (F-, lambda-, prototrophic, ATCC No. 273325), bacilli such as *Bacillus subtilis,* or other enterobacteriaceae such as *Salmonella typhimurium* or *Serratia marcesans,* and various Pseudomonas species may be used. Especially interesting are rapid-growing mycobacteria, e.g. *M. smegmatis,* as these bacteria have a high degree of resemblance with mycobacteria of the tuberculosis complex and therefore stand a good chance of reducing the need of performing post-translational modifications of the expression product.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species (see, e.g., Bolivar et al., 1977, Gene 2: 95). The pBR322 plasmid contains genes for ampicillin and tetracycline resistance and thus provides easy means for identifying transformed cells. The pBR plasmid, or other microbial plasmid or phage must also contain, or be modified to contain, promoters which can be used by the microorganism for expression.

Those promoters most commonly used in recombinant DNA construction include the B-lactamase (penicillinase) and lactose promoter systems (Chang et al., 1978; Itakura et al., 1977; Goeddel et al., 1979) and a tryptophan (trp) promoter system (Goeddel et al., 1979; EPO Appl. Publ. No. 0036776). While these are the most commonly used, other microbial promoters have been discovered and utilized, and details concerning their nucleotide sequences have been published, enabling a skilled worker to ligate them functionally with plasmid vectors (Siebwenlist et al., 1980). Certain genes from prokaryotes may be expressed efficiently in *E. coli* from their own promoter sequences, precluding the need for addition of another promoter by artificial means.

After the recombinant preparation of the polypeptide according to the invention, the isolation of the polypeptide may for instance be carried out by affinity chromatography (or other conventional biochemical procedures based on chromatography), using a monoclonal antibody which substantially specifically binds the polypeptide according to the invention. Another possibility is to employ the simultaneous electroelution technique described by Andersen et al. in J. Immunol. Methods 161: 29–39.

According to the invention the post-translational modifications involves lipidation, glycosylation, cleavage, or elongation of the polypeptide.

In certain aspects, the DNA sequence information provided by this invention allows for the preparation of relatively short DNA (or RNA or PNA) sequences having the ability to specifically hybridize to mycobacterial gene sequences. In these aspects, nucleic acid probes of an appropriate length are prepared based on a consideration of the relevant sequence. The ability of such nucleic acid probes to specifically hybridize to the mycobacterial gene sequences lend them particular utility in a variety of embodiments. Most importantly, the probes can be used in a variety of diagnostic assays for detecting the presence of pathogenic organisms in a given sample. However, either uses are envisioned, including the use of the sequence information for the preparation of mutant species primers, or primers for use in preparing other genetic constructs.

Apart from their use as starting points for the synthesis of polypeptides of the invention and for hybridization probes (useful for direct hybridization assays or as primers in e.g. PCR or other molecular amplification methods) the nucleic acid fragments of the invention may be used for effecting in vivo expression of antigens, i.e. the nucleic acid fragments may be used in so-called DNA vaccines. Recent research have revealed that a DNA fragment cloned in a vector which is non-replicative in eukaryotic cells may be introduced into an animal (including a human being) by e.g. intramuscular injection or percutaneous administration (the so-called "gene gun" approach). The DNA is taken up by e.g. muscle cells and the gene of interest is expressed by a promoter which is functioning in eukaryotes, e.g. a viral promoter, and the gene product thereafter stimulates the immune system. These newly discovered methods are reviewed in Ulmer et al., 1993, which hereby is included by reference.

Hence, the invention also relates to a vaccine comprising a nucleic acid fragment according to the invention, the vaccine effecting in vivo expression of antigen by an animal, including a human being, to whom the vaccine has been administered, the amount of expressed antigen being effective to confer substantially increased resistance to infections with mycobacteria of the tuberculosis complex in an animal, including a human being.

The efficacy of such a "DNA vaccine" can possibly be enhanced by administering the gene encoding the expression product together with a DNA fragment encoding a polypeptide which has the capability of modulating an immune response. For instance, a gene encoding lymphokine precursors or lymphokines (e.g. IFN-γ, IL-2, or IL-12) could be administered together with the gene encoding the immunogenic protein, either by administering two separate DNA fragments or by administering both DNA fragments included in the same vector.

It also is a possibility to administer DNA fragments comprising a multitude of nucleotide sequences which each encode relevant epitopes of the polypeptides disclosed herein so as to effect a continuous sensitization of the immune system with a broad spectrum of these epitopes.

As explained above, the polypeptide fragments of the invention are excellent candidates for vaccine constituents or for constituents in an immune diagnostic agent due to their extracellular presence in culture media containing metabolizing virulent mycobacteria belonging to the tuberculosis complex, or because of their high homologies with such extra-cellular antigens, or because of their absence in *M. bovis* BCG.

Thus, another part of the invention pertains to an immunologic composition comprising a polypeptide or fusion polypeptide according to the invention. In order to ensure optimum performance of such an immunologic composition it is preferred that it comprises an immunologically and pharmaceutically acceptable carrier, vehicle or adjuvant.

Suitable carriers are selected from the group consisting of a polymer to which the polypeptide(s) is/are bound by hydrophobic non-covalent interaction, such as a plastic, e.g. polystyrene, or a polymer to which the polypeptide(s) is/are covalently bound, such as a polysaccharide, or a polypeptide, e.g. bovine serum albumin, ovalbumin or keyhole limpet haemocyanin. Suitable vehicles are selected from the group consisting of a diluent and a suspending agent. The adjuvant is preferably selected from the group consisting of dimethyldioctadecylammonium bromide (DDA), Quil A, poly I:C, Freund's incomplete adjuvant, IFN-γ, IL-2, IL-12, monophosphoryl lipid A (MPL), and muramyl dipeptide (MDP).

A preferred immunologic composition according to the present invention comprising at least two different polypeptide fragments, each different polypeptide fragment being a polypeptide or a fusion polypeptide defined above. It is preferred that the immunologic composition comprises between 3–20 different polypeptide fragments or fusion polypeptides.

Such an immunologic composition may preferably be in the form of a vaccine or in the form of a skin test reagent.

In line with the above, the invention therefore also pertain to a method for producing an immunologic composition according to the invention, the method comprising preparing, synthesizing or isolating a polypeptide according to the invention, and solubilizing or dispersing the polypeptide in a medium for a vaccine, and optionally adding other *M. tuberculosis* antigens and/or a carrier, vehicle and/or adjuvant substance.

Preparation of vaccines which contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables either as liquid solutions or suspensions; solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like, and combinations thereof. In addition, if desired, the vaccine may contain minor amounts of auxiliary substances such as wetting or emulsifying agents, pH buffering agents, or adjuvants which enhance the effectiveness of the vaccines.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10–95% of active ingredient, preferably 25–70%.

The proteins may be formulated into the vaccine as neutral or salt forms. Pharmaceutically acceptable salts include acid addition salts (formed with the free amino groups of the peptide) and which are formed with inorganic acids such as, for example, hydrochloric or phosphoric acids, or such organic acids as acetic oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with a preferred range from about 0.1 $\mu$g to 1000 $\mu$g, such as in the range from about 1 $\mu$g to 300 $\mu$g, and especially in the range from about 10 $\mu$g to 50 $\mu$g. Suitable regimens for initial administration and booster shots are also variable but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the age of the person to be vaccinated and, to a lesser degree, the size of the person to be vaccinated.

Some of the polypeptides of the vaccine are sufficiently immunogenic in a vaccine, but for some of the others the immune response will be enhanced if the vaccine further comprises an adjuvant substance.

Various methods of achieving adjuvant effect for the vaccine include use of agents such as aluminum hydroxide or phosphate (alum), commonly used as 0.05 to 0.1 percent solution in phosphate buffered saline, admixture with synthetic polymers of sugars (Carbopol) used as 0.25 percent solution, aggregation of the protein in the vaccine by heat treatment with temperatures ranging between 700 to 101° C. for 30 second to 2 minute periods respectively. Aggregation by reactivating with pepsin treated (Fab) antibodies to albumin, mixture with bacterial cells such as C. parvum or endotoxins or lipopoly-saccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed. According to the invention DDA (dimethyldioctadecylammonium bromide) is an interesting candidate for an adjuvant, but also Freund's complete and incomplete adjuvants as well as QuilA and RIBI are interesting possibilities. Further possibilities are monophosphoryl lipid A (MPL), and muramyl dipeptide (MDP).

Another highly interesting (and thus, preferred) possibility of achieving adjuvant effect is to employ the technique described in Gosselin et al., 1992 (which is hereby incorporated by reference herein). In brief, the presentation of a relevant antigen such as an antigen of the present invention can be enhanced by conjugating the antigen to antibodies (or antigen binding antibody fragments) against the Fc$\gamma$ receptors on monocytes/macrophages. Especially conjugates between antigen and anti-Fc$\gamma$RI have been demonstrated to enhance immunogenicity for the purposes of vaccination.

Other possibilities involve the use of immune modulating substances such as lymphokines (e.g. IFN-$\gamma$, IL-2 and IL-12) or synthetic IFN-$\gamma$ inducers such as poly I:C in combination with the above-mentioned adjuvants. As discussed in example 3, it is contemplated that such mixtures of antigen and adjuvant will lead to superior vaccine formulations.

In many instances, it will be necessary to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain the desired levels of protective immunity. The course of the immunization may be followed by in vitro proliferation assays of PBL (peripheral blood lymphocytes) co-cultured with ESAT-6 or ST-CF, and especially by measuring the levels of IFN-$\gamma$ released form the primed lymphocytes. The assays may be performed using conventional labels, such as radionuclides, enzymes, fluorescers, and the like. These techniques are well known and may be found in a wide variety of patents, such as U.S. Pat. Nos. 3,791,932; 4,174,384 and 3,949,064, as illustrative of these types of assays.

Due to genetic variation, different individuals may react with immune responses of varying strength to the same polypeptide. Therefore, the vaccine according to the invention may comprise several different polypeptides in order to increase the immune response. The vaccine may comprise two or more polypeptides, where all of the polypeptides are as defined above, or some but not all of the peptides may be derived from a bacterium belonging to the M. tuberculosis complex. In the latter example the polypeptides not necessarily fulfilling the criteria set forth above for polypeptides may either act due to their own immunogenicity or merely act as adjuvants. Examples of such interesting polypeptides are MPB64, MPT64, and MPB59, but any other substance which can be isolated from mycobacteria are possible candidates.

The vaccine may comprise 3–20 different polypeptides, such as 3–10 different polypeptides.

One reason for admixing the polypeptides of the invention with an adjuvant is to effectively activate a cellular immune response. However, this effect can also be achieved in other ways, for instance by expressing the effective antigen in a vaccine in a non-pathogenic microorganism. A well-known example of such a microorganism is *Mycobacterium bovis* BCG.

Therefore, another important aspect of the present invention is an improvement of the living BCG vaccine presently available, which is a vaccine for immunizing an animal, including a human being, against TB caused by mycobacteria belonging to the tuberculosis-complex, comprising as the effective component a microorganism, wherein one or more copies of a DNA sequence encoding a polypeptide as defined above has been incorporated into the genome of the microorganism in a manner allowing the microorganism to express and secrete the polypeptide.

In the present context the term "genome" refers to the chromosome of the microorganisms as well as extrachromosomally DNA or RNA, such as plasmids. It is, however, preferred that the DNA sequence of the present invention has been introduced into the chromosome of the non-pathogenic microorganism, since this will prevent loss of the genetic material introduced.

It is preferred that the non-pathogenic microorganism is a bacterium, e.g. selected from the group consisting of the genera Mycobacterium, Salmonella, Pseudomonas and Eschericia.

It is especially preferred that the non-pathogenic microorganism is *Mycobacterium bovis* BCG, such as *Mycobacterium bovis* BCG strain: Danish 1331.

The incorporation of one or more copies of a nucleotide sequence encoding the polypeptide according to the invention in a mycobacterium from a *M. bovis* BCG strain will enhance the immunogenic effect of the BCG strain. The incorporation of more than one copy of a nucleotide sequence of the invention is contemplated to enhance the immune response even more, and consequently an aspect of the invention is a vaccine wherein at least 2 copies of a DNA sequence encoding a polypeptide is incorporated in the genome of the microorganism, such as at least 5 copies. The copies of DNA sequences may either be identical encoding identical polypeptides or be variants of the same DNA sequence encoding identical or homologues of a polypeptide, or in another embodiment be different DNA sequences encoding different polypeptides where at least one of the polypeptides is according to the present invention.

The living vaccine of the invention can be prepared by cultivating a transformed non-pathogenic cell according to the invention, and transferring these cells to a medium for a vaccine, and optionally adding a carrier, vehicle and/or adjuvant substance.

The invention also relates to a method of diagnosing TB caused by *Mycobacterium tuberculosis, Mycobacterium africanum* or *Mycobacterium bovis* in an animal, including a human being, comprising intradermally injecting, in the animal, a polypeptide according to the invention or a skin test reagent described above, a positive skin response at the location of injection being indicative of the animal having TB, and a negative skin response at the location of injection being indicative of the animal not having TB. A positive response is a skin reaction having a diameter of at least 5 mm, but larger reactions are preferred, such as at least 1 cm, 1.5 cm, and at least 2 cm in diameter. The composition used as the skin test reagent can be prepared in the same manner as described for the vaccines above.

In line with the disclosure above pertaining to vaccine preparation and use, the invention also pertains to a method for immunising an animal, including a human being, against TB caused by mycobacteria belonging to the tuberculosis complex, comprising administering to the animal a polypeptide of the invention, or a vaccine composition of the invention as described above, or a living vaccine described above. Preferred routes of administration are the parenteral (such as intravenous and intraarterially), intraperitoneal, intramuscular, subcutaneous, intradermal, oral, buccal, sublingual, nasal, rectal or transdermal route.

The protein ESAT-6 which is present in short-term culture filtrates from mycobacteria as well as the esat-6 gene in the mycobacterial genome has been demonstrated to have a very limited distribution in other mycobacterial strains that *M. tuberculosis*, e.g. esat-6 is absent in both BCG and the majority of mycobacterial species isolated from the environment, such as *M. avium* and *M. terrae*. It is believed that this is also the case for at least one of the antigens of the present invention and their genes and therefore, the diagnostic embodiments of the invention are especially well-suited for performing the diagnosis of on-going or previous infection with virulent mycobacterial strains of the tuberculosis complex, and it is contemplated that it will be possible to distinguish between 1) subjects (animal or human) which have been previously vaccinated with e.g. BCG vaccines or subjected to antigens from non-virulent mycobacteria and 2) subjects which have or have had active infection with virulent mycobacteria.

A number of possible diagnostic assays and methods can be envisaged:

When diagnosis of previous or ongoing infection with virulent mycobacteria is the aim, a blood sample comprising mononuclear cells (i.a. T-lymphocytes) from a patient could be contacted with a sample of one or more polypeptides of the invention. This contacting can be performed in vitro and a positive reaction could e.g. be proliferation of the T-cells or release cytokines such as γ-interferon into the extracellular phase (e.g. into a culture supernatant); a suitable in vivo test would be a skin test as described above. It is also conceivable to contact a serum sample from a subject to contact with a polypeptide of the invention, the demonstration of a binding between antibodies in the serum sample and the polypeptide being indicative of previous or ongoing infection.

The invention therefore also relates to an in vitro method for diagnosing ongoing or previous sensitization in an animal or a human being with bacteria belonging to the tuberculosis complex, the method comprising providing a blood sample from the animal or human being, and contacting the sample from the animal with the polypeptide of the invention, a significant release into the extracellular phase of at least one cytokine by mononuclear cells in the blood sample being indicative of the animal being sensitized. By the term "significant release" is herein meant that the release of the cytokine is significantly higher than the cytokine release from a blood sample derived from a non-tuberculous subject (e.g. a subject which does not react in a traditional skin test for TB). Normally, a significant release is at least two times the release observed from such a sample.

Alternatively, a sample of a possibly infected organ may be contacted with an antibody raised against a polypeptide of the invention. The demonstration of the reaction by means of methods well-known in the art between the sample and the antibody will be indicative of ongoing infection. It is of course also a possibility to demonstrate the presence of anti-mycobacterial antibodies in serum by contacting a serum sample from a subject with at least one of the polypeptide fragments of the invention and using well-known methods for visualizing the reaction between the antibody and antigen.

Also a method of determining the presence of mycobacterial nucleic acids in an animal, including a human being, or in a sample, comprising administering a nucleic acid fragment of the invention to the animal or incubating the sample with the nucleic acid fragment of the invention or a nucleic acid fragment complementary thereto, and detecting the presence of hybridized nucleic acids resulting from the incubation (by using the hybridization assays which are well-known in the art), is also included in the invention. Such a method of diagnosing TB might involve the use of a composition comprising at least a part of a nucleotide sequence as defined above and detecting the presence of nucleotide sequences in a sample from the animal or human being to be tested which hybridize with the nucleic acid fragment (or a complementary fragment) by the use of PCR technique.

The fact that certain of the disclosed antigens are not present in *M. bovis* BCG but are present in virulent mycobacteria point them out as interesting drug targets; the antigens may constitute receptor molecules or toxins which facilitate the infection by the mycobacterium, and if such functionalities are blocked the infectivity of the mycobacterium will be diminished.

To determine particularly suitable drug targets among the antigens of the invention, the gene encoding at least one of the polypeptides of the invention and the necessary control sequences can be introduced into avirulent strains of mycobacteria (e.g. BCG) so as to determine which of the polypeptides are critical for virulence. Once particular proteins are identified as critical for/contributory to virulence, antimycobacterial agents can be designed rationally to inhibit expression of the critical genes or to attack the critical gene products. For instance, antibodies or fragments thereof (such as Fab and (Fab')$_2$ fragments can be prepared against such critical polypeptides by methods known in the art and thereafter used as prophylactic or therapeutic agents. Alternatively, small molecules can be screened for their ability to selectively inhibit expression of the critical gene products, e.g. using recombinant expression systems which include the gene's endogenous promoter, or for their ability to directly interfere with the action of the target. These small molecules are then used as therapeutics or as prophylactic agents to inhibit mycobacterial virulence.

Alternatively, anti-mycobacterial agents which render a virulent mycobacterium avirulent can be operably linked to expression control sequences and used to transform a virulent mycobacterium. Such anti-mycobacterial agents inhibit the replication of a specified mycobacterium upon transcription or translation of the agent in the mycobacterium. Such a "newly avirulent" mycobacterium would constitute a superb alternative to the above described modified BCG for vaccine purposes since it would be immunologically very similar to a virulent mycobacterium compared to e.g. BCG.

Finally, a monoclonal or polyclonal antibody, which is specifically reacting with a polypeptide of the invention in an immuno assay, or a specific binding fragment of said antibody, is also a part of the invention. The production of such polyclonal antibodies requires that a suitable animal be immunized with the polypeptide and that these antibodies are subsequently isolated, suitably by immune affinity chromatography. The production of monoclonals can be effected by methods well-known in the art, since the present invention provides for adequate amounts of antigen for both immunization and screening of positive hybridomas.

LEGENDS TO THE FIGURES

FIG. 1: Long term memory immune mice are very efficiently protected towards an infection with *M. tuberculosis*. Mice were given a challenge of *M. tuberculosis* and spleens were isolated at different time points. Spleen lymphocytes were stimulated in vitro with ST-CF and the release of IFN-γ investigated (panel A). The counts of CFU in the spleens of the two groups of mice are indicated in panel B. The memory immune mice control infection within the first week and produce large quantities of IFN-γ in response to antigens in ST-CF.

FIG. 2: T cells involved in protective immunity are predominantly directed to molecules from 6–12 and 17–38 kDa. Splenic T cells were isolated four days after the challenge with *M. tuberculosis* and stimulated in vitro with narrow molecular mass fractions of ST-CF. The release of IFN-γ was investigated FIG. 3: Nucleotide sequence (SEQ ID NO: 1) of cfp7. The deduced amino acid sequence (SEQ ID NO: 2) of CFP7 is given in conventional one-letter code below the nucleotide sequence. The putative ribosome-binding site is written in underlined italics as are the putative −10 and −35 regions. Nucleotides written in bold are those encoding CFP7.

FIG. 4. Nucleotide sequence (SEQ ID NO: 3) of cfp9. The deduced amino acid sequence (SEQ ID NO: 4) of CFP9 is given in conventional one-letter code below the nucleotide sequence. The putative ribosome-binding site Shine Delgarno sequence is written in underlined italics as are the putative −10 and −35 regions. Nucleotides in bold writing are those encoding CFP9. The nucleotide sequence obtained from the lambda 226 phage is double underlined.

FIG. 5: Nucleotide sequence of mpt51. The deduced amino acid sequence of MPT51 is given in a one-letter code below the nucleotide sequence. The signal is indicated in italics. the putative potential ribosome-binding site is underlined. The nucleotide difference and amino acid difference compared to the nucleotide sequence of MPB51 (Ohara et al., 1995) are underlined at position 780. The nucleotides given in italics are not present in *M. tuberculosis* H37Rv.

FIG. 6: the position of the purified antigens in the 2DE system have been determined and mapped in a reference gel. The newly purified antigens are encircled and the position of well-known proteins are also indicated.

EXAMPLE 1

Identification of Single Culture Filtrate Antigens Involved in Protective Immunity A group of efficiently protected mice was generated by infecting 8–12 weeks old female C57Bl/6j mice with $5\times10^4$ *M. tuberculosis* i.v. After 30 days of infection the mice were subjected to 60 days of antibiotic treatment with isoniazid and were then left for 200–240 days to ensure the establishment of resting long-term memory immunity. Such memory immune mice are very efficiently protected against a secondary infection (FIG. 1). Long lasting immunity in this model is mediated by a population of highly reactive CD4 cells recruited to the site of infection and triggered to produce large amounts of IFN-γ in response to ST-CF (FIG. 1) (Andersen et al. 1995).

We have used this model to identify single antigens recognized by protective T cells. Memory immune mice were reinfected with $1\times10^6$ *M. tuberculosis* i.v. and splenic lymphocytes were harvested at day 4–6 of reinfection , a time point where this population is highly reactive to ST-CF. The antigens recognized by these T cells were mapped by the multi-elution technique (Andersen and Heron, 1993). This technique divides complex protein mixtures separated in SDS-PAGE into narrow fractions in a physiological buffer. These fractions were used to stimulate spleen lymphocytes in vitro and the release of IFN-γ was monitored (FIG. 2). Long-term memory immune mice did not recognize these fractions before TB infection, but splenic lymphocytes obtained during the recall of protective immunity recognized a range of culture filtrate antigens and peak production of IFN-γ was found in response to proteins of apparent molecular weight 6–12 and 17–30 kDa (FIG. 2). It is therefore concluded that culture filtrate antigens within these regions are the major targets recognized by memory effector T-cells triggered to release IFN-γ during the first phase of a protective immune response.

EXAMPLE 2

Cloning of Genes Expressing Low Mass Culture Filtrate Antigens

In example 1 it was demonstrated that antigens in the low molecular mass fraction are recognized strongly by cells isolated from memory immune mice. Monoclonal antibodies (mAbs) to these antigens were therefore generated by immunizing with the low mass fraction in RIBI adjuvant (first and second immunization) followed by two injections with the fractions in aluminium hydroxide. Fusion and cloning of the reactive cell lines were done according to standard procedures (Kohler and Milstein 1975). The procedure resulted in the provision of two mAbs: ST-3 directed to a 9 kDa culture filtrate antigen (CFP9) and PV-2 directed to a 7 kDa antigen (CFP7), when the molecular weight is estimated from migration of the antigens in an SDS-PAGE.

In order to identify the antigens binding to the Mab's, the following experiments were carried out:

The recombinant λgt11 M. tuberculosis DNA library constructed by R. Young (Young, R. A. et al. 1985) and obtained through the World Health Organization IMMTUB programme (WHO.0032.wibr) was screened for phages expressing gene products which would bind the monoclonal antibodies ST-3 and PV-2.

Approximately 1×10$^5$ pfu of the gene library (containing approximately 25% recombinant phages) were plated on Eschericia coli Y1090 (DlacU169, proA$^+$, Dlon, araD139, supF, trpC22::tn10 [pMC9] ATCC#37197) in soft agar and incubated for 2.5 hours at 42° C.

The plates were overlaid with sheets of nitrocellulose saturated with isopropyl-β-D-thiogalactopyranoside and incubation was continued for 2,5 hours at 37° C. The nitrocellulose was removed and incubated with samples of the monoclonal antibodies in PBS with Tween 20 added to a final concentration of 0.05%. Bound monoclonal antibodies were visualized by horseradish peroxidase-conjugated rabbit anti-mouse immunoglobulins (P260, Dako, Glostrup, DK) and a staining reaction involving 5,5',3,3'-tetramethylbenzidine and $H_2O_2$.

Positive plaques were recloned and the phages originating from a single plaque were used to lysogenize E. coli Y1089 (DlacU169, proA$^+$, Dlon, araD139, strA, hfl150 [chr::tn10] [pMC9] ATCC nr. 37196). The resultant lysogenic strains were used to propagate phage particles for DNA extraction. These lysogenic E. coli strains have been named:

AA226 (expressing ST-3 reactive polypeptide CFP9) which has been deposited Jun. 28, 1993 with the collection of Deutsche Sammlung von Mikroorganismen und Zellkulturen GmbH (DSM) under the accession number DSM 8377 and in accordance with the provisions of the Budapest Treaty, and AA242 (expressing PV-2 reactive polypeptide CFP7) which has been deposited Jun. 28, 1993 with the collection of Deutsche Sammlung von Mikroorganismen und Zellkulturen GmbH (DSM) under the accession number DSM 8379 and in accordance with the provisions of the Budapest Treaty.

These two lysogenic E. coli strains are disclosed in WO 95/01441 as are the mycobacterial polypeptide products expressed thereby. However, no information concerning the amino acid sequences of these polypeptides or their genetic origin are given, and therefore only the direct expression products of AA226 and AA242 are made available to the public.

The st-3 binding protein is expressed as a protein fused to β-galactosidase, whereas the pv-2 binding protein appears to be expressed in an unfused version.

Sequencing of the Nucleotide Sequence Encoding the PV-2 and ST-3 Binding Protein In order to obtain the nucleotide sequence of the gene encoding the pv-2 binding protein, the approximately 3 kb M. tuberculosis derived EcoRI—EcoRI fragment from AA242 was subcloned in the EcoRI site in the pBluescriptSK+(Stratagene) and used to transform E. coli XL-1Blue (Stratagene).

Similarly, to obtain the nucleotide sequence of the gene encoding the st-3 binding protein, the approximately 5 kb M. tuberculosis derived EcoRI-EcoRI fragment from AA226 was subcloned in the EcoRI site in the pBluescriptSK+ (Stratagene) and used to transform E. coli XL-1Blue (Stratagene).

The complete DNA sequence of both genes were obtained by the dideoxy chain termination method adapted for supercoiled DNA by use of the Sequenase DNA sequencing kit version 1.0 (United States Biochemical Corp., Cleveland, Ohio.) and by cycle sequencing using the Dye Terminator system in combination with an automated gel reader (model 373A; Applied Biosystems) according to the instructions provided. The sequences DNA are shown in SEQ ID NO: 1 (CFP7) and in SEQ ID NO: 3 (CFP9) as well as in FIGS. 3 and 4, respectively. Both strands of the DNA were sequenced.

CFP7

An open reading frame (ORF) encoding a sequence of 96 amino acid residues was identified from an ATG start codon at position 91–93 extending to a TAG stop codon at position 379–381. The deduced amino acid sequence is shown in SEQ ID NO: 2 (and in FIG. 3 where conventional one-letter amino acid codes are used).

CFP7 appear to be expressed in E. coli as an unfused version. The nucleotide sequence at position 78–84 is expected to be the Shine Delgarno sequence and the sequences from position 47–50 and 14–19 are expected to be the −10 and −35 regions, respectively:

CFP9

The protein recognised by ST-3 was produced as a β-galactosidase fusion protein, when expressed from the AA226 lambda phage. The fusion protein had an approx. size of 116–117 kDa (Mw for β-galactosidase 116.25 kDa) which may suggest that only part of the CFP9 gene was included in the lambda clone (AA226).

Based on the 90 bp nucleotide sequence obtained on the insert from lambda phage AA226, a search of homology to the nucleotide sequence of the M. tuberculosis genome was performed in the Sanger database (Sanger Mycobacterium tuberculosis database):

http://www.sanger.ac.uk/pathogens/TB-blast-server.html;

Williams, 1996). 100% identity to the cloned sequence was found on the MTCY48 cosmid. An open reading frame (ORF) encoding a sequence of 109 amino acid residues was identified from a GTG start codon at position 141–143 extending to a TGA stop codon at position 465–467. The deduced amino acid sequence is shown in FIG. 4 using conventional one letter code.

The nucleotide sequence at position 123–130 is expected to be the Shine Delgarno sequence and the sequences from position 73–78 and 4–9 are expected to be the −10 and −35 region respectively (FIG. 4). The ORF overlapping with the 5'-end of the sequence of AA229 is shown in FIG. 4 by double underlining.

Subcloning CFP7 and CFP9 in Expression Vectors

The two ORFs encoding CFP7 and CFP9 were PCR cloned into the pMST24 (Theisen et al., 1995) expression vector pRVN01 or the pQE-32 (QIAGEN) expression vector pRVNO2, respectively.

The PCR amplification was carried out in a thermal reactor (Rapid cycler, Idaho Technology, Idaho) by mixing 10 ng plasmid DNA with the mastermix (0.5 µM of each oligonucleotide primer, 0.25 µM BSA (Stratagene), low salt buffer (20 mM Tris-HCl, pH 8.8, 10 mM KCl, 10 mM (NH$_4$)$_2$SO$_4$, 2 mM MgSO$_4$ and 0,1% Triton X-100) (Stratagene), 0.25 mM of each deoxynucleoside triphosphate and 0.5 U Taq Plus Long DNA polymerase (Stratagene)). Final volume was 10 µl (all concentrations given are concentrations in the final volume). Predenaturation was carried out at 94° C. for 30 s. 30 cycles of the following was performed; Denaturation at 94° C. for 30 s, annealing at 55° C. for 30 s and elongation at 72° C. for 1 min.

The oligonucleotide primers were synthesised automatically on a DNA synthesizer (Applied Biosystems, Forster City, Calif., ABI-391, PCR-mode), deblocked, and purified by ethanol precipitation.

The cfp7 oligonucleotides (TABLE 1) were synthesised on the basis of the nucleotide sequence from the CFP7 sequence (FIG. 3). The oligonucleotides were engineered to include an SmaI restriction enzyme site at the 5' end and a BamHI restriction enzyme site at the 3' end for directed subcloning.

The cfp9 oligonucleotides (TABLE 1) were synthesized partly on the basis of the nucleotide sequence from the sequence of the AA229 clone and partly from the identical sequence found in the Sanger database cosmid MTCY48 (FIG. 4). The oligonucleotides were engineered to include a SmaI restriction enzyme site at the 5' end and a HindIII restriction enzyme site at the 3' end for directed subcloning.

CFP7

By the use of PCR a SmaI site was engineered immediately 5' of the first codon of the ORF of 291 bp, encoding the cfp7 gene, so that only the coding region would be expressed, and a BamHI site was incorporated right after the stop codon at the 3' end. The 291 bp PCR fragment was cleaved by SmaI and BamHI, purified from an agarose gel and subcloned into the SmaI—BamHI sites of the pMST24 expression vector. Vector DNA containing the gene fusion was used to transform the E. coli XL1-Blue (pRVN01).

CFP9

By the use of PCR a SmaI site was engineered immediately 5' of the first codon of an ORF of 327 bp, encoding the cfp9 gene, so that only the coding region would be expressed, and a HindIII site was incorporated after the stop codon at the 3' end. The 327 bp PCR fragment was cleaved by SmaI and HindIII, purified from an agarose gel, and subcloned into the SmaI-HindIII sites of the pQE-32 (QIAGEN) expression vector. Vector DNA containing the gene fusion was used to transform the E. coli XL1-Blue (pRVN02).

Purification of Recombinant CFP7 and CFP9

The ORFs were fused N-terminally to the (His)$_6$-tag (cf. EP-A-0 282 242). Recombinant antigen was prepared as follows: Briefly, a single colony of E. coli harbouring either the pRVN01 or the pRVN02 plasmid, was inoculated into Luria-Bertani broth containing 100 µg/ml ampicillin and 12.5 µg/ml tetracycline and grown at 37° C. to OD$_{600nm}$=0.5. IPTG (isopropyl-β-D-thiogalactoside) was then added to a final concentration of 2 mM (expression was regulated either by the strong IPTG inducible P$_{tac}$ or the T5 promoter) and growth was continued for further 2 hours. The cells were harvested by centrifugation at 4,200×g at 4° C. for 8 min. The pelleted bacteria were stored overnight at −20° C. The pellet was resuspended in BC 40/100 buffer (20 mM Tris-HCl pH 7.9, 20% glycerol, 100 mM KCl, 40 mM Imidazole) and cells were broken by sonication (5 times for 30 s with intervals of 30 s) at 40° C. followed by centrifugation at 12,000×g for 30 min at 4° C., the supernatant (crude extract) was used for purification of the recombinant antigens.

The two Histidine fusion proteins (His-rCFP7 and His-rCFP9) were purified from the crude extract by affinity chromatography on a Ni$^{2+}$-NTA column from QIAGEN with a volume of 100 ml. His-rCFP7 and His-rCFP9 binds to Ni$^{2+}$. After extensive washes of the column in BC 40/100 buffer, the fusion protein was eluted with a BC 1000/100 buffer containing 100 mM imidazole, 20 mM Tris pH 7.9, 20% glycerol and 1 M KCl. subsequently, the purified products were dialysed extensively against 10 mM Tris pH 8.0. His-rCFP7 and His-rCFP9 were then separated from contaminants by fast protein liquid chromatography (FPLC) over an anion-exchange column (Mono Q, Pharmacia, Sweden). in 10 mM Tris pH 8.0 with a linear gradient of NaCl from 0 to 1 M. Aliquots of the fractions were analyzed by 10%–20% gradient sodium dodecyl sulphate polyacrylamide gel electrophoresis (SDS-PAGE). Fractions containing purified either purified His-rCFP7 or His-rCFP9 were pooled.

TABLE 1

Sequence of the cfp7 and cfp9 oligonucleotides[a].

| Orientation and oligonucleotide | Sequences (5' → 3') | Position[b] (nucleotide) |
|---|---|---|
| Sense | | |
| pvR3 | GCAACACCCGGGATGTCGCAAATCATG | 91–105 |
| | (SEQ ID NO: 43) | (SEQ ID NO: 1) |
| stR2 | GTAACACCCGGGGTGGCCGCCGACCCG | 141–155 |
| | (SEQ ID NO: 44) | (SEQ ID NO: 3) |

TABLE 1-continued

Sequence of the cfp7 and cfp9 oligonucleotides[a].

| Orientation and oligonucleotide | Sequences (5' → 3') | Position[b] (nucleotide) |
|---|---|---|
| Antisense | | |
| pvF4 | <u>CTACTAAGCTTGGATCCC</u>TAGCCGCCCCATTTGGCGG (SEQ ID NO: 45) | 381–362 (SEQ ID NO: 1) |
| stF2 | <u>CTACTAAGCTTCCATGG</u>TCAGGTCTTTTCGATGCTTAC (SEQ ID NO: 46) | 467–447 (SEQ ID NO: 3) |

[a]The cfp7 oligonucleotides were based on the nucleotide sequence shown in FIG. 3 (SEQ ID NO: 1). The cfp9 oligonucleotides were based on the nucleotide sequence shown in FIG. 4 (SEQ ID NO: 3).
Nucleotides underlined are not contained in the nucleotide sequence of cfp7 and cfp9.
[b]The positions referred to are of the non-underlined part of the primers and correspond to the nucleotide sequence shown in FIG. 3 and FIG. 4, respectively.

EXAMPLE 2A

Identification of Antigens which are not Expressed in BCG Strains

In an effort to control the treat of TB, attenuated bacillus Calmette-Guérin (BCG) has been used as a live attenuated vaccine. BCG is an attenuated derivative of a virulent *Mycobacterium bovis*. The original BCG from the Pasteur Institute in Paris, France was developed from 1908 to 1921 by 231 passages in liquid culture and has never been shown to revert to virulence in animals, indicating that the attenuating mutation(s) in BCG are stable deletions and/or multiple mutations which do not readily revert. While physiological differences between BCG and *M. tuberculosis* and *M. bovis* has been noted, the attenuating mutations which arose during serial passage of the original BCG strain has been unknown until recently. The first mutations described are the loss of the gene encoding MPB64 in some BCG strains (Li et al., 1993, Oettinger and Andersen, 1994) and the gene encoding ESAT-6 in all BCG strain tested (Harboe et al., 1996), later 3 large deletions in BCG have been identified (Mahairas et al., 1996). The region named RD1 includes the gene encoding ESAT-6 and an other (RD2) the gene encoding MPT64. Both antigens have been shown to have diagnostic potential and ESAT-6 has been shown to have properties as a vaccine candidate (cf. PCT/DK94/00273 and PCT/DK/00270). In order to find new *M. tuberculosis* specific diagnostic antigens as well as antigens for a new vaccine against TB, the RD1 region (17.499 bp) of *M. tuberculosis* H37Rv has been analyzed for Open Reading Frames (ORF). ORFs with a minimum length of 96 bp have been predicted using the algorithm described by Borodovsky and McIninch (1993), in total 27 ORFs have been predicted, 20 of these have possible diagnostic and/or vaccine potential, as they are deleted from all known BCG strains. The predicted ORFs include ESAT-6 (RD1-ORF7) and CFP10 (RD1-ORF6) described previously (Sorensen et al., 1995), as a positive control for the ability of the algorithm. In the present is described the potential of 7 of the predicted antigens for diagnosis of TB as well as potential as candidates for a new vaccine against TB.

Seven open reading frames (ORF) from the 17,499 kb RD1 region (Accession no. U34848) with possible diagnostic and vaccine potential have been identified and cloned.

Identification of the ORF's rd1-orf2. rd1-orf3, rd1-orf4, rd1-orf5, rd1-orf8, rd1-orf9a. and rd1-orf9b.

The nucleotide sequence of rd1-orf2 from *M. tuberculosis* H37Rv is set forth in SEQ ID NO: 71. The deduced amino acid sequence of RD1-ORF2 is set forth in SEQ ID NO: 72.

The nucleotide sequence of rd1-orf3 from *M. tuberculosis* H37Rv is set forth in SEQ ID NO: 87. The deduced amino acid sequence of RD1-ORF2 is set forth in SEQ ID NO: 88.

The nucleotide sequence of rd1-orf4 from *M. tuberculosis* H37Rv is set forth in SEQ ID NO: 89. The deduced amino acid sequence of RD1-ORF2 is set forth in SEQ ID NO: 90.

The nucleotide sequence of rd1-orf5 from *M. tuberculosis* H37Rv is set forth in SEQ ID NO: 91. The deduced amino acid sequence of RD1-ORF2 is set forth in SEQ ID NO: 92.

The nucleotide sequence of rd1-orf8 from *M. tuberculosis* H37Rv is set forth in SEQ ID NO: 67. The deduced amino acid sequence of RD1-ORF2 is set forth in SEQ ID NO: 68.

The nucleotide sequence of rd1-orf9a from *M. tuberculosis* H37Rv is set forth in SEQ ID NO: 93. The deduced amino acid sequence of RD1-ORF2 is set forth in SEQ ID NO: 94.

The nucleotide sequence of rd1-orf9b from *M. tuberculosis* H37Rv is set forth in SEQ ID NO: 69. The deduced amino acid sequence of RD1-ORF2 is set forth in SEQ ID NO: 70.

The DNA sequence <u>rd1-orf2</u> (SEQ ID NO: 71) contained an open reading frame starting with an ATG codon at position 889–891 and ending with a termination codon (TAA) at position 2662–2664 (position numbers referring to the location in RD1). The deduced amino acid sequence (SEQ ID NO: 72) contains 591 residues corresponding to a molecular weight of 64,525.

The DNA sequence rb1-orf3 (SEQ ID NO: 87) contained an open reading frame starting with an ATG codon at position 2807–2809 and ending with a termination codon (TAA) at position 3101–3103 (position numbers referring to the location in RD1). The deduced amino acid sequence (SEQ ID NO: 88) contains 98 residues corresponding to a molecular weight of 9,799.

The DNA sequence rd1-orf4 (SEQ ID NO: 89) contained an open reading frame starting with a GTG codon at position 4014–4012 and ending with a termination codon (TAG) at position 3597–3595 (position numbers referring to the location in RD1). The deduced amino acid sequence (SEQ ID NO: 90) contains 139 residues corresponding to a molecular weight of 14,210.

The DNA sequence <u>rb1-orf5</u> (SEQ ID NO: 91) contained an open reading frame starting with a GTG codon at position 3128–3130 and ending with a termination codon (TGA) at position 4241–4243 (position numbers referring to the location in RD1). The deduced amino acid sequence (SEQ ID NO: 92) contains 371 residues corresponding to a molecular weight of 37,647.

The DNA sequence rd1-orf8 (SEQ ID NO: 67) contained an open reading frame starting with a GTG codon at position 5502–5500 and ending with a termination codon (TAG) at position 5084–5082 (position numbers referring to the location in RD1), and the deduced amino acid sequence (SEQ ID NO: 68) contains 139 residues with a molecular weight of 11,737.

The DNA sequence rd1-orf9a (SEQ ID NO: 93) contained an open reading frame starting with a GTG codon at position 6146–6148 and ending with a termination codon (TAA) at position 7070–7072 (position numbers referring to the location in RD1). The deduced amino acid sequence (SEQ ID NO: 94) contains 308 residues corresponding to a molecular weight of 33,453.

The DNA sequence rd1-orf9b (SEQ ID NO: 69) contained an open reading frame starting with an ATG codon at position 5072–5074 and ending with a termination codon (TAA) at position 7070–7072 (position numbers referring to the location in RD1). The deduced amino acid sequence (SEQ ID NO: 70) contains 666 residues corresponding to a molecular weight of 70,650.

Cloning of the ORF's rd1-orf2. rd1-orf3. rd1-orf4. rd1-orf5. rd1-orf8. rd1-orf9a. and rd1-orf9b The ORF's rd1-orf2, rd1-orf3, rd1-orf4, rd1-orf5, rd1-orf8, rd1-orf9a and rd1-orf9b were PCR cloned in the pMST24 (Theisen et al., 1995) (rd1-orf3) or the pQE32 (QIAGEN) (rd1-orf2, rd1-orf4, rd1-orf5, rd1-orf8, rd1-orf9a and rd1-orf9b) expression vector. Preparation of oligonucleotides and PCR amplification of the rd1-orf encoding genes, was carried out as described in example 2. Chromosomal DNA from M. tuberculosis H37Rv was used as template in the PCR reactions. Oligonucleotides were synthesized on the basis of the nucleotide sequence from the RD1 region (Accession no. U34848). The oligonucleotide primers were engineered to include an restriction enzyme site at the 5' end and at the 3' end by which a later subcloning was possible. Primers are listed in TABLE 2.

rd1-orf2. A BamHI site was engineered immediately 5' of the first codon of rd1-orf2, and a HindIII site was incorporated right after the stop codon at the 3' end. The gene rd1-orf2 was subcloned in pQE32, giving pTO96.

rd1-orf3. A SmaI site was engineered immediately 5' of the first codon of rd1-orf3, and a NcoI site was incorporated right after the stop codon at the 3' end. The gene rd1-orf3 was subcloned in pMST24, giving pTO87.

rd1-orf4. A BamHI site was engineered immediately 5' of the first codon of rd1-orf4, and a HindIII site was incorporated right after the stop codon at the 3' end. The gene rd1-orf4 was subcloned in pQE32, giving pTO89.

rd1-orf5. A BamHI site was engineered immediately 5' of the first codon of rd1-orf5, and a HindIII site was incorporated right after the stop codon at the 3' end. The gene rd1-orf5 was subcloned in pQE32, giving pTO88.

rd1-orf8. A BamHI site was engineered immediately 5' of the first codon of rd1-orf8, and a NcoI site was incorporated right after the stop codon at the 3' end. The gene rd1-orf8 as subcloned in pMST24, giving pTO98.

rd1-orf9a. A BamHI site was engineered immediately 5' of the first codon of rd1-orf9a, and a HindIII site was incorporated right after the stop codon at the 3' end. The gene rd1-orf9a was subcloned in pQE32, giving pTO91.

rd1-orf9b. A ScaI site was engineered immediately 5' of the first codon of rd1-orf9b, and a Hind III site was incorporated right after the stop codon at the 3' end. The gene. rd1-orf9b was subcloned in pQE32, giving pTO90.

The PCR fragments were digested with the suitable restriction enzymes, purified from an agarose gel and cloned into either pMST24 or pQE-32. The seven constructs were used to transform the E. coli XL1-Blue. Endpoints of the gene fusions were determined by the dideoxy chain termination method. Both strands of the DNA were sequenced.

Purification of Recombinant RD1-ORF2, RD1-ORF3, RD1-ORF4, RD1-ORF5, RD1-ORF8, RD1-ORF9a and RD1-ORF9b.

The rRD1-ORFs were fused N-terminally to the $(His)_6$-tag. Recombinant antigen was prepared as described in example 2 (with the exception that pTO91 was expressed at 30° C. and not at 37° C.), using a single colony of E. coli harbouring either the pTO87, pTO88, pTO89, pTO90, pTO91, pTO96 or pTO98 for inoculation. Purification of recombinant antigen by $Ni^{2+}$ affinity chromatography was also carried out as described in example 2. Fractions containing purified His-rRD1-ORF2, His-rRD1-ORF3 His-rRD1-ORF4, His-rRD1-ORF5, His-rRD1-ORF8, His-rRD1-ORF9a or His-rRD1-ORF9b were pooled. The His-rRD1-ORF's were extensively dialysed against 10 mM Tris/HCl, pH 8.5, 3 M urea followed by an additional purification step performed on an anion exchange column (Mono Q) using fast protein liquid chromatography (FPLC) (Pharmacia, Uppsala, Sweden). The purification was carried out in 10 mM Tris/HCl, pH 8.5, 3 M urea and protein was eluted by a linear gradient of NaCl from 0 to 1 M. Fractions containing the His-rRD1-ORF's were pooled and subsequently dialysed extensively against 25 mM Hepes, pH 8.0 before use.

TABLE 2

Sequence of the rd1-orf's oligonucleotides[a].

| Orientation and oligonucleotide | Sequences (5' → 3') | Position (nt) |
| --- | --- | --- |
| Sense | | |
| RD1-ORF2f | CTGGGGATCCGCATGACTGCTGAACCG | 886–903 |
| RD1-ORF3f | CTTCCCGGGATGGAAAAAATGTCAC | 2807–2822 |
| RD1-ORF4f | GTAGGATCCTAGGAGACATCAGCGGC | 4028–4015 |
| RD1-ORF5f | CTGGGGATCCGCGTGATCACCATGCTGTGG | 3028–3045 |
| RD1-ORF8f | CTCGGATCCTGTGGGTGCAGGTCCGGCGATGGGC | 5502–5479 |

TABLE 2-continued

Sequence of the rd1-orf's oligonucleotides[a].

| Orientation and oligonucleotide | Sequences (5' → 3') | Position (nt) |
|---|---|---|
| RD1-ORF9af | GTGATGTGAGCTCAGGTGAAGAAGGTGAAG | 6144–6160 |
| RD1-ORF9bf | GTGATGTGAGCTCCTATGGCGGCCGACTACGAC | 5072–5089 |
| Antisense | | |
| RD1-ORF2r | TGCAAGCTTTTAACCGGCGCTTGGGGGTGC | 2664–2644 |
| RD1-ORF3r | GATGCCATGGTTAGGCGAAGACGCCGGC | 3103–3086 |
| RD1-ORF4r | CGATCTAAGCTTGGCAATGGAGGTCTA | 3582–3597 |
| RD1-ORF5r | TGCAAGCTTTCACCAGTCGTCCTCTTCGTC | 4243–4223 |
| RD1-ORF8r | CTCCCATGGCTACGACAAGCTCTTCCGGCCGC | 5083–5105 |
| RD1-ORF9a/br | CGATCTAAGCTTTCAACGACGTCCAGCC | 7073–7056 |

[a]The oligonucleotides were constructed from the Accession number U34484 nucleotide sequence (Mahairas et al., 1996). Nucleotides (nt) underlined are not contained in the nucleotide sequence of RD1-ORF's. The positions correspond to the nucleotide sequence of Accession number U34484.

The nucleotide sequences of rd1-orf2, rd1-orf3, rd1-orf4, rd1-orf5, rd1-orf8, rd1-orf9a, and rd1-orf9b from *M. tuberculosis* H37Rv are set forth in SEQ ID NO: 71, 87, 89, 91, 67, 93, and 69, respectively. The deduced amino acid sequences of rd1-orf2, rd1-orf3, rd1-orf4 rd1-orf5, rd1-orf8, rd1-orf9a, and rd1-orf9b are set forth in SEQ ID NO: 72, 88, 90, 92, 68, 35 94, and 70, respectively.

EXAMPLE 3

Cloning of the Genes Expressing 17–30 kDa Antigens from ST-CF

Isolation of CFP17, CFP20, CFP21, CFP22, CFP25, and CFP28

ST-CF was precipitated with ammonium sulphate at 80% saturation. The precipitated proteins were removed by centrifugation and after resuspension washed with 8 M urea. CHAPS and glycerol were added to a final concentration of 0.5% (w/v) and 5% (v/v) respectively and the protein solution was applied to a Roto for isoelectrical Cell (BioRad). The Rotofor Cell had been equilibrated with an 8 M urea buffer containing 0.5% (w/v) CHAPS, 5% (v/v) glycerol, 3% (v/v) Biolyt 3/5 and 1% (v/v) Biolyt 4/6 (BioRad). Isoelectric focusing was performed in a pH gradient from 3–6. The fractions were analyzed on silver-stained 10–20% SDS-PAGE. Fractions with similar band patterns were pooled and washed three times with PBS on a Centriprep concentrator (Amicon) with a 3 kDa cut off membrane to a final volume of 1–3 ml. An equal volume of SDS containing sample buffer was added and the protein solution boiled for 5 min before further separation on a Prep Cell (BioRad) in a matrix of 16% polyacrylamide under an electrical gradient. Fractions containing pure proteins with an molecular mass from 17–30 kDa were collected.

Isolation of CFP29

Anti-CFP29, reacting with CFP29 was generated by immunization of BALB/c mice with crushed gel pieces in RIBI adjuvant (first and second immunization) or aluminium hydroxide (third immunization and boosting) with two week intervals. SDS-PAGE gel pieces containing 2–5 μg of CFP29 were used for each immunization. Mice were boosted with antigen 3 days before removal of the spleen. Generation of a monoclonal cell line producing antibodies against CFP29 was obtained essentially as described by K öhler and Milstein (1975). Screening of supernatants from growing clones was carried out by immuno-blotting of nitrocellulose strips containing ST-CF separated by SDS-PAGE. Each strip contained approximately 50 μg of ST-CF. The antibody class of anti-CFP29 was identified as IgM by the mouse monoclonal antibody isotyping kit, RPN29 (Amersham) according to the manufacturer's instructions.

CFP29 was purified by the following method: ST-CF was concentrated 10 fold by ultrafiltration, and ammonium sulphate precipitation in the 45 to 55% saturation range was performed. The pellet was redissolved in 50 mM sodium phosphate, 1.5 M ammonium sulphate, pH 8.5, and subjected to thiophilic adsorption chromatography (Porath et al., 1985) on an Affi-T gel column (Kem-En-Tec). Protein was eluted by a linear 1.5 to 0 M gradient of ammonium sulphate and fractions collected in the range 0.44 to 0.31 M ammonium sulphate were identified as CFP29 containing fractions in Western blot experiments with mAb Anti-CFP29. These fractions were pooled and anion exchange chromatography was performed on a Mono Q HR 5/5 column connected to an FPLC system (Pharmacia). The column was equilibrated with 10 mM Tris-HCl, pH 8.5 and the elution was performed with a linear gradient from 0 to 500 mM NaCl. From 400 to 500 mM sodium chloride, rather pure CFP29 was eluted. As a final purification step the Mono Q fractions containing CFP29 were loaded on a 12.5% SDS-PAGE gel and pure CFP29 was obtained by the multi-elution technique (Andersen and Heron, 1993).

N-terminal Sequencing and Amino Acid Analysis

CFP17, CFP20, CFP21, CFP22, CFP25, and CFP28 were washed with water on a Centricon concentrator (Amicon) with cutoff at 10 kDa and then applied to a ProSpin concentrator (Applied Biosystems) where the proteins were collected on a PVDF membrane. The membrane was washed 5 times with 20% methanol before sequencing on a Procise sequencer (Applied Biosystems).

CFP29 containing fractions were blotted to PVDF membrane after tricine SDS-PAGE (Ploug et al., 1989). The relevant bands were excised and subjected to amino acid analysis (Barkholt and Jensen, 1989) and N-terminal sequence analysis on a Procise sequencer (Applied Biosystems).

The following N-terminal sequences were obtained:

```
                                       (SEQ ID NO: 17)
For CFP17: A/S E L D A P A Q A G T E X A V (SEQ ID NO: 18)
For CFP20: A Q I T L R G N A I N T V G E (SEQ ID NO: 19)
For CFP21: D P X S D I A V V F A R G T H (SEQ ID NO: 20)
For CFP22: T N S P L A T A T A T L H T N (SEQ ID NO: 21)
For CFP25: A X P D A E V V F A R G R F E (SEQ ID NO: 22)
For CFP28: X I/V Q K S L E L I V/T V/F T A D/Q E (SEQ ID NO: 23)
For CFP29: M N N L Y R D L A P V T E A A W A E I
```

"X" denotes an amino acid which could not be determined by the sequencing method used, whereas a "/" between two amino acids denotes that the sequencing method could not determine which of the two amino acids is the one actually present.

Cloning the Gene Encoding CFP29

The N-terminal sequence of CFP29 was used for a homology search in the EMBL database using the TFASTA program of the Genetics Computer Group sequence analysis software package. The search identified a protein, Linocin M18, from *Brevibacterium linens* that shares 74% identity with the 19 N-terminal amino acids of CFP29.

Based on this identity between the N-terminal sequence of CFP29 and the sequence of the Linocin M18 protein from *Brevibacterium linens,* a set of degenerated primers were constructed for PCR cloning of the *M. tuberculosis* gene encoding CFP29. PCR reactions were containing 10 ng of *M. tuberculosis* chromosomal DNA in 1×low salt Taq+buffer from Stratagene supplemented with 250 μM of each of the four nucleotides (Boehringer Mannheim), 0,5 mg/ml BSA (IgG technology), 1% DMSO (Merck), 5 pmoles of each primer and 0.5 unit Tag+DNA polymerase (Stratagene) in 10 μl reaction volume. Reactions were initially heated to 94° C. for 25 sec. and run for 30 cycles of the program; 94° C. for 15 sec., 55° C. for 15 sec. and 72° C. for 90 sec, using thermocycler equipment from Idaho Technology.

An approx. 300 bp fragment was obtained using primers with the sequences:

```
                                    (SEQ ID NO: 24)
1:   5'-CCCGGCTCGAGAACCTSTACCGCGACCTSGCSCC (SEQ ID NO: 25)
2:   5'-GGGCCGGATCCGASGCSGCGTCCTTSACSGGYTGCCA
-where S = G/C and Y = T/C
```

The fragment was excised from a 1% agarose gel, purified by Spin-X spinn columns (Costar), cloned into pBluescript SK II+-T vector (Stratagene) and finally sequenced with the Sequenase kit from United States Biochemical.

The first 150 bp of this sequence was used for a homology search using the Blast program of the Sanger *Mycobacterium tuberculosis* database:

(http//www.sanger.ac.uk/projects/M-tuberculosis/blast$_{13}$ server).

This program identified a *Mycobacterium tuberculosis* sequence on cosmid cy444 in the database that is nearly 100% identical to the 150 bp sequence of the CFP29 protein. The sequence is contained within a 795 bp open reading frame of which the 5' end translates into a sequence that is 100% identical to the N-terminally sequenced 19 amino acids of the purified CFP29 protein.

Finally, the 795 bp open reading frame was PCR cloned under the same PCR conditions as described above using the primers:

```
                                    (SEQ ID NO: 26)
3:   5'-GGAAGCCCCATATGAACAATCTCTACCG (SEQ ID NO: 27)
4:   5'-CGCGCTCAGCCCTTAGTGACTGAGCGCGACCG
```

The resulting DNA fragments were purified from agarose gels as described above sequenced with primer 3 and 4 in addition to the following primers:

```
                                    (SEQ ID NO: 115)
5:   5'-GGACGTTCAAGCGACACATCGCCG-3'

(SEQ ID NO: 116)
6:   5'-CAGCACGAACGCGCCGTCGATGGC-3'
```

Three independent cloned were sequenced. All three clones were in 100% agreement with the sequence on cosmid cy444.

All other DNA manipulations were done according to Maniatis et al. (1989).

All enzymes other than Taq polymerase were from New England Biolabs.

Homology Searches in the Sanger Database

For CFP17, CFP20, CFP21, CFP22, CFP25, and CFP28 the N-terminal amino acid sequence from each of the proteins were used for a homology search using the blast program of the Sanger *Mycobacterium tuberculosis* database:

http://www.sanger.ac.uk/pathogens/TB-blast-server.html.

For CFP29 the first 150 bp of the DNA sequence was used for the search. Furthermore, the EMBL database was searched for proteins with homology to CFP29.

Thereby, the following information were obtained:

CFP17

Of the 14 determined amino acids in CFP17 a 93% identical sequence was found with MTCY1A11.16c. The difference between the two sequences is in the first amino acid: It is an A or an S in the N-terminal determined sequenced and a S in MTCY1A11. From the N-terminal sequencing it was not possible to determine amino acid number 13.

Within the. open reading frame the translated protein is 162 amino acids long. The N-terminal of the protein purified from culture filtrate starts at amino acid 31 in agreement with the presence of a signal sequence that has been cleaved off. This gives a length of the mature protein of 132 amino acids, which corresponds to a theoretical molecular mass of 13833 Da and a theoretical pI of 4.4. The observed mass in SDS-PAGE is 17 kDa.

CFP20

A sequence 100% identical to the 15 determined amino acids of CFP20 was found on the translated cosmid cscy09F9. A stop codon is found at amino acid 166 from the amino acid M at position 1. This gives a predicted length of 165 amino acids, which corresponds to a theoretical molecular mass of 16897 Da and a pI of 4.2. The observed molecular weight in a SDS-PAGE is 20 kDa.

Searching the GenEMBL database using the TFASTA algorithm (Pearson and Lipman, 1988) revealed a number of proteins with homology to the predicted 164 amino acids long translated protein.

The highest homology, 51.5% identity in a 163 amino acid overlap, was found to a *Haemophilus influenza* Rd toxR reg. (HIHI0751).

CFP21

A sequence 100% identical to the 14 determined amino acids of CFP21 was found at MTCY39. From the N-terminal sequencing it was not possible to determine amino acid number 3; this amino acid is a C in MTCY39. The amino acid C can not be detected on a Sequencer which is probably the explanation of this difference.

Within the open reading frame the translated protein is 217 amino acids long. The N-terminally determined sequence from the protein purified from culture filtrate starts at amino acid 33 in agreement with the presence of a signal sequence that has been cleaved off. This gives a length of the mature protein of 185 amino acids, which corresponds to a theoretical molecular weigh at 18657 Da, and a theoretical pI at 4,6. The observed weight in a SDS-PAGE is 21 kDa.

In a 193 amino acids overlap the protein has 32,6% identity to a cutinase precursor with a length of 209 amino acids (CUTI_ALTBR P41744).

A comparison of the 14 N-terminal determined amino acids with the translated region (RD2) deleted in *M. bovis* BCG revealed a 100% identical sequence (mb3484) (Mahairas et al. (1996)).

CFP22

A sequence 100% identical to the 15 determined amino acids of CFP22 was found at MTCY10H4. Within the open reading frame the translated protein is 182 amino acids long. The N-terminal sequence of the protein purified from culture filtrate starts at amino acid 8 and therefore the length of the protein occurring in *M. tuberculosis* culture filtrate is 175 amino acids. This gives a theoretical molecular weigh at 18517 Da and a pI at 6.8. The observed weight in a SDS-PAGE is 22 kDa.

In an 182 amino acids overlap the translated protein has 90,1% identity with E235739; a peptidyl-prolyl cis-trans isomerase.

CFP25

A sequence 93% identical to the 15 determined amino acids was found on the cosmid MTCY339.08c. The one amino acid that differs between the two sequences is a C in MTCY339.08c and a X from the N-terminal sequence data. On a Sequencer a C can not be detected which is a probable explanation for this difference.

The N-terminally determined sequence from the protein purified from culture filtrate begins at amino acid 33 in agreement with the presence of a signal sequence that has been cleaved off. This gives a length of the mature protein of 187 amino acids, which corresponds to a theoretical molecular weigh at 19665 Da, and a theoretical pI at 4.9. The observed weight in a SDS-PAGE is 25 kDa.

In a 217 amino acids overlap the protein has 42.9% identity to CFP21 (MTCY39.35).

CFP28

No homology was found when using the 10 determined amino acid residues 2–8, 11, 12, and 14 of SEQ ID NO: 22 in the database search.

CFP29

Sanger database searching: A sequence nearly 100% identical to the 150 bp sequence of the CFP29 protein was found on cosmid cy444. The sequence is contained within a 795 bp open reading frame of which the 5' end translates into a sequence that is 100% identical to the N-terminally sequenced 19 amino acids of the purified CFP29 protein. The open reading frame encodes a 265 amino acid protein.

The amino acid analysis performed on the purified protein further confirmed the identity of CFP29 with the protein encoded in open reading frame on cosmid 444.

EMBL database searching: The open reading frame encodes a 265 amino acid protein that is 58% identical and 74% similar to the Linocin M18 protein (61% identity on DNA level). This is a 28.6 kDa protein with bacteriocin activity (Valdés-Stauber and Scherer, 1994; Valdés-Stauber and Scherer, 1996). The two proteins have the same length (except for 1 amino acid) and share the same theoretical physicochemical properties. We therefore suggest that CFP29 is a mycobacterial homolog to the *Brevibacterium linens* Linocin M18 protein.

The amino acid sequences of the purified antigens as picked from the Sanger database are shown in the following list. The amino acids determined by N-terminal sequencing are marked with bold.

CFP17 (SEQ ID NO: 6)

1 MTDMNPDIEK DQTSDEVTVE TTSVFRADFL SELDAPAQAG TESAVSGVEG
51 LPPGSALLVV KRGPNAGSRF LLDQAITSAG RHPDSDIFLD DVTVSRRHAE
101 FRLENNEFNV VDVGSLNGTY VNREPVDSAV LANGDEVQIG KFRLVFLTGP
151 KQGEDDGSTG GP

CFP20 (SEQ ID NO: 8)

1 MAQITLRGNA INTVGELPAV GSPAPAFTLT GGDLGVISSD QFRGKSVLLN
51 IFPSVDTPVC ATSVRTFDER AAASGATVLC VSKDLPFAQK RFCGAEGTEN
101 VMPASAFRDS FGEDYGVTIA DGPMAGLLAR AIVVIGADGN VAYTELVPEI
151 AQEPNYEAAL AALGA

CFP21 (SEQ ID NO: 10)

1 MTPRSLVRIV GVVVATTLAL VSAPAGGRAA HADPCSDIAV
41 VFARGTHQAS GLGDVGEAFV DSLTSQVGGR SIGVYAVNYP ASDDYRASAS
91 NGSDDASAHI QRTVASCPNT RIVLGGYSQG ATVIDLSTSA MPPAVADHVA
141 AVALFGEPSS GFSSMLWGGG SLPTIGPLYS SKTINLCAPD DPICTGGGNI
191 MAHVSYVQSG MTSQAATFAA NRLDHAG

CFP22 (SEQ ID NO: 12)

1 MADCDSVTNS PLATATATLH TNRGDIKIAL FGNHAPKTVA NFVGLAQGTK
51 DYSTQNASGG PSGPFYDGAV FHRVIQGFMI QGGDPTGTGR GGPGYKFADE

101 FHPELQFDKP YLLAMANAGP GTNGSQFFIT VGKTPHLNRR HTIFGEVIDA
151 ESQRVVEAIS KTATDGNDRP TDPVVIESIT IS

CFP25 (SEQ ID NO: 14)

1 MGAAAAMLAA VLLLTPITVP AGYPGAVAPA TAACPDAEVV FARGRFEPPG
51 IGTVGNAFVS ALRSKVNKNV GVYAVKYPAD NQIDVGANDM SAHIQSMANS
101 CPNTRLVPGG YSLGAAVTDV VLAVPTQMWG FTNPLPPGSD EHIAAVALFG
151 NGSQWVGPIT NFSPAYNDRT IELCHGDDPV CHPADPNTWE ANWPQHLAGA
201 YVSSGMVNQA ADFVAGKLQ

CFP29 (SEQ ID NO: 16)

1 MNNLYRDLAP VTEAAWAEIE LEAARTFKRH IAGR- RVVDVS DPGGPVTAAV
51 STGRLIDVKA PTNGVIAHLR ASKPLVRLRV PFTLSRNEID DVERGSKDSD
101 WEPVKEAAKK LAFVEDRTIF EGYSAASIEG IRSASSNPAL TLPEDPREIP
151 DVISQALSEL RLAGVDGPYS VLLSADVYTK VSETSDHGYP IREHLNRLVD
201 GDIIWAPAID GAFVLTTRGG DFDLQLGTDV AIG- YASHDTD TVRLYLQETL
251 TFLCYTAEAS VALSH

For all six proteins the molecular weights predicted from the sequences are in agreement with the molecular weights observed on SDS-PAGE.

Cloning of the Genes Encoding CFP17, CFP20, CFP21, CFP22 and

CFP25

The genes encoding CFP17, CFP20, CFP21, CFP22 and CFP25 were all cloned into the expression vector pMCT6, by PCR amplification with gene specific primers, for recombinant expression in E. coli of the proteins.

PCR reactions contained 10 ng of M. tuberculosis chromosomal DNA in 1×low salt Taq+buffer from Stratagene supplemented with 250 mM of each of the four nucleotides (Boehringer Mannheim), 0,5 mg/ml BSA (IgG technology), 1% DMSO (Merck), 5 pmoles of each primer and 0.5 unit Tag+DNA polymerase (Stratagene) in 10 μl reaction volume. Reactions were initially heated to 94° C. for 25 sec. and run for 30 cycles according to the following program; 94° C. for 10 sec., 55° C. for 10 sec. and 72° C. for 90 sec, using thermocycler equipment from Idaho Technology.

The DNA fragments were subsequently run on 1% agarose gels, the bands were excised and purified by Spin-X spin columns (Costar) and cloned into pBluescript SK II+-T vector (Stratagene). Plasmid DNA was thereafter prepared from clones harbouring the desired fragments, digested with suitable restriction enzymes and subcloned into the expression vector pMCT6 in frame with 8 histidine residues which are added to the N-terminal of the expressed proteins. The resulting clones were hereafter sequenced by use of the dideoxy chain termination method adapted for supercoiled DNA using the Sequenase DNA sequencing kit version 1.0 (United States Biochemical Corp., USA) and by cycle sequencing using the Dye Terminator system in combination with an automated gel reader (model 373A; Applied Biosystems) according to the instructions provided. Both strands of the DNA were sequenced.

For cloning of the individual antigens, the following gene specific primers were used:

CFP17: Primers used for cloning of cfp17:

(SEQ ID NO: 117)
OPBR-51:   ACAGATCTGTGACGGACATGAACCCG (SEQ ID NO: 118)
OPBR-52:   TTTTCCATGGTCACGGGCCCCCGGTACT

OPBR-51 and OPBR-52 create BglII and NcoI sites, respectively, used for the cloning in pMCT6.

CFP20: Primers used for cloning of cfp20:

(SEQ ID NO: 119)
OPBR-53:   ACAGATCTGTGCCCATGGCACAGATA (SEQ ID NO: 120)
OPBR-54:   TTTAAGCTTCTAGGCGCCCAGCGCGGC

OPBR-53 and OPBR-54 create BglII and HinDIII sites, respectively, used for the cloning in pMCT6.

CFP21: Primers used for cloning of cfp21:
(SEQ ID NO: 121)
OPBR-55:   ACAGATCTGCGCATGCGGATCCGTGT (SEQ ID NO: 122)
OPBR-56:   TTTTCCATGGTCATCCGGCGTGATCGAG OPBR-55 and OPBR-56 create BglII and NcoI sites, respectively, used for the cloning in pMCT6.

CFP22: Primers used for cloning of cfp22:
(SEQ ID NO: 123)
OPBR-57:   ACAGATCTGTAATGGCAGACTGTGAT (SEQ ID NO: 124)
OPBR-58:   TTTTCCATGGTCAGGAGATGGTGATCGA OPBR-57 and OPBR-58 create BglII and NcoI sites, respectively, used for the cloning in pMCT6.

CFP25: Primers used for cloning of cfp25:
(SEQ ID NO: 125)
OPBR-59:   ACAGATCTGCCGGCTACCCCGGTGCC (SEQ ID NO: 126)
OPBR-60:   TTTTCCATGGTATTGCAGCTTTCCGGC OPBR-59 and OPBR-60 create BglII and NcoI sites, respectively, used for the cloning in pMCT6.

Expression/Purification of Recombinant CFP17, CFP20, CFP21, CFP22 and CFP25 Proteins Expression and metal affinity purification of recombinant proteins was undertaken essentially as described by the manufacturers. For each protein, 1 l LB-media containing 100 μg/ml ampicillin, was inoculated with 10 ml of an overnight culture of XL1-Blue cells harbouring recombinant pMCT6 plasmids. Cultures were shaken at 37° C. until they reached a density of $OD_{600}$=0.4–0.6. IPTG was hereafter added to a final concentration of 1 mM and the cultures were further incubated 4–16 hours. Cells were harvested, resuspended in 1× sonication buffer+8 M urea and sonicated 5×30 sec. with 30 sec. pausing between the pulses.

After centrifugation, the lysate was applied to a column containing 25 ml of resuspended Talon resin (Clontech, Palo Alto, USA). The column was washed and eluted as described by the manufacturers.

After elution, all fractions (1.5 ml each) were subjected to analysis by SDS-PAGE using the Mighty Small (Hoefer Scientific Instruments, USA) system and the protein concentrations were estimated at 280 nm. Fractions containing recombinant protein were pooled and dialysed against 3 M urea in 10 mM Tris-HCl, pH 8.5. The dialysed protein was further purified by FPLC (Pharmacia, Sweden) using a 6 ml Resource-Q column, eluted with a linear 0–1 M gradient of NaCl. Fractions were analyzed by SDS-PAGE and protein concentrations were estimated at $OD_{280}$. Fractions containing protein were pooled and dialysed against 25 mM Hepes buffer, pH 8.5.

Finally the protein concentration and the LPS content were determined by the BCA (Pierce, Holland) and LAL (Endosafe, Charleston, USA) tests, respectively.

EXAMPLE 3A

Identification of CFP7A, CFP8A, CFP8B, CFP16, CFP19, CFP19B, CFP22A, CFP23A, CFP23B, CFP25A, CFP27, CFP30A, CWP32 and CFP50

Identification of CFP16 and CFP19B

ST-CF was precipitated with ammonium sulphate at 80% saturation. The precipitated proteins were removed by centrifugation and after resuspension washed with 8 M urea. CHAPS and glycerol were added to a final concentration of 0.5% (w/v) and 5% (v/v) respectively and the protein solution was applied to a Rotofor isoelectrical Cell (BioRad). The Rotofor Cell had been equilibrated with a 8M urea buffer containing 0.5% (w/v) CHAPS, 5% (v/v) glycerol, 3% (v/v) Biolyt 3/5 and 1% (v/v) Biolyt 4/6 (BioRad). Isoelectric focusing was performed in a pH gradient from 3–6. The fractions were analyzed on silver-stained 10–20% SDS-PAGE. Fractions with similar band patterns were pooled and washed three times with PBS on a Centriprep concentrator (Amicon) with a 3 kDa cut off membrane to a final volume of 1–3 ml. An equal volume of SDS containing sample buffer was added and the protein solution boiled for 5 min before further separation on a Prep Cell (BioRad) in a matrix of 16% polyacrylamide under an electrical gradient. Fractions containing well separated bands in SDS-PAGE were selected for N-terminal sequencing after transfer to PVDF membrane.

Isolation of CFP8A, CFP8B, CFP19, CFP23A, and CFP23B

ST-CF was precipitated with ammonium sulphate at 80% saturation and redissolved in PBS, pH 7.4, and dialysed 3 times against 25 mM Piperazin-HCl, pH 5.5, and subjected to chromatofocusing on a matrix of PBE 94 (Pharmacia) in a column connected to an FPLC system (Pharmacia). The column was equilibrated with 25 mM Piperazin-HCl, pH 5.5, and the elution was performed with 10% PB74-HCl, pH 4.0 (Pharmacia).

Fractions with similar band patterns were pooled and washed three times with PBS on a Centriprep concentrator (Amicon) with a 3 kDa cut off membrane to a final volume of 1–3 ml and separated on a Prepcell as described above.

Identification of CFP22A

ST-CF was concentrated approximately 10 fold by ultrafiltration and proteins were precipitated at 80% saturation, redissolved in PBS, pH 7.4, and dialysed 3 times against PBS, pH 7.4. 5.1 ml of the dialysed ST-CF was treated with RNase (0.2 mg/ml, QUIAGEN) and DNase (0.2 mg/ml, Boehringer Mannheim) for 6 h and placed on top of 6.4 ml of 48% (w/v) sucrose in PBS, pH 7.4, in Sorvall tubes (Ultracrimp 03987, DuPont Medical Products) and ultracentrifuged for 20 h at $257,300 \times g_{max}$, 10° C. The pellet was redissolved in 200 µl of 25 mM Tris-192 mM glycine, 0.1% SDS, pH 8.3.

Identification of CFP7A, CFP25A, CFP27, CFP30A and CFP50

For CFP27, CFP30A and CFP50 ST-CF was concentrated approximately 10 fold by ultrafiltration and ammonium sulphate precipitation in the 45 to 55% saturation range was performed. Proteins were redissolved in 50 mM sodium phosphate, 1.5 M ammonium sulphate, pH 8.5, and subjected to thiophilic adsorption chromatography on an Affi-T gel column (Kem-En-Tec). Proteins were eluted by a 1.5 to 0 M decreasing gradient of ammonium sulphate. Fractions with similar band patterns in SDS-PAGE were pooled and anion exchange chromatography was performed on a Mono Q HR 5/5 column connected to an FPLC system (Pharmacia). The column was equilibrated with 10 mM Tris-HCl, pH 8.5, and the elution was performed with a gradient of NaCl from 0 to 1 M. Fractions containing well separated bands in SDS-PAGE were selected.

CFP7A and CFP25A were obtained as described above except for the following modification: ST-CF was concentrated approximately 10 fold by ultrafiltration and proteins were precipitated at 80% saturation, redissolved in PBS, pH 7.4, and dialysed 3 times against PBS, pH 7.4. Ammonium sulphate was added to a concentration of 1.5 M, and ST-CF proteins were loaded on an Affi T-gel column. Elution from the Affi T-gel column and anion exchange were performed as described above.

Isolation of CWP32

Heat treated H37Rv was subfractionated into subcellular fractions as described in Sorensen et al 1995. The Cell wall fraction was resuspended in 8 M urea, 0.2% (w/v) N-octyl β-$_D$ glucopyranoside (Sigma) and 5% (v/v) glycerol and the protein solution was applied to a Rotofor isoelectrical Cell (BioRad) which was equilibrated with the same buffer. Isoelectric focusing was performed in a pH gradient from 3–6. The fractions were analyzed by SDS-PAGE and fractions containing well separated bands were polled and subjected to N-terminal sequencing after transfer to PVDF membrane.

N-terminal Sequencing

Fractions containing CFP7A, CFP8A, CFP8B, CFP16, CFP19, CFP19B, CFP22A, CFP23A, CFP23B, CFP27, CFP30A, CWP32, and CFP50A were blotted to PVDF membrane after Tricine SDS-PAGE (Ploug et al, 1989). The relevant bands were excised and subjected to N-terminal amino acid sequence analysis on a Procise 494 sequencer (Applied Biosystems). The fraction containing CFP25A was blotted to PVDF membrane after 2-DE PAGE (isoelectric focusing in the first dimension and Tricin SDS-PAGE in the second dimension). The relevant spot was excised and sequenced as described above.

The following N-terminal sequences were obtained:

(SEQ ID NO: 81)
CFP7A: AEDVRAEIVA SVLEVVVNEG DQIDKGDVVV LLESMYMEIP
VLAEAAGTVS

| | | |
|---|---|---|
| CFP8A: | DPVDDAFIAKLNTAG | (SEQ ID NO: 73) |
| CFP8B: | DPVDAIINLDNYGX | (SEQ ID NO: 74) |
| CFP16: | AKLSTDELLDAFKEM | (SEQ ID NO: 79) |
| CFP19: | TTSPDPYAALPKLPS | (SEQ ID NO: 82) |
| CFP19B: | DPAXAPDVPTAAQLT | (SEQ ID NO: 80) |
| CFP22A: | TEYEGPKTKF HALMQ | (SEQ ID NO: 83) |
| CFP23A: | VIQ/AGMVT/GHIHXVAG | (SEQ ID NO: 76) |
| CFP23B: | AEMKXFKNAIVQEID | (SEQ ID NO: 75) |
| CFP25A: | AIEVSVLRVF TDSDG | (SEQ ID NO: 78) |
| CWP32: | TNIVVLIKQVPDTWS | (SEQ ID NO: 77) |
| CFP27: | TTIVALKYPG GVVMA | (SEQ ID NO: 84) |
| CFP30A: | SFPYFISPEX AMRE | (SEQ ID NO: 85) |
| CFP50: | THYDVVVLGA GPGGY | (SEQ ID NO: 86) |

N-terminal Homology Searching in the Sanger Database and Identification of the Corresponding Genes The N-terminal amino acid sequence from each of the proteins was used for a homology search using the blast program of the Sanger *Mycobacterium tuberculosis* database:

http://www.sanger.ac.uk/projects/m-tuberculosis/TB-blast-server.

For CFP23B, CFP23A, and CFP19B no similarities were found in the Sanger database. This could be due to the fact that only approximately 70% of the *M. tuberculosis* genome had been sequenced when the searches were performed. The genes encoding these proteins could be contained in the remaining 30% of the genome for which no sequence data is yet available.

For CFP7A, CFP8A, CFP8B, CFP16, CFP19, CFP19B, CFP22A, CFP25A, CFP27, CFP30A, CWP32, and CFP50, the following information was obtained:

CFP7A: Of the 50 determined amino acids in CFP7A a 98% identical sequence was found in cosmid csCY07D1 (contig 256): Score=226 (100.4 bits), Expect=1.4e−24, P=1.4e−24 Identities=49/50 (98%), Positives=49/50 (98%), Frame=−1 data confirmed the identification of the protein. The N-terminally determined sequence from the protein purified from culture filtrate starts at amino acid 29. This gives a length of the mature protein of 82 amino acids corresponding to a theoretical MW of 8337 Da and a pI of 4.23. This is in good agreement with the observed MW on SDS-PAGE at approximately 8 kDa.

Analysis of the amino acid sequence predicts the presence of a signal peptide which has been cleaved of the mature protein found in culture filtrate.

CFP16: The 15 aa N-terminal sequence was found to be 100% identical to a sequence found on cosmid MTCY20H1.

The identity is found within an open reading frame of 130 amino acids length corresponding to a theoretical MW of CFP16 of 13440.4 Da and a pI of 4.59. The observed molecular weight in an SDS-PAGE gel is 16 kDa.

CFP19: The 15 aa N-terminal sequence was found to be 100% identical to a sequence found on cosmid MTCY270.

The identity is found within an open reading frame of 176 amino acids length corresponding to a theoretical MW of CFP19 of 18633.9 Da and a pI of 5.41. The observed molecular weight in an SDS-PAGE gel is 19 kDa.

CFP22A: The 15 aa N-terminal sequence was found to be 100% identical to a sequence found on cosmid MTCY1A6.

The identity is found within an open reading frame of 181 amino acids length corresponding to a theoretical MW of CFP22A of 20441.9 Da and a pI of 4.73. The observed molecular weight in an SDS-PAGE gel is 22 kDa.

CFP25A: The 15 aa N-terminal sequence was found to be 100% identical to a sequence found on contig 255.

The identity is found within an open reading frame of 228 amino acids length corresponding to a theoretical MW of CFP25A of 24574.3 Da and a pI of 4.95. The observed molecular weight in an SDS-PAGE gel is 25 kDa.

CFP27: The 15 aa N-terminal sequence was found to be 100% identical to a sequence found on cosmid MTCY261.

The identity is found within an open reading frame of 291 amino acids length. The N-terminally determined sequence from the protein purified from culture filtrate starts at amino acid 58. This gives a length of the mature protein of 233 amino acids, which corresponds to a theoretical molecular weigh at 24422.4 Da, and a theoretical pI at 4.64. The observed weight in an SDS-PAGE gel is 27 kDa.

CFP30A: Of the 13 determined amino acids in CFP30A, a 100% identical sequence was found on cosmid MTCY261.

```
Query:   1      AEDVRAEIVASVLEVVVNEGDQIDKGDVVVLLESMYMEIPVLAEAAGTVS 50
                AEDVRAEIVASVLEVVVNEGDQIDKGDVVVLLESM MEIPVLAEAAGTVS
Sbjct: 257679   AEDVRAEIVASVLEVVVNEGDQIDKGDVVVLLESMKMEIPVLAEAAGTVS 257530
```

The identity is found within an open reading frame of 71 amino acids length corresponding to a theoretical MW of CFP7A of 7305.9 Da and a pI of 3.762. The observed molecular weight in an SDS-PAGE gel is 7 kDa.

CFP8A: A sequence 80% identical to the 15 N-terminal amino acids was found on contig TB_1884. The N-terminally determined sequence from the protein purified from culture filtrate starts at amino acid 32. This gives a length of the mature protein of 98 amino acids corresponding to a theoretical MW of 9700 Da and a pI of 3.72 This is in good agreement with the observed MW on SDS-PAGE at approximately 8 kDa. The full length protein has a theoretical MW of 12989 Da and a pI of 4.38.

CFP8B: A sequence 71% identical to the 14 N-terminal amino acids was found on contig TB$_{13}$ 653. However, careful re-evaluation of the original N-terminal sequence The identity is found within an open reading frame of 248 amino acids length corresponding to a theoretical MW of CFP30A of 26881.0 Da and a pI of 5.41. The observed molecular weight in an SDS-PAGE gel is 30 kDa.

CWP32: The 15 amino acid N-terminal sequence was found to be 100% identical to a sequence found on contig 281. The identity was found within an open reading frame of 266 amino acids length, corresponding to a theoretical MW of CWP32 of 28083 Da and a pI of 4.563. The observed molecular weight in an SDS-PAGE gel is 32 kDa.

CFP50: The 15 aa N-terminal sequence was found to be 100% identical to a sequence found in MTV038.06. The identity is found within an open reading frame of 464 amino acids length corresponding to a theoretical MW of CFP50 of 49244 Da and a pI of 5.66. The observed molecular weight in an SDS-PAGE gel is 50 kDa.

Use of Homology Searching in the EMBL Database for Identification of CFP19A and CFP23

Homology searching in the EMBL database (using the GCG package of the Biobase, Århus-DK) with the amino acid sequences of two earlier identified highly immunoreactive ST-CF proteins, using the TFASTA algorithm, revealed that these proteins (CFP21 and CFP25, EXAMPLE 3) belong to a family of fungal cutinase homologs. Among the most homologous sequences were also two *Mycobacterium tuberculosis* sequences found on cosmid MTCY13E12. The first, MTCY13E12.04 has 46% and 50% identity to CFP25 and CFP21 respectively. The second, MTCY13E12.05, has also 46% and 50% identity to CFP25 and CFP21. The two proteins share 62.5% aa identity in a 184 residues overlap. On the basis of the high homology to the strong T-cell antigens CFP21 and CFP25, respectively, it is believed that CFP19A and CFP23 are possible new T-cell antigens.

The first reading frame encodes a 254 amino acid protein of which the first 26 aa constitute a putative leader peptide that strongly indicates an extracellular location of the protein. The mature protein is thus 228 aa in length corresponding to a theoretical MW of 23149.0 Da and a Pi of 5.80. The protein is named CFP23.

The second reading frame encodes an 231 aa protein of which the first 44 aa constitute a putative leader peptide that strongly indicates an extracellular location of the protein. The mature protein is thus 187 aa in length corresponding to a theoretical MW of 19020.3 Da and a Pi of 7.03. The protein is named CFP19A.

The presence of putative leader peptides in both proteins (and thereby their presence in the ST-CF) is confirmed by theoretical sequence analysis using the signalP program at the Expasy molecular Biology server (http://expasy.hcuge.ch/www/tools.html).

Searching for Homologies to CFP7A, CFP16, CFP19, CFP19A, CFP19B, CFP22A, CFP23, CFP25A, CFP27, CFP30A, CWP32 and CFP50 in the EMBL Database The amino acid sequences derived from the translated genes of the individual antigens were used for homology searching in the EMBL and Genbank databases using the TFASTA algorithm, in order to find homologous proteins and to address eventual functional roles of the antigens.

CFP7A: CFP7A has 44% identity and 70% similarity to hypothetical *Methanococcus jannaschii* protein (*M. jannaschii* from base 1162199–1175341), as well as 43% and 38% identity and 68 and 64% similarity to the C-terminal part of *B. stearothermophilus* pyruvate carboxylase and *Streptococcus mutans* biotin carboxyl carrier protein.

CFP7A contains a consensus sequence EAMKM for a biotin binding site motif which in this case was slightly modified (ESMKM in amino acid residues 34 to 38). By incubation with alkaline phosphatase conjugated streptavidin after SDS-PAGE and transfer to nitrocellulose it was demonstrated that native CFP7A was biotinylated.

CFP16: RplL gene, 130 aa. Identical to the *M. bovis* 50s ribosomal protein L7/L12 (acc. No P37381).

CFP19: CFP19 has 47% identity and 55% similarity to *E.coli* pectinesterase homolog (ybhc gene) in a 150 aa overlap.

CFP19A: CFP19A has between 38% and 45% identity to several cutinases from different fungal sp.

In addition CFP19A has 46% identity and 61% similarity to CFP25 as well as 50% identity and 64% similarity to CFP21 (both proteins are earlier isolated from the ST-CF).

CFP19B: No apparent homology

CFP22A: No apparent homology

CFP23: CFP23 has between 38% and 46% identity to several cutinases from different fungal sp.

In addition CFP23 has 46% identity and 61% similarity to CFP25 as well as 50% identity and 63% similarity to CFP21 (both proteins are earlier isolated from the ST-CF).

CFP25A: CFP25A has 95% identity in a 241 aa overlap to a putative *M. tuberculosis* thymidylate synthase (450 aa accession No p28176).

CFP27: CFP27 has 81% identity to a hypothetical *M. leprae* protein and 64% identity and 78% similarity to *Rhodococcus* sp. *proteasome* beta-type subunit 2 (prcB(2) gene).

CFP30A: CFP30A has 67% identity to *Rhodococcus proteasome* alfa-type 1 subunit.

CWP32: The CWP32 N-terminal sequence is 100% identical to the *Mycobacterium leprae* sequence MLCB637.03.

CFP50: The CFP50 N-terminal sequence is 100% identical to a putative lipoamide dehydrogenase from *M. leprae* (Accession 415183)

Cloning of the Genes Encoding CFP7A, CFP8A, CFP8B, CFP16, CFP19, CFP19A, CFP22A, CFP23, CFP25A, CFP27, CFP30A, CWP32, and CFP50

The genes encoding CFP7A, CFP8A, CFP8B, CFP16, CFP19, CFP19A, CFP22A, CFP23, CFP25A, CFP27, CFP30A, CWP32 and CFP50 were all cloned into the expression vector pMCT6, by PCR amplification with gene specific primers, for recombinant expression in *E. coli* of the proteins.

PCR reactions contained 10 ng of *M. tuberculosis* chromosomal DNA in 1×low salt Taq+buffer from Stratagene supplemented with 250 mM of each of the four nucleotides (Boehringer Mannheim), 0,5 mg/ml BSA (IgG technology), 1% DMSO (Merck), 5 pmoles of each primer and 0.5 unit Tag+DNA polymerase (Stratagene) in 10 ml reaction volume. Reactions were initially heated to 94° C. for 25 sec. and run for 30 cycles of the program; 94° C. for 10 sec., 55° C. for 10 sec. and 72° C. for 90 sec, using thermocycler equipment from Idaho Technology.

The DNA fragments were subsequently run on 1% agarose gels, the bands were excised and purified by Spin-X spin columns (Costar) and cloned into pBluescript SK II+-T vector (Stratagene). Plasmid DNA was hereafter prepared from clones harbouring the desired fragments, digested with suitable restriction enzymes and subcloned into the expression vector pMCT6 in frame with 8 histidines which are added to the N-terminal of the expressed proteins. The resulting clones were hereafter sequenced by use of the dideoxy chain termination method adapted for supercoiled DNA using the Sequenase DNA sequencing kit version 1.0 (United States Biochemical Corp., USA) and by cycle sequencing using the Dye Terminator system in combination with an automated gel reader (model 373A; Applied Biosystems) according to the instructions provided. Both strands of the DNA were sequenced.

For cloning of the individual antigens, the following gene specific primers were used:

```
CFP7A: Primers used for cloning of cfp7A:

(SEQ ID NO: 95)
OPBR-79:   AAGAGTAGATCTATGATGGCCGAGGATGTTCGCG (SEQ ID NO: 96)
OPBR-80:   CGGCGACGACGGATCCTACCGCGTCGG
```

OPBR-79 and OPBR-80 create BglII and BamHI sites, respectively, used for the cloning in pMCT6.

```
CFP8A: Primers used for cloning of cfp8A:

(SEQ ID NO: 154)
CFP8A-F:   CTGAGATCTATGAACCTACGGCGCC (SEQ ID NO: 155)
CFP8A-R:   CTCCCATGGTACCCTAGGACCCGGGCAGCCCCGGC
```

CFP8A-F and CFP8A-R create BglII and NcoI sites, respectively, used for the cloning in pMCT6.

```
CFP8B: Primers used for cloning of cfp8B:

(SEQ ID NO: 156)
CFP8B-F:   CTGAGATCTATGAGGCTGTCGTTGACCGC (SEQ ID NO: 157)
CFP8B-R:   CTCCCCGGGCTTAATAGTTGTTGCAGGAGC
```

CFP8B-F and CFP8B-R create BglII and SmaI sites, respectively, used for the cloning in pMCT6.

```
CFP16: Primers used for cloning of ctp16:

(SEQ ID NOs: 111 and 130)
OPBR-104:  CCGGGAGATCTATGGCAAAGCTCTCCACCGACG (SEQ ID NOs: 112 and 131)
OPBR-105:  CGCTGGGCAGAGCTACTTGACGGTGACGGTGG
```

OPBR-104 and OPBR-105 create BglII and NcoI sites, respectively, used for the cloning in pMCT6.

```
CFP19: Primers used for cloning of cfp19:

(SEQ ID NO: 107)
OPBR-96:   GAGGAAGATCTATGACAACTTCACCCGACCCG (SEQ ID NO: 108)
OPBR-97.   CATGAAGCCATGGCCCGCAGGCTGCATG
```

OPBR-96 and OPBR-97 create BglII and NcoI sites, respectively, used for the cloning in pMCT6.

```
CFP19A: Primers used for cloning of cfp19A:

(SEQ ID NO: 99)
OPBR-88:   CCCCCCAGATCTGCACCACCGGCATCGGCGGGC (SEQ ID NO: 100)
OPBR-89.   GCGGCGGATCCGTTGCTTAGCCGG
```

OPBR-88 and OPBR-89 create BglII and BamHI sites, respectively, used for the cloning in pMCT6.

```
CFP22A: Primers used for cloning of cfp22A:

(SEQ ID NO: 101)
OPBR-90:   CCGGCTGAGATCTATGACAGAATACGAAGGGC (SEQ ID NO: 102)
OPBR-91:   CCCCGCCAGGGAACTAGAGGCGGC
```

OPBR-90 and OPBR-91 create BglII and NcoI sites, respectively, used for the cloning in pMCT6.

```
CFP23: Primers used for cloning of cfp23:

(SEQ ID NO: 97)
OPBR-86:   CCTTGGGAGATCTTTGGACCCCGGTTGC (SEQ ID NO: 98)
OPBR-87:   GACGAGATCTTATGGGCTTACTGAC
```

OPBR-86 and OPBR-87 both create a BglII site used for the cloning in pMCT6.

```
CFP25A: Primers used for cloning of cfp25A:

(SEQ ID NO: 113)
OPBR-106:  GGCCCAGATCTATGGCCATTGAGGTTTCGGTGTTGC (SEQ ID NO. 114)
OPBR-107:  CGCCGTGTTGCATGGCAGCGCTGAGC
```

OPBR-106 and OPBR-107 create BglII and NcoI sites, respectively, used for the cloning in pMCT6.

```
CFP27: Primers used for cloning of cfp27:

(SEQ ID NO: 103)
OPBR-92:   CTGCCGAGATCTACCACCATTGTCGCGCTGAAATACCC (SEQ ID NO: 104)
OPBR-93:   CGCCATGGCCTTACGCGCCAACTCG
```

OPBR-92 and OPBR-93 create BglII and NcoI sites, respectively, used for the cloning in pMCT6.

```
CFP30A: Primers used for cloning of cfp30A:

(SEQ ID NO: 105)
OPBR-94:   GGCGGAGATCTGTGAGTTTTCCGTATTTCATC (SEQ ID NO: 106)
OPBR-95:   CGCGTCGAGCCATGGTTAGGCGCAG
```

OPBR-94 and OPBR-95 create BglII and NcoI sites, respectively, used for the cloning in pMCT6.

```
CWP32: Primers used for cloning of cwp32:

(SEQ ID NO: 158)
CWP32-F:   GCTTAGATCTATGATTTTCTGGGCAACCAGGTA (SEQ ID NO: 159)
CWP32-R:   GCTTCCATGGGCGAGGCACAGGCGTGGGAA
```

CWP32-F and CWP32-R create BglII and NcoI sites, respectively, used for the cloning in pMCT6.

CFP50: Primers used for cloning of cfp50:

```
                                     (SEQ ID NO: 109)
OPBR-100:    GGCCGAGATCTGTGACCCACTATGACGTCGTCG (SEQ ID NO: 110)
OPBR-101:    GGCGCCCATGGTCAGAAATTGATCATGTGGCCAA
```

OPBR-100 and OPBR-101 create BglII and NcoI sites, respectively, used for the cloning in pMCT6.

Expression/Purification of Recombinant CFP7A, CFP8A, CFP8B, CFP16, CFP19, CFP19A, CFP22A, CFP23, CFP25A, CFP27, CFP30A, CWP32, and CFP50 Proteins Expression and metal affinity purification of recombinant proteins was undertaken essentially as described by the manufacturers. For each protein, 1 l LB-media containing 100 μg/ml ampicillin, was inoculated with 10 ml of an overnight culture of XL1-Blue cells harbouring recombinant pMCT6 plasmids. Cultures were shaken at 37° C. until they reached a density of $OD_{600}$=0.4–0.6. IPTG was hereafter added to a final concentration of 1 mM and the cultures were further incubated 4–16 hours. Cells were harvested, resuspended in 1× sonication buffer+8 M urea and sonicated 5×30 sec. with 30 sec. pausing between the pulses.

After centrifugation, the lysate was applied to a column containing 25 ml of resuspended Talon resin (Clontech, Palo Alto, USA). The column was washed and eluted as described by the manufacturers.

After elution, all fractions (1.5 ml each) were subjected to analysis by SDS-PAGE using the Mighty Small (Hoefer Scientific Instruments, USA) system and the protein concentrations were estimated at 280 nm. Fractions containing recombinant protein were pooled and dialysed against 3 M urea in 10 mM Tris-HCl, pH 8.5. The dialysed protein was further purified by FPLC (Pharmacia, Sweden) using a 6 ml Resource-Q column, eluted with a linear 0–1 M gradient of NaCl. Fractions were analyzed by SDS-PAGE and protein concentrations were estimated at $OD_{280}$. Fractions containing protein were pooled and dialysed against 25 mM Hepes buffer, pH 8.5.

Finally the protein concentration and the LPS content were determined by the BCA (Pierce, Holland) and LAL (Endosafe, Charleston, USA) tests, respectively.

EXAMPLE 3B

Identification of CFP7B, CFP10A, CFP11 and CFP30B Isolation of CFP7B

ST-CF was precipitated with ammonium sulphate at 80% saturation and redissolved in PBS, pH 7.4, and dialyzed 3 times against 25 mM Piperazin-HCl, pH 5.5, and subjected to cromatofocusing on a matrix of PBE 94 (Pharmacia) in a column connected to an FPLC system (Pharmacia). The column was equilibrated with 25 mM Piperazin-HCl, pH 5.5, and the elution was performed with 10% PB74-HCl, pH 4.0 (Pharmacia). Fractions with similar band patterns were pooled and washed three times with PBS on a Centriprep concentrator (Amicon) with a 3 kDa cut off membrane to a final volume of 1–3 ml. An equal volume of SDS containing sample buffer was added and the protein solution boiled for 5 min before further separation on a MultiEluter (BioRad) in a matrix of 10–20% polyacrylamid (Andersen, P. & Heron, I., 1993). The fraction containing a well separated band below 10 kDa was selected for N-terminal sequencing after transfer to a PVDF membrane.

Isolation of CFP11

ST-CF was precipitated with ammonium sulphate at 80% saturation. The precipitated proteins were removed by centrifugation and after resuspension washed with 8 M urea. CHAPS and glycerol were added to a final concentration of 0.5% (w/v) and 5% (v/v) respectively and the protein solution was applied to a Rotofor isoelectrical Cell (BioRad). The Rotofor Cell had been equilibrated with an 8M urea buffer containing 0.5% (w/v) CHAPS, 5% (v/v) glycerol, 3% (v/v) Biolyt 3/5 and 1% (v/v) Biolyt 4/6 (BioRad) Isoelectric focusing was performed in a pH gradient from 3–6. The fractions were analyzed on silverstained 10–20% SDS-PAGE. The fractions in the pH gradient 5.5 to 6 were pooled and washed three times with PBS on a Centriprep concentrator (Amicon) with a 3 kDa cut off membrane to a final volume of 1 ml. 300 mg of the protein preparation was separated on a 10–20% Tricine SDS-PAGE (Ploug et al 1989) and transferred to a PVDF membrane and Coomassie stained. The lowest band occurring on the membrane was excised and submitted for N-terminal sequencing.

Isolation of CFP10A and CFP30B

ST-CF was concentrated approximately 10-fold by ultrafiltration and ammonium sulphate precipitation at 80% saturation. Proteins were redissolved in 50 mM sodium phosphate, 1.5 M ammonium sulphate, pH 8.5, and subjected to thiophilic adsorption chromatography on an Affi-T gel column (Kem-En-Tec). Proteins were eluted by a 1.5 to 0 M decreasing gradient of ammonium sulphate. Fractions with similar band patterns in SDS-PAGE were pooled and anion exchange chromatography was performed on a Mono Q HR 5/5 column connected to an FPLC system (Pharmacia). The column was equilibrated with 10 mM Tris-HCl, pH 8.5, and the elution was performed with a gradient of NaCl from 0 to 1 M. Fractions containing well separated bands in SDS-PAGE were selected.

Fractions containing CFP10A and CFP30B were blotted to PVDF membrane after 2-DE-PAGE (Ploug et al, 1989). The relevant spots were excised and subjected to N-terminal amino acid sequence analysis.

N-terminal Sequencing

N-terminal amino acid sequence analysis was performed on a Procise 494 sequencer (applied Biosystems).

The following N-terminal sequences were obtained:

| CFP7B:  | PQGTVKWFNAEKGFG | (SEQ ID NO: 168) |
|---------|-----------------|------------------|
| CFP10A: | NVTVSIPTILRPXXX | (SEQ ID NO: 169) |
| CFP11:  | TRFMTDPHAMRDMAG | (SEQ ID NO: 170) |
| CFP30B: | PKRSEYRQGTPNWVD | (SEQ ID NO: 171) |

"X" denotes an amino acid which could not be determined by the sequencing method used.

N-terminal Homology Searching in the Sanger Database and Identification of the Corresponding Genes The N-terminal amino acid sequence from each of the proteins was used for a homology search using the blast program of the Sanger *Mycobacterium tuberculosis* genome database:

http//www.sanger.ac.uk/projects/m-tuberculosis/TB-blast-server.

For CFP11 a sequence 100% identical to 15 N-terminal amino acids was found on contig TB_1314. The identity was found within an open reading frame of 98 amino acids length corresponding to a theoretical MW of 10977 Da and a pI of 5.14.

Amino acid number one can also be an Ala (insted of a Thr) as this sequence was also obtained (results not shown), and a 100% identical sequence to this N-terminal is found on contig TB_671 and on locus MTCI364.09.

For CFP7B a sequence 100% identical to 15 N-terminal amino acids was found on contig TB_2044 and on locus MTY15Cl0.04 with EMBL accession number: z95436. The identity was found within an open reading frame of 67 amino acids length corresponding to a theoretical MW of 7240 Da and a pI of 5.18.

For CFP10A a sequence 100% identical to 12 N-terminal amino acids was found on contig TB_752 and on locus CY130.20 with EMBL accession number: Q10646 and Z73902. The identity was found within an open reading frame of 93 amino acids length corresponding to a theoretical MW of 9557 Da and a pI of 4.78.

For CFP30B a sequence 100% identical to 15 N-terminal amino acids was found on contig TB_335. The identity was found within an open reading frame of 261 amino acids length corresponding to a theoretical MW of 27345 Da and a pI of 4.24.

The amino acid sequences of the purified antigens as picked from the Sanger database are shown in the following list.

CFP7B (SEQ ID NO: 147)

1 MPQGTVKWFN AEKGFGFIAP EDGSADVFVH YTEIQGTGFR TLEENQKVEF
51 EIGHSPKGPQ ATGVRSL

CFP10A (SEQ ID NO: 141)

1 MNVTVSIPTI LRPHTGGQKS VSASGDTLGA VISDLEANYS GISERLMDPS
51 SPGKLHRFVN IYVNDEDVRF SGGLATAIAD GDSVTILPAV AGG

CFP11 Protein Sequence (SEQ ID NO: 143)

1 MATRFMTDPH AMRDMAGRFE VHAQTVEDEA RRMWASAQNI SGAGWSGMAE
51 ATSLDTMAQM NQAFRNIVNM LHGVRDGLVR DANNYEQQEQ ASQQILSS

CFP30B (SEQ ID NO: 145)

1 MPKRSEYRQG TPNWVDLQTT DQSAAKKFYT SLFGWGYDDN PVPGGGGVYS
51 MATLNGEAVA AIAPMPPGAP EGMPPIWNTY IAVDDVDAVV DKVVPGGGQV
101 MMPAFDIGDA GRMSFITDPT GAAVGLWQAN RHIGATLVNE TGTLIWNELL
151 TDKPDLALAF YEAVVGLTHS SMEIAAGQNY RVLKAGDAEV GGCMEPPMPG
201 VPNHWHVYFA VDDADATAAK AAAAGGQVIA EPADIPSVGR FAVLSDPQGA
251 IFSVLKPAPQ Q

Cloning of the Genes Encoding CFP7B, CFP10A, CFP11, and CFP30B

PCR reactions contained 10 ng of *M. tuberculosis* chromosomal DNA in 1×low salt Taq+buffer from Stratagene supplemented with 250 mM of each of the four nucleotides (Boehringer Mannheim), 0,5 mg/ml BSA (IgG technology), 1% DMSO (Merck), 5 pmoles of each primer and 0.5 unit Taq+DNA polymerase (Stratagene) in 10 ml reaction volume. Reactions were initially heated to 94° C. for 25 sec. and run for 30 cycles of the program; 94° C. for 10 sec., 55° C. for 10 sec. and 72° C. for 90 sec., using thermocycler equipment from Idaho Technology.

The DNA fragments were subsequently run on 1% agarose gels, the bands were excised and purified by Spin-X spin columns (Costar) and cloned into pBluscript SK II+-T vector (Stratagene). Plasmid DNA was hereafter prepared from clones harbouring the desired fragments, digested with suitable restriction enzymes and subcloned into the expression vector pMCT6 in frame with 8 histidines which are added to the N-terminal of the expressed proteins. The resulting clones were hereafter sequenced by use of the dideoxy chain termination method adapted for supercoiled DNA using the Sequenase DNA sequencing kit version 1.0 (United States Biochemical Corp., USA) and by cycle sequencing using the Dye Terminator system in combination with an automated gel reader (model 373A; Applied Biosystems) according to the instructions provided. Both strands of the DNA were sequenced.

For cloning of the individual antigens, the following gene specific primers were used:

```
CFP7B: Primers used for cloning of cfp7B:

(SEQ ID NO: 160)
CFP7B-F:  CTGAGATCTAGAATGCCACAGGGAACTGTG (SEQ ID NO: 161)
CFP7B-R:  TCTCCCGGGGGTAACTCAGAGCGAGCGGAC
```

CFP7B-F and CFP7B-R create BglII and SmaI sites, respectively, used for the cloning in pMCT6.

```
CFP10A: Primers used for cloning of cfp10A:

(SEQ ID NO: 162)
CFP10A-F:  CTGAGATCTATGAACGTCACCGTATCC (SEQ ID NO: 163)
CFP10A-R:  TCTCCCGGGGCTCACCCACCGGCCACG
```

CFP10A-F and CFP10A-R create BglII and SmaI sites, respectively, used for the cloning in pMCT6.

```
CFP11: Primers used for cloning of cfp11:

(SEQ ID NO: 164)
CFP11-F:  CTGAGATCTATGGCAACACGTTTTATGACG (SEQ ID NO: 165)
CFP11-R:  CTCCCCGGGTTAGCTGCTGAGGATCTGCTH
```

CFP11-F and CFP11-R create BglII and SmaI sites, respectively, used for the cloning in pMCT6.

```
CFP30B: Primers used for cloning of cfp30B:

(SEQ ID NO: 166)
CFP30B-F:  CTGAAGATCTATGCCCAAGAGAAGCGAATAC (SEQ ID NO: 167)
CFP30B-R:  CGGCAGCTGCTAGCATTCTCCGAATCTGCCG
```

CFP30B-F and CFP30B-R create BglII and PvuII sites, respectively, used for the cloning in pMCT6.

Expression/Purification of Recombinant CFP7B, CFP10A, CFP11 and CFP30B Protein

Expression and metal affinity purification of recombinant protein was undertaken essentially as described by the manufacturers. 1 l LB-media containing 100 µg/ml ampicillin, was inoculated with 10 ml of an overnight culture of XL1-Blue cells harbouring recombinant pMCT6 plasmid. The culture was shaken at 37° C. until it reached a density of $OD_{600}$=0.5. IPTG was hereafter added to a final concentration of 1 mM and the culture was further incubated 4 hours. Cells were harvested, resuspended in 1× sonication buffer+8 M urea and sonicated 5×30 sec. with 30 sec. pausing between the pulses.

After centrifugation, the lysate was applied to a column containing 25 ml of resuspended Talon resin (Clontech, Palo Alto, USA). The column was washed and eluted as described by the manufacturers.

After elution, all fractions (1.5 ml each) were subjected to analysis by SDS-PAGE using the Mighty Small (Hoefer Scientific Instruments, USA) system and the protein concentrations were estimated at 280 nm. Fractions containing recombinant protein were pooled and dialysed against 3 M urea in 10 mM Tris-HCl, pH 8.5. The dialysed protein was further purified by FPLC (Pharmacia, Sweden) using a 6 ml Resource-Q column, eluted with a linear 0–1 M gradient of NaCl. Fractions were analysed by SDS-PAGE and protein concentrations were estimated at $OD_{280}$. Fractions containing protein were pooled and dialysed against 25 mM Hepes buffer, pH 8.5.

Finally the protein concentration and the LPS content was determined by the BCA (Pierce, Holland) and LAL (Endosafe, Charleston, USA) tests, respectively.

EXAMPLE 4

Cloning of the Gene Expressing CFP26 (MPT51)
Synthesis and Design of Probes

Oligonucleotide primers were synthesized automatically on a DNA synthesizer (Applied Biosystems, Forster City, Calif., ABI-391, PCR-mode) deblocked and purified by ethanol precipitation.

Three oligonucleotides were synthesized (TABLE 3) on the basis of the nucleotide sequence from mpb51 described by Ohara et al. (1995). The oligonucleotides were engineered to include an EcoRI restriction enzyme site at the 5' end and at the 3' end by which a later subcloning was possible.

Additional four oligonucleotides were synthesized on the basis of the nucleotide sequence from MPT51 (FIG. 5 and SEQ ID NO: 41). The four combinations of the primers were used for the PCR studies.

DNA Cloning and PCR Technology

Standard procedures were used for the preparation and handling of DNA (Sambrook et al., 1989). The gene mpt51 was cloned from *M. tuberculosis* H37Rv chromosomal DNA by the use of the polymerase chain reactions (PCR) technology as described previously (Oettinger and Andersen, 1994). The PCR product was cloned in the pBluescriptSK+ (Stratagene).

Cloning of mpt51

The gene, the signal sequence and the Shine Delgarno region of MPT51 was cloned by use of the PCR technology as two fragments of 952 bp and 815 bp in pBluescript SK+, designated pTO52 and pTO53.

DNA Sequencing

The nucleotide sequence of the cloned 952 bp *M. tuberculosis* H37Rv PCR fragment, pTO52, containing the Shine Dalgarno sequence, the signal peptide sequence and the structural gene of MPT51, and the nucleotide sequence of the cloned 815 bp PCR fragment containing the structural gene of MPT51, pTO53, were determined by the dideoxy chain termination method adapted for supercoiled DNA by use of the Sequenase DNA sequencing kit version 1.0 (United States Biochemical Corp., Cleveland, Ohio.) and by cycle sequencing using the Dye Terminator system in combination with an automated gel reader (model 373A; Applied Biosystems) according to the instructions provided. Both strands of the DNA were sequenced.

The nucleotide sequences of pTO52 and pTO53 and the deduced amino acid sequence are shown in FIG. 5. The DNA sequence contained an open reading frame starting with a ATG codon at position 45–47 and ending with a termination codon (TAA) at position 942–944. The nucleotide sequence of the first 33 codons was expected to encode the signal sequence. On the basis of the known N-terminal amino acid sequence (Ala-Pro-Tyr-Glu-Asn) of the purified MPT51 (Nagai et al., 1991) and the features of the signal peptide, it is presumed that the signal peptidase recognition sequence (Ala-X-Ala) (von Heijne, 1984) is located in front of the N-terminal region of the mature protein at position 144. Therefore, a structural gene encoding MPT51, mpt51, derived from *M. tuberculosis* H37Rv was found to be located at position 144–945 of the sequence shown in FIG. 5. The nucleotide sequence of mpt51 differed with one nucleotide compared to the nucleotide sequence of MPB51 described by Ohara et al. (1995) (FIG. 5). In mpt51 at position 780 was found a substitution of a guanine to an adenine. From the deduced amino acid sequence this change occurs at a first position of the codon giving a amino acid change from alanine to threonine. Thus it is concluded, that mpt51 consists of 801 bp and that the deduced amino acid sequence contains 266 residues with a molecular weight of 27,842, and MPT51 show 99,8% identity to MPB51.

Subcloning of mpt51

An EcoRI site was engineered immediately 5' of the first codon of mpt51so that only the coding region of the gene encoding MPT51 would be expressed, and an EcoRI site was incorporated right after the stop codon at the 3' end.

DNA of the recombinant plasmid pTO53 was cleaved at the EcoRI sites. The 815 bp fragment was purified from an agarose gel and subcloned into the EcoRI site of the pMAL-cR1 expression vector (New England Biolabs), pTO54. Vector DNA containing the gene fusion was used to transform the *E. coli* XL1-Blue by the standard procedures for DNA manipulation.

The endpoints of the gene fusion were determined by the dideoxy chain termination method as described under section DNA sequencing. Both strands of the DNA were sequenced.

Preparation and Purification of rMPT51

Recombinant antigen was prepared in accordance with instructions provided by New England Biolabs. Briefly, single colonies of *E. coli* harbouring the pTO54 plasmid were inoculated into Luria-Bertani broth containing 50

μg/ml ampicillin and 12.5 μg/ml tetracycline and grown at 37° C. to 2×10⁸ cells/ml. Isopropyl-β-D-thiogalactoside (IPTG) was then added to a final concentration of 0.3 mM and growth was continued for further 2 hours. The pelleted bacteria were stored overnight at −20° C. in new column buffer (20 mM Tris/HCl, pH 7.4, 200 mM NaCl, 1 mM EDTA, 1 mM dithiothreitol (DTT))and thawed at 4° C. followed by incubation with 1 mg/ml lysozyme on ice for 30 min and sonication (20 times for 10 sec with intervals of 20 sec). After centrifugation at 9,000×g for 30 min at 4° C., the maltose binding protein -MPT51fusion protein (MBP-rMPT51) was purified from the crude extract by affinity chromatography on amylose resin column. MBP-rMPT51 binds to amylose. After extensive washes of the column, the fusion protein was eluted with 10 mM maltose. Aliquots of the fractions were analyzed on 10% SDS-PAGE. Fractions containing the fusion protein of interest were pooled and was dialysed extensively against physiological saline.

Protein concentration was determined by the BCA method supplied by Pierce (Pierce Chemical Company, Rockford, Ill.).

The nucleotide sequence of complete gene fusion was determined by the dideoxy chain termination method as described under section DNA sequencing. Both strands of the DNA were sequenced.

Preparation and Purification of rMPT51

Recombinant antigen was prepared from single colonies of *E. coli* harbouring the pTO86 plasmid inoculated into Luria-Bertani broth containing 50 μg/ml ampicillin and 12.5 μg/ml tetracycline and grown at 37° C. to 2×10⁸ cells/ml. Isopropyl-β-D-thiogalactoside (IPTG) was then added to a final concentration of 1 mM and growth was continued for further 2 hours. The pelleted bacteria were resuspended in BC 100/20 buffer (100 mM KCl, 20 mM Imidazole, 20 mM Tris/HCl, pH 7.9, 20% glycerol). Cells were broken by sonication (20 times for 10 sec with intervals of 20 sec). After centrifugation at 9,000×g for 30 min. at 4° C. the insoluble matter was resuspended in BC 100/20 buffer with 8 M urea followed by sonication and centrifugation as above. The 6×His tag-MPT51 fusion protein (His-rMPT51) was purified by affinity chromatography on Ni-NTA resin

TABLE 3

Sequence of the mpt51 oligonucleotides[a].

| Orientation and oligonucleotide[a] | Sequences (5' → 3') | Position[b] (nucleotide) |
|---|---|---|
| Sense | | |
| MPT51-1 | CTCGAATTCGCCGGGTGCACACAG (SEQ ID NO: 28) | 6–21 (SEQ ID NO: 41) |
| MPT51-3 | CTCGAATTCGCCCCATACGAGAAC (SEQ ID NO: 29) | 143–158 (SEQ ID NO: 41) |
| MPT51-5 | GTGTATCTGCTGGAC (SEQ ID NO: 30) | 228–242 (SEQ ID NO: 41) |
| MPT51-7 | CCGACTGGCTGGCCG (SEQ ID NO: 31) | 418–432 (SEQ ID NO: 41) |
| Antisense | | |
| MPT51-2 | GAGGAATTCGCTTAGCGGATCGCA (SEQ ID NO: 32) | 946–932 (SEQ ID NO: 41) |
| MPT51-4 | CCCACATTCCGTTGG (SEQ ID NO: 33) | 642–628 (SEQ ID NO: 41) |
| MPT51-6 | GTCCAGCAGATACAC (SEQ ID NO: 34) | 242–228 (SEQ ID NO: 41) |

[a]The oligonucleotides MPT51-1 and MPT51-2 were constructed from the MPB51 nucleotide sequence (Ohara et al., 1995). The other oligonucleotides constructions were based on the nucleotide sequence obtained from mpt51 reported in this work. Nucleotides (nt) underlined are not contained in the nucleotide sequence of MPB/T51.
[b]The positions referred to are of the non-underlined parts of the primers and correspond to the nucleotide sequence shown in SEQ ID NO: 41.

Cloning of mpt51 in the Expression Vector pMST24

A PCR fragment was produced from pTO52 using the primer combination MPT51-F and MPT51-R (TABLE 4). A BamHI site was engineered immediately 5' of the first codon of mpt51 so that only the coding region of the gene encoding MPT51 would be expressed, and an NcoI site was incorporated right after the stop codon at the 3' end.

The PCR product was cleaved at the BamHI and the NcoI site. The 811 bp fragment was purified from an agarose gel and subcloned into the BamHI and the NcoI site of the pMST24 expression vector, pTO86. Vector DNA containing the gene fusion was used to transform the *E. coli* XL1-Blue by the standard procedures for DNA manipulation.

column (Qiagen, Hilden, Germany). His-rMPT51 binds to Ni-NTA. After extensive washes of the column, the fusion protein was eluted with BC 100/40 buffer (100 mM KCl, 40 mM Imidazole, 20 mM Tris/HCl, pH 7.9, 20% glycerol) with 8 M urea and BC 1000/40 buffer (1000 mM KCl, 40 mM Imidazole, 20 mM Tris/HCl, pH 7.9, 20% glycerol) with 8 M urea. His-rMPT51 was extensive dialysed against 10 mM Tris/HCl, pH 8.5, 3 M urea followed by purification using fast protein liquid chromatography (FPLC) (Pharmacia, Uppsala, Sweden), over an anion exchange column (Mono Q) using 10 mM Tris/HCl, pH 8.5, 3 M urea with a 0–1 M NaCl linear gradient. Fractions containing rMPT51 were pooled and subsequently dialysed extensively against 25 mM Hepes, pH 8.0 before use.

Protein concentration was determined by the BCA method supplied by Pierce (Pierce Chemical Company, Rockford, Ill.). The lipopolysaccharide (LPS) content was determined by the limulus amoebocyte lysate test (LAL) to be less than 0.004 ng/μg rMPT51, and this concentration had no influence on cellular activity.

TABLE 4

Sequence of the mpt51 oligonucleotides.

| Orientation and oligo-nucleotide | Sequences (5' → 3') | Position (nt) |
|---|---|---|
| Sense MPT51-F | CTCGGATCCTGCCCCATACGAGAACCTG | 139–156 |
| Antisense MPT51-R | CTCCCATGGTTAGCGGATCGCACCG | 939–924 |

EXAMPLE 4A

Cloning of the ESAT6-MPT59 and the MPT59-ESAT6 Hybrides

Background for ESAT-MPT59 and MPT59-ESAT6 Fusion

Several studies have demonstrated that ESAT-6 is a an immunogen which is relatively difficult to adjuvate in order to obtain consistent results when immunizing therewith. To detect an in vitro recognition of ESAT-6 after immunization with the antigen is very difficult compared to the strong recognition of the antigen that has been found during the recall of memory immunity to M. tuberculosis. ESAT-6 has been found in ST-CF in a truncated version were amino acids 1–15 have been deleted. The deletion includes the main T-cell epitopes recognized by C57BL/6j mice (Brandt et al., 1996). This result indicates that ESAT-6 either is N-terminally processed or proteolytically degraded in STCF. In order to optimize ESAT-6 as an immunogen, a gene fusion between ESAT-6 and another major T cell antigen MPT59 has been constructed. Two different construct have been made: MPT59-ESAT-6 (SEQ ID NO: 172) and ESAT-6-MPT59 (SEQ ID NO: 173). In the first hybrid ESAT-6 is N-terminally protected by MPT59 and in the latter it is expected that the fusion of two dominant T-cell antigens can have a synergistic effect.

The genes encoding the ESAT6-MPT59 and the MPT59-ESAT6 hybrides were cloned into the expression vector pMCT6, by PCR amplification with gene specific primers, for recombinant expression in E. coli of the hybrid proteins.

Construction of the Hybrid MPT59-ESAT6

The cloning was carried out in three steps. First the genes encoding the two components of the hybrid, ESAT6 and MPT59, were PCR amplified using the following primer constructions:

ESAT6:

(SEQ ID NO: 132)
OPBR-4:    GGCGCCGGCAAGCTTGCCATGACAGAGCAGCAGTGG (SEQ ID NO: 133)
OPBR-28:   CGAACTCGCCGGATCCCGTGTTTCGC

OPBR-4 and OPBR-28 create HinDIII and BamHI sites, respectively.

MPT59:

(SEQ ID NO: 134)
OPBR-48:   GGCAACCGCGAGATCTTTCTCCCGGCCGGGGC (SEQ ID NO: 135)
OPBR-3:    GGCAAGCTTGCCGGCGCCTAACGAACT

OPBR-48 and OPBR-3 create BglII and HinDIII, respectively. Additionally OPBR-3 deletes the stop codon of MPT59.

PCR reactions contained 10 ng of M. tuberculosis chromosomal DNA in 1×low salt Taq+buffer from Stratagene supplemented with 250 mM of each of the four nucleotides (Boehringer Mannheim), 0,5 mg/ml BSA (IgG technology), 1% DMSO (Merck), 5 pmoles of each primer and 0.5 unit Tag+DNA polymerase (Stratagene) in 10 μl reaction volume. Reactions were initially heated to 94° C. for 25 sec. and run for 30 cycles of the program; 94° C. for 10 sec., 55° C. for 10 sec. and 72° C. for 90 sec, using thermocycler equipment from Idaho Technology.

The DNA fragments were subsequently run on 1% agarose gels, the bands were excised and purified by Spin-X spin columns (Costar). The two PCR fragments were digested with HinDIII and ligated. A PCR amplification of the ligated PCR fragments encoding MPT59-ESAT6 was carried out using the primers OPBR-48 and OPBR-28. PCR reaction was initially heated to 94° C. for 25 sec. and run for 30 cycles of the program; 94° C. for 30 sec., 55° C. for 30 sec. and 72° C. for 90 sec. The resulting PCR fragment was digested with BglII and BamHI and cloned into the expression vector pMCT6 in frame with 8 histidines which are added to the N-terminal of the expressed protein hybrid. The resulting clones were hereafter sequenced by use of the dideoxy chain termination method adapted for supercoiled DNA using the Sequenase DNA sequencing kit version 1.0 (United States Biochemical Corp., USA) and by cycle sequencing using the Dye Terminator system in combination with an automated gel reader (model 373A; Applied Biosystems) according to the instructions provided. Both strands of the DNA were sequenced.

Construction of the Hybrid ESAT6-MPT59

Construction of the hybrid ESAT6-MPT59 was carried out as described for the hybrid MPT59-ESAT6. The primers used for the construction and cloning were:

ESAT6:

OPBR-75:                                            (SEQ ID NO: 136)
GGACCCAGATCTATGACAGAGCAGCAGTGG

OPBR-76:                                            (SEQ ID NO: 137)
CCGGCAGCCCCGGCCGGGAGAAAAGCTTTGCGAACATCCCAGTGACG

OPBR-75 and OPBR-76 create BglII and HinDIII sites, respectively. Additionally OPBR-76 deletes the stop codon of ESAT6.

MPT59:

OPBR-77:                                            (SEQ ID NO: 138)
GTTCGCAAAGCTTTTCTCCCGGCCGGGGCTGCCGGTCGAGTACC

```
OPBR-18:                                    (SEQ ID NO: 139)
CCTTCGGTGGATCCCGTCAG
```

OPBR-77 and OPBR-18 create HinDIII and BamHI sites, respectively.

Expression/Purification of MPT59-ESAT6 and ESAT6-MPT59 Hybrid Proteins

Expression and metal affinity purification of recombinant proteins was undertaken essentially as described by the manufacturers. For each protein, 1 l LB-media containing 100 µg/ml ampicillin, was inoculated with 10 ml of an overnight culture of XL1-Blue cells harbouring recombinant pMCT6 plasmids. Cultures were shaken at 37° C. until they reached a density of $OD_{600}$=0.4–0.6. IPTG was hereafter added to a final concentration of 1 mM and the cultures were further incubated 4–16 hours. Cells were harvested, resuspended in 1× sonication buffer+8 M urea and sonicated 5×30 sec. with 30 sec. pausing between the pulses.

After centrifugation, the lysate was applied to a column containing 25 ml of resuspended Talon resin (Clontech, Palo Alto, USA). The column was washed and eluted as described by the manufacturers.

After elution, all fractions (1.5 ml each) were subjected to analysis by SDS-PAGE using the Mighty Small (Hoefer Scientific Instruments, USA) system and the protein concentrations were estimated at 280 nm. Fractions containing recombinant protein were pooled and dialysed against 3 M urea in 10 mM Tris-HCl, pH 8.5. The dialysed protein was further purified by FPLC (Pharmacia, Sweden) using a 6 ml Resource-Q column, eluted with a linear 0–1 M gradient of NaCl. Fractions were analyzed by SDS-PAGE and protein concentrations were estimated at $OD_{280}$. Fractions containing protein were pooled and dialysed against 25 mM Hepes buffer, pH 8.5.

Finally the protein concentration and the LPS content were determined by the BCA (Pierce, Holland) and LAL (Endosafe, Charleston, USA) tests, respectively.

The biological activity of the MPT59-ESAT6 fusion protein is described in Example 6A.

EXAMPLE 5

Mapping of the Purified Antigens in a 2DE System

In order to characterize the purified antigens they were mapped in a 2-dimensional electrophoresis (2DE) reference system. This consists of a silver stained gel containing ST-CF proteins separated by isoelectrical focusing followed by a separation according to size in a polyacrylamide gel electrophoresis. The 2DE was performed according to Hochstrasser et al. (1988). 85 µg of ST-CF was applied to the isoelectrical focusing tubes where BioRad ampholytes BioLyt 4–6 (2 parts) and BioLyt 5–7 (3 parts) were included. The first dimension was performed in acrylamide/piperazin diacrylamide tube gels in the presence of urea, the detergent CHAPS and the reducing agent DTT at 400 V for 18 hours and 800 V for 2 hours. The second dimension 10–20% SDS-PAGE was performed at 100 V for 18 hours and silver stained. The identification of CFP7, CFP7A, CFP7B, CFP8A, CFP8B, CFP9, CFP11, CFP16, CFP17, CFP19, CFP20, CFP21, CFP22, CFP25, CFP27, CFP28, CFP29, CFP30A, CFP50, and MPT51 in the 2DE reference gel were done by comparing the spot pattern of the purified antigen with ST-CF with and without the purified antigen. By the assistance of an analytical 2DE software system (Phoretix International, UK) the spots have been identified in FIG. 6. The position of MPT51 and CFP29 were confirmed by a Western blot of the 2DE gel using the Mab's anti-CFP29 and HBT 4.

EXAMPLE 6

Biological Activity of the Purified Antigens

IFN-γ Induction in the Mouse Model of TB Infection

The recognition of the purified antigens in the mouse model of memory immunity to TB (described in example 1) was investigated. The results shown in TABLE 5 are representative for three experiments.

A very high IFN-γ response was induced by two of the antigens CFP17 and CFP21 at almost the same high level as ST-CF.

TABLE 5

IFN-γ release from splenic memory effector cells from C57BL/6J mice isolated after reinfection with *M. tuberculosis* after stimulation with native antigens.

| Antigen[a]      | IFN-γ (pg/ml)[b] |
|-----------------|------------------|
| ST-CF           | 12564            |
| CFP7            | ND[d]            |
| CFP9            | ND               |
| CFP17           | 9251             |
| CFP20           | 2388             |
| CFP21           | 10732            |
| CFP22 + CFP25[c] | 5342            |
| CFP26 (MPT51)   | ND               |
| CFP28           | 2818             |
| CFP29           | 3700             |

The data is derived from a representative experiment out of three.
[a]ST-CF was tested in a concentration of 5 µg/ml and the individual antigens in a concentration of 2 µg/ml.
[b]Four days after rechallenge a pool of cells from three mice were tested. The results are expressed as mean of duplicate values and the difference between duplicate cultures are < 15% of mean. The IFN-γ release of cultures incubated without antigen was 390 pg/ml.
[c]A pool of CFP22 and CFP25 was tested.
[d]ND, not determined.

Skin Test Reaction in TB Infected Guinea Pigs

The skin test activity of the purified proteins was tested in *M. tuberculosis* infected guinea pigs.

1 group of guinea pigs was infected via an ear vein with $1×10^4$ CFU of *M. tuberculosis* H37Rv in 0,2 ml PBS. After 4 weeks skin tests were performed and 24 hours after injection erythema diameter was measured.

As seen in TABLES 6 and 6a all of the antigens induced a significant Delayed Type Hypersensitivity (DTH) reaction.

TABLE 6

DTH erythema diameter in guinea pigs infected with $1 \times 10^4$ CFU of M. tuberculosis, after stimulation with native antigens.

| Antigen[a] | Skin reaction (mm)[b] |
| --- | --- |
| Control | 2.00 |
| PPD[c] | 15.40 (0.53) |
| CFP7 | ND[e] |
| CFP9 | ND |
| CFP17 | 11.25 (0.84) |
| CFP20 | 8.88 (0.13) |
| CFP21 | 12.44 (0.79) |
| CFP22 + CFP25[d] | 9.19 (3.10) |
| CFP26 (MPT51) | ND |
| CFP28 | 2.90 (1.28) |
| CFP29 | 6.63 (0.88) |

The values presented are the mean of erythema diameter of four animals and the SEM's are indicated in the brackets. For PPD and CFP29 the values are mean of erythema diameter of ten animals.
[a]The antigens were tested in a concentration of 0,1 μg except for CFP29 which was tested in a concentration of 0,8 μg.
[b]The skin reactions are measured in mm erythema 24 h after intradermal injection.
[c]10 TU of PPD was used.
[d]A pool of CFP22 and CFP25 was tested.
[e]ND, not determined.

Together these analyses indicate that most of the antigens identified were highly biologically active and recognized during TB infection in different animal models.

TABLE 6a

DTH erythema diameter of recombinant antigens in outbred guinea pigs infected with $1 \times 10^4$ CFU of M. Tuberculosis.

| Antigen[a] | Skin reaction (mm)[b] |
| --- | --- |
| Control | 2.9 (0.3) |
| PPD[c] | 14.5 (1.0) |
| CFP 7a | 13.6 (1.4) |
| CFP 17 | 6.8 (1.9) |
| CFP 20 | 6.4 (1.4) |
| CFP 21 | 5.3 (0.7) |
| CFP 25 | 10.8 (0.8) |
| CFP 29 | 7.4 (2.2) |
| MPT 51 | 4.9 (1.1) |

The values presented are the mean of erythema diameter of four animals and the SEM's are indicated in the brackets. For Control, PPD, and CFP 20 the values are mean of erythema diameter of eight animals.
[a]The antigens were tested in a concentration of 1,0 μg.
[b]The skin test reactions are measured in mm erythema 24 h after intradermal infection.
[c]10 TU of PPD was used.

Biological Activity of the Purified Recombinant Antigens

Interferon-γ Induction in the Mouse Model of TB Infection

Primary infections. 8 to 12 weeks old female C57BL/6j (H-$2^b$), CBA/J(H-$2^k$), DBA.2(H-$2^d$) and A.SW(H-$2^s$) mice (Bomholtegaard, Ry) were given intravenous infections via the lateral tail vein with an inoculum of $5 \times 10^4$ M. tuberculosis suspended in PBS in a vol. of 0.1 ml. 14 days postinfection the animals were sacrificed and spleen cells were isolated and tested for the recognition of recombinant antigen.

As seen in TABLE 7 the recombinant antigens rCFP7A, rCFP17, rCFP21, rCFP25, and rCFP29 were all recognized in at least two strains of mice at a level comparable to ST-CF. rMPT51 and rCFP7 were only recognized in one or two strains respectively, at a level corresponding to no more than ⅓ of the response detected after ST-CF stimulation. Neither of the antigens rCFP20 and rCFP22 were recognized by any of the four mouse strains.

Memory responses. 8–12 weeks old female C57BL/6j(H-$2^b$) mice (Bomholtegaard, Ry) were given intravenous infections via the lateral tail vein with an inoculum of $5 \times 10^4$ M. tuberculosis suspended in PBS in a vol. of 0.1 ml. After 1 month of infection the mice were treated with isoniazid (Merck and Co., Rahway, N.J.) and rifabutin (Farmatalia Carlo Erba, Milano, Italy) in the drinking water, for two months. The mice were rested for 4–6 months before being used in experiments. For the study of the recall of memory immunity, animals were infected with an inoculum of $1 \times 10^6$ bacteria i.v. and sacrificed at day 4 postinfection. Spleen cells were isolated and tested for the recognition of recombinant antigen. As seen from TABLE 8, IFN-γ release after stimulation with rCFP17, rCFP21 and rCFP25 was at the same level as seen from spleen cells stimulated with ST-CF. Stimulation with rCFP7, rCFP7A and rCFP29 all resulted in an IFN-γ no higher than ⅓ of the response seen with ST-CF. rCFP22 was not recognized by IFN-γ producing cells. None of the antigens stimulated IFN-γ release in naive mice. Additionally non of the antigens were toxic to the cell cultures.

TABLE 7

T cell responses in primary TB infection.

| Name | c57BL/6J(H$2^b$) | DBA.2(H$2^d$) | CBA/J(H$2^k$) | A.SW(H$2^s$) |
| --- | --- | --- | --- | --- |
| rCFP7 | + | + | − | − |
| rCFP7A | +++ | +++ | +++ | + |
| rCFP17 | +++ | + | +++ | + |
| rCFP20 | − | − | − | − |
| rCFP21 | +++ | +++ | +++ | + |
| rCFP22 | − | − | − | − |
| rCFP25 | +++ | ++ | +++ | + |
| rCFP29 | +++ | +++ | +++ | ++ |
| rMPT51 | + | − | − | − |

Mouse IFN-γ release during recall of memory immunity to M. tuberculosis.
−: no response; +: ⅓ of ST-CF; ++: ⅔ of ST-CF; +++: level of ST-CF.

TABLE 8

T cell responses in memory immune animals.

| Name | Memory response |
| --- | --- |
| rCFP7 | + |
| rCFP7A | ++ |
| rCFP17 | +++ |
| rCFP21 | +++ |
| rCFP22 | − |
| rCFP29 | + |
| rCFP25 | +++ |
| rMPT51 | + |

Mouse IFN-γ release 14 days after primary infection with M. tuberculosis.
−: no response; +: ⅓ of ST-CF; ++: ⅔ of ST-CF; +++: level of ST-CF.

Interferon-γ Induction in Human TB Patients and BCG Vaccinated People

Human donors: PBMC were obtained from healthy BCG vaccinated donors with no known exposure to patients with TB and from patients with culture or microscopy proven infection with Mycobacterium tuberculosis. Blood samples were drawn from the TB patients 1–4 months after diagnosis.

Lymphocyte preparations and cell culture: PBMC were freshly isolated by gradient centrifugation of heparinized blood on Lymphoprep (Nycomed, Oslo, Norway). The cells were resuspended in complete medium: RPMI 1640 (Gibco, Grand Island, N.Y.) supplemented with 40 μg/ml streptomycin, 40 U/ml penicillin, and 0.04 mM/ml glutamine, (all from Gibco Laboratories, Paisley, Scotland) and 10% normal human ABO serum (NHS) from the local blood bank. The number and the viability of the cells were determined by trypan blue staining. Cultures were established with $2{,}5\times10^5$ PBMC in 200 μl in microtitre plates (Nunc, Roskilde, Denmark) and stimulated with no antigen, ST-CF, PPD (2.5 μg/ml); rCFP7, rCFP7A, rCFP17, rCFP20, rCFP21, rCFP22, rCFP25, rCFP26, rCFP29, in a final concentration of 5 μg/ml. Phytohaemagglutinin, 1 μg/ml (PHA, Difco laboratories, Detroit, Mich. was used as a positive control. Supernatants for the detection of cytokines were harvested after 5 days of culture, pooled and stored at −80° C. until use.

Cytokine analysis: Interferon-γ (IFN-γ) was measured with a standard ELISA technique using a commercially available pair of mab's from Endogen and used according to the instructions for use. Recombinant IFN-γ (Gibco laboratories) was used as a standard. The detection level for the assay was 50 pg/ml. The variation between the duplicate wells did not exceed 10% of the mean. Responses of 9 individual donors are shown in TABLE 9.

A seen in TABLE 9 high levels of IFN-γ release are obtained after stimulation with several of the recombinant antigens. rCFP7a and rCFP17 gives rise to responses comparable to STCF in almost all donors. rCFP7 seems to be most strongly recognized by BCG vaccinated healthy donors. rCFP21, rCFP25, rCFP26, and rCFP29 gives rise to a mixed picture with intermediate responses in each group, whereas low responses are obtained by rCFP20 and rCFP22.

TABLE 9

Mean values of results from the stimulation of human blood cells from 7 BCG vaccinated and 7 TB patients with recombinant antigens. SE values are given for each antigen. ST-CF and *M. avium* culture filtrate are shown for the comparison.

| donor: | no ag | PHA | PPD | STCF | CFP7 | CFP17 | CFP7A | CFP20 | CFP21 | CFP22 | CFP25 | CFP26 | CFP29 |
|---|---|---|---|---|---|---|---|---|---|---|---|---|---|
| Controls, Healthy, BCG vaccinated, no known TB exposure | | | | | | | | | | | | | |
| 1 | 6 | 9564 | 6774 | 3966 | 7034 | 69 | 1799 | 58 | 152 | 73 | 182 | 946 | 86 |
| 2 | 48 | 12486 | 6603 | 8067 | 3146 | 10044 | 5267 | 29 | 6149 | 51 | 1937 | 526 | 2065 |
| 3 | 190 | 11929 | 10000 | 8299 | 8015 | 11563 | 8641 | 437 | 3194 | 669 | 2531 | 8076 | 6098 |
| 4 | 10 | 21029 | 4106 | 3537 | 1323 | 1939 | 5211 | 1 | 284 | 1 | 1344 | 20 | 125 |
| 5 | 1 | 18750 | 14209 | 13027 | 17725 | 8038 | 19002 | 1 | 3008 | 1 | 2103 | 974 | 8181 |
| TB patients, 1–4 month after diagnosis | | | | | | | | | | | | | |
| 6 | 9 | 8973 | 5096 | 6145 | 852 | 4250 | 4019 | 284 | 1131 | 48 | 2400 | 1078 | 4584 |
| 7 | 1 | 12413 | 6281 | 3393 | 168 | 6375 | 4505 | 11 | 4335 | 16 | 3082 | 1370 | 5115 |
| 8 | 4 | 11915 | 7671 | 7375 | 104 | 2753 | 3356 | 119 | 407 | 437 | 2069 | 712 | 5284 |
| 9 | 32 | 22130 | 16417 | 17213 | 8450 | 9783 | 16319 | 91 | 5957 | 67 | 10043 | 13313 | 9953 |

EXAMPLE 6A

Four groups of 6–8 weeks old, female C57Bl/6J mice (Bomholteg årg, Denmark) were immunized subcutaneously at the base of the tail with vaccines of the following compositions:

Group 1: 10 μg ESAT-6/DDA (250 μg)
Group 2: 10 μg MPT59/DDA (250 μg)
Group 3: 10 μg MPT59-ESAT-6/DDA (250 μg)
Group 4: Adjuvant control group: DDA (250 μg) in NaCl The animals were injected with a volume of 0.2 ml. Two weeks after the first injection and 3 weeks after the second injection the mice were boosted a little further up the back. One week after the last immunization the mice were bled and the blood cells were isolated. The immune response induced was monitored by release of IFN-γ into the culture supernatants when stimulated in vitro with relevant antigens (see the following table).

| Immunogen | For restimulation[a)]: Ag in vitro | | | |
|---|---|---|---|---|
| 10 μg/dose | no antigen | ST-CF | ESAT-6 | MPT59 |
| ESAT-6 | 219 ± 219 | 569 ± 569 | 835 ± 633 | — |
| MPT59 | 0 | 802 ± 182 | — | 5647 ± 159 |
| Hybrid: MPT59-ESAT-6 | 127 ± 127 | 7453 ± 581 | 15133 ± 861 | 16363 ± 1002 |

[a)]Blood cells were isolated 1 week after the last immunization and the release of IFN-γ (pg/ml) after 72 h of antigen stimulation (5 μg/ml) was measured.
The values shown are mean of triplicates performed on cells pooled from three mice ± SEM
[b)]— not determined The experiment demonstrates that immunization with the hybrid stimulates T cells which recognize ESAT-6 and MPT59 stronger than after single antigen immunization. Especially the recognition of ESAT-6 was enhanced by immunization with the MPT59-ESAT-6 hybrid. IFN-γ release in control mice immunized with DDA never exceeded 1000 pg/ml.

EXAMPLE 6B

The recombinant antigens were tested individually as subunit vaccines in mice. Eleven groups of 6–8 weeks old, female C57Bl/6j mice (Bomholtegård, Denmark) were immunized subcutaneously at the base of the tail with vaccines of the following composition:

| | |
|---|---|
| Group 1: | 10 μg CFP7 |
| Group 2: | 10 μg CFP17 |
| Group 3: | 10 μg CFP21 |
| Group 4: | 10 μg CFP22 |
| Group 5: | 10 μg CFP25 |
| Group 6: | 10 μg CFP29 |
| Group 7: | 10 μg MPT51 |
| Group 8: | 50 μg ST-CF |
| Group 9: | Adjuvant control group |
| Group 10: | BCG 2,5 × 10$^5$/ml, 0,2 ml |
| Group 11: | Control group: Untreated |

All the subunit vaccines were given with DDA as adjuvant. The animals were vaccinated with a volume of 0.2 ml. Two weeks after the first injection and three weeks after the second injection group 1–9 were boosted a little further up the back. One week after the last injection the mice were bled and the blood cells were isolated. The immune response induced was monitored by release of IFN-γ into the culture supernatant when stimulated in vitro with the homologous protein.

6 weeks after the last immunization the mice were aerosol challenged with 5×10$^6$ viable *Mycobacterium tuberculosis*/ml. After 6 weeks of infection the mice were killed and the number of viable bacteria in lung and spleen of infected mice was determined by plating serial 3-fold dilutions of organ homogenates on 7H11 plates. Colonies were counted after 2–3 weeks of incubation. The protective efficacy is expressed as the difference between $\log_{10}$ values of the geometric mean of counts obtained from five mice of the relevant group and the geometric mean of counts obtained from five mouse of the relevant control group.

The results from the experiments are presented in the following table.

Immunogenicity and protective efficacy in mice, of ST-CF and 7 subunit vaccines

| Subunit Vaccine | Immunogenicity | Protective efficacy |
|---|---|---|
| ST-CF | +++ | +++ |
| CFP7 | ++ | – |
| CFP17 | +++ | +++ |
| CFP21 | +++ | ++ |
| CFP22 | – | – |
| CFP25 | +++ | +++ |
| CFP29 | +++ | +++ |
| MPT51 | +++ | ++ |

+++ Strong immunogen/high protection (level of BCG)
++ Medium immunogen/medium protection
– No recognition/no protection In conclusion, we have identified a number of proteins inducing high levels of protection. Three of these CFP17, CFP25 and CFP29 giving rise to similar levels of protection as ST-CF and BCG while two proteins CFP21 and MPT51 induces protections around ⅔ the level of BCG and ST-CF. Two of the proteins CFP7 and CFP22 did not induce protection in the mouse model.

EXAMPLE 7

Species Distribution of cfp7, cfp9, mpt51, rd1-orf2, rd1-orf3, rd1-orf4, rd1-orf5, rd1-orf8, rd1-orf9a and rd1-orf9b as well as of cfp7a, cfp7b, cfp10a, cfp17, cfp20, cfp21, cfp22, cfp22a, cfp23, cfp25 and cfp25a

Presence of cfp7, cfp9, mpt51, rd1-orf2, rd1-orf3, rd1-orf4, rd1-orf5, rd1-orf8, rd1-orf9a and rd1-orf9b in Different Mycobacterial Species In order to determine the distribution of the cfp7, cfp9, mpt51, rd1-orf2, rd1-orf3, rd1-orf4, rd1-orf5, rd1-orf8, rd1-orf9a and rd1-orf9b genes in species belonging to the *M. tuberculosis*-complex and in other mycobacteria PCR and/or Southern blotting was used. The bacterial strains used are listed in TABLE 10. Genomic DNA was prepared from mycobacterial cells as described previously (Andersen et al. 1992).

PCR analyses were used in order to determine the distribution of the cfp7, cfp9 and mpt51 gene in species belonging to the tuberculosis-complex and in other mycobacteria. The bacterial strains used are listed in TABLE 10. PCR was performed on genomic DNA prepared from mycobacterial cells as described previously (Andersen et al., 1992).

The oligonucleotide primers used were synthesised automatically on a DNA synthesizer (Applied Biosystems, Forster City, Calif., ABI-391, PCR-mode), deblocked, and purified by ethanol precipitation. The primers used for the analyses are shown in TABLE 11.

The PCR amplification was carried out in a thermal reactor (Rapid cycler, Idaho Technology, Idaho) by mixing 20 ng chromosomal with the mastermix (contained 0.5 μM of each oligonucleotide primer, 0.25 μM BSA (Stratagene), low salt buffer (20 mM Tris-HCl, pH8.8 , 10 mM KCl, 10 mM $(NH_4)_2SO_4$, 2 mM $MgSO_4$ and 0,1% Triton X-100) (Stratagene), 0.25 mM of each deoxynucleoside triphosphate and 0.5 U Taq Plus Long DNA polymerase (Stratagene)). Final volume was 10 μl (all concentrations given are concentrations in the final volume). Predenaturation was carried out at 94° C. for 30 s. 30 cycles of the following was performed: Denaturation at 94° C. for 30 s, annealing at 55° C. for 30 s and elongation at 72° C. for 1 min.

The following primer combinations were used (the length of the amplified products are given in parentheses):

mpt51: MPT51-3 and MPT51-2 (820 bp), MPT51-3 and MPT51-6 (108 bp), MPT51-5 and MPT51-4 (415 bp), MPT51-7 and MPT51-4 (325 bp).

cfp7: pVF1 and PVR1 (274 bp), pVF1 and PVR2 (197 bp), pVF3 and PVR1 (302 bp), pVF3 and PVR2 (125 bp).

cfp9: stR3 and stF1 (351 bp).

TABLE 10

Mycobacterial strains used in this Example.

| Species and strain(s) | | Source |
|---|---|---|
| 1. *M. tuberculosis* | H37R v ATCC[a] (ATCC 27294) | |
| 2. | H37R aATCC (ATCC 25177) | |
| 3. | Erdman | Obtained from A. Lazlo, Ottawa, Canada |
| 4. *M. bovis* BCG substrain: Danish 1331 | | SSI[b] |
| 5. | Chinese | SSI[c] |
| 6. | Canadian | SSI[c] |
| 7. | Glaxo | SSI[c] |
| 8. | Russia | SSI[c] |
| 9. | Pasteur | SSI[c] |
| 10. | Japan | WHO[e] |
| 11. *M. bovis* MNC 27 | | SSI[c] |

TABLE 10-continued

Mycobacterial strains used in this Example.

| Species and strain(s) | Source |
|---|---|
| 12. *M. africanum* | Isolated from a Danish patient |
| 13. *M. leprae* (armadillo-derived) | Obtained from J. M. Colston, London, UK |
| 14. *M. avium* (ATCC 15769) | ATCC |
| 15. *M. kansasii* (ATCC 12478) | ATCC |
| 16. *M. marinum* (ATCC 927) | ATCC |
| 17. *M. scrofulaceum* (ATCC 19275) | ATCC |
| 18. *M. intercellulare* (ATCC 15985) | ATCC |
| 19. *M. fortuitum* (ATCC 6841) | ATCC |
| 20. *M. xenopi* | Isolated from a Danish patient |
| 21. *M. flavescens* | Isolated from a Danish patient |
| 22. *M. szulgai* | Isolated from a Danish patient |
| 23. *M. terrae* | SSI[c] |
| 24. *E. coli* | SSI[d] |
| 25. *S. aureus* | SSI[d] |

[a]American Type Culture Collection, USA.
[b]Statens Serum Institut, Copenhagen, Denmark.
[c]Our collection Department of Mycobacteriology, Statens Serum Institut, Copenhagen, Denmark.
[d]Department of Clinical Microbiology, Statens Serum Institut, Denmark.
[e]WHO International Laboratory for Biological Standards, Statens Serum Institut, Copenhagen, Denmark.

TABLE 11

Sequence of the mpt51, cfp7 and cfp9 oligonucleotides.

| Orientation and oligonucleotide | Sequences (5' → 3')[a] | Position[b] (nucleotides) |
|---|---|---|
| Sense | | |
| MPT51-1 | CTCGAATTCGCCGGGTGCACACAG (SEQ ID NO: 28) | 6–21 (SEQ ID NO: 41) |
| MPT51-3 | CTCGAATTCGCCCCATACGAGAAC (SEQ ID NO: 29) | 143–158 (SEQ ID NO: 41) |
| MPT51-5 | GTGTATCTGCTGGAC (SEQ ID NO: 30) | 228–242 (SEQ ID NO: 41) |
| MPT51-7 | CCGACTGGCTGGCCG (SEQ ID NO: 31) | 418–432 (SEQ ID NO: 41) |
| pvR1 | GTACGAGAATTCATGTCGCAAATCATG (SEQ ID NO: 35) | 91–105 (SEQ ID NO: 1) |
| pvR2 | GTACGAGAATTCGAGCTTGGGGTGCCG (SEQ ID NO: 36) | 168–181 (SEQ ID NO: 1) |
| stR3 | CGATTCCAAGCTTGTGGCCGCCGACCCG (SEQ ID NO: 37) | 141–155 (SEQ ID NO: 3) |
| Antisense | | |
| MPT51-2 | GAGGAATTCGCTTAGCGGATCGCA (SEQ ID NO: 32) | 946–932 (SEQ ID NO: 41) |
| MPT51-4 | CCCACATTCCGTTGG (SEQ ID NO: 33) | 642–628 (SEQ ID NO: 41) |
| MPT51-6 | GTCCAGCAGATACAC (SEQ ID NO: 34) | 242–228 (SEQ ID NO: 41) |
| pvF1 | CGTTAGGGATCCTCATCGCCATGGTGTTGG (SEQ ID NO: 38) | 340–323 (SEQ ID NO: 1) |
| pvF3 | CGTTAGGGATCCGGTTCCACTGTGCC (SEQ ID NO: 39) | 268–255 (SEQ ID NO: 1) |
| stF1 | CGTTAGGGATCCTCAGGTCTTTTCGATG (SEQ ID NO: 40) | 467–452 (SEQ ID NO: 3) |

[a]Nucleotides underlined are not contained in the nucleotide sequences of mpt51, cfp7, and cfp9.
[b]The positions referred to are of the non-underlined parts of the primers and correspond to the nucleotide sequence shown in SEQ ID NOs: 41, 1, and 3 for mpt51, cfp7, and cfp9, respectively.

The Southern blotting was carried out as described previously (Oettinger and Andersen, 1994) with the following modifications: 2 μg of genomic DNA was digested with PvuII, electrophoresed in an 0.8% agarose gel, and transferred onto a nylon membrane (Hybond N-plus; Amersham International plc, Little Chalfont, United Kingdom) with a vacuum transfer device (Milliblot, TM-v; Millipore Corp., Bedford, Mass.). The cfp7, cfp9, mpt51, rd1-orf2, rd1-orf3, rd1-orf4, rd1-orf5, rd1-orf8, rd1-orf9a and rd1-orf9b gene fragments were amplified by PCR from the plasmids pRVN01, pRVN02, pTO52, pTO87, pTO88, pTO89, pTO90, pTO91, pTO96 or pTO98 by using the primers shown in TABLE 11 and TABLE 2 (in Example 2a). The probes were labelled non-radioactively with an enhanced chemiluminescence kit (ECL; Amersham International plc, Little Chalfont, United Kingdom). Hybridization and detection was performed according to the instructions provided by the manufacturer. The results are summarized in TABLES 12 and 13.

TABLE 12

Interspecies analysis of the cfp7, cfp9 and mpt51 genes by PCR and/or Southern blotting and of MPT51 protein by Western blotting.

| Species and strain | PCR | | | Southern blot | | | Western blot |
| --- | --- | --- | --- | --- | --- | --- | --- |
| | cfp7 | cfp9 | mpt51 | cfp7 | cfp9 | mpt51 | MPT51 |
| 1. M. tub. H37Rv | + | + | + | + | + | + | + |
| 2. M. tub. H37Ra | + | + | + | N.D. | N.D. | + | + |
| 3. M. tub. Erdmann | + | + | + | + | + | + | + |
| 4. M. bovis | + | + | + | | | + | + |
| 5. M. bovis BCG Danish 1331 | + | + | + | + | + | + | + |
| 6. M. bovis BCG Japan | + | + | N.D. | + | + | + | N.D. |
| 7. M. bovis BCG Chinese | + | + | N.D. | + | + | N.D. | N.D. |
| 8. M. bovis BCG Canadian | + | + | N.D. | + | + | N.D. | N.D. |
| 9. M. bovis BCG Glaxo | + | + | N.D. | + | + | N.D. | N.D. |
| 10. M. bovis BCG Russia | + | + | N.D. | + | + | N.D. | N.D. |
| 11. M. bovis BCG Pasteur | + | + | N.D. | + | + | N.D. | N.D. |
| 12. M. africanum | + | + | + | + | + | + | + |
| 13. M. leprae | − | − | − | − | − | − | − |
| 14. M. avium | + | + | − | + | + | + | − |
| 15. M. kansasii | + | − | − | + | + | + | − |
| 16. M. marinum | − | (+) | − | + | + | + | − |
| 17. M. scrofulaceum | − | − | − | − | − | − | − |
| 18. M. intercellulare | + | (+) | − | + | + | + | − |
| 19. M. fortuitum | − | − | − | − | − | − | − |
| 20. M. flavescens | + | (+) | − | + | + | + | N.D. |
| 21. M. xenopi | − | − | − | N.D. | N.D. | + | − |
| 22. M. szulgai | (+) | (+) | − | − | + | − | − |
| 23. M. terrae | − | − | N.D. | N.D. | N.D. | N.D. | N.D. |

+, positive reaction; −, no reaction; N.D. not determined.

cfp7, cfp9 and mpt51 were found in the M. tuberculosis complex including BCG and the environmental mycobacteria; M. avium, M. kansasii, M. marinum M. intracellular and M. flavescens. cfp9 was additionally found in M. szulgai and mpt51 in M. xenopi.

Furthermore the presence of native MPT51 in culture filtrates from different mycobacterial strains was investigated with western blots developed with Mab HBT4.

There is a strong band at around 26 kDa in M. tuberculosis H37Rv, Ra, Erdman, M. bovis AN5, M. bovis BCG substrain Danish 1331 and M. africanum. No band was seen in the region in any other tested mycobacterial strains.

TABLE 13a

Interspecies analysis of the rd1-orf2, rd1-orf3, rd1-orf4, rd1-orf5, rd1-orf8, rd1-orf9a and rd1-orf9b genes by Southern blotting.

| Species and strain | rd1-orf2 | rd1-orf3 | rd1-orf4 | rd1-orf5 | rd1-orf8 | rd1-orf9a | rd1-orf9b |
| --- | --- | --- | --- | --- | --- | --- | --- |
| 1. M. tub. H37Rv | + | + | + | + | + | + | + |
| 2. M. bovis | + | + | + | + | N.D. | + | + |
| 3. M. bovis BCG Danish 1331 | + | − | − | − | N.D. | − | − |
| 4. M. bovis BCG Japan | + | − | − | − | N.D. | − | − |
| 5. M. avium | − | − | − | − | N.D. | − | − |
| 6. M. kansasii | − | − | − | − | N.D. | − | − |
| 7. M. marinum | + | − | + | − | N.D. | − | − |
| 8. M. scrofulaceum | + | − | − | − | N.D. | − | − |
| 9. M. intercellulare | − | − | − | − | N.D. | − | − |

TABLE 13a-continued

Interspecies analysis of the rd1-orf2, rd1-orf3, rd1-orf4, rd1-orf5, rd1-orf8, rd1-orf9a and rd1-orf9b genes by Southern blotting.

| Species and strain | rd1-orf2 | rd1-orf3 | rd1-orf4 | rd1-orf5 | rd1-orf8 | rd1-orf9a | rd1-orf9b |
|---|---|---|---|---|---|---|---|
| 10. *M. fortuitum* | − | − | − | − | N.D. | − | − |
| 11. *M. xenopi* | − | − | − | − | N.D. | − | − |
| 12. *M. szulgai* | + | − | − | − | N.D. | − | − |

+ positive reaction; − no reaction, N.D. not determined.

Positive results for rd1-orf2, rd1-orf3, rd1-orf4, rd1-orf5, rd1-orf8, rd1-orf9a and rd1-orf9b were only obtained when using genomic DNA from *M. tuberculosis* and *M. bovis,* and not from *M. bovis* BCG or other mycobacteria analyzed except rd1-orf4 which also was found in *M. marinum.*

Presence of cfp7a, cfp7b, cfp10a, cfp17, cfp20, cfp21, cfp22, cfp22a, cfp23, efp25 and cfp25a in Different Mycobacterial Species Southern blotting was carried out as described for rd1-orf2, rd1-orf3, rd1-orf4, rd1-orf5, rd1-orf8, rd1-orf9a and rd1-orf9b, The cfp7a, cfp7b, cfp10a, cfp17, cfp2O, cfp21, cfp22, cfp22a, cfp23, cfp25 and cfp25a gene fragments were amplified by PCR from the recombinant pMCT6 plasmids encoding the individual genes. The primers used (same as the primers used for cloning) are described in example 3, 3A and 3B. The results are summarized in Table 13b.

TABLE 13b

Interspecies analysis of the cfp7a, cfp7b, cfp10a, cfp17, cfp20, cfp21, cfp22, cfp22a, cfp23, cfp25, and cfp25a genes by Southern blotting.

| Species and strain | cfp7a | cfp7b | cfp10a | cfp17 | cfp20 | cfp21 | cfp22 | cfp22a | cfp23 | cfp25 | cfp25a |
|---|---|---|---|---|---|---|---|---|---|---|---|
| 1. *M. tub.* H37Rv | + | + | + | + | + | + | + | + | + | + | + |
| 2. *M. bovis* | + | + | + | + | + | + | + | + | + | + | + |
| 3. *M. bovis* BCG Danish 1331 | + | + | + | + | + | N.D. | + | + | + | + | + |
| 4. *M. bovis* BCG Japan | + | + | + | + | + | + | + | + | + | + | + |
| 5. *M. avium* | + | N.D. | − | + | − | + | + | + | + | + | − |
| 6. *M. kansasii* | − | N.D. | + | − | − | − | + | − | + | − | − |
| 7. *M. marinum* | + | + | − | + | + | + | + | + | + | + | + |
| 8. *M. scrofulaceum* | − | − | + | − | + | + | − | + | + | + | − |
| 9. *M. intercellulare* | + | + | − | + | − | + | + | − | + | + | − |
| 10. *M. fortuitum* | − | N.D. | − | − | − | − | − | − | + | − | − |
| 11. *M. xenopi* | + | + | + | + | + | + | + | + | + | + | + |
| 12. *M. szulgai* | + | + | − | + | + | + | + | + | + | + | + |

+ positive reaction, − no reaction, N.D. not determined.

List of References

Andersen, P. and Heron, I, 1993, J. Immunol. Methods 161: 29–39.
Andersen, Å. B. et al., 1992, Infect. Immun. 60: 2317–2323.
Andersen P., 1994, Infect. Immun. 62: 2536–44.
Andersen P. et al., 1995, J. Immunol. 154: 3359–72
Barkholt, V. and Jensen, A. L., 1989, Anal. Biochem. 177: 318–322.
Borodovsky, M., and J. McIninch. 1993, Computers Chem. 17: 123–133.
van Dyke M. W. et al., 1992. Gene pp. 99–104.
Gosselin et al., 1992, J. Immunol. 149: 3477–3481.
Harboe, M. et al., 1996, Infect. Immun. 64: 16–22.
von Heijne, G., 1984, J. Mol. Biol. 173: 243–251.
Hochstrasser, D. F. et al., 1988, Anal.Biochem. 173: 424–435.
Köhler, G. and Milstein, C., 1975, Nature 256: 495–497.
Li, H. et al., 1993, Infect. Immun. 61: 1730–1734.
Lindblad E. B. et al., 1997, Infect. Immun. 65: 623–629.
Mahairas, G. G. et al., 1996, J. Bacteriol 178: 1274–1282.
Maniatis T. et al., 1989, "Molecular cloning: a laboratory manual", 2nd ed., Cold Spring Harbor Laboratory, Cold Spring Harbor, N.Y.
Nagai, S. et al., 1991, Infect. Immun. 59: 372–382.
Oettinger, T. and Andersen, Å. B., 1994, Infect. Immun. 62: 2058–2064.
Ohara, N. et al., 1995, Scand. J. immunol. 41: 233–442.
Pal P. G. and Horwitz M. A., 1992, Infect. Immun. 60: 4781–92.
Pearson, W. R. and Lipman D. J., 1988. Proc. Natl. Acad. Sci. USA 85: 2444–92.2448.
Ploug, M. et al., 1989, Anal. Biochem. 181: 33–92.39.
Porath, J. et al., 1985, FEBS Lett. 185: 306–310.
Roberts, A. D. et al., 1995, Immunol. 85: 502–508.
Sorensen, A. L. et al., 1995, Infect. Immun. 63: 1710–1717.
Theisen, M. et al., 1995, Clinical and Diagnostic Laboratory Immunology, 2: 30–34.
Valdés-Stauber, N. and Scherer, S., 1994, Appl. Environ. Microbiol. 60: 3809–3814.
Valdes-Stauber, N. and Scherer, S., 1996, Appl. Environ. Microbiol. 62: 1283–1286.
Williams, N., 1996, Science 272: 27.
Young, R. A. et al., 1985, Proc. Natl. Acad. Sci. USA 82: 2583–2587.

What is claimed is:

1. A substantially pure or isolated polypeptide which
   a) consists of the amino acid sequence as shown in SEQ ID NO: 16, or
   b) consists essentially of the amino acid sequence shown in SEQ ID NO: 16 and is immunologically equivalent to the amino acid sequence shown in SEQ ID NO: 16 with respect to the ability of evoking a protective immune response in mice against infections with mycobacteria belonging to the tuberculosis complex or with respect to the ability of eliciting a diagnostically significant immune response indicating previous or ongoing sensitization with antigens derived from mycobacteria belonging to the tuberculosis complex, or
   c) consists essentially of an amino acid sequence with a sequence identity of at least 80% with SEQ ID NO: 16, and which is at least 6 contiguous amino acid residues of SEQ ID NO: 16, and is immunologically equivalent to the amino acid sequence shown in SEQ ID NO: 16 with respect to the ability of evoking a protective immune response in mice against infections with mycobacteria belonging to the tuberculosis complex or with respect to the ability of eliciting a diagnostically significant immune response indicating previous or ongoing sensitization with antigens derived from mycobacteria belonging to the tuberculosis complex; wherein "sequence identity" is a measure of the degree of similarity between two amino acid sequences of equal length, calculated as $(N_{ref}-N_{dif})*100/N_{ref}$, wherein $N_{dif}$ is the total number of non-identical residues in the two sequences when aligned and wherein $N_{ref}$ is the number of residues in one of the sequences.

2. A substantially pure or isolated polypeptide which consists essentially of:
   a) at least 6 contiguous amino acid residues of SEQ ID NO: 16, or
   b) an amino acid sequence with a sequence identity of at least 80% with SEQ ID NO: 16, or
   c) an amino acid sequence with a sequence identity of at least 80% with a); wherein the polypeptide is immunologically equivalent to the amino acid sequence shown in SEQ ID NO: 16 with respect to the ability of evoking a protective immune response in mice against infections with mycobacteria belonging to the tuberculosis complex or with respect to the ability of eliciting a diagnostically significant immune response indicating previous or ongoing sensitization with antigens derived from mycobacteria belonging to the tuberculosis complex, and "sequence identity" is a measure of the degree of similarity between two amino acid sequences of equal length, calculated as $(N_{ref}-N_{dij})*100\ N_{ref}$, wherein $N_{dif}$ is the total number of non-identical residues in the two sequences when aligned and wherein $N_{ref}$ is the number of residues in one of the sequences.

3. A substantially pure or isolated polypeptide which consists of the amino acid sequence as shown in SEQ ID NO: 16.

4. A substantially pure or isolated polypeptide which consists essentially of the amino acid sequence shown in SEQ ID NO: 16.

5. A substantially or isolated polypeptide which consists essentially of an amino acid sequence with a sequence identity of at least 80% with SEQ ID NO: 16, and which is at least 6 contiguous amino acid residues of SEQ ID NO: 16 wherein the polypeptide is immunologically equivalent to the amino acid sequence shown in SEQ ID NO: 16 with respect to the ability of evoking a protective immune response in mice against infections with mycobacteria belonging to the tuberculosis complex or with respect to the ability of eliciting a diagnostically significant immune response indicating previous or ongoing sensitization with antigens derived from mycobacteria belonging to the tuberculosis complex, and "sequence identity" is a measure of the degree of similarity between two amino acid sequences of equal length, calculated as $(N_{ref}-N_{dij})*100/N_{ref}$, wherein $N_{dif}$ is the total number of non-identical residues in the two sequences when aligned and wherein $N_{ref}$ is the number of residues in one of the sequences.

6. A substantially pure or isolated polypeptide which consists essentially of at least 6 contiguous amino acid residues of SEQ ID NO: 16, wherein the polypeptide is immunologically equivalent to the amino acid sequence shown in SEQ ID NO: 16 with respect to the ability of evoking a protective immune response in mice against infections with mycobacteria belonging to the tuberculosis complex or with respect to the ability of eliciting a diagnostically significant immune response indicating previous or ongoing sensitization with antigens derived from mycobacteria belonging to the tuberculosis complex.

7. The polypeptide of claim 1 or 2 consisting essentially of a T cell epitope of SEQ ID NO: 16 that is a non-naturally occurring polypeptide that induces a release of IFN-γ from primed memory T-lymphocytes withdrawn from a mouse within 2 weeks of primary infection or within 4 days after the mouse has been re-challenge infected with mycobacteria belonging to the tuberculosis complex, the induction performed by the addition of the polypeptide to a suspension comprising about 200,000 spleen cells per ml, the addition of the polypeptide resulting in a concentration of 1–4 µg polypeptide per ml suspension, the release of IFN-γ being assessable by determination of IFN-γ in supernatant harvested 2 days after the addition of the polypeptide to the suspension, and elicits a delayed type hypersensitivity reaction.

8. A substantially pure or isolated polypeptide which consists essentially of an amino acid sequence with a sequence identity of at least 80% with SEQ ID NO: 16, or wherein the polypeptide is immunologically equivalent to the amino acid sequence shown in SEQ ID NO: 16 with respect to the ability of evoking a protective immune in mice response against infections with mycobacteria belonging to the tuberculosis complex or with respect to the ability of eliciting a diagnostically significant immune response indicating previous or ongoing sensitization with antigens derived from mycobacteria belonging to the tuberculosis complex, and "sequence identity" is a measure of the degree of similarity between two amino acid sequences of equal length, calculated as $(N_{ref}-N_{dif})*100/N_{ref}$, wherein $N_{dif}$ is the total number of non-identical residues in the two sequences when aligned and wherein $N_{ref}$ is the number of residues in one of the sequences.

9. A substantially pure or isolated polypeptide which consists essentially of a first amino acid sequence with a sequence identity of at least 80% with a second amino acid sequence that consists essentially of at least 6 contiguous amino acid residues of SEQ ID NO: 16, wherein the polypeptide is immunologically equivalent to the amino acid sequence shown in SEQ ID NO: 16 with respect to the ability of evoking a protective immune response in mice against infections with mycobacteria belonging to the tuberculosis complex or with respect to the ability of eliciting a diagnostically significant immune response indicating previous or ongoing sensitization with antigens derived from mycobacteria belonging to the tuberculosis complex, and "sequence identity" is a measure of the degree of similarity between two amino acid sequences of equal length, calculated as $ 25. A composition comprising a polypeptide according to any one of claims 1 or 2 and pharmaceutically acceptable carrier, vehicle or adjuvant.

26. An immunological composition comprising a polypeptide according to any one of claims 1 or 2.

27. The immunological composition according to claim 26, further comprising an immunologically and pharmaceutically acceptable carrier, vehicle or adjuvant.

28. The immunological composition according to claim 27, wherein the carrier is a polymer to which the polypeptide (s) is/are bound by hydrophobic non-covalent interaction; the vehicle is selected from the group consisting of a diluent and a suspending agent; and the adjuvant is Freund's incomplete adjuvant.

29. An immunological composition comprising at least two different polypeptides according to any one of claims 1 or 2.

30. An immunological composition comprising 3–20 different polypeptides according to any one of claims 1 or 2.

31. A skin test reagent comprising the immunological composition of claim 26.

32. A composition for diagnosing tuberculosis in an animal, including a human being, comprising a polypeptide according to any one of claims 1 or 2 optionally in combination with a means for detection.

33. A fusion polypeptide comprising at least one polypeptide according to any one of claims 3 or 4 and at least one fusion partner.

34. A fusion polypeptide, consisting essentially of at least one polypeptide according to any one of claims 3 or 4 and at least one fusion partner selected from the group consisting of ESAT-6, at least one T-cell epitope of ESAT-6, MPB64, at least one T-cell epitope of MPB64, MPT64, at least one T-cell epitope of MPT64, MPB59 and at least one T-cell epitope of MPB59.

35. The polypeptide according to any one of claims 3 or 4 which is lipidated.

36. A composition comprising a polypeptide according to any one of claims 3 or 4 and pharmaceutically acceptable carrier, vehicle or adjuvant.

37. An immunological composition comprising a polypeptide according to any one of claims 3 or 4.

38. The immunological composition according to claim 37, further comprising an immunologically and pharmaceutically acceptable carrier, vehicle or adjuvant.

39. The immunological-composition according to claim 38, wherein the carrier is a polymer to which the polypeptide (s) is/are bound by hydrophobic non-covalent interaction; the vehicle is selected from the-group consisting of a diluent and a suspending agent; and the adjuvant is Freund's incomplete adjuvant.

40. An immunological composition comprising at least two different polypeptides according to claim 4.

41. An immunological composition comprising 3–20 different polypeptides according to claim 4.

42. A skin test reagent comprising the immunological composition of claim 37.

43. A composition for diagnosing tuberculosis in an animal, including a human being, comprising a polypeptide according to any one of claims 3 or 4 optionally in combination with a means for detection.

* * * * *

UNITED STATES PATENT AND TRADEMARK OFFICE
CERTIFICATE OF CORRECTION

PATENT NO. : 6,641,814 B1
DATED : November 4, 2003
INVENTOR(S) : Andersen et al.

It is certified that error appears in the above-identified patent and that said Letters Patent is hereby corrected as shown below:

Column 182,
Lines 64-65, change "immune in mice response" to -- immune response in mice --.

Signed and Sealed this

Twenty-second Day of June, 2004

JON W. DUDAS
*Acting Director of the United States Patent and Trademark Office*

SEQUENCE LISTING

<160> NUMBER OF SEQ ID NOS: 173

<210> SEQ ID NO 1
<211> LENGTH: 381
<212> TYPE: DNA
<213> ORGANISM: Mycobacterium tuberculosis

<400> SEQUENCE: 1

| ggccgccggt | acctatgtgg | ccgccgatgc | tgcggacgcg | tcgacctata | ccgggttctg | 60 |
| atcgaaccct | gctgaccgag | aggacttgtg | atgtcgcaaa | tcatgtacaa | ctaccccgcg | 120 |
| atgttgggtc | acgccgggga | tatgccgga  | tatgccggca | cgctgcagag | cttgggtgcc | 180 |
| gagatcgccg | tggagcaggc | cgcgttgcag | agtgcgtggc | agggcgatac | cgggatcacg | 240 |
| tatcaggcgt | ggcaggcaca | gtggaaccag | gccatggaag | atttggtgcg | ggcctatcat | 300 |
| gcgatgtcca | gcacccatga | agccaacacc | atggcgatga | tggcccgcga | caccgccgaa | 360 |
| gccgccaaat | ggggcggcta | g | | | | 381 |

<210> SEQ ID NO 2
<211> LENGTH: 96
<212> TYPE: PRT
<213> ORGANISM: Mycobacterium tuberculosis

<400> SEQUENCE: 2

```
Met Ser Gln Ile Met Tyr Asn Tyr Pro Ala Met Leu Gly His Ala Gly
  1               5                  10                  15

Asp Met Ala Gly Tyr Ala Gly Thr Leu Gln Ser Leu Gly Ala Glu Ile
             20                  25                  30

Ala Val Glu Gln Ala Ala Leu Gln Ser Ala Trp Gln Gly Asp Thr Gly
         35                  40                  45

Ile Thr Tyr Gln Ala Trp Gln Ala Gln Trp Asn Gln Ala Met Glu Asp
     50                  55                  60

Leu Val Arg Ala Tyr His Ala Met Ser Ser Thr His Glu Ala Asn Thr
 65                  70                  75                  80

Met Ala Met Met Ala Arg Asp Thr Ala Glu Ala Ala Lys Trp Gly Gly
                 85                  90                  95
```

<210> SEQ ID NO 3
<211> LENGTH: 467
<212> TYPE: DNA
<213> ORGANISM: Mycobacterium tuberculosis

<400> SEQUENCE: 3

| gggtagccgg | accacggctg | ggcaaagatg | tgcaggccgc | catcaaggcg | gtcaaggccg | 60 |
| gcgacggcgt | cataaacccg | gacggcacct | tgttggcggg | ccccgcggtg | ctgacgcccg | 120 |
| acgagtacaa | ctcccggctg | gtggccgccg | acccggagtc | caccgcggcg | ttgcccgacg | 180 |
| gcgccgggct | ggtcgttctg | gatggcaccg | tcactgccga | actcgaagcc | gagggctggg | 240 |
| ccaaagatcg | catccgcgaa | ctgcaagagc | tgcgtaagtc | gaccgggctg | acgtttccg  | 300 |
| accgcatccg | ggtggtgatg | tcggtgcctg | cggaacgcga | agactgggcg | cgcacccatc | 360 |
| gcgacctcat | tgccggagaa | atcttggcta | ccgacttcga | attcgccgac | ctcgccgatg | 420 |
| gtgtggccat | cggcgacggc | gtgcgggtaa | gcatcgaaaa | gacctga    |            | 467 |

<210> SEQ ID NO 4
<211> LENGTH: 108

-continued

```
<212> TYPE: PRT
<213> ORGANISM: Mycobacterium tuberculosis

<400> SEQUENCE: 4

Met Ala Ala Asp Pro Glu Ser Thr Ala Ala Leu Pro Asp Gly Ala Gly
  1               5                  10                  15

Leu Val Val Leu Asp Gly Thr Val Thr Ala Glu Leu Glu Ala Glu Gly
             20                  25                  30

Trp Ala Lys Asp Arg Ile Arg Glu Leu Gln Glu Leu Arg Lys Ser Thr
         35                  40                  45

Gly Leu Asp Val Ser Asp Arg Ile Arg Val Val Met Ser Val Pro Ala
     50                  55                  60

Glu Arg Glu Asp Trp Ala Arg Thr His Arg Asp Leu Ile Ala Gly Glu
 65                  70                  75                  80

Ile Leu Ala Thr Asp Phe Glu Phe Ala Asp Leu Ala Asp Gly Val Ala
                 85                  90                  95

Ile Gly Asp Gly Val Arg Val Ser Ile Glu Lys Thr
                100                 105

<210> SEQ ID NO 5
<211> LENGTH: 889
<212> TYPE: DNA
<213> ORGANISM: Mycobacterium tuberculosis

<400> SEQUENCE: 5
cgggtctgca cggatccggg ccgggcaggg caatcgagcc tgggatccgc tggggtgcgc      60
acatcgcgga cccgtgcgcg gtacggtcga cagcggca cgagaaagta gtaagggcga      120
taataggcgg taaagagtag cgggaagccg gccgaacgac tcggtcagac aacgccacag    180
cggccagtga ggagcagcgg gtgacggaca tgaacccgga tattgagaag gaccagacct    240
ccgatgaagt cacggtagag acgacctccg tcttccgcgc agacttcctc agcgagctgg    300
acgctcctgc gcaagcgggt acggagagcg cggtctccgg ggtggaaggg ctcccgccgg    360
gctcggcgtt gctggtagtc aaacgaggcc ccaacgccgg gtcccggttc ctactcgacc    420
aagccatcac gtcggctggt cggcatcccg acagcgacat atttctcgac gacgtgaccg    480
tgagccgtcg ccatgctgaa ttccggttgg aaaacaacga attcaatgtc gtcgatgtcg    540
ggagtctcaa cggcacctac gtcaaccgcg agcccgtgga ttcggcggtg ctggcgaacg    600
gcgacgaggt ccagatcggc aagttccggt tggtgttctt gaccggaccc aagcaaggcg    660
aggatgacgg gagtaccggg ggcccgtgag cgcacccgat agccccgcgc tggccgggat    720
gtcgatcggg gcggtcctcg acctgctacg accggatttt cctgatgtca ccatctccaa    780
gattcgattc ttggaggctg agggtctggt gacgccccgg cgggcctcat cggggtatcg    840
gcggttcacc gcatacgact gcgcacggct gcgattcatt ctcactgcc                 889

<210> SEQ ID NO 6
<211> LENGTH: 162
<212> TYPE: PRT
<213> ORGANISM: Mycobacterium tuberculosis

<400> SEQUENCE: 6

Met Thr Asp Met Asn Pro Asp Ile Glu Lys Asp Gln Thr Ser Asp Glu
  1               5                  10                  15

Val Thr Val Glu Thr Thr Ser Val Phe Arg Ala Asp Phe Leu Ser Glu
             20                  25                  30

Leu Asp Ala Pro Ala Gln Ala Gly Thr Glu Ser Ala Val Ser Gly Val
```

```
                35                  40                  45
Glu Gly Leu Pro Pro Gly Ser Ala Leu Leu Val Val Lys Arg Gly Pro
 50                  55                  60

Asn Ala Gly Ser Arg Phe Leu Leu Asp Gln Ala Ile Thr Ser Ala Gly
 65                  70                  75                  80

Arg His Pro Asp Ser Asp Ile Phe Leu Asp Asp Val Thr Val Ser Arg
                 85                  90                  95

Arg His Ala Glu Phe Arg Leu Glu Asn Asn Glu Phe Asn Val Val Asp
                100                 105                 110

Val Gly Ser Leu Asn Gly Thr Tyr Val Asn Arg Glu Pro Val Asp Ser
            115                 120                 125

Ala Val Leu Ala Asn Gly Asp Glu Val Gln Ile Gly Lys Phe Arg Leu
130                 135                 140

Val Phe Leu Thr Gly Pro Lys Gln Gly Glu Asp Asp Gly Ser Thr Gly
145                 150                 155                 160

Gly Pro

<210> SEQ ID NO 7
<211> LENGTH: 898
<212> TYPE: DNA
<213> ORGANISM: Mycobacterium tuberculosis

<400> SEQUENCE: 7
tcgactccgg cgccaccggg caggatcacg gtgtcgacgg ggtcgccggg gaatcccacg    60
ataaccactc ttcgcgccat gaatgccagt gttggccagg cgctggcctg cgtccacgc   120 cacacaccgc acagattagg acacgccggc ggcgcagccc tgcccgaaag accgtgcacc   180
ggtcttggca gactgtgccc atggcacaga taaccctgcg aggaaacgcg atcaataccg   240
tcggtgagct acctgctgtc ggatccccgg ccccggcctt caccctgacc gggggcgatc   300
tgggggtgat cagcagcgac cagttccggg gtaagtccgt gttgctgaac atctttccat   360
ccgtggacac accggtgtgc gcgacgagtg tgcgaacctt cgacgagcgt gcggcggcaa   420
gtggcgctac cgtgctgtgt gtctcgaagg atctgccgtt cgcccagaag cgcttctgcg   480
gcgccgaggg caccgaaaac gtcatgcccc gtcggcatt ccgggacagc ttcggcgagg   540
attacggcgt gaccatcgcc gacgggccga tggccgggct gctcgcccgc gcaatcgtgg   600
tgatcggcgc ggacggcaac gtcgcctaca cggaattggt gccggaaatc gcgcaagaac   660
ccaactacga agcggcgctg gccgcgctgg gcgcctaggc tttcacaagc cccgcgcgtt   720
cggcgagcag cgcacgattt cgagcgctgc tcccgaaaag cgcctcggtg gtcttggccc   780
ggcggtaata caggtgcagg tcgtgctccc acgtgaaggc gatggcaccg tggatctgaa   840
gagcggagcc ggcgcataac acaaaggttt ccgcggtctg cgccttcgcc agcggcgc    898

<210> SEQ ID NO 8
<211> LENGTH: 165
<212> TYPE: PRT
<213> ORGANISM: Mycobacterium tuberculosis

<400> SEQUENCE: 8

Met Ala Gln Ile Thr Leu Arg Gly Asn Ala Ile Asn Thr Val Gly Glu
  1               5                  10                  15

Leu Pro Ala Val Gly Ser Pro Ala Pro Ala Phe Thr Leu Thr Gly Gly
                 20                  25                  30

Asp Leu Gly Val Ile Ser Ser Asp Gln Phe Arg Gly Lys Ser Val Leu
             35                  40                  45
```

```
Leu Asn Ile Phe Pro Ser Val Asp Thr Pro Val Cys Ala Thr Ser Val
         50                  55                  60

Arg Thr Phe Asp Glu Arg Ala Ala Ser Gly Ala Thr Val Leu Cys
 65                  70                  75                  80

Val Ser Lys Asp Leu Pro Phe Ala Gln Lys Arg Phe Cys Gly Ala Glu
                 85                  90                  95

Gly Thr Glu Asn Val Met Pro Ala Ser Ala Phe Arg Asp Ser Phe Gly
                100                 105                 110

Glu Asp Tyr Gly Val Thr Ile Ala Asp Gly Pro Met Ala Gly Leu Leu
            115                 120                 125

Ala Arg Ala Ile Val Ile Gly Ala Asp Gly Asn Val Ala Tyr Thr
130                 135                 140

Glu Leu Val Pro Glu Ile Ala Gln Glu Pro Asn Tyr Glu Ala Ala Leu
145                 150                 155                 160

Ala Ala Leu Gly Ala
            165
```

<210> SEQ ID NO 9
<211> LENGTH: 1054
<212> TYPE: DNA
<213> ORGANISM: Mycobacterium tuberculosis

<400> SEQUENCE: 9

```
ataatcagct caccgttggg accgacctcg accaggggtc ctttgtgact gccgggcttg      60
acgcggacga ccacagagtc ggtcatcgcc taaggctacc gttctgacct ggggctgcgt     120
gggcgccgac gacgtgaggc acgtcatgtc tcagcggccc accgccacct cggtcgccgg     180
cagtatgtca gcatgtgcag atgactccac gcagccttgt tcgcatcgtt ggtgtcgtgg     240
ttgcgacgac cttggcgctg gtgagcgcac ccgccggcgg tcgtgccgcg catgcggatc     300
cgtgttcgga catcgcggtc gttttcgctc gcggcacgca tcaggcttct ggtcttggcg     360
acgtcggtga ggcgttcgtc gactcgctta cctcgcaagt tggcgggcgg tcgattgggg     420
tctacgcggt gaactaccca gcaagcgacg actaccgcg  gagcgcgtca aacggttccg     480
atgatgcgag cgcccacatc cagcgcaccg tcgccagctg cccgaacacc aggattgtgc     540
ttggtggcta ttcgcagggt gcgacggtca tcgatttgtc cacctcggcg atgccgcccg     600
cggtggcaga tcatgtcgcc gctgtcgccc ttttcggcga gccatccagt ggttctctcca    660
gcatgttgtg gggcggcggg tcgttgccga caatcggtcc gctgtatagc tctaagacca     720
taaacttgtg tgctcccgac gatccaatat gcaccggagg cggcaatatt atggcgcatg     780
tttcgtatgt tcagtcgggg atgacaagcc aggcggcgac attcgcggcg aacaggctcg     840
atcacgccgg atgatcaaag actgttgtcc ctataccgct ggggctgtag tcgatgtaca     900
ccggctggaa tctgaagggc aagaacccgg tattcatcag gccggatgaa atgacggtcg     960
ggcggtaatc gtttgtgttg aacgcgtaga gccgatcacc gccggggctg gtgtagacct    1020
caatgtttgt gttcgccggc agggttccgg atcc                                1054
```

<210> SEQ ID NO 10
<211> LENGTH: 217
<212> TYPE: PRT
<213> ORGANISM: Mycobacterium tuberculosis

<400> SEQUENCE: 10

```
Met Thr Pro Arg Ser Leu Val Arg Ile Val Gly Val Val Val Ala Thr
 1               5                  10                  15
```

-continued

```
Thr Leu Ala Leu Val Ser Ala Pro Ala Gly Arg Ala His Ala
             20                  25                  30
Asp Pro Cys Ser Asp Ile Ala Val Val Phe Ala Arg Gly Thr His Gln
         35                  40                  45
Ala Ser Gly Leu Gly Asp Val Gly Glu Ala Phe Val Asp Ser Leu Thr
     50                  55                  60
Ser Gln Val Gly Gly Arg Ser Ile Gly Val Tyr Ala Val Asn Tyr Pro
 65                  70                  75                  80
Ala Ser Asp Asp Tyr Arg Ala Ser Ala Ser Asn Gly Ser Asp Asp Ala
                 85                  90                  95
Ser Ala His Ile Gln Arg Thr Val Ala Ser Cys Pro Asn Thr Arg Ile
            100                 105                 110
Val Leu Gly Gly Tyr Ser Gln Gly Ala Thr Val Ile Asp Leu Ser Thr
        115                 120                 125
Ser Ala Met Pro Pro Ala Val Ala Asp His Val Ala Val Ala Leu
    130                 135                 140
Phe Gly Glu Pro Ser Ser Gly Phe Ser Ser Met Leu Trp Gly Gly
145                 150                 155                 160
Ser Leu Pro Thr Ile Gly Pro Leu Tyr Ser Ser Lys Thr Ile Asn Leu
                165                 170                 175
Cys Ala Pro Asp Asp Pro Ile Cys Thr Gly Gly Asn Ile Met Ala
                180                 185                 190
His Val Ser Tyr Val Gln Ser Gly Met Thr Ser Gln Ala Ala Thr Phe
            195                 200                 205
Ala Ala Asn Arg Leu Asp His Ala Gly
    210                 215
```

<210> SEQ ID NO 11
<211> LENGTH: 949
<212> TYPE: DNA
<213> ORGANISM: Mycobacterium tuberculosis

<400> SEQUENCE: 11

```
agccgctcgc gtgggtcaa ccgggttcc acctgctcac tcattttgcc gcctttctgt     60
gtccgggccg aggcttgcgc tcaataactc ggtcaagttc cttcacagac tgccatcact    120
ggcccgtcgg cgggctcgtt gcgggtgcgc cgcgtgcggg tttgtgttcc gggcaccggg    180
tgggggcccg cccgggcgta atggcagact gtgattccgt gactaacagc cccttgcga    240
ccgctaccgc cacgctgcac actaaccgcg gcgacatcaa gatcgccctg ttcggaaacc    300
atgcgcccaa gaccgtcgcc aattttgtgg gccttgcgca gggcaccaag gactattcga    360
cccaaaacgc atcaggtggc ccgtccggcc cgttctacga cggcgcggtc tttcaccggg    420
tgatccaggg cttcatgatc cagggtggcg atccaaccgg gacgggtcgc ggcggacccg    480
gctacaagtt cgccgacgag ttccaccccg agctgcaatt cgacaagccc tatctgctcg    540
cgatggccaa cgccggtccg gcaccaacg gctcacagtt tttcatcacc gtcggcaaga    600
ctccgcacct gaaccggcgc cacaccattt tcggtgaagt gatcgacgcg gagtcacagc    660
gggttgtgga ggcgatctcc aagacggcca ccgacggcaa cgatcggccg acggacccgg    720
tggtgatcga gtcgatcacc atctcctgac ccgaagctac gtcggctcgt cgctcgaata    780
caccttgtgg accgccagg gcacgtggcg gtacaccgac acgccgttgg ggccgttcaa    840
ccggacgccc tcacgccaag tccgctcacc tttggccgcg accggcgtaa ccggcagcgg    900
taagcgcatc gagcacctcc actgggtcgg tgccgagatc ccagcggga             949
```

<210> SEQ ID NO 12
<211> LENGTH: 182
<212> TYPE: PRT
<213> ORGANISM: Mycobacterium tuberculosis

<400> SEQUENCE: 12

```
Met Ala Asp Cys Asp Ser Val Thr Asn Ser Pro Leu Ala Thr Ala Thr
 1               5                  10                  15

Ala Thr Leu His Thr Asn Arg Gly Asp Ile Lys Ile Ala Leu Phe Gly
            20                  25                  30

Asn His Ala Pro Lys Thr Val Ala Asn Phe Val Gly Leu Ala Gln Gly
        35                  40                  45

Thr Lys Asp Tyr Ser Thr Gln Asn Ala Ser Gly Gly Pro Ser Gly Pro
    50                  55                  60

Phe Tyr Asp Gly Ala Val Phe His Arg Val Ile Gln Gly Phe Met Ile
 65                  70                  75                  80

Gln Gly Gly Asp Pro Thr Gly Thr Gly Arg Gly Gly Pro Gly Tyr Lys
                85                  90                  95

Phe Ala Asp Glu Phe His Pro Glu Leu Gln Phe Asp Lys Pro Tyr Leu
            100                 105                 110

Leu Ala Met Ala Asn Ala Gly Pro Gly Thr Asn Gly Ser Gln Phe Phe
        115                 120                 125

Ile Thr Val Gly Lys Thr Pro His Leu Asn Arg Arg His Thr Ile Phe
    130                 135                 140

Gly Glu Val Ile Asp Ala Glu Ser Gln Arg Val Val Glu Ala Ile Ser
145                 150                 155                 160

Lys Thr Ala Thr Asp Gly Asn Asp Arg Pro Thr Asp Pro Val Val Ile
                165                 170                 175

Glu Ser Ile Thr Ile Ser
            180
```

<210> SEQ ID NO 13
<211> LENGTH: 1060
<212> TYPE: DNA
<213> ORGANISM: Mycobacterium tuberculosis

<400> SEQUENCE: 13

```
tggaccttca ccggcggtcc cttcgcttcg ggggcgacac ctaacatact ggtcgtcaac     60
ctaccgcgac accgctggga cttcgtgcca ttgccggcca ctcggggccg ctgcggcctg    120
gaaaaattgg tcgggcacgg gcggccgcgg gtcgctacca tcccactgtg aatgatttac    180
tgaccccgcc gactgctcac catgggcgcg gccgccgcaat gctggccgcg gtgcttctgc    240
ttactcccat caccgttccc gccggctacc ccggtgccgt tgcaccggcc actgcagcct    300
gccccgacgc cgaagtggtg ttcgcccgcg gccgcttcga accgcccggg attggcacgg    360
tcggcaacgc attcgtcagc gcgctgcgct cgaaggtcaa caagaatgtc ggggtctacg    420
cggtgaaata ccccgccgac aatcagatcg atgtgggcgc caacgacatg agcgcccaca    480
ttcagagcat ggccaacagc tgtccgaata cccgcctggt gccggcggt tactcgctgg    540
gcgcggccgt caccgacgtg gtactcgcgg tgcccaccca gatgtgggc ttcaccaatc    600
ccctgcctcc cggcagtgat gagcacatcg ccgcggtcgc gctgttcggc aatggcagtc    660
agtgggtcgg cccatcacc aacttcagcc ccgcctacaa cgatcggacc atcgagttgt    720
gtcacggcga cgaccccgtc tgccaccctg ccgaccccaa cacctgggag gccaactggc    780
```

```
cccagcacct cgccggggcc tatgtctcgt cgggcatggt caaccaggcg gctgacttcg      840
ttgccggaaa gctgcaatag ccacctagcc cgtgcgcgag tctttgcttc acgctttcgc      900
taaccgacca acgcgcgcac gatggagggg tccgtggtca tatcaagaca agaagggagt      960
aggcgatgca cgcaaaagtc ggcgactacc tcgtggtgaa gggcacaacc acggaacggc     1020
atgatcaaca tgctgagatc atcgaggtgc gctccgcaga                           1060
```

<210> SEQ ID NO 14
<211> LENGTH: 219
<212> TYPE: PRT
<213> ORGANISM: Mycobacterium tuberculosis

<400> SEQUENCE: 14

Met Gly Ala Ala Ala Met Leu Ala Ala Val Leu Leu Leu Thr Pro
1               5                   10                  15

Ile Thr Val Pro Ala Gly Tyr Pro Gly Ala Val Ala Pro Ala Thr Ala
            20                  25                  30

Ala Cys Pro Asp Ala Glu Val Val Phe Ala Arg Gly Arg Phe Glu Pro
        35                  40                  45

Pro Gly Ile Gly Thr Val Gly Asn Ala Phe Val Ser Ala Leu Arg Ser
    50                  55                  60

Lys Val Asn Lys Asn Val Gly Val Tyr Ala Val Lys Tyr Pro Ala Asp
65                  70                  75                  80

Asn Gln Ile Asp Val Gly Ala Asn Asp Met Ser Ala His Ile Gln Ser
                85                  90                  95

Met Ala Asn Ser Cys Pro Asn Thr Arg Leu Val Pro Gly Gly Tyr Ser
            100                 105                 110

Leu Gly Ala Ala Val Thr Asp Val Val Leu Ala Val Pro Thr Gln Met
        115                 120                 125

Trp Gly Phe Thr Asn Pro Leu Pro Pro Gly Ser Asp Glu His Ile Ala
    130                 135                 140

Ala Val Ala Leu Phe Gly Asn Gly Ser Gln Trp Val Gly Pro Ile Thr
145                 150                 155                 160

Asn Phe Ser Pro Ala Tyr Asn Asp Arg Thr Ile Glu Leu Cys His Gly
                165                 170                 175

Asp Asp Pro Val Cys His Pro Ala Asp Pro Asn Thr Trp Glu Ala Asn
            180                 185                 190

Trp Pro Gln His Leu Ala Gly Ala Tyr Val Ser Ser Gly Met Val Asn
        195                 200                 205

Gln Ala Ala Asp Phe Val Ala Gly Lys Leu Gln
    210                 215

<210> SEQ ID NO 15
<211> LENGTH: 1198
<212> TYPE: DNA
<213> ORGANISM: Mycobacterium tuberculosis

<400> SEQUENCE: 15

```
cagatgctgc gcaacatgtt tctcggcgat ccggcaggca acaccgatcg agtgcttgac       60
ttttccaccg cggtgaccgg cggactgttc ttctcaccca ccatcgactt ctctgaccat      120
ccaccgcccc taccgcaggc ggcgacgcca actctggcag ccgggtcgct atcgatcggc      180
agcttgaaag gaagccccg atgaacaatc tctaccgcga tttggcaccg gtcaccgaag      240
ccgcttgggc ggaaatcgaa ttggaggcgg cgcggacgtt caagcgacac atcgccgggc      300
gccgggtggt cgatgtcagt gatccggggg ggcccgtcac cgcggcggtc agcaccggcc      360
```

-continued

```
ggctgatcga tgttaaggca ccaaccaacg gcgtgatcgc ccacctgcgg gccagcaaac    420
cccttgtccg gctacgggtt ccgtttaccc tgtcgcgcaa cgagatcgac gacgtggaac    480
gtggctctaa ggactccgat tgggaaccgg taaaggaggc ggccaagaag ctggccttcg    540
tcgaggaccg cacaatattc gaaggctaca gcgccgcatc aatcgaaggg atccgcagcg    600
cgagttcgaa cccggcgctg acgttgcccg aggatccccg tgaaatccct gatgtcatct    660
cccaggcatt gtccgaactg cggttggccg gtgtggacgg accgtattcg gtgttgctct    720
ctgctgacgt ctacaccaag gttagcgaga cttccgatca cggctatccc atccgtgagc    780
atctgaaccg gctggtggac ggggacatca tttgggcccc ggccatcgac ggcgcgttcg    840
tgctgaccac tcgaggcggc gacttcgacc tacagctggg caccgacgtt gcaatcgggt    900
acgccagcca cgacacggac accgagcgcc tctacctgca ggagacgctg acgttccttt    960
gctacaccgc cgaggcgtcg gtcgcgctca gccactaagg cacgagcgcg agcaatagct   1020
cctatggcaa gcggccgcgg gttgggtgtg ttcggagctg gctggtgga cggtgcgcag   1080
ggcctggaag acggtgcggg ctaggcggcg tttgaggcag cgtagtgctg cgcgtttggt   1140
tttcccggcg tcttgcagcc tttggtagta ggcctggccc cggctgtcgg tcatccgg     1198
```

<210> SEQ ID NO 16
<211> LENGTH: 265
<212> TYPE: PRT
<213> ORGANISM: Mycobacterium tuberculosis

<400> SEQUENCE: 16

```
Met Asn Asn Leu Tyr Arg Asp Leu Ala Pro Val Thr Glu Ala Ala Trp
  1               5                  10                  15
Ala Glu Ile Glu Leu Glu Ala Ala Arg Thr Phe Lys Arg His Ile Ala
                 20                  25                  30
Gly Arg Arg Val Val Asp Val Ser Asp Pro Gly Pro Val Thr Ala
             35                  40                  45
Ala Val Ser Thr Gly Arg Leu Ile Asp Val Lys Ala Pro Thr Asn Gly
         50                  55                  60
Val Ile Ala His Leu Arg Ala Ser Lys Pro Leu Val Arg Leu Arg Val
 65                  70                  75                  80
Pro Phe Thr Leu Ser Arg Asn Glu Ile Asp Asp Val Glu Arg Gly Ser
                 85                  90                  95
Lys Asp Ser Asp Trp Glu Pro Val Lys Glu Ala Lys Lys Leu Ala
            100                 105                 110
Phe Val Glu Asp Arg Thr Ile Phe Glu Gly Tyr Ser Ala Ala Ser Ile
        115                 120                 125
Glu Gly Ile Arg Ser Ala Ser Ser Asn Pro Ala Leu Thr Leu Pro Glu
    130                 135                 140
Asp Pro Arg Glu Ile Pro Asp Val Ile Ser Gln Ala Leu Ser Glu Leu
145                 150                 155                 160
Arg Leu Ala Gly Val Asp Gly Pro Tyr Ser Val Leu Leu Ser Ala Asp
                165                 170                 175
Val Tyr Thr Lys Val Ser Glu Thr Ser Asp His Gly Tyr Pro Ile Arg
            180                 185                 190
Glu His Leu Asn Arg Leu Val Asp Gly Asp Ile Ile Trp Ala Pro Ala
        195                 200                 205
Ile Asp Gly Ala Phe Val Leu Thr Thr Arg Gly Gly Asp Phe Asp Leu
    210                 215                 220
```

```
Gln Leu Gly Thr Asp Val Ala Ile Gly Tyr Ala Ser His Asp Thr Asp
225                 230                 235                 240

Thr Glu Arg Leu Tyr Leu Gln Glu Thr Leu Thr Phe Leu Cys Tyr Thr
                245                 250                 255

Ala Glu Ala Ser Val Ala Leu Ser His
            260                 265
```

```
<210> SEQ ID NO 17
<211> LENGTH: 15
<212> TYPE: PRT
<213> ORGANISM: Mycobacterium tuberculosis
<220> FEATURE:
<221> NAME/KEY: VARIANT
<222> LOCATION: (1)
<223> OTHER INFORMATION: Ala is Ala or Ser
<220> FEATURE:
<221> NAME/KEY: UNSURE
<222> LOCATION: (13)
<223> OTHER INFORMATION: Xaa is unknown

<400> SEQUENCE: 17

Ala Glu Leu Asp Ala Pro Ala Gln Ala Gly Thr Glu Xaa Ala Val
 1               5                  10                  15
```

```
<210> SEQ ID NO 18
<211> LENGTH: 15
<212> TYPE: PRT
<213> ORGANISM: Mycobacterium tuberculosis

<400> SEQUENCE: 18

Ala Gln Ile Thr Leu Arg Gly Asn Ala Ile Asn Thr Val Gly Glu
 1               5                  10                  15
```

```
<210> SEQ ID NO 19
<211> LENGTH: 15
<212> TYPE: PRT
<213> ORGANISM: Mycobacterium tuberculosis
<220> FEATURE:
<221> NAME/KEY: UNSURE
<222> LOCATION: (3)
<223> OTHER INFORMATION: Xaa is unknown

<400> SEQUENCE: 19

Asp Pro Xaa Ser Asp Ile Ala Val Val Phe Ala Arg Gly Thr His
 1               5                  10                  15
```

```
<210> SEQ ID NO 20
<211> LENGTH: 15
<212> TYPE: PRT
<213> ORGANISM: Mycobacterium tuberculosis

<400> SEQUENCE: 20

Thr Asn Ser Pro Leu Ala Thr Ala Thr Ala Thr Leu His Thr Asn
 1               5                  10                  15
```

```
<210> SEQ ID NO 21
<211> LENGTH: 15
<212> TYPE: PRT
<213> ORGANISM: Mycobacterium tuberculosis
<220> FEATURE:
<221> NAME/KEY: UNSURE
<222> LOCATION: (2)
<223> OTHER INFORMATION: Xaa is unknown

<400> SEQUENCE: 21

Ala Xaa Pro Asp Ala Glu Val Val Phe Ala Arg Gly Arg Phe Glu
 1               5                  10                  15
```

<210> SEQ ID NO 22
<211> LENGTH: 15
<212> TYPE: PRT
<213> ORGANISM: Mycobacterium tuberculosis
<220> FEATURE:
<221> NAME/KEY: UNSURE
<222> LOCATION: (1)
<223> OTHER INFORMATION: Xaa is unknown
<220> FEATURE:
<221> NAME/KEY: VARIANT
<222> LOCATION: (2)
<223> OTHER INFORMATION: Ile is Ile or Val
<220> FEATURE:
<221> NAME/KEY: VARIANT
<222> LOCATION: (10)
<223> OTHER INFORMATION: Val is Val or Thr
<220> FEATURE:
<221> NAME/KEY: VARIANT
<222> LOCATION: (11)
<223> OTHER INFORMATION: Val is Val or Phe
<220> FEATURE:
<221> NAME/KEY: VARIANT
<222> LOCATION: (14)
<223> OTHER INFORMATION: Asp is Asp or Gln

<400> SEQUENCE: 22

Xaa Ile Gln Lys Ser Leu Glu Leu Ile Val Val Thr Ala Asp Glu
 1               5                  10                  15

<210> SEQ ID NO 23
<211> LENGTH: 19
<212> TYPE: PRT
<213> ORGANISM: Mycobacterium tuberculosis

<400> SEQUENCE: 23

Met Asn Asn Leu Tyr Arg Asp Leu Ala Pro Val Thr Glu Ala Ala Trp
 1               5                  10                  15

Ala Glu Ile

<210> SEQ ID NO 24
<211> LENGTH: 34
<212> TYPE: DNA
<213> ORGANISM: Mycobacterium tuberculosis

<400> SEQUENCE: 24
cccggctcga gaacctstac cgcgacctsg cscc                               34

<210> SEQ ID NO 25
<211> LENGTH: 37
<212> TYPE: DNA
<213> ORGANISM: Mycobacterium tuberculosis

<400> SEQUENCE: 25
gggccggatc cgasgcsgcg tccttsacsg gytgcca                            37

<210> SEQ ID NO 26
<211> LENGTH: 28
<212> TYPE: DNA
<213> ORGANISM: Mycobacterium tuberculosis

<400> SEQUENCE: 26
ggaagcccca tatgaacaat ctctaccg                                      28

<210> SEQ ID NO 27
<211> LENGTH: 32
<212> TYPE: DNA

-continued

<213> ORGANISM: Mycobacterium tuberculosis

<400> SEQUENCE: 27
cgcgctcagc ccttagtgac tgagcgcgac cg 32

<210> SEQ ID NO 28
<211> LENGTH: 24
<212> TYPE: DNA
<213> ORGANISM: Mycobacterium tuberculosis

<400> SEQUENCE: 28
ctcgaattcg ccgggtgcac acag 24

<210> SEQ ID NO 29
<211> LENGTH: 25
<212> TYPE: DNA
<213> ORGANISM: Mycobacterium tuberculosis

<400> SEQUENCE: 29
ctcgaattcg cccccatacg agaac 25

<210> SEQ ID NO 30
<211> LENGTH: 15
<212> TYPE: DNA
<213> ORGANISM: Mycobacterium tuberculosis

<400> SEQUENCE: 30
gtgtatctgc tggac 15

<210> SEQ ID NO 31
<211> LENGTH: 15
<212> TYPE: DNA
<213> ORGANISM: Mycobacterium tuberculosis

<400> SEQUENCE: 31
ccgactggct ggccg 15

<210> SEQ ID NO 32
<211> LENGTH: 24
<212> TYPE: DNA
<213> ORGANISM: Mycobacterium tuberculosis

<400> SEQUENCE: 32
gaggaattcg cttagcggat cgca 24

<210> SEQ ID NO 33
<211> LENGTH: 15
<212> TYPE: DNA
<213> ORGANISM: Mycobacterium tuberculosis

<400> SEQUENCE: 33
cccacattcc gttgg 15

<210> SEQ ID NO 34
<211> LENGTH: 15
<212> TYPE: DNA
<213> ORGANISM: Mycobacterium tuberculosis

<400> SEQUENCE: 34
gtccagcaga tacac 15

<210> SEQ ID NO 35
<211> LENGTH: 27

```
<210> SEQ ID NO 35
<211> LENGTH: 27 (implied)
<212> TYPE: DNA
<213> ORGANISM: Mycobacterium tuberculosis

<400> SEQUENCE: 35
gtacgagaat tcatgtcgca aatcatg                                           27

<210> SEQ ID NO 36
<211> LENGTH: 27
<212> TYPE: DNA
<213> ORGANISM: Mycobacterium tuberculosis

<400> SEQUENCE: 36
gtacgagaat tcgagcttgg ggtgccg                                           27

<210> SEQ ID NO 37
<211> LENGTH: 28
<212> TYPE: DNA
<213> ORGANISM: Mycobacterium tuberculosis

<400> SEQUENCE: 37
cgattccaag cttgtggccg ccgacccg                                          28

<210> SEQ ID NO 38
<211> LENGTH: 30
<212> TYPE: DNA
<213> ORGANISM: Mycobacterium tuberculosis

<400> SEQUENCE: 38
cgttagggat cctcatcgcc atggtgttgg                                        30

<210> SEQ ID NO 39
<211> LENGTH: 26
<212> TYPE: DNA
<213> ORGANISM: Mycobacterium tuberculosis

<400> SEQUENCE: 39
cgttagggat ccggttccac tgtgcc                                            26

<210> SEQ ID NO 40
<211> LENGTH: 28
<212> TYPE: DNA
<213> ORGANISM: Mycobacterium tuberculosis

<400> SEQUENCE: 40
cgttagggat cctcaggtct tttcgatg                                          28

<210> SEQ ID NO 41
<211> LENGTH: 952
<212> TYPE: DNA
<213> ORGANISM: Mycobacterium tuberculosis

<400> SEQUENCE: 41
gaattcgccg ggtgcacaca gccttacacg acggaggtgg acacatgaag ggtcggtcgg       60
cgctgctgcg ggcgctctgg attgccgcac tgtcattcgg gttgggcggt gtcgcggtag      120
ccgcggaacc caccgccaag gccgccccat acgagaacct gatggtgccg tcgccctcga      180
tgggccggga catcccggtg gccttcctag ccggtgggcc gcacgcggtg tatctgctgg      240
acgccttcaa cgccggcccg gatgtcagta actgggtcac cgcgggtaac gcgatgaaca      300 cgttggcgg caagggggatt tcggtggtgg caccggccgg tgtgcgtac agcatgtaca      360 ccaactggga gcaggatggc agcaagcagt gggacaccct cttgtccgct gagctgcccg      420
```

-continued

```
actggctggc cgctaaccgg ggcttggccc ccggtggcca tgcggccgtt ggcgccgctc    480
agggcggtta cggggcgatg cgctggcgg ccttccaccc cgaccgcttc ggcttcgctg    540
gctcgatgtc gggcttttg tacccgtcga acaccaccac caacggtgcg atcgcggcgg    600
gcatgcagca attcggcggt gtggacacca acggaatgtg gggagcacca cagctgggtc    660
ggtggaagtg gcacgacccg tgggtgcatg ccagcctgct ggcgcaaaac aacacccggg    720
tgtgggtgtg gagcccgacc aacccgggag ccagcgatcc cgccgccatg atcggccaaa    780
ccgccgaggc gatgggtaac agccgcatgt tctacaacca gtatcgcagc gtcggcgggc    840
acaacggaca cttcgacttc ccagccagcg gtgacaacgg ctggggctcg tgggcgcccc    900
agctgggcgc tatgtcgggc gatatcgtcg gtgcgatccg ctaagcgaat tc    952
```

<210> SEQ ID NO 42
<211> LENGTH: 299
<212> TYPE: PRT
<213> ORGANISM: Mycobacterium tuberculosis

<400> SEQUENCE: 42

```
Met Lys Gly Arg Ser Ala Leu Leu Arg Ala Leu Trp Ile Ala Ala Leu
  1               5                  10                  15

Ser Phe Gly Leu Gly Gly Val Ala Val Ala Ala Glu Pro Thr Ala Lys
             20                  25                  30

Ala Ala Pro Tyr Glu Asn Leu Met Val Pro Ser Pro Ser Met Gly Arg
         35                  40                  45

Asp Ile Pro Val Ala Phe Leu Ala Gly Gly Pro His Ala Val Tyr Leu
     50                  55                  60

Leu Asp Ala Phe Asn Ala Gly Pro Asp Val Ser Asn Trp Val Thr Ala
 65                  70                  75                  80

Gly Asn Ala Met Asn Thr Leu Ala Gly Lys Gly Ile Ser Val Val Ala
                 85                  90                  95

Pro Ala Gly Gly Ala Tyr Ser Met Tyr Thr Asn Trp Glu Gln Asp Gly
            100                 105                 110

Ser Lys Gln Trp Asp Thr Phe Leu Ser Ala Glu Leu Pro Asp Trp Leu
        115                 120                 125

Ala Ala Asn Arg Gly Leu Ala Pro Gly Gly His Ala Ala Val Gly Ala
    130                 135                 140

Ala Gln Gly Gly Tyr Gly Ala Met Ala Leu Ala Ala Phe His Pro Asp
145                 150                 155                 160

Arg Phe Gly Phe Ala Gly Ser Met Ser Gly Phe Leu Tyr Pro Ser Asn
                165                 170                 175

Thr Thr Thr Asn Gly Ala Ile Ala Ala Gly Met Gln Gln Phe Gly Gly
            180                 185                 190

Val Asp Thr Asn Gly Met Trp Gly Ala Pro Gln Leu Gly Arg Trp Lys
        195                 200                 205

Trp His Asp Pro Trp Val His Ala Ser Leu Leu Ala Gln Asn Asn Thr
    210                 215                 220

Arg Val Trp Val Trp Ser Pro Thr Asn Pro Gly Ala Ser Asp Pro Ala
225                 230                 235                 240

Ala Met Ile Gly Gln Thr Ala Glu Ala Met Gly Asn Ser Arg Met Phe
                245                 250                 255

Tyr Asn Gln Tyr Arg Ser Val Gly Gly His Asn Gly His Phe Asp Phe
            260                 265                 270

Pro Ala Ser Gly Asp Asn Gly Trp Gly Ser Trp Ala Pro Gln Leu Gly
        275                 280                 285
```

Ala Met Ser Gly Asp Ile Val Gly Ala Ile Arg
        290                 295

<210> SEQ ID NO 43
<211> LENGTH: 27
<212> TYPE: DNA
<213> ORGANISM: Mycobacterium tuberculosis

<400> SEQUENCE: 43
gcaacacccg ggatgtcgca aatcatg                                         27

<210> SEQ ID NO 44
<211> LENGTH: 27
<212> TYPE: DNA
<213> ORGANISM: Mycobacterium tuberculosis

<400> SEQUENCE: 44
gtaacacccg gggtggccgc cgacccg                                         27

<210> SEQ ID NO 45
<211> LENGTH: 37
<212> TYPE: DNA
<213> ORGANISM: Mycobacterium tuberculosis

<400> SEQUENCE: 45
ctactaagct tggatcccta gccgccccat ttggcgg                              37

<210> SEQ ID NO 46
<211> LENGTH: 38
<212> TYPE: DNA
<213> ORGANISM: Mycobacterium tuberculosis

<400> SEQUENCE: 46
ctactaagct tccatggtca ggtcttttcg atgcttac                             38

<210> SEQ ID NO 47
<211> LENGTH: 450
<212> TYPE: DNA
<213> ORGANISM: Mycobacterium tuberculosis

<400> SEQUENCE: 47
gtgccgcgct ccccaggggtt cttatggttc gatatacctg agtttgatgg aagtccgatg    60
accagcagtc agcatacggc atggccgaaa agagtggggt gatgatgcc gaggatgttc     120
gcgccgagat cgtggccagc gttctcgaag tcgttgtcaa cgaaggcgat cagatcgaca   180
agggcgacgt cgtggtgctg ctggagtcga tgaagatgga gatccccgtc ctggccgaag   240
ctgccggaac ggtcagcaag gtggcggtat cggtgggcga tgtcattcag gccggcgacc   300
ttatcgcggt gatcagctag tcgttgatag tcactcatgt ccacactcgg tgatctgctc   360
gccgaacaca cggtgctgcc gggcagcgcg gtggaccacc tgcatgcggt ggtcggggag   420
tggcagctcc ttgccgactt gtcgtttgcc                                      450

<210> SEQ ID NO 48
<211> LENGTH: 71
<212> TYPE: PRT
<213> ORGANISM: Mycobacterium tuberculosis

<400> SEQUENCE: 48

Met Ala Glu Asp Val Arg Ala Glu Ile Val Ala Ser Val Leu Glu Val
  1               5                  10                  15

```
Val Val Asn Glu Gly Asp Gln Ile Asp Lys Gly Asp Val Val Val Leu
         20                  25                  30

Leu Glu Ser Met Lys Met Glu Ile Pro Val Leu Ala Glu Ala Ala Gly
         35                  40                  45

Thr Val Ser Lys Val Ala Val Ser Val Gly Asp Val Ile Gln Ala Gly
    50                  55                  60

Asp Leu Ile Ala Val Ile Ser
65                  70

<210> SEQ ID NO 49
<211> LENGTH: 750
<212> TYPE: DNA
<213> ORGANISM: Mycobacterium tuberculosis

<400> SEQUENCE: 49
gggtacccat cgatgggttg cggttcggca ccgaggtgct aacgcacttg ctgacacact    60
gctagtcgaa aacgaggcta gtcgcaacgt cgatcacacg agaggactga ccatgacaac   120
ttcacccgac ccgtatgccg cgctgcccaa gctgccgtcc ttcagcctga cgtcaacctc   180
gatcaccgat gggcagccgc tggctacacc ccaggtcagc gggatcatgg gtgcgggcgg   240
ggcggatgcc agtccgcagc tgaggtggtc gggatttccc agcgagaccc gcagcttcgc   300
ggtaaccgtc tacgaccctg atgcccccac cctgtccggg ttctggcact gggcggtggc   360
caacctgcct gccaacgtca ccgagttgcc cgagggtgtc ggcgatggcc gcgaactgcc   420
gggcggggca ctgacattgg tcaacgacgc cggtatgcgc cggtatgtgg gtgcggcgcc   480
gcctcccggt catggggtgc atcgctacta cgtcgcggta cacgcggtga aggtcgaaaa   540
gctcgacctc cccgaggacg cgagtcctgc atatctggga ttcaacctgt tccagcacgc   600
gattgcacga gcggtcatct tcggcaccta cgagcagcgt tagcgctttta gctgggttgc   660 cgacgtcttg ccgagccgac cgcttcgtgc agcgagccga acccgccgtc atgcagcctg   720
cgggcaatgc cttcatggat gtccttggcc                                    750

<210> SEQ ID NO 50
<211> LENGTH: 176
<212> TYPE: PRT
<213> ORGANISM: Mycobacterium tuberculosis

<400> SEQUENCE: 50

Met Thr Thr Ser Pro Asp Pro Tyr Ala Ala Leu Pro Lys Leu Pro Ser
1               5                  10                  15

Phe Ser Leu Thr Ser Thr Ser Ile Thr Asp Gly Gln Pro Leu Ala Thr
            20                  25                  30

Pro Gln Val Ser Gly Ile Met Gly Ala Gly Ala Asp Ala Ser Pro
         35                  40                  45

Gln Leu Arg Trp Ser Gly Phe Pro Ser Glu Thr Arg Ser Phe Ala Val
    50                  55                  60

Thr Val Tyr Asp Pro Asp Ala Pro Thr Leu Ser Gly Phe Trp His Trp
65                  70                  75                  80

Ala Val Ala Asn Leu Pro Ala Asn Val Thr Glu Leu Pro Glu Gly Val
                85                  90                  95

Gly Asp Gly Arg Glu Leu Pro Gly Gly Ala Leu Thr Leu Val Asn Asp
            100                 105                 110

Ala Gly Met Arg Arg Tyr Val Gly Ala Ala Pro Pro Gly His Gly
        115                 120                 125

Val His Arg Tyr Tyr Val Ala Val His Ala Val Lys Val Glu Lys Leu
```

|      |     | 130 |     |     |     | 135 |     |     |     | 140 |     |
| ---- | --- | --- | --- | --- | --- | --- | --- | --- | --- | --- | --- |

Asp Leu Pro Glu Asp Ala Ser Pro Ala Tyr Leu Gly Phe Asn Leu Phe
145                 150                 155                 160

Gln His Ala Ile Ala Arg Ala Val Ile Phe Gly Thr Tyr Glu Gln Arg
                165                 170                 175

<210> SEQ ID NO 51
<211> LENGTH: 800
<212> TYPE: DNA
<213> ORGANISM: Mycobacterium tuberculosis

<400> SEQUENCE: 51

| tcatgaggtt | catcggggtg | atcccacgcc | cgcagccgca | ttcgggccgc | tggcgagccg | 60  |
| gtgccgcacg | ccgcctcacc | agcctggtgg | ccgccgcctt | tgcggcggcc | acactgttgc | 120 |
| ttaccccgc  | gctggcacca | ccggcatcgg | cgggctgccc | ggatgccgag | gtggtgttcg | 180 |
| cccgcggaac | cggcgaacca | cctggcctcg | gtcgggtagg | ccaagctttc | gtcagttcat | 240 |
| tgcgccagca | gaccaacaag | agcatcggga | catacggagt | caactacccg | gccaacggtg | 300 |
| atttcttggc | cgccgctgac | ggcgcgaacg | acgccagcga | ccacattcag | cagatggcca | 360 |
| gcgcgtgccg | ggccacgagg | ttggtgctcg | gcggctactc | ccagggtgcg | gccgtgatcg | 420 |
| acatcgtcac | cgccgcacca | ctgccccgcc | tcgggttcac | gcagccgttg | ccgcccgcag | 480 |
| cggacgatca | catcgccgcg | atcgccctgt | tcgggaatcc | ctcggccgc  | gctggcgggc | 540 |
| tgatgagcgc | cctgacccct | caattcgggt | ccaagaccat | caacctctgc | aacaacggcg | 600 |
| acccgatttg | ttcggacggc | aaccggtggc | gagcgcacct | aggctacgtg | cccgggatga | 660 |
| ccaaccaggc | ggcgcgtttc | gtcgcgagca | ggatctaacg | cgagccgccc | catagattcc | 720 |
| ggctaagcaa | cggctgcgcc | gccgcccggc | cacgagtgac | cgccgccgac | tggcacaccg | 780 |
| cttaccacgg | ccttatgctg |            |            |            |            | 800 |

<210> SEQ ID NO 52
<211> LENGTH: 226
<212> TYPE: PRT
<213> ORGANISM: Mycobacterium tuberculosis

<400> SEQUENCE: 52

Met Ile Pro Arg Pro Gln Pro His Ser Gly Arg Trp Arg Ala Gly Ala
 1               5                  10                  15

Ala Arg Arg Leu Thr Ser Leu Val Ala Ala Phe Ala Ala Ala Thr
                20                  25                  30

Leu Leu Leu Thr Pro Ala Leu Ala Pro Pro Ala Ser Ala Gly Cys Pro
            35                  40                  45

Asp Ala Glu Val Val Phe Ala Arg Gly Thr Gly Glu Pro Pro Gly Leu
     50                  55                  60

Gly Arg Val Gly Gln Ala Phe Val Ser Ser Leu Arg Gln Gln Thr Asn
 65                  70                  75                  80

Lys Ser Ile Gly Thr Tyr Gly Val Asn Tyr Pro Ala Asn Gly Asp Phe
                85                  90                  95

Leu Ala Ala Ala Asp Gly Ala Asn Asp Ala Ser Asp His Ile Gln Gln
            100                 105                 110

Met Ala Ser Ala Cys Arg Ala Thr Arg Leu Val Leu Gly Gly Tyr Ser
        115                 120                 125

Gln Gly Ala Ala Val Ile Asp Ile Val Thr Ala Ala Pro Leu Pro Gly
    130                 135                 140

```
Leu Gly Phe Thr Gln Pro Leu Pro Pro Ala Ala Asp Asp His Ile Ala
145                 150                 155                 160

Ala Ile Ala Leu Phe Gly Asn Pro Ser Gly Arg Ala Gly Gly Leu Met
                165                 170                 175

Ser Ala Leu Thr Pro Gln Phe Gly Ser Lys Thr Ile Asn Leu Cys Asn
                180                 185                 190

Asn Gly Asp Pro Ile Cys Ser Asp Gly Asn Arg Trp Arg Ala His Leu
            195                 200                 205

Gly Tyr Val Pro Gly Met Thr Asn Gln Ala Ala Arg Phe Val Ala Ser
    210                 215                 220

Arg Ile
225

<210> SEQ ID NO 53
<211> LENGTH: 700
<212> TYPE: DNA
<213> ORGANISM: Mycobacterium tuberculosis

<400> SEQUENCE: 53
ctaggaaagc ctttcctgag taagtattgc cttcgttgca taccgccctt tacctgcgtt    60
aatctgcatt ttatgacaga atacgaaggg cctaagacaa aattccacgc gttaatgcag   120
gaacagattc ataacgaatt cacagcggca caacaatatg tcgcgatcgc ggtttatttc   180
gacagcgaag acctgccgca gttggcgaag cattttttaca gccaagcggt cgaggaacga   240
aaccatgcaa tgatgctcgt gcaacacctg ctcgaccgcg accttcgtgt cgaaattccc   300
ggcgtagaca cggtgcgaaa ccagttcgac agaccccgcg aggcactggc gctggcgctc   360
gatcaggaac gcacagtcac cgaccaggtc ggtcggctga cagcggtggc ccgcgacgag   420
ggcgatttcc tcggcgagca gttcatgcag tggttcttgc aggaacagat cgaagaggtg   480
gccttgatgg caaccctggt gcgggttgcc gatcgggccg gggccaacct gttcgagcta   540
gagaacttcg tcgcacgtga agtggatgtg gcgccggccg catcaggcgc cccgcacgct   600
gccgggggcc gcctctagat ccctggcggg gatcagcgag tggtcccgtt cgcccgcccg   660
tcttccagcc aggccttggt gcggccgggg tggtgagtac                         700

<210> SEQ ID NO 54
<211> LENGTH: 181
<212> TYPE: PRT
<213> ORGANISM: Mycobacterium tuberculosis

<400> SEQUENCE: 54

Met Thr Glu Tyr Glu Gly Pro Lys Thr Lys Phe His Ala Leu Met Gln
1               5                   10                  15

Glu Gln Ile His Asn Glu Phe Thr Ala Ala Gln Gln Tyr Val Ala Ile
                20                  25                  30

Ala Val Tyr Phe Asp Ser Glu Asp Leu Pro Gln Leu Ala Lys His Phe
            35                  40                  45

Tyr Ser Gln Ala Val Glu Glu Arg Asn His Ala Met Met Leu Val Gln
    50                  55                  60

His Leu Leu Asp Arg Asp Leu Arg Val Glu Ile Pro Gly Val Asp Thr
65                  70                  75                  80

Val Arg Asn Gln Phe Asp Arg Pro Arg Glu Ala Leu Ala Leu Ala Leu
                85                  90                  95

Asp Gln Glu Arg Thr Val Thr Asp Gln Val Gly Arg Leu Thr Ala Val
            100                 105                 110
```

Ala Arg Asp Glu Gly Asp Phe Leu Gly Glu Gln Phe Met Gln Trp Phe
        115                 120                 125

Leu Gln Glu Gln Ile Glu Glu Val Ala Leu Met Ala Thr Leu Val Arg
    130                 135                 140

Val Ala Asp Arg Ala Gly Ala Asn Leu Phe Glu Leu Glu Asn Phe Val
145                 150                 155                 160

Ala Arg Glu Val Asp Val Ala Pro Ala Ala Ser Gly Ala Pro His Ala
                165                 170                 175

Ala Gly Gly Arg Leu
            180

<210> SEQ ID NO 55
<211> LENGTH: 950
<212> TYPE: DNA
<213> ORGANISM: Mycobacterium tuberculosis

<400> SEQUENCE: 55
tgggctcggc actggctctc ccacggtggc gcgctgattt ctccccacgg taggcgttgc      60
gacgcatgtt cttcaccgtc tatccacagc taccgacatt tgctccggct ggatcgcggg    120
taaaattccg tcgtgaacaa tcgacccatc cgcctgctga catccggcag ggctggtttg    180
ggtgcgggcg cattgatcac cgccgtcgtc ctgctcatcg ccttgggcgc tgtttggacc    240
ccggttgcct tcgccgatgg atgcccggac gccgaagtca cgttcgcccg cggcaccggc    300
gagccgcccg gaatcgggcg cgttggccag gcgttcgtcg actcgctgcg ccagcagact    360
ggcatggaga tcggagtata cccggtgaat tacgccgcca gccgcctaca gctgcacggg    420
ggagacggcg ccaacgacgc catatcgcac attaagtcca tggcctcgtc atgcccgaac    480
accaagctgg tcttgggcgg ctattcgcag gccgcaaccg tgatcgatat cgtggccggg    540
gttccgttgg gcagcatcag ctttggcagt ccgctacctg cggcatacgc agacaacgtc    600
gcagcggtcg cggtcttcgg caatccgtcc aaccgcgccg gcggatcgct gtcgagcctg    660
agcccgctat tcggttccaa ggcgattgac ctgtgcaatc ccaccgatcc gatctgccat    720
gtgggccccg caacgaatt cagcggacac atcgacggct acatacccac ctacaccacc    780
caggcggcta gtttcgtcgt gcagaggctc cgcgccgggt cggtgccaca tctgcctgga    840
tccgtcccgc agctgcccgg gtctgtcctt cagatgcccg gcactgccgc accggctccc    900
gaatcgctgc acggtcgctg acgctttgtc agtaagccca taaaatcgcg              950

<210> SEQ ID NO 56
<211> LENGTH: 262
<212> TYPE: PRT
<213> ORGANISM: Mycobacterium tuberculosis

<400> SEQUENCE: 56

Met Asn Asn Arg Pro Ile Arg Leu Leu Thr Ser Gly Arg Ala Gly Leu
  1               5                  10                  15

Gly Ala Gly Ala Leu Ile Thr Ala Val Val Leu Leu Ile Ala Leu Gly
                20                  25                  30

Ala Val Trp Thr Pro Val Ala Phe Ala Asp Gly Cys Pro Asp Ala Glu
            35                  40                  45

Val Thr Phe Ala Arg Gly Thr Gly Glu Pro Pro Gly Ile Gly Arg Val
        50                  55                  60

Gly Gln Ala Phe Val Asp Ser Leu Arg Gln Gln Thr Gly Met Glu Ile
 65                  70                  75                  80

Gly Val Tyr Pro Val Asn Tyr Ala Ala Ser Arg Leu Gln Leu His Gly

```
                    85                  90                  95
Gly Asp Gly Ala Asn Asp Ala Ile Ser His Ile Lys Ser Met Ala Ser
                100                 105                 110
Ser Cys Pro Asn Thr Lys Leu Val Leu Gly Gly Tyr Ser Gln Gly Ala
            115                 120                 125
Thr Val Ile Asp Ile Val Ala Gly Val Pro Leu Gly Ser Ile Ser Phe
        130                 135                 140
Gly Ser Pro Leu Pro Ala Ala Tyr Ala Asp Asn Val Ala Ala Val Ala
145                 150                 155                 160
Val Phe Gly Asn Pro Ser Asn Arg Ala Gly Gly Ser Leu Ser Ser Leu
                165                 170                 175
Ser Pro Leu Phe Gly Ser Lys Ala Ile Asp Leu Cys Asn Pro Thr Asp
            180                 185                 190
Pro Ile Cys His Val Gly Pro Gly Asn Glu Phe Ser Gly His Ile Asp
        195                 200                 205
Gly Tyr Ile Pro Thr Tyr Thr Thr Gln Ala Ala Ser Phe Val Val Gln
    210                 215                 220
Arg Leu Arg Ala Gly Ser Val Pro His Leu Pro Gly Ser Val Pro Gln
225                 230                 235                 240
Leu Pro Gly Ser Val Leu Gln Met Pro Gly Thr Ala Ala Pro Ala Pro
                245                 250                 255
Glu Ser Leu His Gly Arg
                260

<210> SEQ ID NO 57
<211> LENGTH: 1000
<212> TYPE: DNA
<213> ORGANISM: Mycobacterium tuberculosis

<400> SEQUENCE: 57
cgaggagacc gacgatctgc tcgacgaaat cgacgacgtc ctcgaggaga acgccgagga      60
cttcgtccgc gcatacgtcc aaaagggcgg acagtgacct ggccgttgcc cgatcgcctg     120
tccattaatt cactctctgg aacacccgct gtagacctat cttctttcac tgacttcctg     180
cgccgccagg cgccggagtt gctgccggca agcatcagcg gcggtgcgcc actcgcaggc     240
ggcgatgcgc aactgccgca cggcaccacc attgtcgcgc tgaaataccc cggcggtgtt     300
gtcatggcgg gtgaccggcg ttcgacgcag gcaacatgat ttctgggcg tgatgtgcgc      360 aaggtgtata tcaccgatga ctacaccgct accggcatcc tggcacggc tgcggtcgcg      420 gttgagtttg cccggctgta tgccgtggaa cttgagcact acgagaagct cgagggtgtg     480
ccgctgacgt ttgccggcaa aatcaaccgg ctggcgatta tggtgcgtgg caatctggcg     540
gccgcgatgc agggtctgct ggcgttgccg ttgctggcgg gctacgacat tcatgcgtct     600
gacccgcaga gcgcgggtcg tatcgtttcg ttcgacgccg ccggcggttg gaacatcgag     660
gaagagggct atcaggcggt gggctcgggt tcgctgttcg cgaagtcgtc gatgaagaag     720
ttgtattcgc aggttaccga cggtgattcg gggctgcggg tggcggtcga ggcgctctac     780
gacgccgccg acgacgactc cgccaccggc ggtccggacc tggtgcgggg catctttccg     840
acggcggtga tcatcgacgc cgacggggcg gttgacgtgc cggagagccg gattgccgaa     900
ttggcccgcg cgatcatcga aagccgttcg ggtgcggata ctttcggctc cgatggcggt     960
gagaagtgag ttttccgtat ttcatctcgc ctgagcaggc                          1000

<210> SEQ ID NO 58
```

-continued

```
<211> LENGTH: 291
<212> TYPE: PRT
<213> ORGANISM: Mycobacterium tuberculosis

<400> SEQUENCE: 58

Met Thr Trp Pro Leu Pro Asp Arg Leu Ser Ile Asn Ser Leu Ser Gly
  1               5                  10                  15

Thr Pro Ala Val Asp Leu Ser Ser Phe Thr Asp Phe Leu Arg Arg Gln
             20                  25                  30

Ala Pro Glu Leu Leu Pro Ala Ser Ile Ser Gly Gly Ala Pro Leu Ala
         35                  40                  45

Gly Gly Asp Ala Gln Leu Pro His Gly Thr Thr Ile Val Ala Leu Lys
 50                  55                  60

Tyr Pro Gly Gly Val Val Met Ala Gly Asp Arg Arg Ser Thr Gln Gly
 65                  70                  75                  80

Asn Met Ile Ser Gly Arg Asp Val Arg Lys Val Tyr Ile Thr Asp Asp
             85                  90                  95

Tyr Thr Ala Thr Gly Ile Ala Gly Thr Ala Ala Val Ala Val Glu Phe
            100                 105                 110

Ala Arg Leu Tyr Ala Val Glu Leu Glu His Tyr Glu Lys Leu Glu Gly
        115                 120                 125

Val Pro Leu Thr Phe Ala Gly Lys Ile Asn Arg Leu Ala Ile Met Val
130                 135                 140

Arg Gly Asn Leu Ala Ala Ala Met Gln Gly Leu Leu Ala Leu Pro Leu
145                 150                 155                 160

Leu Ala Gly Tyr Asp Ile His Ala Ser Asp Pro Gln Ser Ala Gly Arg
                165                 170                 175

Ile Val Ser Phe Asp Ala Ala Gly Gly Trp Asn Ile Glu Glu Glu Gly
            180                 185                 190

Tyr Gln Ala Val Gly Ser Gly Ser Leu Phe Ala Lys Ser Ser Met Lys
        195                 200                 205

Lys Leu Tyr Ser Gln Val Thr Asp Gly Asp Ser Gly Leu Arg Val Ala
210                 215                 220

Val Glu Ala Leu Tyr Asp Ala Ala Asp Asp Ser Ala Thr Gly Gly
225                 230                 235                 240

Pro Asp Leu Val Arg Gly Ile Phe Pro Thr Ala Val Ile Ile Asp Ala
                245                 250                 255

Asp Gly Ala Val Asp Val Pro Glu Ser Arg Ile Ala Glu Leu Ala Arg
            260                 265                 270

Ala Ile Ile Glu Ser Arg Ser Gly Ala Asp Thr Phe Gly Ser Asp Gly
        275                 280                 285

Gly Glu Lys
    290

<210> SEQ ID NO 59
<211> LENGTH: 900
<212> TYPE: DNA
<213> ORGANISM: Mycobacterium tuberculosis

<400> SEQUENCE: 59
ttggcccgcg cgatcatcga aagccgttcg ggtgcggata ctttcggctc cgatggcggt     60
gagaagtgag ttttccgtat ttcatctcgc ctgagcaggc gatgcgcgag cgcagcgagt    120
tggcgcgtaa gggcattgcg cgggccaaaa gcgtggtggc gctggcctat gccggtggtg    180
tgctgttcgt cgcggagaat ccgtcgcggt cgctgcagaa gatcagtgag ctctacgatc    240
```

-continued

```
gggtggtttt tgcggctgcg ggcaagttca acgagttcga caatttgcgc cgcggcggga    300
tccagttcgc cgacacccgc ggttacgcct atgaccgtcg tgacgtcacg ggtcggcagt    360
tggccaatgt ctacgcgcag actctaggca ccatcttcac cgaacaggcc aagccctacg    420
aggttgagtt gtgtgtggcc gaggtggcgc attacggcga gacgaaacgc cctgagttgt    480
atcgtattac ctacgacggg tcgatcgccg acgagccgca tttcgtggtg atgggcggca    540
ccacggagcc gatcgccaac gcgctcaaag agtcgtatgc cgagaacgcc agcctgaccg    600
acgccctgcg tatcgcggtc gctgcattgc gggccggcag tgccgacacc tcgggtggtg    660
atcaacccac ccttggcgtg gccagcttag aggtggccgt tctcgatgcc aaccggccac    720
ggcgcgcgtt ccggcgcatc accggctccg ccctgcaagc gttgctggta gaccaggaaa    780
gcccgcagtc tgacggcgaa tcgtcgggct gagtccgaaa gtccgacgcg tgtctgggac    840
cccgctgcga cgttaactgc gcctaacccc ggctcgacgc gtcgccggcc gtcctgactt    900
```

<210> SEQ ID NO 60
<211> LENGTH: 248
<212> TYPE: PRT
<213> ORGANISM: Mycobacterium tuberculosis

<400> SEQUENCE: 60

```
Met Ser Phe Pro Tyr Phe Ile Ser Pro Glu Gln Ala Met Arg Glu Arg
  1               5                  10                  15

Ser Glu Leu Ala Arg Lys Gly Ile Ala Arg Ala Lys Ser Val Val Ala
             20                  25                  30

Leu Ala Tyr Ala Gly Gly Val Leu Phe Val Ala Glu Asn Pro Ser Arg
         35                  40                  45

Ser Leu Gln Lys Ile Ser Glu Leu Tyr Asp Arg Val Gly Phe Ala Ala
     50                  55                  60

Ala Gly Lys Phe Asn Glu Phe Asp Asn Leu Arg Arg Gly Gly Ile Gln
 65                  70                  75                  80

Phe Ala Asp Thr Arg Gly Tyr Ala Tyr Asp Arg Arg Asp Val Thr Gly
                 85                  90                  95

Arg Gln Leu Ala Asn Val Tyr Ala Gln Thr Leu Gly Thr Ile Phe Thr
            100                 105                 110

Glu Gln Ala Lys Pro Tyr Glu Val Glu Leu Cys Val Ala Glu Val Ala
        115                 120                 125

His Tyr Gly Glu Thr Lys Arg Pro Glu Leu Tyr Arg Ile Thr Tyr Asp
    130                 135                 140

Gly Ser Ile Ala Asp Glu Pro His Phe Val Val Met Gly Gly Thr Thr
145                 150                 155                 160

Glu Pro Ile Ala Asn Ala Leu Lys Glu Ser Tyr Ala Glu Asn Ala Ser
                165                 170                 175

Leu Thr Asp Ala Leu Arg Ile Ala Val Ala Ala Leu Arg Ala Gly Ser
            180                 185                 190

Ala Asp Thr Ser Gly Gly Asp Gln Pro Thr Leu Gly Val Ala Ser Leu
        195                 200                 205

Glu Val Ala Val Leu Asp Ala Asn Arg Pro Arg Arg Ala Phe Arg Arg
    210                 215                 220

Ile Thr Gly Ser Ala Leu Gln Ala Leu Leu Val Asp Gln Glu Ser Pro
225                 230                 235                 240

Gln Ser Asp Gly Glu Ser Ser Gly
                245
```

```
<210> SEQ ID NO 61
<211> LENGTH: 1560
<212> TYPE: DNA
<213> ORGANISM: Mycobacterium tuberculosis

<400> SEQUENCE: 61
gagtcattgc ctggtcggcg tcattccgta ctagtcggtt gtcggacttg acctactggg      60
tcaggccgac gagcactcga ccattagggt aggggccgtg acccactatg acgtcgtcgt     120
tctcggagcc ggtcccggcg ggtatgtcgc ggcgattcgc gccgcacagc tcggcctgag     180
cactgcaatc gtcgaaccca agtactgggg cggagtatgc ctcaatgtcg gctgtatccc     240
atccaaggcg ctgttgcgca acgccgaact ggtccacatc ttcaccaagg acgccaaagc     300
atttggcatc agcggcgagg tgaccttcga ctacggcatc gcctatgacc gcagccgaaa     360
ggtagccgag ggcagggtgg ccggtgtgca cttcctgatg aagaagaaca agatcaccga     420
gatccacggg tacggcacat tgccgacgc caacacgttg ttggttgatc tcaacgacgg     480
cggtacagaa tcggtcacgt tcgacaacgc catcatcgcg accggcagta gcacccggct     540
ggttcccggc acctcactgt cggccaacgt agtcacctac gaggaacaga tcctgtcccg     600
agagctgccg aaatcgatca ttattgccgg agctggtgcc attggcatgg agttcggcta     660
cgtgctgaag aactacggcg ttgacgtgac catcgtggaa ttccttccgc gggcgctgcc     720
caacgaggac gccgatgtgt ccaaggagat cgagaagcag ttcaaaaagc tgggtgtcac     780
gatcctgacc gccacgaagg tcgagtccat cgccgatggc gggtcgcagg tcaccgtgac     840
cgtcaccaag gacggcgtgg cgcaagagct taaggcggaa aaggtgttgc aggccatcgg     900
atttgcgccc aacgtcgaag ggtacgggct ggacaaggca ggcgtcgcgc tgaccgaccg     960
caaggctatc ggtgtcgacg actacatgcg taccaacgtg ggccacatct acgctatcgg    1020
cgatgtcaat ggattactgc agctggcgca cgtcgccgag gcacaaggcg tggtagccgc    1080
cgaaaccatt gccggtgcag agactttgac gctgggcgac catcggatgt tgccgcgcgc    1140
gacgttctgt cagccaaacg ttgccagctt cgggctcacc gagcagcaag cccgcaacga    1200
aggttacgac gtggtggtgg ccaagttccc gttcacggcc aacgccaagg cgcacggcgt    1260
gggtgacccc agtgggttcg tcaagctggt ggccgacgcc aagcacgcg agctactggg    1320 tgggcacctg gtcggccacg acgtggccga gctgctgccg gagctcacgc tggcgcagag    1380
gtgggacctg accgccagcg agctggctcg caacgtccac acccacccaa cgatgtctga    1440
ggcgctgcag gagtgcttcc acggcctggt tggccacatg atcaatttct gagcggctca    1500
tgacgaggcg cgcgagcact gacacccccc agatcatcat gggtgccatc ggtggtgtgg    1560

<210> SEQ ID NO 62
<211> LENGTH: 464
<212> TYPE: PRT
<213> ORGANISM: Mycobacterium tuberculosis

<400> SEQUENCE: 62

Met Thr His Tyr Asp Val Val Leu Gly Ala Gly Pro Gly Gly Tyr
 1               5                  10                  15

Val Ala Ala Ile Arg Ala Ala Gln Leu Gly Leu Ser Thr Ala Ile Val
             20                  25                  30

Glu Pro Lys Tyr Trp Gly Gly Val Cys Leu Asn Val Gly Cys Ile Pro
         35                  40                  45

Ser Lys Ala Leu Leu Arg Asn Ala Glu Leu Val His Ile Phe Thr Lys
     50                  55                  60
```

-continued

Asp Ala Lys Ala Phe Gly Ile Ser Gly Glu Val Thr Phe Asp Tyr Gly
65                  70                  75                  80

Ile Ala Tyr Asp Arg Ser Arg Lys Val Ala Glu Gly Arg Val Ala Gly
            85                  90                  95

Val His Phe Leu Met Lys Lys Asn Lys Ile Thr Glu Ile His Gly Tyr
                100                 105                 110

Gly Thr Phe Ala Asp Ala Asn Thr Leu Leu Val Asp Leu Asn Asp Gly
        115                 120                 125

Gly Thr Glu Ser Val Thr Phe Asp Asn Ala Ile Ile Ala Thr Gly Ser
    130                 135                 140

Ser Thr Arg Leu Val Pro Gly Thr Ser Leu Ser Ala Asn Val Val Thr
145                 150                 155                 160

Tyr Glu Glu Gln Ile Leu Ser Arg Glu Leu Pro Lys Ser Ile Ile Ile
                165                 170                 175

Ala Gly Ala Gly Ala Ile Gly Met Glu Phe Gly Tyr Val Leu Lys Asn
            180                 185                 190

Tyr Gly Val Asp Val Thr Ile Val Glu Phe Leu Pro Arg Ala Leu Pro
        195                 200                 205

Asn Glu Asp Ala Asp Val Ser Lys Glu Ile Glu Lys Gln Phe Lys Lys
    210                 215                 220

Leu Gly Val Thr Ile Leu Thr Ala Thr Lys Val Glu Ser Ile Ala Asp
225                 230                 235                 240

Gly Gly Ser Gln Val Thr Val Thr Val Thr Lys Asp Gly Val Ala Gln
                245                 250                 255

Glu Leu Lys Ala Glu Lys Val Leu Gln Ala Ile Gly Phe Ala Pro Asn
            260                 265                 270

Val Glu Gly Tyr Gly Leu Asp Lys Ala Gly Val Ala Leu Thr Asp Arg
        275                 280                 285

Lys Ala Ile Gly Val Asp Asp Tyr Met Arg Thr Asn Val Gly His Ile
    290                 295                 300

Tyr Ala Ile Gly Asp Val Asn Gly Leu Leu Gln Leu Ala His Val Ala
305                 310                 315                 320

Glu Ala Gln Gly Val Val Ala Ala Glu Thr Ile Ala Gly Ala Glu Thr
                325                 330                 335

Leu Thr Leu Gly Asp His Arg Met Leu Pro Arg Ala Thr Phe Cys Gln
            340                 345                 350

Pro Asn Val Ala Ser Phe Gly Leu Thr Glu Gln Gln Ala Arg Asn Glu
        355                 360                 365

Gly Tyr Asp Val Val Ala Lys Phe Pro Phe Thr Ala Asn Ala Lys
    370                 375                 380

Ala His Gly Val Gly Asp Pro Ser Gly Phe Val Lys Leu Val Ala Asp
385                 390                 395                 400

Ala Lys His Gly Glu Leu Leu Gly Gly His Leu Val Gly His Asp Val
                405                 410                 415

Ala Glu Leu Leu Pro Glu Leu Thr Leu Ala Gln Arg Trp Asp Leu Thr
            420                 425                 430

Ala Ser Glu Leu Ala Arg Asn Val His Thr His Pro Thr Met Ser Glu
        435                 440                 445

Ala Leu Gln Glu Cys Phe His Gly Leu Val Gly His Met Ile Asn Phe
    450                 455                 460

<210> SEQ ID NO 63
<211> LENGTH: 550
<212> TYPE: DNA

-continued

<213> ORGANISM: Mycobacterium tuberculosis

<400> SEQUENCE: 63

```
ggcccggctc gcggccgccc tgcaggaaaa gaaggcctgc ccaggcccag actcagccga      60
gtagtcaccc agtaccccac accaggaagg accgcccatc atggcaaagc tctccaccga     120
cgaactgctg gacgcgttca aggaaatgac cctgttggag ctctccgact cgtcaagaa      180
gttcgaggag accttcgagg tcaccgccgc cgctccagtc gccgtcgccg ccgccggtgc     240
cgccccggcc ggtgccgccg tcgaggctgc gaggagcag tccgagttcg acgtgatcct      300
tgaggccgcc ggcgacaaga agatcggcgt catcaaggtg gtccgggaga tcgtttccgg     360
cctgggcctc aaggaggcca aggacctggt cgacggcgcg cccaagccgc tgctggagaa     420
ggtcgccaag gaggccgccg acgaggccaa ggccaagctg gaggccgccg gcgccaccgt     480
caccgtcaag tagctctgcc cagcgtgttc ttttgcgtct gctcggcccg tagcgaacac     540
tgcgcccgct                                                            550
```

<210> SEQ ID NO 64
<211> LENGTH: 130
<212> TYPE: PRT
<213> ORGANISM: Mycobacterium tuberculosis

<400> SEQUENCE: 64

```
Met Ala Lys Leu Ser Thr Asp Glu Leu Leu Asp Ala Phe Lys Glu Met
  1               5                  10                  15
Thr Leu Leu Glu Leu Ser Asp Phe Val Lys Lys Phe Glu Glu Thr Phe
                 20                  25                  30
Glu Val Thr Ala Ala Ala Pro Val Ala Val Ala Ala Ala Gly Ala Ala
             35                  40                  45
Pro Ala Gly Ala Ala Val Glu Ala Ala Glu Glu Gln Ser Glu Phe Asp
         50                  55                  60
Val Ile Leu Glu Ala Ala Gly Asp Lys Lys Ile Gly Val Ile Lys Val
 65                  70                  75                  80
Val Arg Glu Ile Val Ser Gly Leu Gly Leu Lys Glu Ala Lys Asp Leu
                 85                  90                  95
Val Asp Gly Ala Pro Lys Pro Leu Leu Glu Lys Val Ala Lys Glu Ala
                100                 105                 110
Ala Asp Glu Ala Lys Ala Lys Leu Glu Ala Ala Gly Ala Thr Val Thr
            115                 120                 125
Val Lys
    130
```

<210> SEQ ID NO 65
<211> LENGTH: 900
<212> TYPE: DNA
<213> ORGANISM: Mycobacterium tuberculosis

<400> SEQUENCE: 65

```
tgaacgccat cgggtccaac gaacgcagcg ctacctgatc accaccgggt ctgttagggc      60
tcttccccag gtcgtacagt cgggccatgg ccattgaggt ttcggtgttg cgggttttca     120
ccgattcaga cgggaatttc ggtaatccgc tgggggtgat caacgccagc aaggtcgaac     180
accgcgacag gcagcagctg gcagcccaat cgggctacag cgaaaccata ttcgtcgatc     240
ttcccagccc cggctcaacc accgcacacg ccaccatcca tactccccgc accgaaattc     300
cgttcgccgg acacccgacc gtgggagcgt cctggtggct gcgcgagagg gggacgccaa     360
```

```
ttaacacgct gcaggtgccg gccggcatcg tccaggtgag ctaccacggt gatctcaccg      420
ccatcagcgc ccgctcggaa tgggcacccg agttcgccat ccacgacctg gattcacttg      480
atgcgcttgc cgccgccgac cccgccgact tccggacgga catcgcgcac tacctctgga      540
cctggaccga ccgctccgct ggctcgctgc gcgcccgcat gtttgccgcc aacttgggcg      600
tcaccgaaga cgaagcgacc ggtgccgcgg ccatccggat taccgattac ctcagccgtg      660
acctcaccat cacccagggc aaaggatcgt tgatccacac cacctggagt cccgagggct      720
gggttcgggt agccggccga gttgtcagcg acggtgtggc acaactcgac tgacgtagag      780
ctcagcgctg ccgatgcaac acggcggcaa ggtgatcctg caggggttgc ccgaccgcgc      840
gcatctgcaa cgagtacgaa agctcgtcgc cgtcgatgcg gtaggaacgg tcaagggcgg      900

<210> SEQ ID NO 66
<211> LENGTH: 228
<212> TYPE: PRT
<213> ORGANISM: Mycobacterium tuberculosis

<400> SEQUENCE: 66

Met Ala Ile Glu Val Ser Val Leu Arg Val Phe Thr Asp Ser Asp Gly
  1               5                  10                  15

Asn Phe Gly Asn Pro Leu Gly Val Ile Asn Ala Ser Lys Val Glu His
             20                  25                  30

Arg Asp Arg Gln Gln Leu Ala Ala Gln Ser Gly Tyr Ser Glu Thr Ile
         35                  40                  45

Phe Val Asp Leu Pro Ser Pro Gly Ser Thr Thr Ala His Ala Thr Ile
     50                  55                  60

His Thr Pro Arg Thr Glu Ile Pro Phe Ala Gly His Pro Thr Val Gly
 65                  70                  75                  80

Ala Ser Trp Trp Leu Arg Glu Arg Gly Thr Pro Ile Asn Thr Leu Gln
                 85                  90                  95

Val Pro Ala Gly Ile Val Gln Val Ser Tyr His Gly Asp Leu Thr Ala
            100                 105                 110

Ile Ser Ala Arg Ser Glu Trp Ala Pro Glu Phe Ala Ile His Asp Leu
        115                 120                 125

Asp Ser Leu Asp Ala Leu Ala Ala Asp Pro Ala Asp Phe Pro Asp
    130                 135                 140

Asp Ile Ala His Tyr Leu Trp Thr Trp Thr Asp Arg Ser Ala Gly Ser
145                 150                 155                 160

Leu Arg Ala Arg Met Phe Ala Ala Asn Leu Gly Val Thr Glu Asp Glu
                165                 170                 175

Ala Thr Gly Ala Ala Ala Ile Arg Ile Thr Asp Tyr Leu Ser Arg Asp
            180                 185                 190

Leu Thr Ile Thr Gln Gly Lys Gly Ser Leu Ile His Thr Thr Trp Ser
        195                 200                 205

Pro Glu Gly Trp Val Arg Val Ala Gly Arg Val Val Ser Asp Gly Val
    210                 215                 220

Ala Gln Leu Asp
225

<210> SEQ ID NO 67
<211> LENGTH: 500
<212> TYPE: DNA
<213> ORGANISM: Mycobacterium tuberculosis

<400> SEQUENCE: 67
```

-continued

```
gtttgtggtg tcggtggtct ggggggcgcc aactgggatt cggttggggt gggtgcaggt     60
ccggcgatgg gcatcggagg tgtgggtggt ttgggtgggg ccggttcggg tccggcgatg    120
ggcatggggg gtgtgggtgg tttgggtggg gccggttcgg gtccggcgat gggcatgggg    180
ggtgtgggtg gtttagatgc ggccggttcc ggcgagggcg gctctcctgc ggcgatcggc    240
atcggagttg gcggaggcgg aggtgggggt gggggtggcg gcggcggggc cgacacgaac    300
cgctccgaca ggtcgtcgga cgtcgggggc ggagtctggc cgttgggctt cggtaggttt    360
gccgatgcgg gcgccggcgg aaacgaagca ctggggtcga agaacggctg cgctgccata    420
tcgtccggag cttccatacc ttcgtgcggc cggaagagct tgtcgtagtc ggccgccatg    480
acaacctctc agagtgcgct                                                500
```

<210> SEQ ID NO 68
<211> LENGTH: 139
<212> TYPE: PRT
<213> ORGANISM: Mycobacterium tuberculosis

<400> SEQUENCE: 68

```
Met Gly Ala Gly Pro Ala Met Gly Ile Gly Gly Val Gly Gly Leu Gly
  1               5                  10                  15

Gly Ala Gly Ser Gly Pro Ala Met Gly Met Gly Gly Val Gly Gly Leu
             20                  25                  30

Gly Gly Ala Gly Ser Gly Pro Ala Met Gly Met Gly Gly Val Gly Gly
         35                  40                  45

Leu Asp Ala Ala Gly Ser Gly Glu Gly Gly Ser Pro Ala Ala Ile Gly
     50                  55                  60

Ile Gly Val Gly Gly Gly Gly Gly Gly Gly Gly Gly Gly Gly Gly Gly
 65                  70                  75                  80

Ala Asp Thr Asn Arg Ser Asp Arg Ser Ser Asp Val Gly Gly Gly Val
                 85                  90                  95

Trp Pro Leu Gly Phe Gly Arg Phe Ala Asp Ala Gly Ala Gly Gly Asn
            100                 105                 110

Glu Ala Leu Gly Ser Lys Asn Gly Cys Ala Ala Ile Ser Ser Gly Ala
        115                 120                 125

Ser Ile Pro Ser Cys Gly Arg Lys Ser Leu Ser
    130                 135
```

<210> SEQ ID NO 69
<211> LENGTH: 2050
<212> TYPE: DNA
<213> ORGANISM: Mycobacterium tuberculosis

<400> SEQUENCE: 69

```
agcgcactct gagaggttgt catggcggcc gactacgaca agctcttccg gccgcacgaa     60
ggtatggaag ctccggacga tatggcagcg cagccgttct tcgaccccag tgcttcgttt    120
ccgccggcgc ccgcatcggc aaacctaccg aagcccaacg gccagactcc gcccccgacg    180
tccgacgacc tgtcggagcg gttcgtgtcg gccccgccgc cgccaccccc acccccacct    240
ccgcctccgc caactccgat gccgatcgcc gcaggagagc cgccctcgcc ggaaccggcc    300
gcatctaaac cacccacacc ccccatgccc atcgccggac ccgaaccggc cccacccaaa    360
ccacccacac cccccatgcc catcgccgga cccgaaccgg ccccacccaa accacccaca    420
cctccgatgc ccatcgccgg acctgcaccc accccaaccg aatcccagtt ggcgcccccc    480
agaccaccga caccacaaac gccaaccgga gcgccgcagc aaccggaatc accggcgccc    540
```

-continued

```
cacgtaccct cgcacgggcc acatcaaccc cggcgcaccg caccagcacc gccctgggca    600
aagatgccaa tcggcgaacc cccgcccgct ccgtccagac cgtctgcgtc cccggccgaa    660
ccaccgaccc ggcctgcccc ccaacactcc cgacgtgcgc gccggggtca ccgctatcgc    720
acagacaccg aacgaaacgt cgggaaggta gcaactggtc catccatcca ggcgcggctg    780
cgggcagagg aagcatccgg cgcgcagctc gcccccggaa cggagccctc gccagcgccg    840
ttgggccaac cgagatcgta tctggctccg cccacccgcc ccgcgccgac agaacctccc    900
cccagcccct cgccgcagcg caactccggt cggcgtgccg agcgacgcgt ccaccccgat    960
ttagccgccc aacatgccgc ggcgcaacct gattcaatta cggccgcaac cactggcggt   1020
cgtcgccgca agcgtgcagc gccggatctc gacgcgacac agaaatcctt aaggccggcg   1080
gccaagggc cgaaggtgaa gaaggtgaag ccccagaaac cgaaggccac gaagccgccc    1140
aaagtggtgt cgcagcgcgg ctggcgacat tgggtgcatg cgttgacgcg aatcaacctg   1200
ggcctgtcac ccgacgagaa gtacgagctg gacctgcacg ctcgagtccg ccgcaatccc   1260
cgcgggtcgt atcagatcgc cgtcgtcggt ctcaaaggtg gggctggcaa accacgctg    1320
acagcagcgt tggggtcgac gttggctcag gtgcgggccg accggatcct ggctctagac   1380
gcggatccag gcgccggaaa cctcgccgat cgggtagggc gacaatcggg cgcgaccatc   1440
gctgatgtgc ttgcagaaaa agagctgtcg cactacaacg acatccgcgc acacactagc   1500
gtcaatgcgg tcaatctgga agtgctgccg gcaccggaat acagctcggc gcagcgcgcg   1560
ctcagcgacg ccgactggca tttcatcgcc gatcctgcgt cgaggtttta caacctcgtc   1620
ttggctgatt gtggggccgg cttcttcgac ccgctgaccc gcggcgtgct gtccacggtg   1680
tccggtgtcg tggtcgtggc aagtgtctca atcgacggcg cacaacaggc gtcggtcgcg   1740
ttggactggt tgcgcaacaa cggttaccaa gatttggcga gccgcgcatg cgtggtcatc   1800
aatcacatca tgccgggaga acccaatgtc gcagttaaag acctggtgcg gcatttcgaa   1860
cagcaagttc aacccggccg ggtcgtggtc atgccgtggg acaggcacat tgcggccgga   1920
accgagattt cactcgactt gctcgaccct atctacaagc gcaaggtcct cgaattggcc   1980
gcagcgctat ccgacgattt cgagagggct ggacgtcgtt gagcgcacct gctgttgctg   2040
ctggtcctac                                                          2050
```

<210> SEQ ID NO 70
<211> LENGTH: 666
<212> TYPE: PRT
<213> ORGANISM: Mycobacterium tuberculosis

<400> SEQUENCE: 70

```
Met Ala Ala Asp Tyr Asp Lys Leu Phe Arg Pro His Glu Gly Met Glu
  1               5                  10                  15

Ala Pro Asp Asp Met Ala Ala Gln Pro Phe Phe Asp Pro Ser Ala Ser
             20                  25                  30

Phe Pro Pro Ala Pro Ala Ser Ala Asn Leu Pro Lys Pro Asn Gly Gln
         35                  40                  45

Thr Pro Pro Pro Thr Ser Asp Asp Leu Ser Glu Arg Phe Val Ser Ala
     50                  55                  60

Pro Pro Pro Pro Pro Pro Pro Pro Pro Pro Pro Thr Pro Met
 65                  70                  75                  80

Pro Ile Ala Ala Gly Glu Pro Pro Ser Pro Glu Pro Ala Ala Ser Lys
                 85                  90                  95

Pro Pro Thr Pro Pro Met Pro Ile Ala Gly Pro Glu Pro Ala Pro Pro
```

-continued

```
            100                 105                 110
Lys Pro Pro Thr Pro Pro Met Pro Ile Ala Gly Pro Glu Pro Ala Pro
            115                 120                 125

Pro Lys Pro Pro Thr Pro Pro Met Pro Ile Ala Gly Pro Ala Pro Thr
130                 135                 140

Pro Thr Glu Ser Gln Leu Ala Pro Pro Arg Pro Pro Thr Pro Gln Thr
145                 150                 155                 160

Pro Thr Gly Ala Pro Gln Gln Pro Glu Ser Pro Ala Pro His Val Pro
                165                 170                 175

Ser His Gly Pro His Gln Pro Arg Arg Thr Ala Pro Ala Pro Pro Trp
                180                 185                 190

Ala Lys Met Pro Ile Gly Glu Pro Pro Ala Pro Ser Arg Pro Ser
            195                 200                 205

Ala Ser Pro Ala Glu Pro Pro Thr Arg Pro Ala Pro Gln His Ser Arg
            210                 215                 220

Arg Ala Arg Arg Gly His Arg Tyr Arg Thr Asp Thr Glu Arg Asn Val
225                 230                 235                 240

Gly Lys Val Ala Thr Gly Pro Ser Ile Gln Ala Arg Leu Arg Ala Glu
                245                 250                 255

Glu Ala Ser Gly Ala Gln Leu Ala Pro Gly Thr Glu Pro Ser Pro Ala
                260                 265                 270

Pro Leu Gly Gln Pro Arg Ser Tyr Leu Ala Pro Pro Thr Arg Pro Ala
            275                 280                 285

Pro Thr Glu Pro Pro Ser Pro Ser Pro Gln Arg Asn Ser Gly Arg
            290                 295                 300

Arg Ala Glu Arg Arg Val His Pro Asp Leu Ala Ala Gln His Ala Ala
305                 310                 315                 320

Ala Gln Pro Asp Ser Ile Thr Ala Ala Thr Thr Gly Arg Arg
                325                 330                 335

Lys Arg Ala Ala Pro Asp Leu Asp Ala Thr Gln Lys Ser Leu Arg Pro
            340                 345                 350

Ala Ala Lys Gly Pro Lys Val Lys Val Lys Pro Gln Lys Pro Lys
            355                 360                 365

Ala Thr Lys Pro Pro Lys Val Val Ser Gln Arg Gly Trp Arg His Trp
370                 375                 380

Val His Ala Leu Thr Arg Ile Asn Leu Gly Leu Ser Pro Asp Glu Lys
385                 390                 395                 400

Tyr Glu Leu Asp Leu His Ala Arg Val Arg Arg Asn Pro Arg Gly Ser
                405                 410                 415

Tyr Gln Ile Ala Val Val Gly Leu Lys Gly Gly Ala Gly Lys Thr Thr
                420                 425                 430

Leu Thr Ala Ala Leu Gly Ser Thr Leu Ala Gln Val Arg Ala Asp Arg
            435                 440                 445

Ile Leu Ala Leu Asp Ala Asp Pro Gly Ala Gly Asn Leu Ala Asp Arg
            450                 455                 460

Val Gly Arg Gln Ser Gly Ala Thr Ile Ala Asp Val Leu Ala Glu Lys
465                 470                 475                 480

Glu Leu Ser His Tyr Asn Asp Ile Arg Ala His Thr Ser Val Asn Ala
                485                 490                 495

Val Asn Leu Glu Val Leu Pro Ala Pro Glu Tyr Ser Ser Ala Gln Arg
                500                 505                 510

Ala Leu Ser Asp Ala Asp Trp His Phe Ile Ala Asp Pro Ala Ser Arg
            515                 520                 525
```

```
Phe Tyr Asn Leu Val Leu Ala Asp Cys Gly Ala Gly Phe Phe Asp Pro
    530                 535                 540

Leu Thr Arg Gly Val Leu Ser Thr Val Ser Gly Val Val Val Ala
545                 550                 555                 560

Ser Val Ser Ile Asp Gly Ala Gln Gln Ala Ser Val Ala Leu Asp Trp
                565                 570                 575

Leu Arg Asn Asn Gly Tyr Gln Asp Leu Ala Ser Arg Ala Cys Val Val
            580                 585                 590

Ile Asn His Ile Met Pro Gly Glu Pro Asn Val Ala Val Lys Asp Leu
        595                 600                 605

Val Arg His Phe Glu Gln Gln Val Gln Pro Gly Arg Val Val Val Met
610                 615                 620

Pro Trp Asp Arg His Ile Ala Ala Gly Thr Glu Ile Ser Leu Asp Leu
625                 630                 635                 640

Leu Asp Pro Ile Tyr Lys Arg Lys Val Leu Glu Leu Ala Ala Ala Leu
                645                 650                 655

Ser Asp Asp Phe Glu Arg Ala Gly Arg Arg
            660                 665
```

<210> SEQ ID NO 71
<211> LENGTH: 1890
<212> TYPE: DNA
<213> ORGANISM: Mycobacterium tuberculosis

<400> SEQUENCE: 71

```
gcagcgatga ggaggagcgg cgccaacggc ccgcgccggc gacgatgcaa agcgcagcga      60
tgaggaggag cggcgcgcat gactgctgaa ccggaagtac ggacgctgcg cgaggttgtg     120
ctggaccagc tcggcactgc tgaatcgcgt gcgtacaaga tgtggctgcc gccgttgacc     180
aatccggtcc cgctcaacga gctcatcgcc cgtgatcggc gacaacccct gcgatttgcc     240
ctggggatca tggatgaacc gcgccgccat ctacaggatg tgtggggcgt agacgtttcc     300
ggggccggcg gcaacatcgg tattggggc gcacctcaaa ccgggaagtc gacgctactg     360
cagacgatgg tgatgtcggc gccgccaca cactcaccgc gcaacgttca gttctattgc     420
atcgacctag gtggcggcgg gctgatctat ctcgaaaacc ttccacacgt cggtggggta     480
gccaatcggt ccgagcccga caaggtcaac cgggtggtcg cagagatgca agccgtcatg     540
cggcaacggg aaaccaccat caaggaacac cgagtgggct cgatcgggat gtaccggcag     600
ctgcgtgacg atccaagtca acccgttgcg tccgatccat acggcgacgt ctttctgatc     660
atcgacggat ggccccggttt tgtcggcgag ttccccgacc ttgagggggca ggttcaagat     720
ctggccgccc aggggctggg gttcggcgtc cacgtcatca tctccacgcc acgctggaca     780
gagctgaagt cgcgtgttcg cgactacctc ggcaccaaga tcgagttccg gcttggtgac     840
gtcaatgaaa cccagatcga ccggattacc cgcgagatcc cggcgaatcg tccgggtcgg     900
gcagtgtcga tggaaaagca ccatctgatg atcggcgtgc caggttcga cggcgtgcac     960
agcgccgata acctggtgga ggcgatcacc gcggggtga cgcagatcgc ttcccagcac    1020
accgaacagg cacctccggt gcgggtcctg ccggagcgta tccacctgca cgaactcgac    1080
ccgaacccgc cgggaccaga gtccgactac cgcactcgct gggagattcc gatcggcttg    1140
cgcgagacgg acctgacgcc ggctcactgc cacatgcaca cgaacccgca cctactgatc    1200
ttcggtgcgg ccaaatcggg caagacgacc attgcccacg cgatcgcgcg cgccatttgt    1260
gcccgaaaca gtccccagca ggtgcggttc atgctcgcgg actaccgctc gggcctgctg    1320
```

-continued

```
gacgcggtgc cggacaccca tctgctgggc gccggcgcga tcaaccgcaa cagcgcgtcg   1380
ctagacgagg ccgctcaagc actggcggtc aacctgaaga agcggttgcc gccgaccgac   1440
ctgacgacgg cgcagctacg ctcgcgttcg tggtggagcg gatttgacgt cgtgcttctg   1500
gtcgacgatt ggcacatgat cgtgggtgcc gcgggggga tgccgccgat ggcaccgctg    1560
gccccgttat tgccggcggc ggcagatatc gggttgcaca tcattgtcac ctgtcagatg   1620
agccaggctt acaaggcaac catggacaag ttcgtcggcg ccgcattcgg gtcgggcgct   1680
ccgacaatgt tcctttcggg cgagaagcag gaattcccat ccagtgagtt caaggtcaag   1740
cggcgccccc ctggccaggc atttctcgtc tcgccagacg gcaaagaggt catccaggcc   1800
ccctacatcg agcctccaga agaagtgttc gcagcacccc caagcgccgg ttaagattat   1860
ttcattgccg gtgtagcagg acccgagctc                                    1890
```

<210> SEQ ID NO 72
<211> LENGTH: 591
<212> TYPE: PRT
<213> ORGANISM: Mycobacterium tuberculosis

<400> SEQUENCE: 72

```
Met Thr Ala Glu Pro Glu Val Arg Thr Leu Arg Glu Val Val Leu Asp
  1               5                  10                  15

Gln Leu Gly Thr Ala Glu Ser Arg Ala Tyr Lys Met Trp Leu Pro Pro
             20                  25                  30

Leu Thr Asn Pro Val Pro Leu Asn Glu Leu Ile Ala Arg Asp Arg Arg
         35                  40                  45

Gln Pro Leu Arg Phe Ala Leu Gly Ile Met Asp Glu Pro Arg Arg His
     50                  55                  60

Leu Gln Asp Val Trp Gly Val Asp Val Ser Gly Ala Gly Asn Ile
 65                  70                  75                  80

Gly Ile Gly Gly Ala Pro Gln Thr Gly Lys Ser Thr Leu Leu Gln Thr
                 85                  90                  95

Met Val Met Ser Ala Ala Thr His Ser Pro Arg Asn Val Gln Phe
            100                 105                 110

Tyr Cys Ile Asp Leu Gly Gly Gly Leu Ile Tyr Leu Glu Asn Leu
        115                 120                 125

Pro His Val Gly Gly Val Ala Asn Arg Ser Glu Pro Asp Lys Val Asn
    130                 135                 140

Arg Val Val Ala Glu Met Gln Ala Val Met Arg Gln Arg Glu Thr Thr
145                 150                 155                 160

Phe Lys Glu His Arg Val Gly Ser Ile Gly Met Tyr Arg Gln Leu Arg
                165                 170                 175

Asp Asp Pro Ser Gln Pro Val Ala Ser Asp Pro Tyr Gly Asp Val Phe
            180                 185                 190

Leu Ile Ile Asp Gly Trp Pro Gly Phe Val Gly Glu Phe Pro Asp Leu
        195                 200                 205

Glu Gly Gln Val Gln Asp Leu Ala Ala Gln Gly Leu Gly Phe Gly Val
    210                 215                 220

His Val Ile Ile Ser Thr Pro Arg Trp Thr Glu Leu Lys Ser Arg Val
225                 230                 235                 240

Arg Asp Tyr Leu Gly Thr Lys Ile Glu Phe Arg Leu Gly Asp Val Asn
                245                 250                 255

Glu Thr Gln Ile Asp Arg Ile Thr Arg Glu Ile Pro Ala Asn Arg Pro
            260                 265                 270
```

-continued

```
Gly Arg Ala Val Ser Met Glu Lys His His Leu Met Ile Gly Val Pro
        275                 280                 285

Arg Phe Asp Gly Val His Ser Ala Asp Asn Leu Val Glu Ala Ile Thr
        290                 295                 300

Ala Gly Val Thr Gln Ile Ala Ser Gln His Thr Glu Gln Ala Pro Pro
305                 310                 315                 320

Val Arg Val Leu Pro Glu Arg Ile His Leu His Glu Leu Asp Pro Asn
                325                 330                 335

Pro Pro Gly Pro Glu Ser Asp Tyr Arg Thr Arg Trp Glu Ile Pro Ile
            340                 345                 350

Gly Leu Arg Glu Thr Asp Leu Thr Pro Ala His Cys His Met His Thr
        355                 360                 365

Asn Pro His Leu Leu Ile Phe Gly Ala Ala Lys Ser Gly Lys Thr Thr
370                 375                 380

Ile Ala His Ala Ile Ala Arg Ala Ile Cys Ala Arg Asn Ser Pro Gln
385                 390                 395                 400

Gln Val Arg Phe Met Leu Ala Asp Tyr Arg Ser Gly Leu Leu Asp Ala
                405                 410                 415

Val Pro Asp Thr His Leu Leu Gly Ala Gly Ala Ile Asn Arg Asn Ser
                420                 425                 430

Ala Ser Leu Asp Glu Ala Ala Gln Ala Leu Ala Val Asn Leu Lys Lys
            435                 440                 445

Arg Leu Pro Pro Thr Asp Leu Thr Thr Ala Gln Leu Arg Ser Arg Ser
        450                 455                 460

Trp Trp Ser Gly Phe Asp Val Val Leu Leu Val Asp Asp Trp His Met
465                 470                 475                 480

Ile Val Gly Ala Ala Gly Gly Met Pro Pro Met Ala Pro Leu Ala Pro
                485                 490                 495

Leu Leu Pro Ala Ala Asp Ile Gly Leu His Ile Ile Val Thr Cys
            500                 505                 510

Gln Met Ser Gln Ala Tyr Lys Ala Thr Met Asp Lys Phe Val Gly Ala
        515                 520                 525

Ala Phe Gly Ser Gly Ala Pro Thr Met Phe Leu Ser Gly Glu Lys Gln
530                 535                 540

Glu Phe Pro Ser Ser Glu Phe Lys Val Lys Arg Arg Pro Pro Gly Gln
545                 550                 555                 560

Ala Phe Leu Val Ser Pro Asp Gly Lys Glu Val Ile Gln Ala Pro Tyr
                565                 570                 575

Ile Glu Pro Pro Glu Glu Val Phe Ala Ala Pro Pro Ser Ala Gly
            580                 585                 590
```

<210> SEQ ID NO 73
<211> LENGTH: 15
<212> TYPE: PRT
<213> ORGANISM: Mycobacterium tuberculosis

<400> SEQUENCE: 73

```
Asp Pro Val Asp Asp Ala Phe Ile Ala Lys Leu Asn Thr Ala Gly
 1               5                  10                  15
```

<210> SEQ ID NO 74
<211> LENGTH: 14
<212> TYPE: PRT
<213> ORGANISM: Mycobacterium tuberculosis
<220> FEATURE:
<221> NAME/KEY: UNSURE

```
<222> LOCATION: (14)
<223> OTHER INFORMATION: Xaa is unknown

<400> SEQUENCE: 74

Asp Pro Val Asp Ala Ile Ile Asn Leu Asp Asn Tyr Gly Xaa
  1               5                  10

<210> SEQ ID NO 75
<211> LENGTH: 15
<212> TYPE: PRT
<213> ORGANISM: Mycobacterium tuberculosis
<220> FEATURE:
<221> NAME/KEY: UNSURE
<222> LOCATION: (5)
<223> OTHER INFORMATION: Xaa is unknown

<400> SEQUENCE: 75

Ala Glu Met Lys Xaa Phe Lys Asn Ala Ile Val Gln Glu Ile Asp
  1               5                  10                  15

<210> SEQ ID NO 76
<211> LENGTH: 14
<212> TYPE: PRT
<213> ORGANISM: Mycobacterium tuberculosis
<220> FEATURE:
<221> NAME/KEY: VARIANT
<222> LOCATION: (3)
<223> OTHER INFORMATION: Ala is Ala or Gln
<220> FEATURE:
<221> NAME/KEY: VARIANT
<222> LOCATION: (7)
<223> OTHER INFORMATION: Thr is Gly or Thr
<220> FEATURE:
<221> NAME/KEY: UNSURE
<222> LOCATION: (11)
<223> OTHER INFORMATION: Xaa is unknown

<400> SEQUENCE: 76

Val Ile Ala Gly Met Val Thr His Ile His Xaa Val Ala Gly
  1               5                  10

<210> SEQ ID NO 77
<211> LENGTH: 15
<212> TYPE: PRT
<213> ORGANISM: Mycobacterium tuberculosis

<400> SEQUENCE: 77

Thr Asn Ile Val Val Leu Ile Lys Gln Val Pro Asp Thr Trp Ser
  1               5                  10                  15

<210> SEQ ID NO 78
<211> LENGTH: 15
<212> TYPE: PRT
<213> ORGANISM: Mycobacterium tuberculosis

<400> SEQUENCE: 78

Ala Ile Glu Val Ser Val Leu Arg Val Phe Thr Asp Ser Asp Gly
  1               5                  10                  15

<210> SEQ ID NO 79
<211> LENGTH: 15
<212> TYPE: PRT
<213> ORGANISM: Mycobacterium tuberculosis

<400> SEQUENCE: 79

Ala Lys Leu Ser Thr Asp Glu Leu Leu Asp Ala Phe Lys Glu Met
  1               5                  10                  15
```

```
<210> SEQ ID NO 80
<211> LENGTH: 15
<212> TYPE: PRT
<213> ORGANISM: Mycobacterium tuberculosis
<220> FEATURE:
<221> NAME/KEY: VARIANT
<222> LOCATION: (4)
<223> OTHER INFORMATION: Asp is Asp or Glu

<400> SEQUENCE: 80

Asp Pro Ala Asp Ala Pro Asp Val Pro Thr Ala Ala Gln Leu Thr
 1               5                  10                  15

<210> SEQ ID NO 81
<211> LENGTH: 50
<212> TYPE: PRT
<213> ORGANISM: Mycobacterium tuberculosis

<400> SEQUENCE: 81

Ala Glu Asp Val Arg Ala Glu Ile Val Ala Ser Val Leu Glu Val Val
 1               5                  10                  15

Val Asn Glu Gly Asp Gln Ile Asp Lys Gly Asp Val Val Leu Leu
            20                  25                  30

Glu Ser Met Tyr Met Glu Ile Pro Val Leu Ala Glu Ala Gly Thr
        35                  40                  45

Val Ser
    50

<210> SEQ ID NO 82
<211> LENGTH: 15
<212> TYPE: PRT
<213> ORGANISM: Mycobacterium tuberculosis

<400> SEQUENCE: 82

Thr Thr Ser Pro Asp Pro Tyr Ala Ala Leu Pro Lys Leu Pro Ser
 1               5                  10                  15

<210> SEQ ID NO 83
<211> LENGTH: 15
<212> TYPE: PRT
<213> ORGANISM: Mycobacterium tuberculosis

<400> SEQUENCE: 83

Thr Glu Tyr Glu Gly Pro Lys Thr Lys Phe His Ala Leu Met Gln
 1               5                  10                  15

<210> SEQ ID NO 84
<211> LENGTH: 15
<212> TYPE: PRT
<213> ORGANISM: Mycobacterium tuberculosis

<400> SEQUENCE: 84

Thr Thr Ile Val Ala Leu Lys Tyr Pro Gly Gly Val Val Met Ala
 1               5                  10                  15

<210> SEQ ID NO 85
<211> LENGTH: 15
<212> TYPE: PRT
<213> ORGANISM: Mycobacterium tuberculosis
<220> FEATURE:
<221> NAME/KEY: UNSURE
<222> LOCATION: (10)
<223> OTHER INFORMATION: Xaa is unknown
<220> FEATURE:
<221> NAME/KEY: UNSURE
```

```
<222> LOCATION: (15)
<223> OTHER INFORMATION: Xaa is unknown

<400> SEQUENCE: 85

Ser Phe Pro Tyr Phe Ile Ser Pro Glu Xaa Ala Met Arg Glu Xaa
 1               5                  10                  15

<210> SEQ ID NO 86
<211> LENGTH: 15
<212> TYPE: PRT
<213> ORGANISM: Mycobacterium tuberculosis

<400> SEQUENCE: 86

Thr His Tyr Asp Val Val Leu Gly Ala Gly Pro Gly Gly Tyr
 1               5                  10                  15

<210> SEQ ID NO 87
<211> LENGTH: 450
<212> TYPE: DNA
<213> ORGANISM: Mycobacterium tuberculosis

<400> SEQUENCE: 87
agcccggtaa tcgagttcgg gcaatgctga ccatcgggtt tgtttccggc tataaccgaa      60
cggtttgtgt acgggataca aatacaggga gggaagaagt aggcaaatgg aaaaaatgtc    120
acatgatccg atcgctgccg acattggcac gcaagtgagc gacaacgctc tgcacggcgt    180
gacggccggc tcgacggcgc tgacgtcggt gaccgggctg gttcccgcgg gggccgatga    240
ggtctccgcc caagcggcga cggcgttcac atcggagggc atccaattgc tggcttccaa    300
tgcatcggcc caagaccagc tccaccgtgc gggcgaagcg gtccaggacg tcgcccgcac    360
ctattcgcaa atcgacgacg gcgccgccgg cgtcttcgcc taataggccc ccaacacatc    420
ggagggagtg atcaccatgc tgtggcacgc                                     450

<210> SEQ ID NO 88
<211> LENGTH: 98
<212> TYPE: PRT
<213> ORGANISM: Mycobacterium tuberculosis

<400> SEQUENCE: 88

Met Glu Lys Met Ser His Asp Pro Ile Ala Ala Asp Ile Gly Thr Gln
 1               5                  10                  15

Val Ser Asp Asn Ala Leu His Gly Val Thr Ala Gly Ser Thr Ala Leu
                20                  25                  30

Thr Ser Val Thr Gly Leu Val Pro Ala Gly Ala Asp Glu Val Ser Ala
            35                  40                  45

Gln Ala Ala Thr Ala Phe Thr Ser Glu Gly Ile Gln Leu Leu Ala Ser
        50                  55                  60

Asn Ala Ser Ala Gln Asp Gln Leu His Arg Ala Gly Glu Ala Val Gln
 65                  70                  75                  80

Asp Val Ala Arg Thr Tyr Ser Gln Ile Asp Asp Gly Ala Ala Gly Val
                85                  90                  95

Phe Ala

<210> SEQ ID NO 89
<211> LENGTH: 460
<212> TYPE: DNA
<213> ORGANISM: Mycobacterium tuberculosis

<400> SEQUENCE: 89
```

```
gcaaccggct tttcgatcag ctgagacatc agcggcgtgc gggtcaacga cccacctgcg    60
ccaggtagcg actccgcgcg cagcaggccc gcgcccgcgc tggggcctga tccaccagcc   120
agcggatggt tcgacagcgg actggtgccg agcaggccca tctgcgcggc ttcctcgtcg   180
gctgggttgc cgccgccggt gccgcccacc tggctgaaca acgacgtcac ctgctgcagc   240
ggctgggtca gctgctgcat cgggccgctc atctcaccca gttggccgag ggtctgggta   300
gccgccggcg gcaactggcc aaccggtgtt gagctgccag gggagggcat tccgaagatc   360
gggttcgtcg tgctctggct cgcgccggga tcaaggatcg acgccatcgg ctcgagcttc   420
tcgaaaagcg tgttaaccgc ggtctcggcc tggtagacct                         460
```

<210> SEQ ID NO 90
<211> LENGTH: 139
<212> TYPE: PRT
<213> ORGANISM: Mycobacterium tuberculosis

<400> SEQUENCE: 90

```
Met Arg Val Asn Asp Pro Pro Ala Pro Gly Ser Asp Ser Ala Arg Ser
  1               5                  10                  15

Arg Pro Ala Pro Ala Leu Gly Pro Asp Pro Pro Ala Ser Gly Trp Phe
             20                  25                  30

Asp Ser Gly Leu Val Pro Ser Arg Pro Ile Cys Ala Ala Ser Ser Ser
         35                  40                  45

Ala Gly Leu Pro Pro Pro Val Pro Pro Thr Trp Leu Asn Asn Asp Val
     50                  55                  60

Thr Cys Cys Ser Gly Trp Val Ser Cys Cys Ile Gly Pro Leu Ile Ser
 65                  70                  75                  80

Pro Ser Trp Pro Arg Val Trp Val Ala Ala Gly Gly Asn Trp Pro Thr
                 85                  90                  95

Gly Val Glu Leu Pro Gly Glu Gly Ile Pro Lys Ile Gly Phe Val Val
            100                 105                 110

Leu Trp Leu Ala Pro Gly Ser Arg Ile Asp Ala Ile Gly Ser Ser Phe
        115                 120                 125

Ser Lys Ser Val Leu Thr Ala Val Ser Ala Trp
    130                 135
```

<210> SEQ ID NO 91
<211> LENGTH: 1200
<212> TYPE: DNA
<213> ORGANISM: Mycobacterium tuberculosis

<400> SEQUENCE: 91

```
taataggccc ccaacacatc ggagggagtg atcaccatgc tgtggcacgc aatgccaccg    60
gagctaaata ccgcacggct gatggccggc gcgggtccgg ctccaatgct gcggcggcc   120 gcgggatggc agacgctttc ggcggctctg gacgctcagg ccgtcgagtt gaccgcgcgc   180
ctgaactctc tgggagaagc ctggactgga ggtggcagcg acaaggcgct gcggctgca   240 acgccgatgg tggtctggct acaaaccgcg tcaacacagg ccaagacccg tgcgatgcag   300
gcgacggcgc aagccgcggc atacacccag gccatggcca cgacgccgtc gctgccggag   360
atcgccgcca accacatcac ccaggccgtc cttacgccca ccaacttctt cggtatcaac   420
acgatcccga tcgcgttgac cgagatggat tatttcatcc gtatgtggaa ccaggcagcc   480
ctggcaatgg aggtctacca ggccgagacc gcggttaaca cgcttttcga aagctcgag   540 ccgatggcgt cgatccttga tcccggcgcg agccagagca cgacgaaccc gatcttcgga   600
```

-continued

```
atgccctccc ctggcagctc aacaccggtt ggccagttgc cgccggcggc tacccagacc    660
ctcggccaac tgggtgagat gagcggcccg atgcagcagc tgacccagcc gctgcagcag    720
gtgacgtcgt tgttcagcca ggtgggcggc accggcggcg gcaacccagc cgacgaggaa    780
gccgcgcaga tgggcctgct cggcaccagt ccgctgtcga accatccgct ggctggtgga    840
tcaggcccca gcgcgggcgc gggcctgctg cgcgcggagt cgctacctgg cgcaggtggg    900
tcgttgaccc gcacgccgct gatgtctcag ctgatcgaaa agccggttgc ccctcggtg     960 atgccggcgg ctgctgccgg atcgtcggcg acgggtggcg ccgctccggt gggtgcggga    1020
gcgatgggcc aggtgcgca atccggcggc tccaccaggc cgggtctggt cgcgccggca     1080
ccgctcgcgc aggagcgtga agaagacgac gaggacgact gggacgaaga ggacgactgg    1140
tgagctcccg taatgacaac agacttcccg gccacccggg ccggaagact tgccaacatt    1200
```

<210> SEQ ID NO 92
<211> LENGTH: 371
<212> TYPE: PRT
<213> ORGANISM: Mycobacterium tuberculosis

<400> SEQUENCE: 92

```
Met Ile Thr Met Leu Trp His Ala Met Pro Pro Glu Leu Asn Thr Ala
  1               5                  10                  15

Arg Leu Met Ala Gly Ala Gly Pro Ala Pro Met Leu Ala Ala Ala Ala
             20                  25                  30

Gly Trp Gln Thr Leu Ser Ala Ala Leu Asp Ala Gln Ala Val Glu Leu
         35                  40                  45

Thr Ala Arg Leu Asn Ser Leu Gly Glu Ala Trp Thr Gly Gly Gly Ser
     50                  55                  60

Asp Lys Ala Leu Ala Ala Ala Thr Pro Met Val Val Trp Leu Gln Thr
 65                  70                  75                  80

Ala Ser Thr Gln Ala Lys Thr Arg Ala Met Gln Ala Thr Ala Gln Ala
                 85                  90                  95

Ala Ala Tyr Thr Gln Ala Met Ala Thr Thr Pro Ser Leu Pro Glu Ile
            100                 105                 110

Ala Ala Asn His Ile Thr Gln Ala Val Leu Thr Ala Thr Asn Phe Phe
        115                 120                 125

Gly Ile Asn Thr Ile Pro Ile Ala Leu Thr Glu Met Asp Tyr Phe Ile
    130                 135                 140

Arg Met Trp Asn Gln Ala Ala Leu Ala Met Glu Val Tyr Gln Ala Glu
145                 150                 155                 160

Thr Ala Val Asn Thr Leu Phe Glu Lys Leu Glu Pro Met Ala Ser Ile
                165                 170                 175

Leu Asp Pro Gly Ala Ser Gln Ser Thr Thr Asn Pro Ile Phe Gly Met
            180                 185                 190

Pro Ser Pro Gly Ser Ser Thr Pro Val Gly Gln Leu Pro Pro Ala Ala
        195                 200                 205

Thr Gln Thr Leu Gly Gln Leu Gly Glu Met Ser Gly Pro Met Gln Gln
    210                 215                 220

Leu Thr Gln Pro Leu Gln Gln Val Thr Ser Leu Phe Ser Gln Val Gly
225                 230                 235                 240

Gly Thr Gly Gly Gly Asn Pro Ala Asp Glu Glu Ala Ala Gln Met Gly
                245                 250                 255

Leu Leu Gly Thr Ser Pro Leu Ser Asn His Pro Leu Ala Gly Gly Ser
            260                 265                 270
```

Gly Pro Ser Ala Gly Ala Gly Leu Leu Arg Ala Glu Ser Leu Pro Gly
            275                 280                 285

Ala Gly Gly Ser Leu Thr Arg Thr Pro Leu Met Ser Gln Leu Ile Glu
        290                 295                 300

Lys Pro Val Ala Pro Ser Val Met Pro Ala Ala Ala Gly Ser Ser
305                 310                 315                 320

Ala Thr Gly Gly Ala Ala Pro Val Gly Ala Gly Ala Met Gly Gln Gly
                325                 330                 335

Ala Gln Ser Gly Gly Ser Thr Arg Pro Gly Leu Val Ala Pro Ala Pro
            340                 345                 350

Leu Ala Gln Glu Arg Glu Glu Asp Glu Asp Asp Trp Asp Glu Glu
        355                 360                 365

Asp Asp Trp
    370

<210> SEQ ID NO 93
<211> LENGTH: 1000
<212> TYPE: DNA
<213> ORGANISM: Mycobacterium tuberculosis

<400> SEQUENCE: 93
gacgcgacac agaaatcctt aaggccggcg gccaaggggc cgaaggtgaa gaaggtgaag      60
ccccagaaac cgaaggccac gaagccgccc aaagtggtgt cgcagcgcgg ctggcgacat     120
tgggtgcatg cgttgacgcg aatcaacctg gcctgtcac ccgacgagaa gtacgagctg      180
gacctgcacg ctcgagtccg ccgcaatccc cgcgggtcgt atcagatcgc cgtcgtcggt     240
ctcaaaggtg gggctggcaa accacgctg acagcagcgt tggggtcgac gttggctcag      300
gtgcgggccg accggatcct ggctctagac gcggatccag gcgccggaaa cctcgccgat     360
cgggtagggc gacaatcggg cgcgaccatc gctgatgtgc ttgcagaaaa agagctgtcg     420
cactacaacg acatccgcgc acacactagc gtcaatgcgg tcaatctgga agtgctgccg     480
gcaccggaat acagctcggc gcagcgcgcg ctcagcgacg ccgactggca tttcatcgcc     540
gatcctgcgt cgaggtttta caacctcgtc ttggctgatt gtggggccgg cttcttcgac     600
ccgctgaccc gcggcgtgct gtccacggtg tccggtgtcg tggtcgtggc aagtgtctca     660
atcgacggcg cacaacaggc gtcggtcgcg ttggactggt gcgcaacaa cggttaccaa      720 gatttggcga ccgcgcatg cgtggtcatc aatcacatca tgccgggaga acccaatgtc     780
gcagttaaag acctggtgcg gcatttcgaa cagcaagttc aacccggccg ggtcgtggtc     840
atgccgtggg acaggcacat tgcggccgga accgagattt cactcgactt gctcgaccct     900
atctacaagc gcaaggtcct cgaattggcc gcagcgctat ccgacgattt cgagagggct     960
ggacgtcgtt gagcgcacct gctgttgctg ctggtcctac                         1000

<210> SEQ ID NO 94
<211> LENGTH: 308
<212> TYPE: PRT
<213> ORGANISM: Mycobacterium tuberculosis

<400> SEQUENCE: 94

Met Lys Lys Val Lys Pro Gln Lys Pro Lys Ala Thr Lys Pro Pro Lys
1               5                   10                  15

Val Val Ser Gln Arg Gly Trp Arg His Trp Val His Ala Leu Thr Arg
            20                  25                  30

Ile Asn Leu Gly Leu Ser Pro Asp Glu Lys Tyr Glu Leu Asp Leu His
        35                  40                  45

Ala Arg Val Arg Arg Asn Pro Arg Gly Ser Tyr Gln Ile Ala Val Val
        50                  55                  60

Gly Leu Lys Gly Gly Ala Gly Lys Thr Thr Leu Thr Ala Ala Leu Gly
 65                  70                  75                  80

Ser Thr Leu Ala Gln Val Arg Ala Asp Arg Ile Leu Ala Leu Asp Ala
                 85                  90                  95

Asp Pro Gly Ala Gly Asn Leu Ala Asp Arg Val Gly Arg Gln Ser Gly
            100                 105                 110

Ala Thr Ile Ala Asp Val Leu Ala Glu Lys Glu Leu Ser His Tyr Asn
        115                 120                 125

Asp Ile Arg Ala His Thr Ser Val Asn Ala Val Asn Leu Glu Val Leu
130                 135                 140

Pro Ala Pro Glu Tyr Ser Ser Ala Gln Arg Ala Leu Ser Asp Ala Asp
145                 150                 155                 160

Trp His Phe Ile Ala Asp Pro Ala Ser Arg Phe Tyr Asn Leu Val Leu
                165                 170                 175

Ala Asp Cys Gly Ala Gly Phe Phe Asp Pro Leu Thr Arg Gly Val Leu
            180                 185                 190

Ser Thr Val Ser Gly Val Val Val Ala Ser Val Ser Ile Asp Gly
        195                 200                 205

Ala Gln Gln Ala Ser Val Ala Leu Asp Trp Leu Arg Asn Asn Gly Tyr
        210                 215                 220

Gln Asp Leu Ala Ser Arg Ala Cys Val Val Ile Asn His Ile Met Pro
225                 230                 235                 240

Gly Glu Pro Asn Val Ala Val Lys Asp Leu Val Arg His Phe Glu Gln
                245                 250                 255

Gln Val Gln Pro Gly Arg Val Val Met Pro Trp Asp Arg His Ile
            260                 265                 270

Ala Ala Gly Thr Glu Ile Ser Leu Asp Leu Leu Asp Pro Ile Tyr Lys
        275                 280                 285

Arg Lys Val Leu Glu Leu Ala Ala Ala Leu Ser Asp Asp Phe Glu Arg
        290                 295                 300

Ala Gly Arg Arg
305

<210> SEQ ID NO 95
<211> LENGTH: 34
<212> TYPE: DNA
<213> ORGANISM: Mycobacterium tuberculosis

<400> SEQUENCE: 95
aagagtagat ctatgatggc cgaggatgtt cgcg                                34

<210> SEQ ID NO 96
<211> LENGTH: 27
<212> TYPE: DNA
<213> ORGANISM: Mycobacterium tuberculosis

<400> SEQUENCE: 96
cggcgacgac ggatcctacc gcgtcgg                                         27

<210> SEQ ID NO 97
<211> LENGTH: 28
<212> TYPE: DNA
<213> ORGANISM: Mycobacterium tuberculosis

<400> SEQUENCE: 97

-continued ccttgggaga tctttggacc ccggttgc     28

<210> SEQ ID NO 98
<211> LENGTH: 25
<212> TYPE: DNA
<213> ORGANISM: Mycobacterium tuberculosis

<400> SEQUENCE: 98
gacgagatct tatgggctta ctgac     25

<210> SEQ ID NO 99
<211> LENGTH: 33
<212> TYPE: DNA
<213> ORGANISM: Mycobacterium tuberculosis

<400> SEQUENCE: 99 cccccccagat ctgcaccacc ggcatcggcg ggc     33

<210> SEQ ID NO 100
<211> LENGTH: 24
<212> TYPE: DNA
<213> ORGANISM: Mycobacterium tuberculosis

<400> SEQUENCE: 100
gcggcggatc cgttgcttag ccgg     24

<210> SEQ ID NO 101
<211> LENGTH: 32
<212> TYPE: DNA
<213> ORGANISM: Mycobacterium tuberculosis

<400> SEQUENCE: 101
ccggctgaga tctatgacag aatacgaagg gc     32

<210> SEQ ID NO 102
<211> LENGTH: 24
<212> TYPE: DNA
<213> ORGANISM: Mycobacterium tuberculosis

<400> SEQUENCE: 102
ccccgccagg gaactagagg cggc     24

<210> SEQ ID NO 103
<211> LENGTH: 38
<212> TYPE: DNA
<213> ORGANISM: Mycobacterium tuberculosis

<400> SEQUENCE: 103
ctgccgagat ctaccaccat tgtcgcgctg aaataccc     38

<210> SEQ ID NO 104
<211> LENGTH: 25
<212> TYPE: DNA
<213> ORGANISM: Mycobacterium tuberculosis

<400> SEQUENCE: 104
cgccatggcc ttacgcgcca actcg     25

<210> SEQ ID NO 105
<211> LENGTH: 32
<212> TYPE: DNA
<213> ORGANISM: Mycobacterium tuberculosis

```
<400> SEQUENCE: 105
ggcggagatc tgtgagtttt ccgtatttca tc                              32

<210> SEQ ID NO 106
<211> LENGTH: 25
<212> TYPE: DNA
<213> ORGANISM: Mycobacterium tuberculosis

<400> SEQUENCE: 106
cgcgtcgagc catggttagg cgcag                                      25

<210> SEQ ID NO 107
<211> LENGTH: 32
<212> TYPE: DNA
<213> ORGANISM: Mycobacterium tuberculosis

<400> SEQUENCE: 107
gaggaagatc tatgacaact tcacccgacc cg                              32

<210> SEQ ID NO 108
<211> LENGTH: 28
<212> TYPE: DNA
<213> ORGANISM: Mycobacterium tuberculosis

<400> SEQUENCE: 108
catgaagcca tggcccgcag gctgcatg                                   28

<210> SEQ ID NO 109
<211> LENGTH: 33
<212> TYPE: DNA
<213> ORGANISM: Mycobacterium tuberculosis

<400> SEQUENCE: 109
ggccgagatc tgtgacccac tatgacgtcg tcg                             33

<210> SEQ ID NO 110
<211> LENGTH: 36
<212> TYPE: DNA
<213> ORGANISM: Mycobacterium tuberculosis

<400> SEQUENCE: 110
ggcgcccatg gtcagaaatt gatcatgtgg ccaacc                          36

<210> SEQ ID NO 111
<211> LENGTH: 33
<212> TYPE: DNA
<213> ORGANISM: Mycobacterium tuberculosis

<400> SEQUENCE: 111
ccgggagatc tatggcaaag ctctccaccg acg                             33

<210> SEQ ID NO 112
<211> LENGTH: 32
<212> TYPE: DNA
<213> ORGANISM: Mycobacterium tuberculosis

<400> SEQUENCE: 112
cgctgggcag agctacttga cggtgacggt gg                              32

<210> SEQ ID NO 113
<211> LENGTH: 36
<212> TYPE: DNA
<213> ORGANISM: Mycobacterium tuberculosis
```

```
<400> SEQUENCE: 113
ggcccagatc tatggccatt gaggtttcgg tgttgc                         36

<210> SEQ ID NO 114
<211> LENGTH: 26
<212> TYPE: DNA
<213> ORGANISM: Mycobacterium tuberculosis

<400> SEQUENCE: 114
cgccgtgttg catggcagcg ctgagc                                    26

<210> SEQ ID NO 115
<211> LENGTH: 24
<212> TYPE: DNA
<213> ORGANISM: Mycobacterium tuberculosis

<400> SEQUENCE: 115
ggacgttcaa gcgacacatc gccg                                      24

<210> SEQ ID NO 116
<211> LENGTH: 24
<212> TYPE: DNA
<213> ORGANISM: Mycobacterium tuberculosis

<400> SEQUENCE: 116
cagcacgaac gcgccgtcga tggc                                      24

<210> SEQ ID NO 117
<211> LENGTH: 26
<212> TYPE: DNA
<213> ORGANISM: Mycobacterium tuberculosis

<400> SEQUENCE: 117
acagatctgt gacggacatg aacccg                                    26

<210> SEQ ID NO 118
<211> LENGTH: 28
<212> TYPE: DNA
<213> ORGANISM: Mycobacterium tuberculosis

<400> SEQUENCE: 118
ttttccatgg tcacgggccc ccggtact                                  28

<210> SEQ ID NO 119
<211> LENGTH: 26
<212> TYPE: DNA
<213> ORGANISM: Mycobacterium tuberculosis

<400> SEQUENCE: 119
acagatctgt gcccatggca cagata                                    26

<210> SEQ ID NO 120
<211> LENGTH: 27
<212> TYPE: DNA
<213> ORGANISM: Mycobacterium tuberculosis

<400> SEQUENCE: 120
tttaagcttc taggcgccca gcgcggc                                   27

<210> SEQ ID NO 121
<211> LENGTH: 26
<212> TYPE: DNA
```

```
<213> ORGANISM: Mycobacterium tuberculosis

<400> SEQUENCE: 121
acagatctgc gcatgcggat ccgtgt                                         26

```
<212> TYPE: PRT
<213> ORGANISM: Mycobacterium tuberculosis

<400> SEQUENCE: 128

Ala Glu Asp Val Arg Ala Glu Ile Val Ala Ser Val Leu Glu Val Val
 1               5                  10                  15

Val Asn Glu Gly Asp Gln Ile Asp Lys Gly Asp Val Val Leu Leu
            20                  25                  30

Glu Ser Met Met Glu Ile Pro Val Leu Ala Glu Ala Ala Gly Thr Val
        35                  40                  45

Ser

<210> SEQ ID NO 129
<211> LENGTH: 50
<212> TYPE: PRT
<213> ORGANISM: Mycobacterium tuberculosis

<400> SEQUENCE: 129

Ala Glu Asp Val Arg Ala Glu Ile Val Ala Ser Val Leu Glu Val Val
 1               5                  10                  15

Val Asn Glu Gly Asp Gln Ile Asp Lys Gly Asp Val Val Leu Leu
            20                  25                  30

Glu Ser Met Lys Met Glu Ile Pro Val Leu Ala Glu Ala Ala Gly Thr
        35                  40                  45

Val Ser
    50

<210> SEQ ID NO 130
<211> LENGTH: 33
<212> TYPE: DNA
<213> ORGANISM: Mycobacterium tuberculosis

<400> SEQUENCE: 130
ccgggagatc tatggcaaag ctctccaccg acg                            33

<210> SEQ ID NO 131
<211> LENGTH: 32
<212> TYPE: DNA
<213> ORGANISM: Mycobacterium tuberculosis

<400> SEQUENCE: 131
cgctgggcag agctacttga cggtgacggt gg                             32

<210> SEQ ID NO 132
<211> LENGTH: 36
<212> TYPE: DNA
<213> ORGANISM: Mycobacterium tuberculosis

<400> SEQUENCE: 132
ggcgccggca agcttgccat gacagagcag cagtgg                         36

<210> SEQ ID NO 133
<211> LENGTH: 26
<212> TYPE: DNA
<213> ORGANISM: Mycobacterium tuberculosis

<400> SEQUENCE: 133
cgaactcgcc ggatcccgtg tttcgc                                    26

<210> SEQ ID NO 134
<211> LENGTH: 32
```

```
<212> TYPE: DNA
<213> ORGANISM: Mycobacterium tuberculosis

<400> SEQUENCE: 134
ggcaaccgcg agatctttct cccggccggg gc                          32

<210> SEQ ID NO 135
<211> LENGTH: 27
<212> TYPE: DNA
<213> ORGANISM: Mycobacterium tuberculosis

<400> SEQUENCE: 135
ggcaagcttg ccggcgccta acgaact                                27

<210> SEQ ID NO 136
<211> LENGTH: 30
<212> TYPE: DNA
<213> ORGANISM: Mycobacterium tuberculosis

<400> SEQUENCE: 136
ggacccagat ctatgacaga gcagcagtgg                             30

<210> SEQ ID NO 137
<211> LENGTH: 47
<212> TYPE: DNA
<213> ORGANISM: Mycobacterium tuberculosis

<400> SEQUENCE: 137
ccggcagccc cggccgggag aaaagctttg cgaacatccc agtgacg          47

<210> SEQ ID NO 138
<211> LENGTH: 44
<212> TYPE: DNA
<213> ORGANISM: Mycobacterium tuberculosis

<400> SEQUENCE: 138
gttcgcaaag cttttctccc ggccggggct gccggtcgag tacc             44

<210> SEQ ID NO 139
<211> LENGTH: 20
<212> TYPE: DNA
<213> ORGANISM: Mycobacterium tuberculosis

<400> SEQUENCE: 139
ccttcggtgg atcccgtcag                                        20

<210> SEQ ID NO 140
<211> LENGTH: 450
<212> TYPE: DNA
<213> ORGANISM: Mycobacterium tuberculosis

<400> SEQUENCE: 140
tggcgctgtc accgaggaac ctgtcaatgt cgtcgagcag tactgaaccg ttccgagaaa    60
ggccagcatg aacgtcaccg tatccattcc gaccatcctg cggccccaca ccggcggcca   120
gaagagtgtc tcggccagcg gcgataccct gggtgccgtc atcagcgacc tggaggccaa   180
ctattcgggc atttccgagc gcctgatgga cccgtcttcc ccaggtaagt tgcaccgctt   240
cgtgaacatc tacgtcaacg acgaggacgt gcggttctcc ggcggcttgg ccaccgcgat   300
cgctgacggt gactcggtca ccatcctccc gccgtggcc  ggtgggtgag cggagcacat   360
gacacgatac gactcgctgt tgcaggcctt gggcaacacg ccgctggttg gcctgcagcg   420
```

```
attgtcgcca cgctgggatg acgggcgaga                                     450
```

<210> SEQ ID NO 141
<211> LENGTH: 93
<212> TYPE: PRT
<213> ORGANISM: Mycobacterium tuberculosis

<400> SEQUENCE: 141

```
Met Asn Val Thr Val Ser Ile Pro Thr Ile Leu Arg Pro His Thr Gly
  1               5                  10                  15

Gly Gln Lys Ser Val Ser Ala Ser Gly Asp Thr Leu Gly Ala Val Ile
             20                  25                  30

Ser Asp Leu Glu Ala Asn Tyr Ser Gly Ile Ser Glu Arg Leu Met Asp
         35                  40                  45

Pro Ser Ser Pro Gly Lys Leu His Arg Phe Val Asn Ile Tyr Val Asn
     50                  55                  60

Asp Glu Asp Val Arg Phe Ser Gly Gly Leu Ala Thr Ala Ile Ala Asp
 65                  70                  75                  80

Gly Asp Ser Val Thr Ile Leu Pro Ala Val Ala Gly Gly
                 85                  90
```

<210> SEQ ID NO 142
<211> LENGTH: 480
<212> TYPE: DNA
<213> ORGANISM: Mycobacterium tuberculosis

<400> SEQUENCE: 142

```
ggtgttcccg cggccggcta tgacaacagt caatgtgcat gacaagttac aggtattagg    60
tccaggttca acaaggagac aggcaacatg gcaaacgttt ttatgacgga tccgcacgcg   120
atgcgggaca tggcgggccg ttttgaggtg cacgcccaga cggtggagga cgaggctcgc   180
cggatgtggg cgtccgcgca aaacatctcg ggcgcgggct ggagtggcat ggccgaggcg   240
acctcgctag acaccatggc ccagatgaat caggcgtttc gcaacatcgt gaacatgctg   300
cacggggtgc gtgacgggct ggttcgcgac gccaacaact acgagcagca agagcaggcc   360
tcccagcaga tcctcagcag ctaacgtcag ccgctgcagc acaatacttt tacaagcgaa   420
ggagaacagg ttcgatgacc atcaactatc agttcggtga tgtcgacgct catggcgcca   480
```

<210> SEQ ID NO 143
<211> LENGTH: 98
<212> TYPE: PRT
<213> ORGANISM: Mycobacterium tuberculosis

<400> SEQUENCE: 143

```
Met Ala Thr Arg Phe Met Thr Asp Pro His Ala Met Arg Asp Met Ala
  1               5                  10                  15

Gly Arg Phe Glu Val His Ala Gln Thr Val Glu Asp Glu Ala Arg Arg
             20                  25                  30

Met Trp Ala Ser Ala Gln Asn Ile Ser Gly Ala Gly Trp Ser Gly Met
         35                  40                  45

Ala Glu Ala Thr Ser Leu Asp Thr Met Ala Gln Met Asn Gln Ala Phe
     50                  55                  60

Arg Asn Ile Val Asn Met Leu His Gly Val Arg Asp Gly Leu Val Arg
 65                  70                  75                  80

Asp Ala Asn Asn Tyr Glu Gln Gln Glu Gln Ala Ser Gln Gln Ile Leu
                 85                  90                  95

Ser Ser
```

<210> SEQ ID NO 144
<211> LENGTH: 940
<212> TYPE: DNA
<213> ORGANISM: Mycobacterium tuberculosis

<400> SEQUENCE: 144

```
gccccagtcc tcgatcgcct catcgccttc accggccgcc agccgaccgc aggccacgtg      60
tccgccacct aacgaaagga tgatcatgcc caagagaagc gaatacagga aaggcacgcc     120
gaactgggtc gaccttcaga ccaccgatca gtccgccgca aaaagttct acacatcgtt      180
gttcggctgg ggttacgacg acaacccggt ccccggaggc ggtggggtct attccatggc     240
cacgctgaac ggcgaagccg tggccgccat cgcaccgatg cccccgggtg caccggaggg     300
gatgccgccg atctggaaca cctatatcgc ggtggacgac gtcgatgcgg tggtggacaa     360
ggtggtgccc ggggcgggc aggtgatgat gccggccttc gacatcggcg atgccggccg      420
gatgtcgttc atcaccgatc cgaccggcgc tgccgtgggc ctatggcagg ccaatcggca     480
catcggagcg acgttggtca acgagacggg cacgctcatc tggaacgaac tgctcacgga     540
caagccggat ttggcgctag cgttctacga ggctgtggtt ggcctcaccc actcgagcat     600
ggagatagct gcgggccaga actatcgggt gctcaaggcc ggcgacgcgg aagtcggcgg     660
ctgtatggaa ccgccgatgc ccggcgtgcc gaatcattgg cacgtctact ttgcggtgga     720
tgacgccgac gccacggcgg ccaaagccgc cgcagcgggc ggccaggtca ttgcggaacc     780
ggctgacatt ccgtcggtgg gccggttcgc cgtgttgtcc gatccgcagg gcgcgatctt     840
cagtgtgttg aagcccgcac cgcagcaata gggagcatcc cgggcaggcc cgccggccgg     900
cagattcgga gaatgctaga agctgccgcc ggcgccgccg                             940
```

<210> SEQ ID NO 145
<211> LENGTH: 261
<212> TYPE: PRT
<213> ORGANISM: Mycobacterium tuberculosis

<400> SEQUENCE: 145

```
Met Pro Lys Arg Ser Glu Tyr Arg Gln Gly Thr Pro Asn Trp Val Asp
  1               5                  10                  15

Leu Gln Thr Thr Asp Gln Ser Ala Ala Lys Lys Phe Tyr Thr Ser Leu
                 20                  25                  30

Phe Gly Trp Gly Tyr Asp Asp Asn Pro Val Pro Gly Gly Gly Val
         35                  40                  45

Tyr Ser Met Ala Thr Leu Asn Gly Glu Ala Val Ala Ala Ile Ala Pro
     50                  55                  60

Met Pro Pro Gly Ala Pro Glu Gly Met Pro Pro Ile Trp Asn Thr Tyr
 65                  70                  75                  80

Ile Ala Val Asp Asp Val Asp Ala Val Val Asp Lys Val Val Pro Gly
                 85                  90                  95

Gly Gly Gln Val Met Met Pro Ala Phe Asp Ile Gly Asp Ala Gly Arg
            100                 105                 110

Met Ser Phe Ile Thr Asp Pro Thr Gly Ala Ala Val Gly Leu Trp Gln
        115                 120                 125

Ala Asn Arg His Ile Gly Ala Thr Leu Val Asn Glu Thr Gly Thr Leu
    130                 135                 140

Ile Trp Asn Glu Leu Leu Thr Asp Lys Pro Asp Leu Ala Leu Ala Phe
145                 150                 155                 160
```

-continued

```
Tyr Glu Ala Val Val Gly Leu Thr His Ser Ser Met Glu Ile Ala Ala
                165                 170                 175

Gly Gln Asn Tyr Arg Val Leu Lys Ala Gly Asp Ala Glu Val Gly Gly
            180                 185                 190

Cys Met Glu Pro Pro Met Pro Gly Val Pro Asn His Trp His Val Tyr
        195                 200                 205

Phe Ala Val Asp Asp Ala Asp Ala Thr Ala Ala Lys Ala Ala Ala Ala
    210                 215                 220

Gly Gly Gln Val Ile Ala Glu Pro Ala Asp Ile Pro Ser Val Gly Arg
225                 230                 235                 240

Phe Ala Val Leu Ser Asp Pro Gln Gly Ala Ile Phe Ser Val Leu Lys
                245                 250                 255

Pro Ala Pro Gln Gln
            260
```

<210> SEQ ID NO 146
<211> LENGTH: 280
<212> TYPE: DNA
<213> ORGANISM: Mycobacterium tuberculosis

<400> SEQUENCE: 146

```
ccgaaaggcg gtgcaccgca cccagaagaa aaggaaagat cgagaaatgc cacagggaac     60
tgtgaagtgg ttcaacgcgg agaaggggtt cggctttatc gcccccgaag acggttccgc    120
ggatgtattt gtccactaca cggagatcca gggaacgggc ttccgcaccc ttgaagaaaa    180
ccagaaggtc gagttcgaga tcggccacag ccctaagggc ccccaggcca ccggagtccg    240
ctcgctctga gttacccccg cgagcagacg caaaaagccc                          280
```

<210> SEQ ID NO 147
<211> LENGTH: 67
<212> TYPE: PRT
<213> ORGANISM: Mycobacterium tuberculosis

<400> SEQUENCE: 147

```
Met Pro Gln Gly Thr Val Lys Trp Phe Asn Ala Glu Lys Gly Phe Gly
  1               5                  10                  15

Phe Ile Ala Pro Glu Asp Gly Ser Ala Asp Val Phe Val His Tyr Thr
             20                  25                  30

Glu Ile Gln Gly Thr Gly Phe Arg Thr Leu Glu Glu Asn Gln Lys Val
         35                  40                  45

Glu Phe Glu Ile Gly His Ser Pro Lys Gly Pro Gln Ala Thr Gly Val
     50                  55                  60

Arg Ser Leu
 65
```

<210> SEQ ID NO 148
<211> LENGTH: 540
<212> TYPE: DNA
<213> ORGANISM: Mycobacterium tuberculosis

<400> SEQUENCE: 148

```
atcgtgtcgt atcgagaacc ccggccggta tcagaacgcg ccagagcgca aacctttata     60
acttcgtgtc ccaaatgtga cgaccatgga ccaaggttcc tgagatgaac ctacggcgcc    120
atcagaccct gacgctgcga ctgctggcgg catccgcggg cattctcagc gccgcggcct    180
tcgccgcgcc agcacaggca aaccccgtcg acgacgcgtt catcgccgcg ctgaacaatg    240
ccggcgtcaa ctacggcgat ccggtcgacg ccaaagcgct gggtcagtcc gtctgcccga    300

```
tcctggccga gcccggcggg tcgtttaaca ccgcggtagc cagcgttgtg gcgcgcgccc    360
aaggcatgtc ccaggacatg gcgcaaacct tcaccagtat cgcgatttcg atgtactgcc    420
cctcggtgat ggcagacgtc gccagcggca acctgccggc cctgccagac atgccggggc    480
tgcccgggtc ctaggcgtgc gcggctccta gccggtccct aacggatcga tcgtggatgc    540
```

<210> SEQ ID NO 149
<211> LENGTH: 129
<212> TYPE: PRT
<213> ORGANISM: Mycobacterium tuberculosis

<400> SEQUENCE: 149

```
Met Asn Leu Arg Arg His Gln Thr Leu Thr Leu Arg Leu Leu Ala Ala
 1               5                  10                  15

Ser Ala Gly Ile Leu Ser Ala Ala Ala Phe Ala Ala Pro Ala Gln Ala
                20                  25                  30

Asn Pro Val Asp Asp Ala Phe Ile Ala Ala Leu Asn Asn Ala Gly Val
            35                  40                  45

Asn Tyr Gly Asp Pro Val Asp Ala Lys Ala Leu Gly Gln Ser Val Cys
 50                  55                  60

Pro Ile Leu Ala Glu Pro Gly Gly Ser Phe Asn Thr Ala Val Ala Ser
 65                  70                  75                  80

Val Val Ala Arg Ala Gln Gly Met Ser Gln Asp Met Ala Gln Thr Phe
                85                  90                  95

Thr Ser Ile Ala Ile Ser Met Tyr Cys Pro Ser Val Met Ala Asp Val
            100                 105                 110

Ala Ser Gly Asn Leu Pro Ala Leu Pro Asp Met Pro Gly Leu Pro Gly
        115                 120                 125

Ser
```

<210> SEQ ID NO 150
<211> LENGTH: 400
<212> TYPE: DNA
<213> ORGANISM: Mycobacterium tuberculosis

<400> SEQUENCE: 150

```
atagtttggg gaaggtgtcc ataaatgagg ctgtcgttga ccgcattgag cgccggtgta     60
ggcgccgtgg caatgtcgtt gaccgtcggg gccggggtcg cctccgcaga tcccgtggac    120
gcggtcatta acaccacctg caattacggg caggtagtag ctgcgctcaa cgcgacggat    180 ccggggctg ccgcacagtt caacgcctca ccggtggcgc agtcctatt tgcgcaatttc    240 ctcgccgcac cgccacctca gcgcgctgcc atggccgcgc aattgcaagc tgtgccgggg    300
gcggcacagt acatcggcct tgtcgagtcg gttgccggct cctgcaacaa ctattaagcc    360
catgcgggcc ccatcccgcg accggcatc gtcgccgggg                           400
```

<210> SEQ ID NO 151
<211> LENGTH: 110
<212> TYPE: PRT
<213> ORGANISM: Mycobacterium tuberculosis

<400> SEQUENCE: 151

```
Met Arg Leu Ser Leu Thr Ala Leu Ser Ala Gly Val Gly Ala Val Ala
 1               5                  10                  15

Met Ser Leu Thr Val Gly Ala Gly Val Ala Ser Ala Asp Pro Val Asp
                20                  25                  30
```

```
Ala Val Ile Asn Thr Thr Cys Asn Tyr Gly Gln Val Ala Ala Leu
         35                  40                  45

Asn Ala Thr Asp Pro Gly Ala Ala Gln Phe Asn Ala Ser Pro Val
 50                  55                  60

Ala Gln Ser Tyr Leu Arg Asn Phe Leu Ala Ala Pro Pro Pro Gln Arg
 65                  70                  75                  80

Ala Ala Met Ala Ala Gln Leu Gln Ala Val Pro Gly Ala Ala Gln Tyr
                 85                  90                  95

Ile Gly Leu Val Glu Ser Val Ala Gly Ser Cys Asn Asn Tyr
                100                 105                 110

<210> SEQ ID NO 152
<211> LENGTH: 990
<212> TYPE: DNA
<213> ORGANISM: Mycobacterium tuberculosis

<400> SEQUENCE: 152
aatagtaata tcgctgtgcg gttgcaaaac gtgtgaccga ggttccgcag tcgagcgctg     60
cgggccgcct tcgaggagga cgaaccacag tcatgacgaa catcgtggtc ctgatcaagc    120
aggtcccaga tacctggtcg gagcgcaagc tgaccgacgg cgatttcacg ctggaccgcg    180
aggccgccga cgcggtgctg gacgagatca acgagcgcgc cgtggaggaa gcgctacaga    240
ttcgggagaa agaggccgcc gacggcatcg aaggtcggt aaccgtgctg acggcgggcc    300
ccgagcgcgc caccgaggcg atccgcaagg cgctgtcgat gggtgccgac aaggccgtcc    360
acctaaagga cgacggcatg cacggctcgg acgtcatcca aaccgggtgg gctttggcgc    420
gcgcgttggg caccatcgag ggcaccgagc tggtgatcgc aggcaacgaa tcgaccgacg    480
gggtgggcgg tgcggtgccg gccatcatcg ccgagtacct gggcctgccg cagctcaccc    540
acctgcgcaa agtgtcgatc gagggcggca agatcaccgg cgagcgtgag accgatgagg    600
gcgtattcac cctcgaggcc acgctgcccg cggtgatcag cgtgaacgag aagatcaacg    660
agccgcgctt cccgtccttc aaaggcatca tggccgccaa gaagaaggaa gttaccgtgc    720
tgaccctggc cgagatcggt gtcgagagcg acgaggtggg gctggccaac gccggatcca    780
ccgtgctggc gtcgacgccc aaaccggcca agactgccgg ggagaaggtc accgacgagg    840
gtgaaggcgg caaccagatc gtgcagtacc tggttgccca gaaaatcatc taagacatac    900
gcacctccca aagacgagag cgatataacc catggctgaa gtactggtgc tcgttgagca    960
cgctgaaggc gcgttaaaga aggtcagcgc                                     990

<210> SEQ ID NO 153
<211> LENGTH: 266
<212> TYPE: PRT
<213> ORGANISM: Mycobacterium tuberculosis

<400> SEQUENCE: 153

Met Thr Asn Ile Val Val Leu Ile Lys Gln Val Pro Asp Thr Trp Ser
 1               5                  10                  15

Glu Arg Lys Leu Thr Asp Gly Asp Phe Thr Leu Asp Arg Glu Ala Ala
                 20                  25                  30

Asp Ala Val Leu Asp Glu Ile Asn Glu Arg Ala Val Glu Glu Ala Leu
         35                  40                  45

Gln Ile Arg Glu Lys Glu Ala Ala Asp Gly Ile Glu Gly Ser Val Thr
 50                  55                  60

Val Leu Thr Ala Gly Pro Glu Arg Ala Thr Glu Ala Ile Arg Lys Ala
 65                  70                  75                  80
```

```
Leu Ser Met Gly Ala Asp Lys Ala Val His Leu Lys Asp Asp Gly Met
                85                  90                  95

His Gly Ser Asp Val Ile Gln Thr Gly Trp Ala Leu Ala Arg Ala Leu
            100                 105                 110

Gly Thr Ile Glu Gly Thr Glu Leu Val Ile Ala Gly Asn Glu Ser Thr
        115                 120                 125

Asp Gly Val Gly Gly Ala Val Pro Ala Ile Ile Ala Glu Tyr Leu Gly
    130                 135                 140

Leu Pro Gln Leu Thr His Leu Arg Lys Val Ser Ile Glu Gly Gly Lys
145                 150                 155                 160

Ile Thr Gly Glu Arg Glu Thr Asp Glu Gly Val Phe Thr Leu Glu Ala
                165                 170                 175

Thr Leu Pro Ala Val Ile Ser Val Asn Glu Lys Ile Asn Glu Pro Arg
            180                 185                 190

Phe Pro Ser Phe Lys Gly Ile Met Ala Ala Lys Lys Lys Glu Val Thr
        195                 200                 205

Val Leu Thr Leu Ala Glu Ile Gly Val Glu Ser Asp Glu Val Gly Leu
    210                 215                 220

Ala Asn Ala Gly Ser Thr Val Leu Ala Ser Thr Pro Lys Pro Ala Lys
225                 230                 235                 240

Thr Ala Gly Glu Lys Val Thr Asp Glu Gly Glu Gly Asn Gln Ile
                245                 250                 255

Val Gln Tyr Leu Val Ala Gln Lys Ile Ile
            260                 265

<210> SEQ ID NO 154
<211> LENGTH: 25
<212> TYPE: DNA
<213> ORGANISM: Mycobacterium tuberculosis

<400> SEQUENCE: 154
ctgagatcta tgaacctacg gcgcc                                         25

<210> SEQ ID NO 155
<211> LENGTH: 35
<212> TYPE: DNA
<213> ORGANISM: Mycobacterium tuberculosis

<400> SEQUENCE: 155
ctcccatggt accctaggac ccgggcagcc ccggc                              35

<210> SEQ ID NO 156
<211> LENGTH: 29
<212> TYPE: DNA
<213> ORGANISM: Mycobacterium tuberculosis

<400> SEQUENCE: 156
ctgagatcta tgaggctgtc gttgaccgc                                     29

<210> SEQ ID NO 157
<211> LENGTH: 30
<212> TYPE: DNA
<213> ORGANISM: Mycobacterium tuberculosis

<400> SEQUENCE: 157
ctccccgggc ttaatagttg ttgcaggagc                                    30

<210> SEQ ID NO 158
```

-continued

```
<210> SEQ ID NO 158
<211> LENGTH: 33
<212> TYPE: DNA
<213> ORGANISM: Mycobacterium tuberculosis

<400> SEQUENCE: 158
gcttagatct atgattttct gggcaaccag gta                           33

<210> SEQ ID NO 159
<211> LENGTH: 30
<212> TYPE: DNA
<213> ORGANISM: Mycobacterium tuberculosis

<400> SEQUENCE: 159
gcttccatgg gcgaggcaca ggcgtgggaa                              30

<210> SEQ ID NO 160
<211> LENGTH: 30
<212> TYPE: DNA
<213> ORGANISM: Mycobacterium tuberculosis

<400> SEQUENCE: 160
ctgagatcta gaatgccaca gggaactgtg                              30

<210> SEQ ID NO 161
<211> LENGTH: 30
<212> TYPE: DNA
<213> ORGANISM: Mycobacterium tuberculosis

<400> SEQUENCE: 161
tctcccgggg gtaactcaga gcgagcggac                              30

<210> SEQ ID NO 162
<211> LENGTH: 27
<212> TYPE: DNA
<213> ORGANISM: Mycobacterium tuberculosis

<400> SEQUENCE: 162
ctgagatcta tgaacgtcac cgtatcc                                 27

<210> SEQ ID NO 163
<211> LENGTH: 27
<212> TYPE: DNA
<213> ORGANISM: Mycobacterium tuberculosis

<400> SEQUENCE: 163
tctcccgggg ctcacccacc ggccacg                                 27

<210> SEQ ID NO 164
<211> LENGTH: 30
<212> TYPE: DNA
<213> ORGANISM: Mycobacterium tuberculosis

<400> SEQUENCE: 164
ctgagatcta tggcaacacg ttttatgacg                              30

<210> SEQ ID NO 165
<211> LENGTH: 30
<212> TYPE: DNA
<213> ORGANISM: Mycobacterium tuberculosis

<400> SEQUENCE: 165
ctccccgggt tagctgctga ggatctgcth                              30
```

```
<210> SEQ ID NO 166
<211> LENGTH: 31
<212> TYPE: DNA
<213> ORGANISM: Mycobacterium tuberculosis

<400> SEQUENCE: 166
ctgaagatct atgcccaaga gaagcgaata c                              31

<210> SEQ ID NO 167
<211> LENGTH: 31
<212> TYPE: DNA
<213> ORGANISM: Mycobacterium tuberculosis

<400> SEQUENCE: 167
cggcagctgc tagcattctc cgaatctgcc g                              31

<210> SEQ ID NO 168
<211> LENGTH: 15
<212> TYPE: PRT
<213> ORGANISM: Mycobacterium tuberculosis

<400> SEQUENCE: 168

Pro Gln Gly Thr Val Lys Trp Phe Asn Ala Glu Lys Gly Phe Gly
 1               5                  10                  15

<210> SEQ ID NO 169
<211> LENGTH: 15
<212> TYPE: PRT
<213> ORGANISM: Mycobacterium tuberculosis
<220> FEATURE:
<221> NAME/KEY: UNSURE
<222> LOCATION: (15)
<223> OTHER INFORMATION: Xaa is unknown

<400> SEQUENCE: 169

Asn Val Thr Val Ser Ile Pro Thr Ile Leu Arg Pro Xaa Xaa Xaa
 1               5                  10                  15

<210> SEQ ID NO 170
<211> LENGTH: 15
<212> TYPE: PRT
<213> ORGANISM: Mycobacterium tuberculosis
<220> FEATURE:
<221> NAME/KEY: VARIANT
<222> LOCATION: (1)
<223> OTHER INFORMATION: Thr could also be Ala

<400> SEQUENCE: 170

Thr Arg Phe Met Thr Asp Pro His Ala Met Arg Asp Met Ala Gly
 1               5                  10                  15

<210> SEQ ID NO 171
<211> LENGTH: 15
<212> TYPE: PRT
<213> ORGANISM: Mycobacterium tuberculosis

<400> SEQUENCE: 171

Pro Lys Arg Ser Glu Tyr Arg Gln Gly Thr Pro Asn Trp Val Asp
 1               5                  10                  15

<210> SEQ ID NO 172
<211> LENGTH: 404
<212> TYPE: PRT
<213> ORGANISM: Mycobacterium tuberculosis

<400> SEQUENCE: 172
```

```
Met Ala Thr Val Asn Arg Ser Arg His His His His His His
 1               5                  10                  15

Ile Glu Gly Arg Ser Phe Ser Arg Pro Gly Leu Pro Val Glu Tyr Leu
                 20                  25                  30

Gln Val Pro Ser Pro Ser Met Gly Arg Asp Ile Lys Val Gln Phe Gln
             35                  40                  45

Ser Gly Gly Asn Asn Ser Pro Ala Val Tyr Leu Leu Asp Gly Leu Arg
 50                  55                  60

Ala Gln Asp Asp Tyr Asn Gly Trp Asp Ile Asn Thr Pro Ala Phe Glu
 65                  70                  75                  80

Trp Tyr Tyr Gln Ser Gly Leu Ser Ile Val Met Pro Val Gly Gly Gln
                 85                  90                  95

Ser Ser Phe Tyr Ser Asp Trp Tyr Ser Pro Ala Cys Gly Lys Ala Gly
             100                 105                 110

Cys Gln Thr Tyr Lys Trp Glu Thr Phe Leu Thr Ser Glu Leu Pro Gln
             115                 120                 125

Trp Leu Ser Ala Asn Arg Ala Val Lys Pro Thr Gly Ser Ala Ala Ile
 130                 135                 140

Gly Leu Ser Met Ala Gly Ser Ser Ala Met Ile Leu Ala Ala Tyr His
145                 150                 155                 160

Pro Gln Gln Phe Ile Tyr Ala Gly Ser Leu Ser Ala Leu Leu Asp Pro
                 165                 170                 175

Ser Gln Gly Met Gly Pro Ser Leu Ile Gly Leu Ala Met Gly Asp Ala
             180                 185                 190

Gly Gly Tyr Lys Ala Ala Asp Met Trp Gly Pro Ser Ser Asp Pro Ala
             195                 200                 205

Trp Glu Arg Asn Asp Pro Thr Gln Gln Ile Pro Lys Leu Val Ala Asn
 210                 215                 220

Asn Thr Arg Leu Trp Val Tyr Cys Gly Asn Gly Thr Pro Asn Glu Leu
225                 230                 235                 240

Gly Gly Ala Asn Ile Pro Ala Glu Phe Leu Glu Asn Phe Val Arg Ser
                 245                 250                 255

Ser Asn Leu Lys Phe Gln Asp Ala Tyr Asn Ala Ala Gly Gly His Asn
             260                 265                 270

Ala Val Phe Asn Phe Pro Pro Asn Gly Thr His Ser Trp Glu Tyr Trp
             275                 280                 285

Gly Ala Gln Leu Asn Ala Met Lys Gly Asp Leu Gln Ser Ser Leu Gly
 290                 295                 300

Ala Gly Lys Leu Ala Met Thr Glu Gln Gln Trp Asn Phe Ala Gly Ile
305                 310                 315                 320

Glu Ala Ala Ala Ser Ala Ile Gln Gly Asn Val Thr Ser Ile His Ser
                 325                 330                 335

Leu Leu Asp Glu Gly Lys Gln Ser Leu Thr Lys Leu Ala Ala Ala Trp
             340                 345                 350

Gly Gly Ser Gly Ser Glu Ala Tyr Gln Gly Val Gln Gln Lys Trp Asp
             355                 360                 365

Ala Thr Ala Thr Glu Leu Asn Asn Ala Leu Gln Asn Leu Ala Arg Thr
 370                 375                 380

Ile Ser Glu Ala Gly Gln Ala Met Ala Ser Thr Glu Gly Asn Val Thr
385                 390                 395                 400

Gly Met Phe Ala

<210> SEQ ID NO 173
```

```
<211> LENGTH: 403
<212> TYPE: PRT
<213> ORGANISM: Mycobacterium tuberculosis

<400> SEQUENCE: 173

Met Ala Thr Val Asn Arg Ser Arg His His His His His His
  1               5                  10                  15

Ile Glu Gly Arg Ser Met Thr Glu Gln Gln Trp Asn Phe Ala Gly Ile
                 20                  25                  30

Glu Ala Ala Ala Ser Ala Ile Gln Gly Asn Val Thr Ser Ile His Ser
             35                  40                  45

Leu Leu Asp Glu Gly Lys Gln Ser Leu Thr Lys Leu Ala Ala Ala Trp
 50                  55                  60

Gly Gly Ser Gly Ser Glu Ala Tyr Gln Gly Val Gln Gln Lys Trp Asp
 65                  70                  75                  80

Ala Thr Ala Thr Glu Leu Asn Asn Ala Leu Gln Asn Leu Ala Arg Thr
                 85                  90                  95

Ile Ser Glu Ala Gly Gln Ala Met Ala Ser Thr Glu Gly Asn Val Thr
                100                 105                 110

Gly Met Phe Ala Lys Leu Phe Ser Arg Pro Gly Leu Pro Val Glu Tyr
            115                 120                 125

Leu Gln Val Pro Ser Pro Ser Met Gly Arg Asp Ile Lys Val Gln Phe
130                 135                 140

Gln Ser Gly Gly Asn Asn Ser Pro Ala Val Tyr Leu Leu Asp Gly Leu
145                 150                 155                 160

Arg Ala Gln Asp Asp Tyr Asn Gly Trp Asp Ile Asn Thr Pro Ala Phe
                165                 170                 175

Glu Trp Tyr Tyr Gln Ser Gly Leu Ser Ile Val Met Pro Val Gly Gly
            180                 185                 190

Gln Ser Ser Phe Tyr Ser Asp Trp Tyr Ser Pro Ala Cys Gly Lys Ala
        195                 200                 205

Gly Cys Gln Thr Tyr Lys Trp Glu Thr Phe Leu Thr Ser Glu Leu Pro
    210                 215                 220

Gln Trp Leu Ser Ala Asn Arg Ala Val Lys Pro Thr Gly Ser Ala Ala
225                 230                 235                 240

Ile Gly Leu Ser Met Ala Gly Ser Ser Ala Met Ile Leu Ala Ala Tyr
                245                 250                 255

His Pro Gln Gln Phe Ile Tyr Ala Gly Ser Leu Ser Ala Leu Leu Asp
            260                 265                 270

Pro Ser Gln Gly Met Gly Pro Ser Leu Ile Gly Leu Ala Met Gly Asp
        275                 280                 285

Ala Gly Gly Tyr Lys Ala Ala Asp Met Trp Gly Pro Ser Ser Asp Pro
    290                 295                 300

Ala Trp Glu Arg Asn Asp Pro Thr Gln Gln Ile Pro Lys Leu Val Ala
305                 310                 315                 320

Asn Asn Thr Arg Leu Trp Val Tyr Cys Gly Asn Gly Thr Pro Asn Glu
                325                 330                 335

Leu Gly Gly Ala Asn Ile Pro Ala Glu Phe Leu Glu Asn Phe Val Arg
            340                 345                 350

Ser Ser Asn Leu Lys Phe Gln Asp Ala Tyr Asn Ala Ala Gly Gly His
        355                 360                 365
```

-continued

```
Asn Ala Val Phe Asn Phe Pro Pro Asn Gly Thr His Ser Trp Glu Tyr
    370                 375                 380

Trp Gly Ala Gln Leu Asn Ala Met Lys Gly Asp Leu Gln Ser Ser Leu
385                 390                 395                 400

Gly Ala Gly
```